US008680236B2

(12) United States Patent
Luft et al.

(10) Patent No.: US 8,680,236 B2
(45) Date of Patent: Mar. 25, 2014

(54) **ALTERED OSPA OF *BORRELIA BURGDORFERI***

(75) Inventors: Benjamin J. Luft, East Setauket, NY (US); John J. Dunn, Bellport, NY (US); Shohei Koide, Chicago, IL (US); Catherine L. Lawson, Piscataway, NJ (US)

(73) Assignees: Brookhaven Sciences Associates, LLC, Upton, NY (US); University of Rochester, Rochester, NY (US); Research Foundation of the State University of New York, Stony Brook, NY (US)

( * ) Notice: Subject to any disclaimer, the term of this patent is extended or adjusted under 35 U.S.C. 154(b) by 578 days.

(21) Appl. No.: 12/313,443

(22) Filed: Nov. 19, 2008

(65) Prior Publication Data

US 2009/0326200 A1    Dec. 31, 2009

Related U.S. Application Data

(63) Continuation of application No. 10/369,339, filed on Feb. 18, 2003, now abandoned, which is a continuation of application No. PCT/US01/25852, filed on Aug. 17, 2001.

(60) Provisional application No. 60/226,484, filed on Aug. 18, 2000.

(51) Int. Cl.
*C07K 14/00* (2006.01)
*C07K 14/20* (2006.01)
*C12N 15/00* (2006.01)
*C12N 15/31* (2006.01)

(52) U.S. Cl.
USPC ... 530/350; 435/69.1; 435/320.1; 435/252.33

(58) Field of Classification Search
None
See application file for complete search history.

(56) References Cited

U.S. PATENT DOCUMENTS

| | | |
|---|---|---|
| 5,217,872 A | 6/1993 | Dorward et al. |
| 5,470,712 A | 11/1995 | Simpson et al. |
| 5,523,089 A | 6/1996 | Bergstrom et al. |
| 5,571,718 A | 11/1996 | Dunn et al. |
| 5,620,862 A | 4/1997 | Padula |
| 5,688,512 A | 11/1997 | Bergstrom et al. |
| 5,747,294 A | 5/1998 | Flavell et al. |
| 5,777,095 A | 7/1998 | Barbour et al. |
| 5,780,041 A | 7/1998 | Simpson et al. |
| 6,113,914 A | 9/2000 | Lobet et al. |
| 6,197,301 B1 | 3/2001 | Flavell et al. |
| 6,210,676 B1 | 4/2001 | Callister et al. |
| 6,248,562 B1 | 6/2001 | Dunn et al. |
| 2004/0023325 A1 | 2/2004 | Luft et al. |
| 2004/0033236 A1 | 2/2004 | Dattwyler et al. |

FOREIGN PATENT DOCUMENTS

| | | |
|---|---|---|
| EP | 0 418 827 A1 | 3/1991 |
| EP | 0 465 204 A2 | 1/1992 |
| EP | 0 492 964 A2 | 7/1992 |
| EP | 0 522 560 A2 | 1/1993 |
| EP | 0 540 457 A1 | 5/1993 |
| EP | 0 643 974 B1 | 3/1995 |
| EP | 0 711 563 A1 | 5/1996 |
| EP | 0598 816 B1 | 6/1999 |
| EP | 1 016 416 A2 | 7/2000 |
| EP | 1 311 540 | 5/2003 |
| WO | WO 90/04411 | 5/1990 |
| WO | WO 91/09870 | 7/1991 |
| WO | WO 92/00055 | 1/1992 |
| WO | WO 93/04175 | 3/1993 |
| WO | WO 93/08286 | 4/1993 |
| WO | WO 93/08299 | 4/1993 |
| WO | WO 93/10237 | 5/1993 |
| WO | WO 94/19697 | 9/1994 |
| WO | WO 94/20536 | 9/1994 |
| WO | WO 94/25596 | 11/1994 |
| WO | WO 95/12676 | 5/1995 |
| WO | WO 96/40290 | 12/1996 |
| WO | WO 96/49718 | 12/1996 |
| WO | WO 97/42221 | 11/1997 |
| WO | WO 98/00549 | 1/1998 |
| WO | WO 99/14345 | 3/1999 |
| WO | WO 00/06745 | 2/2000 |
| WO | WO 91/13630 | 9/2001 |
| WO | WO 02/16421 A2 | 2/2002 |

OTHER PUBLICATIONS

Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Eiffert et al, Nucleotide Sequence of the ospAB Operon of a *Borrelia burgdorferi* Strain Expressing OspA but Not OspB, Infection and Immunity, May 1992, vol. 60, No. 5, p. 1864-1868.*
Balmelli et al, Association between different clinical manifestations of Lyme disease and of *Borrelia burgdoferi* sensu lato, Res Microbiol, 1995, 146, 329-340.*
Willett et al, An effective second-generation outer surface protein A-derived Lyme vaccine that eliminates a potentially autoreactive T cell epitope, PNAS, Feb. 3, 2004, vol. 101 (No. 5), 1303-1308.*
Wallich, R. et al., "DNA Vaccines Expressing a Fusion Product of Outer Surface Proteins A and C from *Borrelia burgdorferi* Induce Protective Antibodies Suitable for Prophylaxis But Not for Resolution of Lyme Disease," Infect. Immun., 69(4):2130-2136 (Apr. 2001).

(Continued)

*Primary Examiner* — Maria Marvich
(74) *Attorney, Agent, or Firm* — Hamilton, Brook, Smith & Reynolds, P.C.

(57) ABSTRACT

Provided herein are OspA polypeptides from Lyme Disease-causing *Borrelia* having certain alteration(s). In one embodiment, the alteration(s) increase the conformational stability of the OspA polypeptide containing the alteration(s) while maintaining at least some of the antigenicity of the corresponding unaltered OspA polypeptide. In another embodiment, the altered OspA polypeptide has reduced cross-reactivity to hLFA-1, as compared to the corresponding unaltered OspA polypeptide.

4 Claims, 138 Drawing Sheets

(56) References Cited

OTHER PUBLICATIONS

Kalish, R.S., et al., "Lyme Disease: Human T-cell Response to OspA and OspC *Borrelia Lipoproteins* Includes Both CD8+and CD4+T-Cells," J. Invest. Dermatol., 114(4):836 Abstract 523 (2000) (month not available).

Luft, B.J., et al., "A New Multi-Target OspA-OspC Vaccine for Lyme Disease," Abstracts of the Interscience Conference on Antimicrobial Agents and Chemotherapy, 40:248 Abstract 1932 (Sep. 2000).

Gomes-Solecki, M.J.C., et al., "Recombinant Chimeric *Borrelia* Proteins for Diagnosis of Lyme Disease," J. Clin. Microbiol., 38(7):2530-2535 (Jul. 2000).

Bakken, L.L., et al., "Interlaboratory Comparison of Test Results for Detection of Lyme Disease by 516 Participants in the Wisconsin State Laboratory of Hygiene/College of American Pathologists Proficiency Testing Program," J. Clin. Microbiol., 35(3):537-543 (Mar. 1997).

Chang, Y-F., et al., "Expression and Secretion of Outer Surface Protein (OSP-A) of *Borrelia burgdorferi* From *Escherichia coli*," FEMS Microbiol. Lett. 109:297-301 (Mar. 1993).

De, B.K., et al., "Purification and Characterization of *Streptococcus pneumoniae Palmitoylated Pneumococcal* Surface Adhesin a Expressed in *Escherichia coli*," Vaccine, 18:1811-1821 (2000) (month not available).

de Silva, A.M., et al., "*Borrelia burgdorferi* OspA Is an Arthropod-Specific Transmission-Blocking Lyme Disease Vaccine," J. Exp. Med. 183(1):271-275 (Jan. 1996).

de Silva, A.M. And E. Fikrig, "Arthopod- and Host-Specific Gene Expression by *Borrelia burgdorferi*," J. Clin. Invest. 99(3):377-379 (Feb. 1997).

Fingerle, V., et al., "Expression of Outer Surface Proteins A and C of *Borrelia burgdorferi* in Ixodes ricinus Ticks Removed from Humans," Med. Microbiol. Immunol. 187(2):121-126 (Jul. 1998).

Dykhuizen, D.E., et al., "*Borrelia burgdorferi* is Clonal: Implications for Taxonomy and Vaccine Development," Proc. Natl. Acad. Sci. USA 90:10163-10167 (Jul. 1993).

Gilmore, R.D., Jr., et al., "Outer Surface Protein C (OspC), but Not P39, Is a Protective Immunogen Against a Tick-Transmitted *Borrelia burgdorferi* Challenge: Evidence for a Conformational Protective Epitope in OspC," Infect. Immun. (64)6:2234-2239 (Jun. 1996).

Montgomery, R.R., et al., "Direct Demonstration of Antigenic Substitution of *Borrelia burgdorferi* Ex Vivo: Exploration of the Paradox of the Early Immune Response to Outer Surface Proteins A and C in Lyme Disease," J. Exp. Med. 183 (1):261-269 (Jan. 1996).

Probert, W.S. And R.B. LeFebvre, "Protection of C3H/HeN Mice from Challenge with *Borrelia burgdorferi* through Active Immunization with OspA, OspB, or OspC, but Not OspD or the 83-Kilodalton Antigen," Infect. Immun. 62(5):1920-1926 (Mar. 1994).

Probert, W.S., et al., "Immunization with Outer Surface Protein (Osp) A, but Not OspC, Provides Cross-Protection of Mice Challenged with North American Isolates of *Borrelia burgdorferi*," J. Infect. Dis. 175(2):400-405 (1997) (month not available).

Schwan, T.G., et al., "Induction of an Outer Surface Protein on *Borrelia burgdorferi* During Tick Feeding," Proc. Natl. Acad. Sci. USA 92:2909-2913 (Mar. 1995).

Simon, M.M., et al., "Protective Immunization with Plasmid DNA Containing the Outer Surface Lipoprotein a Gene of *Borrelia burgdorferi* is Independent of an Eukaryotic Promoter," Eur. J. Immunol. 26(12):2831-2840 (Aug. 1996).

Simon, M.M., et al., "Lyme Disease: Pathogenesis and Vaccine Development," Zent.bl. Bakteriol. 289:690-695 (1999) (month not available).

Solé, M., et al., "*Borrelia burgdorferi* Escape Mutants That Survive in the Presence of Antiserum to the OspA Vaccine Are Killed When Complement Is Also Present," Infect. Immun. 66(6):2540-2546 (Jun. 1998).

Steigbigel, R.T. And J.L. Benach, "Immunization Against Lyme Disease—An Important First Step," N. Engl. J. Med. 339(4):263-264 (Jul. 1998).

Stover, C.K., et al., "Protective Immunity Elicited by rBCG Vaccines," Dev. Biol. Stand. 82:163170 (1994) (month not available).

Thanassi, W.T. And R.T. Schoen, "The Lyme Disease Vaccine: Conception, Development, and Implementation," Ann. Intern. Med. 132:661-668 (2000) (month not available).

Wahlberg, P., "Vaccination Against Lyme *borreliosis*," Ann. Med. 31:233-235 (1999) (month not available).

Wang, I-N., et al., "Genetic Diversity of ospC in a Local Population of *Borrelia burgdorferi* sensu stricto," Genetics 151:15-30 (Jan. 1999).

Wieneke, C.A., et al., "Evaluation of Whole-Cell and OspC Enzyme-Linked Immunosorbent Assays for Discrimination of Early Lyme *Borreliosis* from OspA Vaccination," J. Clin. Microbiol., 38(1):313-317 (Jan. 2000).

Wilske, B., et al., "Diversity of OspA and OspC among Cerebrospinal Fluid Isolates of *Borrelia burgdorferi* sensu lato from Patients with Neuroborreliosis in Germany," Med. Microbiol. Immunol. 184:195-201 (1996) (month not available).

Wilske, B., et al., "Immunological and Molecular Variability of OspA and OspC. Implications for *Borrelia* Vaccine Development," Infection 24(2):208-212 (1996) (month not available).

Wilske, B., et al., "Immunological and Molecular Polymorphisms of OspC, an Immunodominant Major Outer Surface Protein of *Borrelia burgdorferi*," Infect. Immun. 61(5):2182-2191 (May 1993).

Zhong, W. et al., "Therapeutic Passive Vaccination Against Chronic Lyme Disease in Mice," Proc. Natl. Acad. Sci. USA 94:12533-12538 (Nov. 1997).

Zhong, W. et al., "Resolution of Experimental and Tick-borne *Borrelia burgdorferi* Infection in Mice by Passive, But Not Active Immunization Using Recombinant OspC," Eur. J. Immunol. 29:946-957 (1999) (month not available).

Fikrig, E., et al., "Selection of Variant *Borrelia burgdorferi* Isolates From Mice Immunized With Outer Surface Protein A or B," Infect. Immun., 63(5):1658-1662 (May 1995).

Sellati, T.J., et al., "Outer Surface Lipoproteins of *Borrelia burgdorferi* Activate Vascular Endothelium in Vitro," Infect. Immun. 64(8):3180-3187 (Aug. 1996).

Zhang, Y-Q., et al., "*Borrelia burgdorferi* Enzyme-Linked Immunosorbent Assay for Discrimination of OspA Vaccination from Spirochete Infection," J. Clin. Microbiol., 35(1):233238 (Jan. 1997).

Bunikis, J., et al., "Access of Antibody or Trypsin to an Integral Outer Membrane Protein (P66) of *Borrelia burgdorferi* Is Hindered by Osp Lipoproteins," Infect. Immun., 67(6):2874-2883 (Jun. 1999).

Hughes, C.A.N., et al., "Protective Immunity Is Induced by a *Borrelia burgdorferi* Mutant That Lacks OspA and OspB," Infect. Immun. 61(12):5115-5122 (Dec. 1993).

Wallich, R., et al., "A Recombinant Vaccine for Lyme Disease," Behring Inst. Mitt., 95:106-108 (1994) (month not available).

Rosa, P.A., et al., "Recombination Between Genes Encoding Major Outer Surface Proteins A and B of *Borrelia burgdorferi*," Mol. Microbiol., 6(20):3031-3040 (Jul. 1992).

Stover, C.K., et al., "Protective Immunity Elicited by Recombinant Bacille Calmette-Guerin (BCG) Expressing Outer Surface Protein A (OspA) Lipoprotein: A Candidate Lyme Disease Vaccine," J. Exp. Med., 178:197-209 (Jul. 1993).

Schwan, T.G., et al., "Distribution and Molecular Analysis of Lyme Disease Spirochetes, *Borrelia burgdorferi*, Isolated From Ticks Throughout California," J. Clin. Microbiol., 31(12):3096-3108 (Dec. 1993).

Hu, C.M., et al., "Comparison in the Immunological Properties of *Borrelia burgdorferi* Isolates from Ixodes Ricinus Derived From Three Endemic Areas in Switzerland," Epidemiol. Infect., 112:533-542 (Jan. 1994).

Schubach, W.H., et al., "Mapping Antibody-Binding Domains of the Major Outer Surface Membrane Protein (OspA) of *Borrelia burgdorferi*," Infect. Immun. 59(6):1911-1915 (Jun. 1991).

Kitten, T., et al., "Intragenic Recombination and a Chimeric Outer Membrane Protein in the Relapsing Fever Agent *Borrelia hermsii*," J. Bacteriol., 175(9):2516-2522 (May 1993).

McGrath, B.C., et al., "Biochemical and Biophysical Characterization of the Major Outer Surface Protein from North American and European Isolates of *Borrelia burgdorferi*", Vaccines 93:365-370 (1993) (month not available).

(56) References Cited

OTHER PUBLICATIONS

France, L.L., et al., "Evidence for an ÿ-Helical Epitope on Outer Surface Protein A From the Lyme Disease Spirochete, *Borrelia burgdorferi* : An Application of Steady-State and Time-Resolved Fluorescence Quenching Techniques," Biochim. Biophys. Acta., 1202:287-296 (May 1993).
Kantor, F.S., "Disarming Lyme Disease," Sci. Am. 271(3):34-39 (Sep. 1994).
McGrath, B.C., et al., "Identification of an Immunologically Important Hypervariable Domain of Major Outer Surface Protein a of *Borrelia burgdorferi* ," Infect. Immun., 63(4):1356-1361 (Apr. 1995).
Wilske, B., et al., "An OspA Serotyping System for *Borrelia burgdorferi* Based on Reactivity With Monoclonal Antibodies and OspA Sequence Analysis," J. Clin. Microbiol., 31(2):340-350 (Feb. 1993).
Marconi, R.T., et al., "Variability of osp Genes and Gene Products Among Species of Lyme Disease Spirochetes," Infect. Immun., 61(6):2611-2617 (Jun. 1993).
Fikrig, E., et al., "*Borrelia burgdorferi* Strain 25015: Characterization of Outer Surface Protein A and Vaccination Against Infection, " J. Immunol. 148(7):2256-2260 (1992) (month not available).
Schaible, U., et al., "Immune Sera to Individual *Borrelia burgdorferi* Isolates or Recombinant OspA Thereof Protect SCID Mice Against Infection With Homologous Strains But Only Partially or Not At All Against Those of Different OspA/OspB Genotype," Vaccine 11(10):1049-1054 (1993) (month not available).
Masuzawa, T., et al., "Protective Activity of Antisera Against Isolates of *Borrelia burgdorferi* From Various Geographical Origins," Microbiol. Immunol., 37(1):79-83 (1993) (month not available).
Wallich, R., et al., "Evaluation of Genetic Divergence Among *Borrelia burgdorferi* Isolates by Use of OspA, fla, HSP60, and HSP70 Gene Probes," Infect. Immun., 60(11):4856-4866 (Nov. 1992).
Simon, M.M., et al., "A Mouse Model for *Borrelia burgdorferi* Infection: Approach to a Vaccine Against Lyme Disease," Immunol. Today, 12(1):11-16 (1991) (month not available).
Schaible, U.E., et al., "Monoclonal Antibodies Specific for the Outer Surface Protein a (OspA) of *Borrelia Burgdorferi* Prevent Lyme Borreliosis in Severe Combined Immunodeficiency (scid) Mice," Proc. Natl. Acad. Sci. USA, 87:3768-3772 (May 1990).
Preac-Mursic, V., et al., "Active Immunization With pC Protein of *Borrelia burgdorferi* Protects Gerbils Against *B. burgdorferi* Infection," Infection, 20(6):342-349 (Oct. 1992).
Simon, M., et al., "Spirochetes: Vaccines, Animal Models and Diagnostics," Res. Microbiol., 143:641-647 (1992) (month not available).
Simon, M.M., et al., "Recombinant Outer Surface Protein a from *Borrelia burgdorferi* Induces Antibodies Protective against Spirochetal Infection in Mice," J. Infect. Dis., 164:123-132 (Feb. 1991).
Howe, T.R., et al., "A Single Recombinant Plasmid Expressing Two Major Outer Surface Proteins of the Lyme Disease Spirochete," Science, 227:645-46 (Feb. 1985).
Johnson, R.C., et al., "Experimental Infection of the Hamster with *Borrelia burgdorferi* ," Ann. N.Y. Acad. Sci., 539:258-263 (1988) (month not available).
France, L.L., et al., "Structural Analysis of an Outer Surface Protein From the Lyme Disease Spirochete, *Borrelia burgdorferi* , Using Circular Dichroism and Fluorescence Spectroscopy," Biochim. Biophys. Acta, 1120:59-68 (1992) (month not available).
Howe, T.R., et al., "Organization of Genes Encoding Two Outer Membrane Proteins of the Lyme Disease Agent *Borrelia burgdorferi* within a Single Transcriptional Unit," Infect. Immun., 54(1):207-212 (Oct. 1986).
Johnson, R.C., et al., "Vaccination of Hamsters Against Experimental Infection with *Borrelia burgdorferi* ," Zbl. Bakt. Hyg. A, 263:45-48 (1986) (month not available).
Johnson, R.C., et al., "Passive Immunization of Hamsters Against Experimental Infection with the Lyme Disease Spirochete," Infect. And Immun., 53(3):713-714 (Sep. 1986).

Johnson, R.C., et al., "Active Immunization of Hamsters Against Experimental Infection with *Borrelia burgdorferi* ," Infect. Immun., 54(3):897-898 (Dec. 1986).
Fikrig, E., et al., "Elimination of *Borrelia burgdorferi* from Vector Ticks Feeding on OspAImmunized Mice," Proc. Natl. Acad. Sci. USA, 89:5418-5421 (Jun. 1992).
Fikrig, E., et al., "Long-Term Protection of Mice From Lyme Disease by Vaccination with OspA," Infect. Immun., 60(3):773-777 (Mar. 1992).
Fikrig, E., et al., "Protection of Mice Against the Lyme Disease Agent by Immunizing with Recombinant OspA," Science, 250:553-556 (Oct. 1990).
Erdile, L. F. et al., "Role of Attached Lipid in Immunogenicity of *Borrelia burgdorferi* OspA," Infect. Immun., 61(1):81-90 (Jan. 1993).
Bockenstedt, L.K., et al., "Inability of Truncated Recombinant OspA Proteins to Elicit Protective Immunity to *Borrelia burgdorferi* in Mice," J. Immun., 151(2):900-906 (Jul. 1993).
Lovrich, S.D., et al., "Seroprotective Groups Among Isolates of *Borrelia burgdorferi* ," Infect. Immun., 61(10):4367-4374 (Oct. 1993).
Wilske, B., et al., "Molecular Analysis of the Outer Surface Protein a (OspA) of *Borrelia burgdorferi* for Conserved and Variable Antibody Binding Domains," Med. Microbiol. Immunol., 181:191-207 (May 1992).
Sears, J.E., et al., "Molecular Mapping of Osp-A Mediated Immunity Against *Borrelia burgdorferi* , The Agent of Lyme Disease," J. Immunol., 147(6):1995-2000 (Sep. 1991).
Lovrich, S.D., et al., "Seroprotective Groups of Lyme *Borreliosis Spirochetes* from North America and Europe," J. Infect. Dis. 170:115-121 (Feb. 1994).
Gern, L., et al., "Immunization With a Polyvalent OspA Vaccine Protects Mice Against Ixodes ricinus Tick Bites Infected by *Borrelia burgdorferi* ss, *Borrelia garinii* and *Borrelia afzelli* ," Vaccine 15(14):1551-1557 (Mar. 1997).
Golde, W.T., et al., "The Lyme Disease Vaccine Candidate Outer Surface Protein a (OspA) in a Formulation Compatible With Human Use Protects Mice Against Natural Tick Transmission of *B. Burgdorferi* ," Vaccine 13(5):435-441 (1995) (month not available).
Masuzawa, T., et al., "Negative Finding in Cross-Protective Activity of Japanese Borrelia Isolates Against Infection with Three Species of Lyme Disease Borrelia in Outbred Mice," Microbiol. Immunol., 41(9):733-736 (Jun. 1997).
Bowie, J.U., et al., "Deciphering the Message in Protein Sequences: Tolerance to Amino acid Substitutions," Science, 247:1306-1310 (Mar. 1990).
Li, H., et al., "Crystal Structure of Lyme Disease Antigen Outer Surface Protein A Complexed With an Fab," Proc. Natl. Acad. Sci. USA, 94:3584-3589 (Apr. 1997).
Gross, D.M., et al., "Identification of LFA-1 As a Candidate Autoantigen in Treatment-Resistant Lyme Arthritis," Science, 281:703-706 (Jul. 1998).
Kumaran, D., et al., "Crystal Structure of Outer Surface Protein C (OspC) From the Lyme Disease Spirochete, *Borrelia burgdorferi* ," Embo J., 20(5):971-978 (2001) (month not available).
Golde, W.T., et al., "T Cell Antigen Reactivity to Recombinant OspA and the Homologous Self Peptide of LFA-1 in Patients with Lyme Disease," Faseb J., 14(6):A950 (Apr. 2000).
Malawista, S.E., et al., "Geographic Clustering of an Outer Surface Protein a Mutant of *Borrelia burgdorferi* . Possible Implications of Multiple Variants for Lyme Disease Persistence," Rheumatology 39(5):537-541 (May 2000).
Huang, X., et al., "Formation of the Single-Layer ÿ-Sheet of *Borrelia burgdorferi* OspA in the Absence of the C-Terminal Capping Globular Domain," J. Mol. Biol. 308:367-375 (2001) (month not available).
Koide, S., et al., "Design of Single-Layer ÿ-Sheets without a Hydrophobic Core," Nature 403(6768):456-460 (Jan. 2000).
Barbour, A.G., et al., "Lyme Disease Spirochetes and Ixodid Tick Spirochetes Share a Common Surface Antigenic Determinant Defined by a Monoclonal Antibody," Infect. Immun. 41(2):795804 (Aug. 1983).

(56) References Cited

OTHER PUBLICATIONS

Koide, S., et al., "Structure-Based Design of a Second-Generation Lyme Disease Vaccine Based on a C-Terminal Fragment of *Borrelia Burgforferi* OspA," J. Mol. Biol., 350:290-299 (Jul. 2005).

Purcell, A.W., et al., "Dissecting the Role of Peptides in the Immune Response: Theory, Practice and the Application to Vaccine Design," *J. Pept. Sci.* 9(5): 255-281 (2003) (month not available).

Ding, W., et al., "Structural Identification of a Key Protective B-Cell Epitope in Lyme Disease Antigen OspA," *J. Mol. Biol.* 302(5): 1153-1164 (2000) (month not available).

Richards, F.M., "Protein Stability: Still an Unsolved Problem," *Cell. Mol. Life Sci.* 53(10):790802 (1997) (month not available).

\* cited by examiner

|  | Domain 1 | | | | | | | | |
|---|---|---|---|---|---|---|---|---|---|
|  | 34 | 35 | 36 | 37 | 38 | 39 | 40 | 41 | |
| A-B31 | L | P | G | E | M | K | V | L | SEQ ID NO:131 |
| A-TRo | L | P | G | E | M | K | V | L | SEQ ID NO:132 |
| A-K48 | L | P | G | G | M | T | V | L | SEQ ID NO:133 |
| A-DK29 | L | P | G | G | M | T | V | L | SEQ ID NO:134 |
| A-P/Gau | L | P | G | E | M | K | V | L | SEQ ID NO:135 |
| A-PKo | L | P | G | E | M | K | V | L | SEQ ID NO:136 |
| A-IP3 | L | P | G | E | I | K | V | L | SEQ ID NO:137 |
| A-IP90 | L | P | G | G | M | G | V | L | SEQ ID NO:138 |
| A-25015 | L | P | G | E | M | K | V | L | SEQ ID NO:139 |

FIG. 2A

|  | 65 | 66 | 67 | 68 | 69 | 70 | 71 | 72 | 73 | 74 | 75 |  |
|---|---|---|---|---|---|---|---|---|---|---|---|---|
| | | | | | | Domain 2 | | | | | | |
| A-B31 | G | T | S | D | K | N | N | G | S | G | V | SEQ ID NO:140 |
| A-TRo | G | T | S | D | K | S | N | G | S | G | T | SEQ ID NO:141 |
| A-K48 | G | T | S | D | K | N | N | G | S | G | T | SEQ ID NO:142 |
| A-DK29 | G | T | S | D | K | N | N | G | S | G | T | SEQ ID NO:143 |
| A-P/Gau | G | T | S | D | K | D | N | G | S | G | T | SEQ ID NO:144 |
| A-PKo | G | T | S | D | K | D | N | G | S | G | T | SEQ ID NO:145 |
| A-IP3 | G | T | S | D | K | D | N | G | S | G | V | SEQ ID NO:146 |
| A-IP90 | G | T | S | D | K | N | N | G | S | G | T | SEQ ID NO:147 |
| A-25015 | G | T | S | D | K | N | N | G | S | G | V | SEQ ID NO:148 |

FIG. 2B

Domain 3

| | 190 200 210 220 | |
|---|---|---|
| A-B31 | NISKSGEVSVELNDTDSSAATKKTAAWNSGT | SEQ ID NO:149 |
| A-TRo | HIPNSGEITVELNDSNSTQATKKTGKWDSNT | SEQ ID NO:150 |
| A-K48 | NILKSGEITVALDDSDTTQATKKTGKWDSKT | SEQ ID NO:151 |
| A-DK29 | NILKSGEITAALDDSDTTRATKKTGKWDSKT | SEQ ID NO:152 |
| A-P/Gau | EIAKSGEVTVALNDTNTTQATKKTGAWDSKT | SEQ ID NO:153 |
| A-PKo | EIAKSGEVTVALNDTNTTQATKKTGAWDSKT | SEQ ID NO:154 |
| A-IP3 | EIAKSGEVTVALNDTNTTQATKKTGAWDSKT | SEQ ID NO:155 |
| A-IP90 | HISNSGEITVELNDSDTTQATKKTGTWDSKT | SEQ ID NO:156 |
| A-25015 | HISKSGEVTAELNDTDSTQATKKTGKWDAGT | SEQ ID NO:157 |

FIG. 2C

Domain 4

| | 250 | 260 | 270 | |
|---|---|---|---|---|
| A-B31 | SNGTKLEGSAVEITKLDEIKN | | | SEQ ID NO:158 |
| A-TRo | SAGTNLEGNAVEIKTLDELKN | | | SEQ ID NO:159 |
| A-K48 | SAGTNLEGKAVEITTLKELKN | | | SEQ ID NO:160 |
| A-DK29 | SAGTNLEGKAVEITTLKELKN | | | SEQ ID NO:161 |
| A-P/Gau | SAGTNLEGTAVEIKTLDELKN | | | SEQ ID NO:162 |
| A-PKo | SAGTNLEGTAVEIKTLDELKN | | | SEQ ID NO:163 |
| A-IP3 | SAGTNLEGTAVEIKTLDELKN | | | SEQ ID NO:164 |
| A-IP90 | SAGTNLEGKAVEITTLKELKN | | | SEQ ID NO:165 |
| A-25015 | SAGTNLEGTAVEIKTLDEIKN | | | SEQ ID NO:166 |

FIG. 2D

Protein sequence of OspAs from B31, K48 and site-directed mutants from amino acids 200-220

↓

| | | |
|---|---|---|
| B31: | ELNDTDSSAATKKTAAWNSGT | (SEQ ID NO:167) |
| K48: | ALDDSDTTQATKKTGKWDSKT | (SEQ ID NO:168) |
| 613: | ELNDSDTSAATKKTAAWNSGT | (SEQ ID NO:169) |
| 625: | ELNDTDSSAATKKTGKWNSGT | (SEQ ID NO:170) |
| 640: | ELNDTDSSAATKKTAAWDSKT | (SEQ ID NO:171) |
| 613/625: | ELNDSDTSAATKKTGKWNSGT | (SEQ ID NO:172) |
| 613/640: | ELNDSDTSAATKKTAAWDSKT | (SEQ ID NO:173) |

```
          10              20              30              40
           •       •       •       •       •       •       •       •
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50              60              70              80              90
       •       •       •       •       •       •       •       •       •
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100             110             120             130             140
       •       •       •       •       •       •       •       •       •
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150             160             170             180             190
       •       •       •       •       •       •       •       •       •
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200             210             220             230             240
       •       •       •       •       •       •       •       •       •
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250             260             270             280
       •       •       •       •       •       •       •       •       •
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290             300             310             320             330
   •       •       •       •       •       •       •       •       •
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340             350             360             370             380
       •       •       •       •       •       •       •       •       •
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 6A

```
       390            400            410            420           430
        .              .              .              .             .
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

440            450            460            470           480
        .              .              .              .             .
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490            500            510            520
        .              .              .              .
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530            540            550            560            570
 .              .              .              .              .
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580            590            600            610           620
 .              .              .              .             .
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630            640            650            660           670
        .              .              .              .             .
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

680            690            700            710           720
        .              .              .              .             .
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

730            740            750            760
        .              .              .              .
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770            780            790            800            810
 .              .              .              .              .
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

820
 *
AAA TAA
TTT ATT
Lys ***>
```

FIG. 6B

```
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50            60            70            80            90

TGT AAG CAA AAT GTT AGC AGC CTT GAT GAA AAA AAT AGC GTT TCA GTA
ACA TTC GTT TTA CAA TCG TCG GAA CTA CTT TTT TTA TCG CAA AGT CAT
Cys Lys Gln Asn Val Ser Ser Leu Asp Glu Lys Asn Ser Val Ser Val>

100           110           120           130           140

GAT TTA CCT GGT GGA ATG ACA GTT CTT GTA AGT AAA GAA AAA GAC AAA
CTA AAT GGA CCA CCT TAC TGT CAA GAA CAT TCA TTT CTT TTT CTG TTT
Asp Leu Pro Gly Gly Met Thr Val Leu Val Ser Lys Glu Lys Asp Lys>

150           160           170           180           190

GAC GGT AAA TAC AGT CTA GAG GCA ACA GTA GAC AAG CTT GAG CTT AAA
CTG CCA TTT ATG TCA GAT CTC CGT TGT CAT CTG TTC GAA CTC GAA TTT
Asp Gly Lys Tyr Ser Leu Glu Ala Thr Val Asp Lys Leu Glu Leu Lys>

200           210           220           230           240

GGA ACT TCT GAT AAA AAC AAC GGT TCT GGA ACA CTT GAA GGT GAA AAA
CCT TGA AGA CTA TTT TTG TTG CCA AGA CCT TGT GAA CTT CCA CTT TTT
Gly Thr Ser Asp Lys Asn Asn Gly Ser Gly Thr Leu Glu Gly Glu Lys>

250           260           270           280

ACT GAC AAA AGT AAA GTA AAA TTA ACA ATT GCT GAT GAC CTA AGT CAA
TGA CTG TTT TCA TTT CAT TTT AAT TGT TAA CGA CTA CTG GAT TCA GTT
Thr Asp Lys Ser Lys Val Lys Leu Thr Ile Ala Asp Asp Leu Ser Gln>

290          300           310           320           330

ACT AAA TTT GAA ATT TTC AAA GAA GAT GCC AAA ACA TTA GTA TCA AAA
TGA TTT AAA CTT TAA AAG TTT CTT CTA CGG TTT TGT AAT CAT AGT TTT
Thr Lys Phe Glu Ile Phe Lys Glu Asp Ala Lys Thr Leu Val Ser Lys>

340           350           360           370           380

AAA GTA ACC CTT AAA GAC AAG TCA TCA ACA GAA GAA AAA TTC AAC GAA
TTT CAT TGG GAA TTT CTG TTC AGT AGT TGT CTT CTT TTT AAG TTG CTT
Lys Val Thr Leu Lys Asp Lys Ser Ser Thr Glu Glu Lys Phe Asn Glu>
```

FIG. 7A

```
          390            400            410            420            430
           *              *              *              *              *
 AAG  GGT  GAA  ACA  TCT  GAA  AAA  ACA  ATA  GTA  AGA  GCA  AAT  GGA  ACC  AGA
 TTC  CCA  CTT  TGT  AGA  CTT  TTT  TGT  TAT  CAT  TCT  CGT  TTA  CCT  TGG  TCT
 Lys  Gly  Glu  Thr  Ser  Glu  Lys  Thr  Ile  Val  Arg  Ala  Asn  Gly  Thr  Arg>

440            450            460            470            480
                 *              *              *              *              *
 CTT  GAA  TAC  ACA  GAC  ATA  AAA  AGC  GAT  GGA  TCC  GGA  AAA  GCT  AAA  GAA
 GAA  CTT  ATG  TGT  CTG  TAT  TTT  TCG  CTA  CCT  AGG  CCT  TTT  CGA  TTT  CTT
 Leu  Glu  Tyr  Thr  Asp  Ile  Lys  Ser  Asp  Gly  Ser  Gly  Lys  Ala  Lys  Glu>

490            500            510            520
                 *              *              *              *
 GTT  TTA  AAA  GAC  TTT  ACT  CTT  GAA  GGA  ACT  CTA  GCT  GCT  GAC  GGC  AAA
 CAA  AAT  TTT  CTG  AAA  TGA  GAA  CTT  CCT  TGA  GAT  CGA  CGA  CTG  CCG  TTT
 Val  Leu  Lys  Asp  Phe  Thr  Leu  Glu  Gly  Thr  Leu  Ala  Ala  Asp  Gly  Lys>

530            540            550            560            570
  *              *              *              *              *
 ACA  ACA  TTG  AAA  GTT  ACA  GAA  GGC  ACT  GTT  GTT  TTA  AGC  AAG  AAC  ATT
 TGT  TGT  AAC  TTT  CAA  TGT  CTT  CCG  TGA  CAA  CAA  AAT  TCG  TTC  TTG  TAA
 Thr  Thr  Leu  Lys  Val  Thr  Glu  Gly  Thr  Val  Val  Leu  Ser  Lys  Asn  Ile>

580            590            600            610            620
        *              *              *              *              *
 TTA  AAA  TCC  GGA  GAA  ATA  ACA  GTT  GCA  CTT  GAT  GAC  TCT  GAC  ACT  ACT
 AAT  TTT  AGG  CCT  CTT  TAT  TGT  CAA  CGT  GAA  CTA  CTG  AGA  CTG  TGA  TGA
 Leu  Lys  Ser  Gly  Glu  Ile  Thr  Val  Ala  Leu  Asp  Asp  Ser  Asp  Thr  Thr>

630            640            650            660            670
        *              *              *              *              *
 CAG  GCT  ACT  AAA  AAA  ACT  GGA  AAA  TGG  GAT  TCA  AAA  ACT  TCC  ACT  TTA
 GTC  CGA  TGA  TTT  TTT  TGA  CCT  TTT  ACC  CTA  AGT  TTT  TGA  AGG  TGA  AAT
 Gln  Ala  Thr  Lys  Lys  Thr  Gly  Lys  Trp  Asp  Ser  Lys  Thr  Ser  Thr  Leu>

680            690            700            710            720
             *              *              *              *              *
 ACA  ATT  AGT  GTG  AAT  AGC  CAA  AAA  ACC  AAA  AAC  CTT  GTA  TTC  ACA  AAA
 TGT  TAA  TCA  CAC  TTA  TCG  GTT  TTT  TGG  TTT  TTG  GAA  CAT  AAG  TGT  TTT
 Thr  Ile  Ser  Val  Asn  Ser  Gln  Lys  Thr  Lys  Asn  Leu  Val  Phe  Thr  Lys>

730            740            750            760
                 *              *              *              *
 GAA  GAC  ACA  ATA  ACA  GTA  CAA  AAA  TAC  GAC  TCA  GCA  GGC  ACC  AAT  CTA
 CTT  CTG  TGT  TAT  TGT  CAT  GTT  TTT  ATG  CTG  AGT  CGT  CCG  TGG  TTA  GAT
 Glu  Asp  Thr  Ile  Thr  Val  Gln  Lys  Tyr  Asp  Ser  Ala  Gly  Thr  Asn  Leu>
```

FIG. 7B

```
       770           780           790           800           810
         .             .             .             .             .
GAA GGC AAA GCA GTC GAA ATT ACA ACA CTT AAA GAA CTT AAA AAC GCT
CTT CCG TTT CGT CAG CTT TAA TGT TGT GAA TTT CTT GAA TTT TTG CGA
Glu Gly Lys Ala Val Glu Ile Thr Thr Leu Lys Glu Leu Lys Asn Ala>

820
      .
TTA AAA TAA
AAT TTT ATT
Leu Lys ***>
```

FIG. 7C

```
            10              20              30              40
     •       •       •       •       •       •       •       •       •
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50              60              70              80              90
     •       •       •       •       •       •       •       •       •
TGC AAG CAA AAT GTT AGC AGC CTT GAT GAA AAA AAC AGC GCT TCA GTA
ACG TTC GTT TTA CAA TCG TCG GAA CTA CTT TTT TTG TCG CGA AGT CAT
Cys Lys Gln Asn Val Ser Ser Leu Asp Glu Lys Asn Ser Ala Ser Val>

100             110             120             130             140
     •       •       •       •       •       •       •       •       •
GAT TTG CCT GGT GAG ATG AAA GTT CTT GTA AGT AAA GAA AAA GAC AAA
CTA AAC GGA CCA CTC TAC TTT CAA GAA CAT TCA TTT CTT TTT CTG TTT
Asp Leu Pro Gly Glu Met Lys Val Leu Val Ser Lys Glu Lys Asp Lys>

150             160             170             180             190
     •       •       •       •       •       •       •       •       •
GAC GGT AAG TAC AGT CTA AAG GCA ACA GTA GAC AAG ATT GAG CTA AAA
CTG CCA TTC ATG TCA GAT TTC CGT TGT CAT CTG TTC TAA CTC GAT TTT
Asp Gly Lys Tyr Ser Leu Lys Ala Thr Val Asp Lys Ile Glu Leu Lys>

200             210             220             230             240
     •       •       •       •       •       •       •       •       •
GGA ACT TCT GAT AAA GAC AAT GGT TCT GGA GTG CTT GAA GGT ACA AAA
CCT TGA AGA CTA TTT CTG TTA CCA AGA CCT CAC GAA CTT CCA TGT TTT
Gly Thr Ser Asp Lys Asp Asn Gly Ser Gly Val Leu Glu Gly Thr Lys>

250             260             270             280
     •       •       •       •       •       •       •       •       •
GAT GAC AAA AGT AAA GCA AAA TTA ACA ATT GCT GAC GAT CTA AGT AAA
CTA CTG TTT TCA TTT CGT TTT AAT TGT TAA CGA CTG CTA GAT TCA TTT
Asp Asp Lys Ser Lys Ala Lys Leu Thr Ile Ala Asp Asp Leu Ser Lys>

290             300             310             320             330
  •       •       •       •       •       •       •       •       •
ACC ACA TTC GAA CTT TTA AAA GAA GAT GGC AAA ACA TTA GTG TCA AGA
TGG TGT AAG CTT GAA AAT TTT CTT CTA CCG TTT TGT AAT CAC AGT TCT
Thr Thr Phe Glu Leu Leu Lys Glu Asp Gly Lys Thr Leu Val Ser Arg>

340             350             360             370             380
     •       •       •       •       •       •       •       •       •
AAA GTA AGT TCT AGA GAC AAA ACA TCA ACA GAT GAA ATG TTC AAT GAA
TTT CAT TCA AGA TCT CTG TTT TGT AGT TGT CTA CTT TAC AAG TTA CTT
Lys Val Ser Ser Arg Asp Lys Thr Ser Thr Asp Glu Met Phe Asn Glu>
```

FIG. 8A

```
         390           400           410           420           430
    •      •      •      •      •      •      •      •      •      •
AAA GGT GAA TTG TCT GCA AAA ACC ATG ACA AGA GAA AAT GGA ACC AAA
TTT CCA CTT AAC AGA CGT TTT TGG TAC TGT TCT CTT TTA CCT TGG TTT
Lys Gly Glu Leu Ser Ala Lys Thr Met Thr Arg Glu Asn Gly Thr Lys>

440           450           460           470           480
    •      •      •      •      •      •      •      •      •      •
CTT GAA TAT ACA GAA ATG AAA AGC GAT GGA ACC GGA AAA GCT AAA GAA
GAA CTT ATA TGT CTT TAC TTT TCG CTA CCT TGG CCT TTT CGA TTT CTT
Leu Glu Tyr Thr Glu Met Lys Ser Asp Gly Thr Gly Lys Ala Lys Glu>

490           500           510           520
    •      •      •      •      •      •      •      •      •
GTT TTA AAA AAG TTT ACT CTT GAA GGA AAA GTA GCT AAT GAT AAA GTA
CAA AAT TTT TTC AAA TGA GAA CTT CCT TTT CAT CGA TTA CTA TTT CAT
Val Leu Lys Lys Phe Thr Leu Glu Gly Lys Val Ala Asn Asp Lys Val>

530           540           550           560           570
 •      •      •      •      •      •      •      •      •      •
ACA TTG GAA GTA AAA GAA GGA ACC GTT ACT TTA AGT AAG GAA ATT GCA
TGT AAC CTT CAT TTT CTT CCT TGG CAA TGA AAT TCA TTC CTT TAA CGT
Thr Leu Glu Val Lys Glu Gly Thr Val Thr Leu Ser Lys Glu Ile Ala>

580           590           600           610           620
    •      •      •      •      •      •      •      •      •      •
AAA TCT GGA GAA GTA ACA GTT GCT CTT AAT GAC ACT AAC ACT ACT CAG
TTT AGA CCT CTT CAT TGT CAA CGA GAA TTA CTG TGA TTG TGA TGA GTC
Lys Ser Gly Glu Val Thr Val Ala Leu Asn Asp Thr Asn Thr Thr Gln>

630           640           650           660           670
    •      •      •      •      •      •      •      •      •      •
GCT ACT AAA AAA ACT GGC GCA TGG GAT TCA AAA ACT TCT ACT TTA ACA
CGA TGA TTT TTT TGA CCG CGT ACC CTA AGT TTT TGA AGA TGA AAT TGT
Ala Thr Lys Lys Thr Gly Ala Trp Asp Ser Lys Thr Ser Thr Leu Thr>

680           690           700           710           720
    •      •      •      •      •      •      •      •      •      •
ATT AGT GTT AAC AGC AAA AAA ACT ACA CAA CTT GTG TTT ACT AAA CAA
TAA TCA CAA TTG TCG TTT TTT TGA TGT GTT GAA CAC AAA TGA TTT GTT
Ile Ser Val Asn Ser Lys Lys Thr Thr Gln Leu Val Phe Thr Lys Gln>

730           740           750           760
    •      •      •      •      •      •      •      •      •
TAC ACA ATA ACT GTA AAA CAA TAC GAC TCC GCA GGT ACC AAT TTA GAA
ATG TGT TAT TGA CAT TTT GTT ATG CTG AGG CGT CCA TGG TTA AAT CTT
Tyr Thr Ile Thr Val Lys Gln Tyr Asp Ser Ala Gly Thr Asn Leu Glu>
```

FIG. 8B

```
     770           780           790           800           810
      .             .             .             .             .
     .             .             .             .             .
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

820
      .
     .
AAA TAA
TTT ATT
Lys ***>
```

FIG. 8C

```
         10              20              30              40
          *               *               *               *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50              60              70              80              90
    *               *               *               *               *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100             110             120             130             140
        *               *               *               *               *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150             160             170             180             190
        *               *               *               *               *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200             210             220             230             240
        *               *               *               *               *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250             260             270             280
        *               *               *               *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290             300             310             320             330
 *               *               *               *               *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340             350             360             370             380
    *               *               *               *               *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

```
              10              20              30              40
     *    *    *    *    *    *    *    *    *
ATG  AAA  AAA  TAT  TTA  TTG  GGA  ATA  GGT  CTA  ATA  TTA  GCC  TTA  ATA  GCA
TAC  TTT  TTT  ATA  AAT  AAC  CCT  TAT  CCA  GAT  TAT  AAT  CGG  AAT  TAT  CGT
Met  Lys  Lys  Tyr  Leu  Leu  Gly  Ile  Gly  Leu  Ile  Leu  Ala  Leu  Ile  Ala>

50              60              70              80              90
     *    *    *    *    *    *    *    *    *    *
TGT  AAG  CAA  AAT  GTT  AGC  AGC  CTT  GAT  GAA  AAA  AAT  AGC  GTT  TCA  GTA
ACA  TTC  GTT  TTA  CAA  TCG  TCG  GAA  CTA  CTT  TTT  TTA  TCG  CAA  AGT  CAT
Cys  Lys  Gln  Asn  Val  Ser  Ser  Leu  Asp  Glu  Lys  Asn  Ser  Val  Ser  Val>

100             110             120             130             140
     *    *    *    *    *    *    *    *    *    *
GAT  TTA  CCT  GGT  GGA  ATG  ACA  GTT  CTT  GTA  AGT  AAA  GAA  AAA  GAC  AAA
CTA  AAT  GGA  CCA  CCT  TAC  TGT  CAA  GAA  CAT  TCA  TTT  CTT  TTT  CTG  TTT
Asp  Leu  Pro  Gly  Gly  Met  Thr  Val  Leu  Val  Ser  Lys  Glu  Lys  Asp  Lys>

150             160             170             180             190
     *    *    *    *    *    *    *    *    *    *
GAC  GGT  AAA  TAC  AGT  CTA  GAG  GCA  ACA  GTA  GAC  AAG  CTT  GAG  CTT  AAA
CTG  CCA  TTT  ATG  TCA  GAT  CTC  CGT  TGT  CAT  CTG  TTC  GAA  CTC  GAA  TTT
Asp  Gly  Lys  Tyr  Ser  Leu  Glu  Ala  Thr  Val  Asp  Lys  Leu  Glu  Leu  Lys>

200             210             220             230             240
     *    *    *    *    *    *    *    *    *    *
GGA  ACT  TCT  GAT  AAA  AAC  AAC  GGT  TCT  GGA  ACA  CTT  GAA  GGT  GAA  AAA
CCT  TGA  AGA  CTA  TTT  TTG  TTG  CCA  AGA  CCT  TGT  GAA  CTT  CCA  CTT  TTT
Gly  Thr  Ser  Asp  Lys  Asn  Asn  Gly  Ser  Gly  Thr  Leu  Glu  Gly  Glu  Lys>

250             260             270             280
     *    *    *    *    *    *    *    *    *    *
ACT  GAC  AAA  AGT  AAA  GTA  AAA  TTA  ACA  ATT  GCT  GAT  GAC  CTA  AGT  CAA
TGA  CTG  TTT  TCA  TTT  CAT  TTT  AAT  TGT  TAA  CGA  CTA  CTG  GAT  TCA  GTT
Thr  Asp  Lys  Ser  Lys  Val  Lys  Leu  Thr  Ile  Ala  Asp  Asp  Leu  Ser  Gln>

290             300             310             320             330
     *    *    *    *    *    *    *    *    *    *
ACT  AAA  TTT  GAA  ATT  TTC  AAA  GAA  GAT  GCC  AAA  ACA  TTA  GTA  TCA  AAA
TGA  TTT  AAA  CTT  TAA  AAG  TTT  CTT  CTA  CGG  TTT  TGT  AAT  CAT  AGT  TTT
Thr  Lys  Phe  Glu  Ile  Phe  Lys  Glu  Asp  Ala  Lys  Thr  Leu  Val  Ser  Lys>

340             350             360             370             380
     *    *    *    *    *    *    *    *    *    *
AAA  GTA  ACC  CTT  AAA  GAC  AAG  TCA  TCA  ACA  GAA  GAA  AAA  TTC  AAC  GAA
TTT  CAT  TGG  GAA  TTT  CTG  TTC  AGT  AGT  TGT  CTT  CTT  TTT  AAG  TTG  CTT
Lys  Val  Thr  Leu  Lys  Asp  Lys  Ser  Ser  Thr  Glu  Glu  Lys  Phe  Asn  Glu>
```

FIG. 10A

```
           390         400         410         420         430
    .     .     .     .     .     .     .     .     .     .
   AAG GGT GAA ACA TCT GAA AAA ACA ATA GTA AGA GCA AAT GGA ACC AGA
   TTC CCA CTT TGT AGA CTT TTT TGT TAT CAT TCT CGT TTA CCT TGG TCT
   Lys Gly Glu Thr Ser Glu Lys Thr Ile Val Arg Ala Asn Gly Thr Arg>

440         450         460         470         480
    .     .     .     .     .     .     .     .     .     .
   CTT GAA TAC ACA GAC ATA AAA AGC GAT GGA TCC GGA AAA GCT AAA GAA
   GAA CTT ATG TGT CTG TAT TTT TCG CTA CCT AGG CCT TTT CGA TTT CTT
   Leu Glu Tyr Thr Asp Ile Lys Ser Asp Gly Ser Gly Lys Ala Lys Glu>

490         500         510         520
    .     .     .     .     .     .     .     .
   GTT TTA AAA GAC TTT ACT CTT GAA GGA ACT CTA GCT GCT GAC GGC AAA
   CAA AAT TTT CTG AAA TGA GAA CTT CCT TGA GAT CGA CGA CTG CCG TTT
   Val Leu Lys Asp Phe Thr Leu Glu Gly Thr Leu Ala Ala Asp Gly Lys>

530         540         550         560         570
  .     .     .     .     .     .     .     .     .     .
   ACA ACA TTG AAA GTT ACA GAA GGC ACT GTT GTT TTA AGC AAG AAC ATT
   TGT TGT AAC TTT CAA TGT CTT CCG TGA CAA CAA AAT TCG TTC TTG TAA
   Thr Thr Leu Lys Val Thr Glu Gly Thr Val Val Leu Ser Lys Asn Ile>

580         590         600         610         620
    .     .     .     .     .     .     .     .     .     .
   TTA AAA TCC GGA GAA ATA ACA GTT GCA CTT GAT GAC TCT GAC ACT ACT
   AAT TTT AGG CCT CTT TAT TGT CAA CGT GAA CTA CTG AGA CTG TGA TGA
   Leu Lys Ser Gly Glu Ile Thr Val Ala Leu Asp Asp Ser Asp Thr Thr>

630         640         650         660         670
    .     .     .     .     .     .     .     .     .     .
   CAG GCT ACT AAA AAA ACT GGA AAA TGG GAT TCA AAA ACT TCT ACT TTA
   GTC CGA TGA TTT TTT TGA CCT TTT ACC CTA AGT TTT TGA AGA TGA AAT
   Gln Ala Thr Lys Lys Thr Gly Lys Trp Asp Ser Lys Thr Ser Thr Leu>

680         690         700         710         720
    .     .     .     .     .     .     .     .     .     .
   ACA ATT AGT GTT AAC AGC AAA AAA ACT ACA CAA CTT GTG TTT ACT AAA
   TGT TAA TCA CAA TTG TCG TTT TTT TGA TGT GTT GAA CAC AAA TGA TTT
   Thr Ile Ser Val Asn Ser Lys Lys Thr Thr Gln Leu Val Phe Thr Lys>

730         740         750         760
    .     .     .     .     .     .     .     .
   CAA TAC ACA ATA ACT GTA AAA CAA TAC GAC TCC GCA GGT ACC AAT TTA
   GTT ATG TGT TAT TGA CAT TTT GTT ATG CTG AGG CGT CCA TGG TTA AAT
   Gln Tyr Thr Ile Thr Val Lys Gln Tyr Asp Ser Ala Gly Thr Asn Leu>
```

FIG. 10B

```
      770         780         790         800         810
       .    .      .    .      .    .      .    .      .    .
      GAA GGC ACA GCA GTC GAA ATT AAA ACA CTT GAT GAA CTT AAA AAC GCT
      CTT CCG TGT CGT CAG CTT TAA TTT TGT GAA CTA CTT GAA TTT TTG CGA
      Glu Gly Thr Ala Val Glu Ile Lys Thr Leu Asp Glu Leu Lys Asn Ala>

820
       .    .
      TTA AAA TAA
      AAT TTT ATT
      Leu Lys ***>
```

FIG. 10C

```
              10             20             30             40
               .              .              .              .
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50             60             70             80             90
     .              .              .              .              .
TGC AAG CAA AAT GTT AGC AGC CTT GAT GAA AAA AAC AGC GCT TCA GTA
ACG TTC GTT TTA CAA TCG TCG GAA CTA CTT TTT TTG TCG CGA AGT CAT
Cys Lys Gln Asn Val Ser Ser Leu Asp Glu Lys Asn Ser Ala Ser Val>

100            110            120            130            140
     .              .              .              .              .
GAT TTG CCT GGT GAG ATG AAA GTT CTT GTA AGT AAA GAA AAA GAC AAA
CTA AAC GGA CCA CTC TAC TTT CAA GAA CAT TCA TTT CTT TTT CTG TTT
Asp Leu Pro Gly Glu Met Lys Val Leu Val Ser Lys Glu Lys Asp Lys>

150            160            170            180            190
     .              .              .              .              .
GAC GGT AAG TAC AGT CTA AAG GCA ACA GTA GAC AAG ATT GAG CTA AAA
CTG CCA TTC ATG TCA GAT TTC CGT TGT CAT CTG TTC TAA CTC GAT TTT
Asp Gly Lys Tyr Ser Leu Lys Ala Thr Val Asp Lys Ile Glu Leu Lys>

200            210            220            230            240
     .              .              .              .              .
GGA ACT TCT GAT AAA GAC AAT GGT TCT GGA GTG CTT GAA GGT ACA AAA
CCT TGA AGA CTA TTT CTG TTA CCA AGA CCT CAC GAA CTT CCA TGT TTT
Gly Thr Ser Asp Lys Asp Asn Gly Ser Gly Val Leu Glu Gly Thr Lys>

250            260            270            280
     .              .              .              .
GAT GAC AAA AGT AAA GCA AAA TTA ACA ATT GCT GAC GAT CTA AGT AAA
CTA CTG TTT TCA TTT CGT TTT AAT TGT TAA CGA CTG CTA GAT TCA TTT
Asp Asp Lys Ser Lys Ala Lys Leu Thr Ile Ala Asp Asp Leu Ser Lys>

290            300            310            320            330
  .              .              .              .              .
ACC ACA TTC GAA CTT TTA AAA GAA GAT GGC AAA ACA TTA GTG TCA AGA
TGG TGT AAG CTT GAA AAT TTT CTT CTA CCG TTT TGT AAT CAC AGT TCT
Thr Thr Phe Glu Leu Leu Lys Glu Asp Gly Lys Thr Leu Val Ser Arg>

340            350            360            370            380
     .              .              .              .              .
AAA GTA AGT TCT AGA GAC AAA ACA TCA ACA GAT GAA ATG TTC AAT GAA
TTT CAT TCA AGA TCT CTG TTT TGT AGT TGT CTA CTT TAC AAG TTA CTT
Lys Val Ser Ser Arg Asp Lys Thr Ser Thr Asp Glu Met Phe Asn Glu>
```

FIG. 11A

```
         390           400           410           420           430
  .     .     .     .     .     .     .     .     .     .
AAA GGT GAA TTG TCT GCA AAA ACC ATG ACA AGA GAA AAT GGA ACC AAA
TTT CCA CTT AAC AGA CGT TTT TGG TAC TGT TCT CTT TTA CCT TGG TTT
Lys Gly Glu Leu Ser Ala Lys Thr Met Thr Arg Glu Asn Gly Thr Lys>

440           450           460           470           480
  .     .     .     .     .     .     .     .     .     .
CTT GAA TAT ACA GAA ATG AAA AGC GAT GGA ACC GGA AAA GCT AAA GAA
GAA CTT ATA TGT CTT TAC TTT TCG CTA CCT TGG CCT TTT CGA TTT CTT
Leu Glu Tyr Thr Glu Met Lys Ser Asp Gly Thr Gly Lys Ala Lys Glu>

490           500           510           520
  .     .     .     .     .     .     .     .     .
GTT TTA AAA AAG TTT ACT CTT GAA GGA AAA GTA GCT AAT GAT AAA GTA
CAA AAT TTT TTC AAA TGA GAA CTT CCT TTT CAT CGA TTA CTA TTT CAT
Val Leu Lys Lys Phe Thr Leu Glu Gly Lys Val Ala Asn Asp Lys Val>

530           540           550           560           570
  .     .     .     .     .     .     .     .     .     .
ACA TTG GAA GTA AAA GAA GGA ACC GTT ACT TTA AGT AAG GAA ATT GCA
TGT AAC CTT CAT TTT CTT CCT TGG CAA TGA AAT TCA TTC CTT TAA CGT
Thr Leu Glu Val Lys Glu Gly Thr Val Thr Leu Ser Lys Glu Ile Ala>

580           590           600           610           620
  .     .     .     .     .     .     .     .     .     .
AAA TCT GGA GAA GTA ACA GTT GCT CTT AAT GAC ACT AAC ACT ACT CAG
TTT AGA CCT CTT CAT TGT CAA CGA GAA TTA CTG TGA TTG TGA TGA GTC
Lys Ser Gly Glu Val Thr Val Ala Leu Asn Asp Thr Asn Thr Thr Gln>

630           640           650           660           670
  .     .     .     .     .     .     .     .     .     .
GCT ACT AAA AAA ACT GGC GCA TGG GAT TCA AAA ACT TCT ACT TTA ACA
CGA TGA TTT TTT TGA CCG CGT ACC CTA AGT TTT TGA AGA TGA AAT TGT
Ala Thr Lys Lys Thr Gly Ala Trp Asp Ser Lys Thr Ser Thr Leu Thr>

680           690           700           710           720
  .     .     .     .     .     .     .     .     .     .
ATT AGT GTT AAC AGC AAA AAA ACT ACA CAA CTT GTG TTT ACT AAA CAA
TAA TCA CAA TTG TCG TTT TTT TGA TGT GTT GAA CAC AAA TGA TTT GTT
Ile Ser Val Asn Ser Lys Lys Thr Thr Gln Leu Val Phe Thr Lys Gln>

730           740           750           760
  .     .     .     .     .     .     .     .     .
TAC ACA ATA ACT GTA AAA CAA TAC GAC TCC GCA GGT ACC AAT TTA GAA
ATG TGT TAT TGA CAT TTT GTT ATG CTG AGG CGT CCA TGG TTA AAT CTT
Tyr Thr Ile Thr Val Lys Gln Tyr Asp Ser Ala Gly Thr Asn Leu Glu>
```

FIG. 11B

```
      770           780           790           800           810
       *             *             *             *             *
   *             *             *             *             *
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

820
       *
AAA TAA
TTT ATT.
Lys ***>
```

FIG. 11C

```
                10                  20                  30                  40
                 *                   *                   *                   *
        ATG AAA AAA TAT TTA TTG GGA ATA GGT CTA ATA TTA GCC TTA ATA GCA
        TAC TTT TTT ATA AAT AAC CCT TAT CCA GAT TAT AAT CGG AAT TAT CGT
        Met Lys Lys Tyr Leu Leu Gly Ile Gly Leu Ile Leu Ala Leu Ile Ala>

50                  60                  70                  80                  90
         *                   *                   *                   *                   *
        TGT AAG CAA AAT GTT AGC AGC CTT GAC GAG AAA AAC AGC GTT TCA GTA
        ACA TTC GTT TTA CAA TCG TCG GAA CTG CTC TTT TTG TCG CAA AGT CAT
        Cys Lys Gln Asn Val Ser Ser Leu Asp Glu Lys Asn Ser Val Ser Val>

100                 110                 120                 130                 140
                 *                   *                   *                   *                   *
        GAT TTG CCT GGT GAA ATG AAA GTT CTT GTA AGC AAA GAA AAA AAC AAA
        CTA AAC GGA CCA CTT TAC TTT CAA GAA CAT TCG TTT CTT TTT TTG TTT
        Asp Leu Pro Gly Glu Met Lys Val Leu Val Ser Lys Glu Lys Asn Lys>

150                 160                 170                 180                 190
                 *                   *                   *                   *                   *
        GAC GGC AAG TAC GAT CTA ATT GCA ACA GTA GAC AAG CTT GAG CTT AAA
        CTG CCG TTC ATG CTA GAT TAA CGT TGT CAT CTG TTC GAA CTC GAA TTT
        Asp Gly Lys Tyr Asp Leu Ile Ala Thr Val Asp Lys Leu Glu Leu Lys>

200                 210                 220                 230                 240
                 *                   *                   *                   *                   *
        GGA ACT TCT GAT AAA AAC AAT GGA TCT GGA GTA CTT GAA GGC GTA AAA
        CCT TGA AGA CTA TTT TTG TTA CCT AGA CCT CAT GAA CTT CCG CAT TTT
        Gly Thr Ser Asp Lys Asn Asn Gly Ser Gly Val Leu Glu Gly Val Lys>

250                 260                 270                 280
                 *                   *                   *                   *
        GCT GAC AAA AGT AAA GTA AAA TTA ACA ATT TCT GAC GAT CTA GGT CAA
        CGA CTG TTT TCA TTT CAT TTT AAT TGT TAA AGA CTG CTA GAT CCA GTT
        Ala Asp Lys Ser Lys Val Lys Leu Thr Ile Ser Asp Asp Leu Gly Gln>

290                 300                 310                 320                 330
         *                   *                   *                   *                   *
        ACC ACA CTT GAA GTT TTC AAA GAA GAT GGC AAA ACA CTA GTA TCA AAA
        TGG TGT GAA CTT CAA AAG TTT CTT CTA CCG TTT TGT GAT CAT AGT TTT
        Thr Thr Leu Glu Val Phe Lys Glu Asp Gly Lys Thr Leu Val Ser Lys>

340                 350                 360                 370                 380
         *                   *                   *                   *                   *
        AAA GTA ACT TCC AAA GAC AAG TCA TCA ACA GAA GAA AAA TTC AAT GAA
        TTT CAT TGA AGG TTT CTG TTC AGT AGT TGT CTT CTT TTT AAG TTA CTT
        Lys Val Thr Ser Lys Asp Lys Ser Ser Thr Glu Glu Lys Phe Asn Glu>

390                 400                 410                 420                 430
         *                   *                   *                   *                   *
        AAA GGT GAA GTA TCT GAA AAA ATA ATA ACA AGA GCA GAC GGA ACC AGA
        TTT CCA CTT CAT AGA CTT TTT TAT TAT TGT TCT CGT CTG CCT TGG TCT
        Lys Gly Glu Val Ser Glu Lys Ile Ile Thr Arg Ala Asp Gly Thr Arg>
```

FIG. 12A

```
            440           450           460           470           480
    •   •      •   •        •   •        •   •        •   •        •   •
   CTT GAA TAC ACA GGA ATT AAA AGC GAT GGA TCT GGA AAA GCT AAA GAG
   GAA CTT ATG TGT CCT TAA TTT TCG CTA CCT AGA CCT TTT CGA TTT CTC
   Leu Glu Tyr Thr Gly Ile Lys Ser Asp Gly Ser Gly Lys Ala Lys Glu>

490           500           510           520
         •   •      •   •        •   •        •   •        •   •
   GTT TTA AAA GGC TAT GTT CTT GAA GGA ACT CTA ACT GCT GAA AAA ACA
   CAA AAT TTT CCG ATA CAA GAA CTT CCT TGA GAT TGA CGA CTT TTT TGT
   Val Leu Lys Gly Tyr Val Leu Glu Gly Thr Leu Thr Ala Glu Lys Thr>

530           540           550           560           570
     •      •   •        •   •        •   •        •   •        •   •
   ACA TTG GTG GTT AAA GAA GGA ACT GTT ACT TTA AGC AAA AAT ATT TCA
   TGT AAC CAC CAA TTT CTT CCT TGA CAA TGA AAT TCG TTT TTA TAA AGT
   Thr Leu Val Val Lys Glu Gly Thr Val Thr Leu Ser Lys Asn Ile Ser>

580           590           600           610           620
           •   •        •   •        •   •        •   •        •   •
   AAA TCT GGG GAA GTT TCA GTT GAA CTT AAT GAC ACT GAC AGT AGT GCT
   TTT AGA CCC CTT CAA AGT CAA CTT GAA TTA CTG TGA CTG TCA TCA CGA
   Lys Ser Gly Glu Val Ser Val Glu Leu Asn Asp Thr Asp Ser Ser Ala>

630           640           650           660           670
    •   •      •   •        •   •        •   •        •   •        •   •
   GCT ACT AAA AAA ACT GCA GCT TGG AAT TCA AAA ACT TCC ACT TTA ACA
   CGA TGA TTT TTT TGA CGT CGA ACC TTA AGT TTT TGA AGG TGA AAT TGT
   Ala Thr Lys Lys Thr Ala Ala Trp Asn Ser Lys Thr Ser Thr Leu Thr>

680           690           700           710           720
         •   •      •   •        •   •        •   •        •   •        •   •
   ATT AGT GTG AAT AGC CAA AAA ACC AAA AAC CTT GTA TTC ACA AAA GAA
   TAA TCA CAC TTA TCG GTT TTT TGG TTT TTG GAA CAT AAG TGT TTT CTT
   Ile Ser Val Asn Ser Gln Lys Thr Lys Asn Leu Val Phe Thr Lys Glu>

730           740           750           760
         •   •      •   •        •   •        •   •        •   •
   GAC ACA ATA ACA GTA CAA AAA TAC GAC TCA GCA GGC ACC AAT CTA GAA
   CTG TGT TAT TGT CAT GTT TTT ATG CTG AGT CGT CCG TGG TTA GAT CTT
   Asp Thr Ile Thr Val Gln Lys Tyr Asp Ser Ala Gly Thr Asn Leu Glu>

770           780           790           800           810
     •      •   •        •   •        •   •        •   •        •   •
   GGC AAA GCA GTC GAA ATT ACA ACA CTT AAA GAA CTT AAA AAC GCT TTA
   CCG TTT CGT CAG CTT TAA TGT TGT GAA TTT CTT GAA TTT TTG CGA AAT
   Gly Lys Ala Val Glu Ile Thr Thr Leu Lys Glu Leu Lys Asn Ala Leu>

820
     •
   AAA TAA
   TTT ATT
   Lys ***>
```

FIG. 12B

```
         10            20            30            40
         *             *             *             *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50            60            70            80            90
     *             *             *             *             *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100           110           120           130           140
     *             *             *             *             *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150           160           170           180           190
     *             *             *             *             *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200           210           220           230           240
     *             *             *             *             *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250           260           270           280
     *             *             *             *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290           300           310           320           330
*             *             *             *             *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340           350           360           370           380
     *             *             *             *             *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 13A

```
         390           400           410           420           430
    .     *       .     *       .     *       .     *       .     *
   AAA GGT GAA GTA TCT GAA AAA ATA ATA ACA AGA GCA GAC GGA ACC AGA
   TTT CCA CTT CAT AGA CTT TTT TAT TAT TGT TCT CGT CTG CCT TGG TCT
   Lys Gly Glu Val Ser Glu Lys Ile Ile Thr Arg Ala Asp Gly Thr Arg>

440           450           460           470           480
    .     *       .     *       .     *       .     *       .     *
   CTT GAA TAC ACA GGA ATT AAA AGC GAT GGA TCT GGA AAA GCT AAA GAG
   GAA CTT ATG TGT CCT TAA TTT TCG CTA CCT AGA CCT TTT CGA TTT CTC
   Leu Glu Tyr Thr Gly Ile Lys Ser Asp Gly Ser Gly Lys Ala Lys Glu>

490           500           510           520
    .     *       .     *       .     *       .     *       .
   GTT TTA AAA GGC TAT GTT CTT GAA GGA ACT CTA ACT GCT GAA AAA ACA
   CAA AAT TTT CCG ATA CAA GAA CTT CCT TGA GAT TGA CGA CTT TTT TGT
   Val Leu Lys Gly Tyr Val Leu Glu Gly Thr Leu Thr Ala Glu Lys Thr>

530           540           550           560           570
    .     *       .     *       .     *       .     *       .     *
   ACA TTG GTG GTT AAA GAA GGA ACT GTT ACT TTA AGC AAA AAT ATT TCA
   TGT AAC CAC CAA TTT CTT CCT TGA CAA TGA AAT TCG TTT TTA TAA AGT
   Thr Leu Val Val Lys Glu Gly Thr Val Thr Leu Ser Lys Asn Ile Ser>

580           590           600           610           620
    .     *       .     *       .     *       .     *       .     *
   AAA TCT GGG GAA GTT TCA GTT GAA CTT AAT GAC ACT GAC AGT AGT GCT
   TTT AGA CCC CTT CAA AGT CAA CTT GAA TTA CTG TGA CTG TCA TCA CGA
   Lys Ser Gly Glu Val Ser Val Glu Leu Asn Asp Thr Asp Ser Ser Ala>

630           640           650           660           670
    .     *       .     *       .     *       .     *       .     *
   GCT ACT AAA AAA ACT GCA GCT TGG AAT GCA GGC ACT TCA ACT TTA ACA
   CGA TGA TTT TTT TGA CGT CGA ACC TTA CGT CCG TGA AGT TGA AAT TGT
   Ala Thr Lys Lys Thr Ala Ala Trp Asn Ala Gly Thr Ser Thr Leu Thr>

680           690           700           710           720
    .     *       .     *       .     *       .     *       .     *
   ATT ACT GTA AAC AAC AAA AAA ACT AAA GCC CTT GTA TTT ACA AAA CAA
   TAA TGA CAT TTG TTG TTT TTT TGA TTT CGG GAA CAT AAA TGT TTT GTT
   Ile Thr Val Asn Asn Lys Lys Thr Lys Ala Leu Val Phe Thr Lys Gln>

730           740           750           760
    .     *       .     *       .     *       .     *       .
   GAC ACA ATT ACA TCA CAA AAA TAC GAC TCA GCA GGA ACC AAC TTG GAA
   CTG TGT TAA TGT AGT GTT TTT ATG CTG AGT CGT CCT TGG TTG AAC CTT
   Asp Thr Ile Thr Ser Gln Lys Tyr Asp Ser Ala Gly Thr Asn Leu Glu>
```

FIG. 13B

```
      770         780         790         800         810
       .           .           .           .           .
       *           *           *           *           *
  GGC ACA GCA GTC GAA ATT AAA ACA CTT GAT GAA CTT AAA AAC GCT TTA
  CCG TGT CGT CAG CTT TAA TTT TGT GAA CTA CTT GAA TTT TTG CGA AAT
  Gly Thr Ala Val Glu Ile Lys Thr Leu Asp Glu Leu Lys Asn Ala Leu>

AGA
  TCT
  Arg>
```

FIG. 13C

```
          10          20          30          40
           *           *           *           *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
     *           *           *           *           *
TGT AAG CAA AAT GTT AGC AGC CTT GAT GAA AAA AAT AGC GTT TCA GTA
ACA TTC GTT TTA CAA TCG TCG GAA CTA CTT TTT TTA TCG CAA AGT CAT
Cys Lys Gln Asn Val Ser Ser Leu Asp Glu Lys Asn Ser Val Ser Val>

100         110         120         130         140
        *           *           *           *           *
GAT TTA CCT GGT GGA ATG ACA GTT CTT GTA AGT AAA GAA AAA GAC AAA
CTA AAT GGA CCA CCT TAC TGT CAA GAA CAT TCA TTT CTT TTT CTG TTT
Asp Leu Pro Gly Gly Met Thr Val Leu Val Ser Lys Glu Lys Asp Lys>

150         160         170         180         190
        *           *           *           *           *
GAC GGT AAA TAC AGT CTA GAG GCA ACA GTA GAC AAG CTT GAG CTT AAA
CTG CCA TTT ATG TCA GAT CTC CGT TGT CAT CTG TTC GAA CTC GAA TTT
Asp Gly Lys Tyr Ser Leu Glu Ala Thr Val Asp Lys Leu Glu Leu Lys>

200         210         220         230         240
        *           *           *           *           *
GGA ACT TCT GAT AAA AAC AAC GGT TCT GGA ACA CTT GAA GGT GAA AAA
CCT TGA AGA CTA TTT TTG TTG CCA AGA CCT TGT GAA CTT CCA CTT TTT
Gly Thr Ser Asp Lys Asn Asn Gly Ser Gly Thr Leu Glu Gly Glu Lys>

250         260         270         280
        *           *           *           *
ACT GAC AAA AGT AAA GTA AAA TTA ACA ATT GCT GAT GAC CTA AGT CAA
TGA CTG TTT TCA TTT CAT TTT AAT TGT TAA CGA CTA CTG GAT TCA GTT
Thr Asp Lys Ser Lys Val Lys Leu Thr Ile Ala Asp Asp Leu Ser Gln>

290        300         310         320         330
  *          *           *           *           *
ACT AAA TTT GAA ATT TTC AAA GAA GAT GCC AAA ACA TTA GTA TCA AAA
TGA TTT AAA CTT TAA AAG TTT CTT CTA CGG TTT TGT AAT CAT AGT TTT
Thr Lys Phe Glu Ile Phe Lys Glu Asp Ala Lys Thr Leu Val Ser Lys>

340         350         360         370         380
     *           *           *           *           *
AAA GTA ACC CTT AAA GAC AAG TCA TCA ACA GAA GAA AAA TTC AAC GAA
TTT CAT TGG GAA TTT CTG TTC AGT AGT TGT CTT CTT TTT AAG TTG CTT
Lys Val Thr Leu Lys Asp Lys Ser Ser Thr Glu Glu Lys Phe Asn Glu>
```

FIG. 14A

```
         390          400          410          420          430
    .    .       .    .       .    .       .    .       .    .
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

440          450          460          470          480
    .    .       .    .       .    .       .    .       .    .
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

490          500          510          520
    .    .       .    .       .    .       .    .       .    .
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530          540          550          560          570
    .    .       .    .       .    .       .    .       .    .
ACA ACA TTG AAA GTT ACA GAA GGC ACT GTT GTT TTA AGC AAG ATT TCA
TGT TGT AAC TTT CAA TGT CTT CCG TGA CAA CAA AAT TCG TTC TAA AGT
Thr Thr Leu Lys Val Thr Glu Gly Thr Val Val Leu Ser Lys Ile Ser>

580          590          600          610          620
    .    .       .    .       .    .       .    .       .    .
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630          640          650          660          670
    .    .       .    .       .    .       .    .       .    .
GCT ACT AAA AAA ACT GCA GCT TGG AAT TCA AAA ACT TCC ACT TTA ACA
CGA TGA TTT TTT TGA CGT CGA ACC TTA AGT TTT TGA AGG TGA AAT TGT
Ala Thr Lys Lys Thr Ala Ala Trp Asn Ser Lys Thr Ser Thr Leu Thr>

680          690          700          710          720
    .    .       .    .       .    .       .    .       .    .
ATT AGT GTG AAT AGC CAA AAA ACC AAA AAC CTT GTA TTC ACA AAA GAA
TAA TCA CAC TTA TCG GTT TTT TGG TTT TTG GAA CAT AAG TGT TTT CTT
Ile Ser Val Asn Ser Gln Lys Thr Lys Asn Leu Val Phe Thr Lys Glu>

730          740          750          760
    .    .       .    .       .    .       .    .       .
GAC ACA ATA ACA GTA CAA AAA TAC GAC TCA GCA GGC ACC AAT CTA GAA
CTG TGT TAT TGT CAT GTT TTT ATG CTG AGT CGT CCG TGG TTA GAT CTT
Asp Thr Ile Thr Val Gln Lys Tyr Asp Ser Ala Gly Thr Asn Leu Glu>

FIG. 14B
```

```
    770         780         790         800         810
     .           .           .           .           .
GGC AAA GCA GTC GAA ATT ACA ACA CTT AAA GAA CTT AAA AAC GCT TTA
CCG TTT CGT CAG CTT TAA TGT TGT GAA TTT CTT GAA TTT TTG CGA AAT
Gly Lys Ala Val Glu Ile Thr Thr Leu Lys Glu Leu Lys Asn Ala Leu>

820
     .
AAA TAA
TTT ATT
Lys ***>
```

FIG. 14C

```
              10            20            30            40
     .    .    .    .    .    .    .    .    .    .
ATG  AAA  AAA  TAT  TTA  TTG  GGA  ATA  GGT  CTA  ATA  TTA  GCC  TTA  ATA  GCA
TAC  TTT  TTT  ATA  AAT  AAC  CCT  TAT  CCA  GAT  TAT  AAT  CGG  AAT  TAT  CGT
Met  Lys  Lys  Tyr  Leu  Leu  Gly  Ile  Gly  Leu  Ile  Leu  Ala  Leu  Ile  Ala>

50            60            70            80            90
     .    .    .    .    .    .    .    .    .    .
TGT  AAG  CAA  AAT  GTT  AGC  AGC  CTT  CAT  GAA  AAA  AAT  AGC  GTT  TCA  GTA
ACA  TTC  GTT  TTA  CAA  TCG  TCG  GAA  CTA  CTT  TTT  TTA  TCG  CAA  AGT  CAT
Cys  Lys  Gln  Asn  Val  Ser  Ser  Leu  Asp  Glu  Lys  Asn  Ser  Val  Ser  Val>

100           110           120           130           140
     .    .    .    .    .    .    .    .    .    .
GAT  TTA  CCT  GGT  GGA  ATG  ACA  GTT  CTT  GTA  AGT  AAA  GAA  AAA  GAC  AAA
CTA  AAT  GGA  CCA  CCT  TAC  TGT  CAA  GAA  CAT  TCA  TTT  CTT  TTT  CTG  TTT
Asp  Leu  Pro  Gly  Gly  Met  Thr  Val  Leu  Val  Ser  Lys  Glu  Lys  Asp  Lys>

150           160           170           180           190
     .    .    .    .    .    .    .    .    .    .
GAC  GGT  AAA  TAC  AGT  CTA  GAG  GCA  ACA  GTA  GAC  AAG  CTT  GAG  CTT  AAA
CTG  CCA  TTT  ATG  TCA  GAT  CTC  CGT  TGT  CAT  CTG  TTC  GAA  CTC  GAA  TTT
Asp  Gly  Lys  Tyr  Ser  Leu  Glu  Ala  Thr  Val  Asp  Lys  Leu  Glu  Leu  Lys>

200           210           220           230           240
     .    .    .    .    .    .    .    .    .    .
GGA  ACT  TCT  GAT  AAA  AAC  AAC  GGT  TCT  GGA  ACA  CTT  GAA  GGT  GAA  AAA
CCT  TGA  AGA  CTA  TTT  TTG  TTG  CCA  AGA  CCT  TGT  GAA  CTT  CCA  CTT  TTT
Gly  Thr  Ser  Asp  Lys  Asn  Asn  Gly  Ser  Gly  Thr  Leu  Glu  Gly  Glu  Lys>

250           260           270           280
     .    .    .    .    .    .    .    .    .
ACT  GAC  AAA  AGT  AAA  GTA  AAA  TTA  ACA  ATT  GCT  GAT  GAC  CTA  AGT  CAA
TGA  CTG  TTT  TCA  TTT  CAT  TTT  AAT  TGT  TAA  CGA  CTA  CTG  GAT  TCA  GTT
Thr  Asp  Lys  Ser  Lys  Val  Lys  Leu  Thr  Ile  Ala  Asp  Asp  Leu  Ser  Gln>

290           300           310           320           330
     .    .    .    .    .    .    .    .    .    .
ACT  AAA  TTT  GAA  ATT  TTC  AAA  GAA  GAT  GCC  AAA  ACA  TTA  GTA  TCA  AAA
TGA  TTT  AAA  CTT  TAA  AAG  TTT  CTT  CTA  CGG  TTT  TGT  AAT  CAT  AGT  TTT
Thr  Lys  Phe  Glu  Ile  Phe  Lys  Glu  Asp  Ala  Lys  Thr  Leu  Val  Ser  Lys>

340           350           360           370           380
     .    .    .    .    .    .    .    .    .    .
AAA  GTA  ACC  CTT  AAA  GAC  AAG  TCA  TCA  ACA  GAA  GAA  AAA  TTC  AAC  GAA
TTT  CAT  TGG  GAA  TTT  CTG  TTC  AGT  AGT  TGT  CTT  CTT  TTT  AAG  TTG  CTT
Lys  Val  Thr  Leu  Lys  Asp  Lys  Ser  Ser  Thr  Glu  Glu  Lys  Phe  Asn  Glu>
```

FIG. 15A

```
        390           400           410           420           430
   *     *      *      *      *     *      *      *      *     *
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

440           450           460           470           480
     *      *      *      *     *     *      *      *      *      *
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

490           500           510           520
       *      *      *      *     *     *      *      *      *
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530           540           550           560           570
   *     *      *      *     *     *      *      *      *     *
ACA ACA TTG AAA GTT ACA GAA GGC ACT GTT GTT TTA AGC AAG ATT TCA
TGT TGT AAC TTT CAA TGT CTT CCG TGA CAA CAA AAT TCG TTC TAA AGT
Thr Thr Leu Lys Val Thr Glu Gly Thr Val Val Leu Ser Lys Ile Ser>

580           590           600           610           620
     *      *      *      *     *     *      *      *     *     *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630           640           650           660           670
     *      *      *      *     *     *      *      *      *     *
GCT ACT AAA AAA ACT GCA GCT TGG AAT TCA AAA ACT TCC ACT TTA ACA
CGA TGA TTT TTT TGA CGT CGA ACC TTA AGT TTT TGA AGG TGA AAT TGT
Ala Thr Lys Lys Thr Ala Ala Trp Asn Ser Lys Thr Ser Thr Leu Thr>

680           690           700           710           720
       *      *      *      *     *     *      *      *     *     *
ATT AGT GTG AAT AGC CAA AAA ACC AAA AAC CTT GTA TTC ACA AAA GAA
TAA TCA CAC TTA TCG GTT TTT TGG TTT TTG GAA CAT AAG TGT TTT CTT
Ile Ser Val Asn Ser Gln Lys Thr Lys Asn Leu Val Phe Thr Lys Glu>

730           740           750           760
       *      *      *      *     *     *      *      *      *
GAC ACA ATA ACA GTA CAA AAA TAC GAC TCA GCA GGC ACC AAT CTA GAA
CTG TGT TAT TGT CAT GTT TTT ATG CTG AGT CGT CCG TGG TTA GAT CTT
Asp Thr Ile Thr Val Gln Lys Tyr Asp Ser Ala Gly Thr Asn Leu Glu>
```

FIG. 15B

```
        770         780         790         800         810
          .           .           .           .           .
GGC AAA GCA GTC GAA ATT ACA ACA CTT AAA GAA CTT AAA AAC GCT TTA
CCG TTT CGT CAG CTT TAA TGT TGT GAA TTT CTT GAA TTT TTG CGA AAT
Gly Lys Ala Val Glu Ile Thr Thr Leu Lys Glu Leu Lys Asn Ala Leu>

820
     .
AAA TAA
TTT ATT
Lys ***>
```

FIG. 15C

```
          10             20             30             40
           .              .              .              .
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50             60             70             80             90
     .              .              .              .              .
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100            110            120            130            140
          .              .              .              .              .
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150            160            170            180            190
          .              .              .              .              .
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200            210            220            230            240
          .              .              .              .              .
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250            260            270            280
          .              .              .              .
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290            300            310            320            330
 .              .              .              .              .
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340            350            360            370            380
     .              .              .              .              .
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 16A

```
            390         400         410         420         430
     •       •   •       •   •       •   •       •   •       •
    AAA GGT GAA GTA TCT GAA AAA ATA ATA ACA AGA GCA GAC GGA ACC AGA
    TTT CCA CTT CAT AGA CTT TTT TAT TAT TGT TCT CGT CTG CCT TGG TCT
    Lys Gly Glu Val Ser Glu Lys Ile Ile Thr Arg Ala Asp Gly Thr Arg>

440         450         460         470         480
     •       •   •       •   •       •   •       •   •       •
    CTT GAA TAC ACA GGA ATT AAA AGC GAT GGA TCT GGA AAA GCT AAA GAG
    GAA CTT ATG TGT CCT TAA TTT TCG CTA CCT AGA CCT TTT CGA TTT CTC
    Leu Glu Tyr Thr Gly Ile Lys Ser Asp Gly Ser Gly Lys Ala Lys Glu>

490         500         510         520
     •       •   •       •   •       •   •       •   •       •
    GTT TTA AAA GGC TAT GTT CTT GAA GGA ACT CTA ACT GCT GAA AAA ACA
    CAA AAT TTT CCG ATA CAA GAA CTT CCT TGA GAT TGA CGA CTT TTT TGT
    Val Leu Lys Gly Tyr Val Leu Glu Gly Thr Leu Thr Ala Glu Lys Thr>

530         540         550         560         570
     •   •       •   •       •   •       •   •       •   •
    ACA TTG GTG GTT AAA GAA GGA ACT GTT ACT TTA AGC AAA AAT ATT TCA
    TGT AAC CAC CAA TTT CTT CCT TGA CAA TGA AAT TCG TTT TTA TAA AGT
    Thr Leu Val Val Lys Glu Gly Thr Val Thr Leu Ser Lys Asn Ile Ser>

580         590         600         610         620
     •       •   •       •   •       •   •       •   •       •
    AAA TCT GGG GAA GTT TCA GTT GAA CTT AAT GAC ACT GAC AGT AGT GCT
    TTT AGA CCC CTT CAA AGT CAA CTT GAA TTA CTG TGA CTG TCA TCA CGA
    Lys Ser Gly Glu Val Ser Val Glu Leu Asn Asp Thr Asp Ser Ser Ala>

630         640         650         660         670
     •       •   •       •   •       •   •       •   •       •
    GCT ACT AAA AAA ACT GCA GCT TGG AAT GAC AGT ACT AGC ACT TTA ACA
    CGA TGA TTT TTT TGA CGT CGA ACC TTA CTG TCA TGA TCG TGA AAT TGT
    Ala Thr Lys Lys Thr Ala Ala Trp Asn Asp Ser Thr Ser Thr Leu Thr>

680         690         700         710         720
     •       •   •       •   •       •   •       •   •       •
    ATT AGT GCT GAC AGC AAA AAA ACT AAA GAT TTG GTG TTC TTA ACA GAT
    TAA TCA CGA CTG TCG TTT TTT TGA TTT CTA AAC CAC AAG AAT TGT CTA
    Ile Ser Ala Asp Ser Lys Lys Thr Lys Asp Leu Val Phe Leu Thr Asp>

730         740         750         760
     •       •   •       •   •       •   •       •   •
    GGT ACA ATT ACA GTA CAA CAA TAC AAC ACA GCT GGA ACC AGC CTA GAA
    CCA TGT TAA TGT CAT GTT GTT ATG TTG TGT CGA CCT TGG TCG GAT CTT
    Gly Thr Ile Thr Val Gln Gln Tyr Asn Thr Ala Gly Thr Ser Leu Glu>
```

FIG. 16B

```
       770         780         790         800         810
        •     •     •     •     •     •     •     •     •     •
GGA TCA GCA AGT GAA ATT AAA AAT CTT TCA GAG CTT AAA AAC GCT TTA
CCT AGT CGT TCA CTT TAA TTT TTA GAA AGT CTC GAA TTT TTG CGA AAT
Gly Ser Ala Ser Glu Ile Lys Asn Leu Ser Glu Leu Lys Asn Ala Leu>

820
     •
AAA TAA
TTT ATT
Lys ***>
```

FIG. 16C

Sequence Range: 1 to 822

```
                        10          20          30          40
OspA-B31        ATG AAA AAA TAT TTA TTG GGA ATA GGT CTA ATA TTA GCC TTA ATA GCA
                TAC TTT TTT ATA AAT AAC CCT TAT CCA GAT TAT AAT CGG AAT TAT CGT 10          20          30          40
OspA-B31
[ 3288 ]        ... ... ... ... ... ... ... ... ... ... ... ... ... ... ...>

10          20          30          40
OspA-KA
[ 3288 ]        ... ... ... ... ... ... ... ... ... ... ... ... ... ... ...>

10          20          30          40
OspA-N40
[ 3276 ]        ... ... ... ... ... ... ... ... ... ... ... ... ... ... ...>

10          20          30          40
OspA-ZS7
[ 3264 ]        ... ... ... ... ... ... ... ... ... ... ... ... ... ... ...>

10          20          30          40
OspA-25015
[ 2802 ]        ... ... ... ... ... ... ... ... ... ... ... ..t ... ... ...>

10          20          30          40
OspA-TRO
[ 2648 ]        ... ... ... ... ... ... ... ... ... ... ... ... ... ... ...>

10          20          30          40
OspA-K48
[ 2584 ]        ... ... ... ... ... ... ... ... ... ... ... ... ... ... ...>

10          20          30          40
OspA-HB 11
[ 2580 ]        ... ... ... ... ... ... ... ... ... ... ... ... ... ... ...>

10          20          30          40
OspA-DK29
[ 2566 ]        ... ... ... ... ... ... ... ... ... ... ... ... ... ... ...>

10          20          30          40
OspA-Ip90
[ 2562 ]        ... ... ... ... ... ... ... ... ... ... ... ..a ... ... ...>

10          20          30          40
OspA-BO
[ 2558 ]        ... ... ... ... ... ... ... ... ... ... ... ... ... ... ...>

10          20          30          40
OSPA-IP3
[ 2558 ]        ... ... ... ... ... ... ... ... ... ... ... ... ... ... ...>

10          20          30          40
OspA-PKO
[ 2558 ]        ... ... ... ... ... ... ... ... ... ... ... ... ... ... ...>

10          20          30          40
OspA-ACAI
[ 2556 ]        ... ... ... ... ... ... ... ... ... ... ... ... ... ... ...>

10          20          30          40
OspA-P-GAU
[ 2544 ]        ... ... ... ... ... ... ... ... ... ... ... ... ... ... ...>

50          60          70          80          90
OspA-B31        TGT AAG CAA AAT GTT AGC AGC CTT GAC CAG AAA AAC AGC GTT TCA GTA
                ACA TTC GTT TTA CAA TCG TCG GAA CTG CTC TTT TTG TCG CAA AGT CAT
```

FIG. 17A

| | | | | | |
|---|---|---|---|---|---|
| OspA-B31 [3298] | 50 ... ... ... | 60 ... ... ... | 70 ... ... ... | 80 ... ... ... | 90 ... ... ... ...> |
| OspA-KA [3288] | 50 ... ... ... | 60 ... ... ... | 70 ... ... ... | 80 ... ... ... | 90 ... ... ... ...> |
| OspA-N40 [3276] | 50 ... ... ... | 60 ... ... ... | 70 ... ... ... | 80 ... ... ... | 90 ... ... ... ...> |
| OspA-Z67 [3264] | 50 ... ... ... | 60 ... ... ... | 70 ... ... ... | 80 ... ... ... | 90 ... ... ... ...> |
| OspA-25015 [2802] | 50 ... ... ... | 60 ... ... ... | 70 ... ... ... | 80 ... ... ... | 90 ... ... ... ...> |
| OspA-TRO [2648] | 50 ... ... ... | 60 ... ... ... | 70 ... ... ... | 80 ..t ... ... | 90 ... ... ... ...> |
| OspA-K48 [2584] | 50 ... ... ... | 60 ... ... ... | 70 ... ... ... | 80 ..t ..a ... ..t ... | 90 ... ... ... ...> |
| OspA-HB11 [2580] | 50 ... ... ... | 60 ... ... ... | 70 ... ... ... | 80 ..t ..a ... ..t ... | 90 ... ... ... ...> |
| OspA-DK29 [2566] | 50 ... ... ... | 60 ... ... ... | 70 ... ... ... | 80 ..t ..a ... ..t ... | 90 ... ... ... ...> |
| OspA-Ip90 [2562] | 50 ... ... ... | 60 ... ... ... | 70 ... ... ... | 80 ..t ..a ... ..t ... | 90 ... ... ... ...> |
| OspA-BO [2558] | 50 ..c ... ... | 60 ... ... ... | 70 ... ... ... | 80 ..t ..a ... | 90 .c. ... ...> |
| OspA-IP3 [2558] | 50 ..c ... ... | 60 ... ... ... | 70 ... ... ... | 80 ..t ..a ... | 90 .c. ... ...> |
| OspA-PKO [2558] | 50 ..c ... ... | 60 ... ... ... | 70 ... ... ... | 80 ..t ... ... | 90 .c. ... ...> |
| OspA-ACAI [2556] | 50 ..c ... ... | 60 ... ... ... | 70 ... ... ... | 80 ..t ..a ... | 90 .c. ... ...> |
| OspA-P-GAU [2544] | 50 ..c ... ... | 60 ... ... ... | 70 ... ... ... | 80 ..t ..a ... | 90 .c. ... ...> |

| | 100 | 110 | 120 | 130 | 140 |
|---|---|---|---|---|---|
| OspA-B31 | GAT TTG CCT CTA AAC GGA | GGT GAA ATG CCA CTT TAC | AAA GTT CTT TTT CAA GAA | GTA AGC AAA CAT TCG TTT | GAA AAA AAC AAA CTT TTT TTG TTT |
| OspA-B31 [3288] | 100 ... ... ... | 110 ... ... ... | 120 ... ... ... | 130 ... ... ... | 140 ... ... ... ...> |
| OspA-KA [3288] | 100 ... ... ... | 110 ... ... ... | 120 ... ... ... | 130 ... ... ... | 140 ... ... ... ...> |
| OspA-N40 | 100 | 110 | 120 | 130 | 140 |

FIG. 17B

| | | | | | |
|---|---|---|---|---|---|
| [ 3276 ] | ... ... ... ... ... ... ..c ... ... ... ... ... ... ... ...> | | | | |
| OspA-ZS7 | 100 | 110 | 120 | 130 | 140 |
| [ 3264 ] | ... ... ... ... ... ... ..c ... ... ... ... ... ... ... ...> | | | | |
| OspA-25015 | 100 | 110 | 120 | 130 | 140 |
| [ 2802 ] | ... ... ... ... ... ... ... ... ... ... ... ... ... g.. ...> | | | | |
| OspA-TRO | 100 | 110 | 120 | 130 | 140 |
| [ 2648 ] | ... ..a ... ... ... ... ... ... ... ... ... ... ... g.. ...> | | | | |
| OspA-K48 | 100 | 110 | 120 | 130 | 140 |
| [ 2584 ] | ... ..a ... ... .g. ... .c. ... ... ... ..t ... ... g.. ...> | | | | |
| OspA-HE11 | 100 | 110 | 120 | 130 | 140 |
| [ 2580 ] | ... ..a ... ... .g. ... ... ... ... ... ..t ... ... g.. ...> | | | | |
| OspA-DK29 | 100 | 110 | 120 | 130 | 140 |
| [ 2566 ] | ... ..a ... ... .g. ... .c. ... ... ... ..t ... ... g.. ...> | | | | |
| OspA-Ip90 | 100 | 110 | 120 | 130 | 140 |
| [ 2562 ] | ... ..a ... ... .g. ... c.. ... ... ... ..t ... ... g.. ...> | | | | |
| OspA-BO | 100 | 110 | 120 | 130 | 140 |
| [ 2558 ] | ... ... ... ... .g ... ... ... ... ... ..t ... ... g.. ...> | | | | |
| OSPA-IP3 | 100 | 110 | 120 | 130 | 140 |
| [ 2558 ] | ... ... ... ... .g ..t ... ... ... ... ..t ... ... g.. ...> | | | | |
| OspA-PKO | 100 | 110 | 120 | 130 | 140 |
| [ 2558 ] | ... ... ... ... .g ... ... ... ... ... ..t ... ... g.. ...> | | | | |
| OspA-ACAI | 100 | 110 | 120 | 130 | 140 |
| [ 2556 ] | ... ... ... ... .g ... ... ... ... ... ..t ... ... g.. ...> | | | | |
| OspA-P-GAU | 100 | 110 | 120 | 130 | 140 |
| [ 2544 ] | ... ... ... ... .g ... ... ... ... ... ..t

```
OspA-TRO          150         160         170         180         190
[ 2648 ]       ..t ..t ..a ... ag. ... ..g ... ... ... ... ... ..a ... ... ...>

OspA-K48          150         160         170         180         190
[ 2584 ]       ... ..t ..a ... ag. ... gag ... ... ... ... ... ... ... ... ...>

OspA-HB 11        150         160         170         180         190
[ 2580 ]       ..t ..t ..a ... ag. ... ..g ... ... ... ... ... ..a ... ... ...>

OspA-DK29         150         160         170         180         190
[ 2566 ]       ... ..t ..a ... ag. ... gag ... ... ... ... ... ... ... ... ...>

OspA-Ip90         150         160         170         180         190
[ 2562 ]       ..t ..t ..a ... ag. ... ..g ... ... ... ... ... ... ... ... ...>

OspA-BO           150         160         170         180         190
[ 2558 ]       ... ..t ... ... ag. ... .ag ... ... ... ... ... a.. ... ..a ...>

OSPA-IP3          150         160         170         180         190
[ 2558 ]       ... ..t ... ... ag. ... .ag ... ... ... ... ... a.. ... ..a ...>

OspA-PKO          150         160         170         180         190
[ 2558 ]       ... ..t ... ... ag. ... .ag ... ... ... ... ... a.. ... ..a ...>

OspA-ACAI         150         160         170         180         190
[ 2556 ]       ... ..t ... ... ag. ... .ag ... ... ... ... ... a.. ... ..a ...> ospA-P-GAU        150         160         170         180         190
[ 2544 ]       ... ..t ... ... ag. ... .ag ... ... ... ... ... a.. ... ..a ...>

200         210         220         230         240
                   *           *           *           *           *
OspA-B31       GGA ACT TCT GAT AAA AAC AAT GGA TCT GGA GTA CTT GAA GGC GTA AAA
               CCT TGA AGA CTA TTT TTG TTA CCT AGA CCT CAT GAA CTT CCG CAT TTT

OspA-B31          200         210         220         230         240
[ 3288 ]       ... ... ... ... ... ... ... ... ... ... ... ... ... ... ... ...>

OspA-HA           200         210         220         230         240
[ 3288 ]       ... ... ... ... ... ... ... ... ... ... ... ... ... ... ... ...>

OspA-N40          200         210         220         230         240
[ 3276 ]       ... ... ... ... ... ... ... ... ... ... ... ... ... ... ... ...>

OspA-ZS7          200         210         220         230         240
[ 3264 ]       ... ... ... ... ... ... ... ... ... ... ... ... ... ... ... ...>

OspA-25015        200         210         220         230         240
[ 2802 ]       ... ..a ... ... ... ... ... ... ... ..g ..g ... ... ... ... ...>

OspA-TRO          200         210         220         230         240
[ 2648 ]       ... ... ... ... ... .g. ..c ..t ... ... ac. ... ... ..t .a. ...>

OspA-K48          200         210         220         230         240
[ 2584 ]       ... ... ... ... ... ... ..c ..t ... ... ac. ... ... ..t .a. ...>
```

FIG. 17D

```
OspA-HE 11          200       210       220       230       240
[ 2580 ]            ... ... ... ... ... ... ..c ..t ... ... ac. ... ... ..t ..a. ...>

OspA-DK29           200       210       220       230       240
[ 2566 ]            ... ... ... ... ... ... ..c ..t ... ... ac. ... ... ..t ..a. ...>

OspA-Ip90           200       210       220       230       240
[ 2562 ]            ... ... ... ... ... ... ..c ..t ... ... ac. ... ... ..t ..a. ...>

OspA-BO             200       210       220       230       240
[ 2558 ]            ... ... ... ... ... g.. ... ..t ... ..g ..g ... ... ..t ac. ...>

OspA-IP3            200       210       220       230       240
[ 2558 ]            ... ... ... ... ... g.. ... ..t ... ... ..g ... ... ..t ac. ...>

OspA-PKO            200       210       220       230       240
[ 2558 ]            ... ... ... ... ... g.. ... ..t ... ..g ..g ... ... ..t ac. ...>

OspA-ACAI           200       210       220       230       240
[ 2556 ]            ... ... ... ... ... g.. ... ..t ... ... ..g ... ... ..t ac. ...>

OspA-P-CAU          200       210       220       230       240
[ 2544 ]            ... ... ... ... ... g.. ... ..t ... ... ..g ... ... ..t ac. ...>

250       260       270       280

OspA-B31            GCT GAC AAA AGT AAA GTA AAA TTA ACA ATT TCT GAC GAT CTA GGT CAA
                    CGA CTG TTT TCA TTT CAT TTT AAT TGT TAA AGA CTG CTA GAT CCA GTT

OspA-B31                 250       260       270       280
[ 3288 ]            ... ... ... ... ... ... ... ... ... ... ... ... ... ... ... ...>

OspA-FR                  250       260       270       280
[ 3288 ]            ... ... ... ... ... ... ... ... ... ... ... ... ... ... ... ...>

OspA-N40                 250       260       270       280
[ 3276 ]            ... ... ... ... ... ... ... ... ... ... ... ... ... ... ... ...>

OspA-ZS7                 250       260       270       280
[ 3264 ]            ... ... ... ... ... ... ... ... ... ... ... ... ... ... ... ...>

OspA-25015               250       260       270       280
[ 2802 ]            ... ... ... ..c ... ... ... ... ... g.. ... ... ... ... a..c ac.>

OspA-TRO                 250       260       270       280
[ 2648 ]            t.. ... ... ... ... .c. ... ... ... ... ..a ... ... a... a...>

OspA-K48                 250       260       270       280
[ 2584 ]            a.. ... ... ... ... ... ... ... ... ... g.. ..t ..c ... a... ...>

OspA-HE 11               250       260       270       280
[ 2580 ]            ... ... ... ... ... ... ... ... ... ... g.. ..g ... ... a... a..>

OspA-DK29                250       260       270       280
[ 2566 ]            a.. ... ... ... ... .c. ... ... ... g.. ..t ..c ... a... ...>

OspA-Ip90                250       260       270       280
```

FIG. 17E

| | | | | | |
|---|---|---|---|---|---|
| [ 2562 ] | a... ... ... ... ... | .c. ... ... ... ... | ... g.. ..g | ... ... a.. a..> |  |
| OspA-EO | 250 | 260 | 270 | 280 | |
| [ 2558 ] | .a. ... ... ... ... | .c. ... ... ... ... | ... g.. ... | ... ... ... a..> | |
| OspA-IP3 | 250 | 260 | 270 | 280 | |
| [ 2558 ] | .a. ... ... ... ... | .c. ... ... ... ... | ... g.. ... ... | ... a.. a..> | |
| OspA-PKO | 250 | 260 | 270 | 280 | |
| [ 2558 ] | .a. ... ... ... ... | .c. ... ... ... ... | ... g.. ... ... | ... ... ... a..> | |
| OspA-ACAI | 250 | 260 | 270 | 280 | |
| [ 2556 ] | .a. ... ... ... ... | .c. ... ... ... ... | ... g.. ... ...,... | a.. a..> | |
| OspA-P-CAU | 250 | 260 | 270 | 280 | |
| [ 2544 ] | .a. ... ... ... .... | .c. ... ... ... .... | g.. ... ... ... | a.. a..> | |

```
              290           300          310          320         330
               *             *            *            *           *
OspA-B31     ACC ACA CTT GAA GTT TTC AAA GAA GAT GGC AAA ACA CTA GTA TCA AAA
             TGG TGT GAA CTT CAA AAG TTT CTT CTA CCG TTT TGT GAT CAT AGT TTT
```

| | | | | | |
|---|---|---|---|---|---|
| OspA-B31 | 290 | 300 | 310 | 320 | 330 |
| [ 3288 ] | ... ... ... | ... ... ... | ... ... ... | ... ... ... | ... ...> |
| OspA-IR | 290 | 300 | 310 | 320 | 330 |
| [ 3288 ] | ... ... ... | ... ... ... | ... ... ... | ... ... ... | ... ...> |
| OspA-N40 | 290 | 300 | 310 | 320 | 330 |
| [ 3276 ] | ... ... ... | ... ... ... | ... ... ... | ... ... ... | ... ...> |
| OspA-257 | 290 | 300 | 310 | 320 | 330 |
| [ 3264 ] | ... ... ... | ... ... ... | ... ... ... | ... ... ... | ..., ... ...> |
| OspA-25015 | 290 | 300 | 310 | 320 | 330 |
| [ 2902 ] | ... ... ... | ... ..a ... | ... ... ... | ... t.. ..g | ... ...> |
| OspA-TRO | 290 | 300 | 310 | 320 | 330 |
| [ 2648 ] | ... ... t.. | ... a.. ... | ... ... ... | ... t.. ... | ... ...> |
| OspA-K4S | 290 | 300 | 310 | 320 | 330 |
| [ 2594 ] | ..t .a. t.. | ... a.. ... | ... ... ... | .c. ... t.. | ... ...> |
| OspA-HB 11 | 290 | 300 | 310 | 320 | 330 |
| [ 2580 ] | ... ... t.. | ... a.c ... | ... ... ... | ... t.. ... | ..g ...> |
| OspA-DK29 | 290 | 300 | 310 | 320 | 330 |
| [ 2566 ] | ..t .a. t.. | ... a.. ... | ... ... ... | ... t.. ... | ... ...> |
| OspA-IP90 | 290 | 300 | 310 | 320 | 330 |
| [ 2562 ] | ... ... t.. | ... a.c ... | ... ... ... | ... t.. ... | ... ...> |
| OspA-EO | 290 | 300 | 310 | 320 | 330 |
| [ 2558 ] | ... ... t.c | ... c.. ... | ... ... ... | ... t.. ..g | ... .g.> |
| OspA-IP3 | 290 | 300 | 310 | 320 | 330 |
| [ 2558 ] | ... ... t.c | ... c.. ... | ... ... ... | ... t.. ..g | ... .g.> |

FIG. 17F

```
OspA-PKO   290          300          310          320          330
[ 2558 ]   ... ... t.c ... c.. ... ... ... ... ... ... t.. ..g ... .g.>

OspA-ACAI  290          300          310          320          330
[ 2556 ]   ... ... t.c ... c.. ... ... ... ... ... ... t.. ..g ... .g.>

OspA-P-GAU 290          300          310          320          330
[ 2544 ]   ... ... t.c ... c.. ..a ... ... ... ... ... t.. ..g ... .g.>

340          350          360          370          380
OspA-B31    AAA GTA ACT TCC AAA GAC AAG TCA TCA ACA GAA GAA AAA TTC AAT GAA
            TTT CAT TGA AGG TTT CTG TTC AGT AGT TGT CTT CTT TTT AAG TTA CTT

OspA-B31    340          350          360          370          380
[ 3288 ]    ... ... ... ... ... ... ... ... ... ... ... ... ... ... ......>

OspA-HA     340          350          360          370          380
[ 3298 ]    ... ... ... ... ... ... ... ... ... ... ... ... ... ... ... ...>

OspA-N40    340          350          360          370          380
[ 3276 ]    ... ... ... ... ... ... ... ... ... ... ... ... ... ... ... ...>

OspA-ZS7    340          350          360          370          380
[ 3254 ]    ... ... ... ... ... ... ... ... ... ... ... ... ... ... ... ...>

OspA-25015  340          350          360          370          380
[ 2802 ]    ... ag. ... ..t ... ..t ... ... ... ... ... ..g ... ... ... ...>

OspA-TRO    340          350          360          370          380
[ 2648 ]    ... ... .a. ..t ... ..t ... ... ... .t. ... ... ... ... ..c .c.>

OspA-K48    340          350          360          370          380
[ 2584 ]    ... ... ..c ctt ... ... ... ... ... ... ... ... ... ... ..c ...>

OspA-KE 11  340          350          360          370          380
[ 2580 ]    ... ... ..c ctt ... ... ... ... ... ... ... ... ... ... ..c ...>

OspA-DK29   340          350          360          370          380
[.2566 ]    ... ... ..c ctt ... ... ... ... ... ... ... ... ... ... ..c .g.>

OspA-Ip90   340          350          360          370          380
[ 2562 ]    ... ... ..c ctt ... ... ... ... ... ... ... ... ... ... ..c .c.>

OspA-BO     340          350          360          370          380
[ 2558 ]    ... ... .g. ..t ... ... ..a a.. ... ... ..t ... .tg ... ... ...>

OSPA-IP3    340          350          360          370          380
[ 2558 ]    ... ... .g. ..t ... ... ..a a.. ... ... ..t ... .tg ... ... ...>

OspA-PKO    340          350          360          370          380
[ 2558 ]    ... ... .g. ..t ... ... ..a a.. ... ... ..t ... .tg ... ... ...>

OspA-ACAI   340          350          360          370          380
[ 2556 ]    ... ... .g. ..t ... ... ..a a.. ... ... ..t ... .tg ... ... ...>
```

FIG. 17G

```
OspA-P-GAU     340         350         360         370         380
[ 2544 ]       ... ... .g. ..t .g. ... ..a a.. ... ... ...t ... .tg ... ... ...>

390         400         410         420         430
OspA-B31       AAA GGT GAA GTA TCT GAA AAA ATA ATA ACA AGA GCA GAC GGA ACC AGA
               TTT CCA CTT CAT AGA CTT TTT TAT TAT TGT TCT CGT CTG CCT TGG TCT

OspA-B31       390         400         410         420         430
[ 3288 ]       ... ... ... ... ... ... ... ... ... ... ... ... ... ... ... ...>

OspA-KA        390         400         410         420         430
[ 3288 ]       ... ... ... ... ... ... ... ... ... ... ... ... ... ... ... ...>

OspA-N40       390         400         410         420         430
[ 3276 ]       ... ... ... ... ... ... ... ... ... ... ... ... ... ... ... ...>

OspA-ZS7       390         400         410         420         430
[ 3264 ]       ... ... ... ... ... ... ... ... ... ... ... ... ... ... ... ...>

OspA-25015     390         400         410         420         430
[ 2802 ]       ... ..c ... t.. gt. ... ... ... ..g g.. ... ... a.. ... ... .t.>

OspA-TRO       390         400         410         420         430
[ 2648 ]       ... ... ... t.. ... ... ... .c. ... cc. ... ... a.. ... ... .g>

OspA-K48       390         400         410         420         430
[ 2584 ]       ..g ... ... ac. ... ... .c. ... gt. ... ... a.t ... ... ...>

OspA-PHe11     390         400         410         420         430
[ 2580 ]       ..g t.. ... a.. ... ... .c. ... gt. ... ... a.t ... ... ...>

OspA-DK29      390         400         410         420         430
[ 2566 ]       ..g ... ... ac. ... ... .c. ... gt. ... ... a.t ... ... ...>

OspA-Ip90      390         400         410         420         430
[ 2562 ]       ..g ... ... .c. ... ... .c. ... gt. ... ... a.t ... ... ...>

OspA-BO        390         400         410         420         430
[ 2558 ]       ... ... ... t.g ... .c. ... .cc ..g ... .a. a.t ... ... .a.>

OspA-IP3       390         400         410         420         430
[ 2558 ]       ... ... ... t.g ... .c. ... .cc ..g ... .a. a.t ... ... .a.>

OspA-PKO       390         400         410         420         430
[ 2558 ]       ... ... ... t.g ... .c. ... .cc ..g ... .a. a.t ... ... .a.>

OspA-ACAI      390         400         410         420         430
[ 2556 ]       ... ... ... t.g ... .c. ... .cc ..g ... .a. a.t ... ... .a.>

OspA-P-GAU     390         400         410         420         430
[ 2544 ]       ... ... ... t.g ... .c. ... .cc ..g ... .a. a.t ... ... .a.>

440         450         460         470         480
OspA-B31       CTT GAA TAC ACA GGA ATT AAA AGC GAT GGA TCT GGA AAA GCT AAA GAG
```

FIG. 17H

```
                    GAA CTT ATG TGT CCT TAA TTT TCG CTA CCT AGA CCT TTT CGA TTT CTC
OspA-B31            440         450         460         470         480
[ 3298 ]            ... ... ... ... ... ... ... ... ... ... ... ... ... ... ... ...>

OspA-KA             440         450         460         470         480
[ 3289 ]            ... ... ... ... ... ... ... ... ... ... ... ... ... ... ... ...>

OspA-N40            440         450         460         470         480
[ 3276 ]            ... ... ... ... .a. ... ... ... ... ... ... ... ... ... ... ...>

OspA-ZS7            440         450         460         470         480
[ 3264 ]            ... ... ... ... .a. ... ... ... ... ... ... ... ... ... ... ...>

OspA-25015          440         450         460         470         480
[ 2802 ]            ... ... ... ... ... ... ... ... ... ... ..c ... ... ... ... ..a>

OspA-TRO            440         450         460         470         480
[ 2648 ]            ... ... ... ... .a. ..a ... ... ... ... a.c ... ... ... ... ..a>

OspA-K48            440         450         460         470         480
[ 2584 ]            ... ... ... ... .ac ..a ... ... ... ... ..c ... ... ... ... ..a>

OspA-HB11           440         450         460         470         480
[ 2580 ]            ... ... ... ... .ac ..a ... ... ... aa. a.c ... ... ... ... ..a>

OspA-DK29           440         450         460         470         480
[ 2566 ]            ... ... ... ... .ac ..a ... ... ... ... ..c ... ... ... ... ..a>

OspA-Ip90           440         450         460         470         480
[ 2562 ]            ... ... ... ... .ac ..a ... ... ... aa. a.c ... ... ... ... ..a>

OspA-BO             440         450         460         470         480
[ 2558 ]            ... ... ..t ... .a. ..g ... ... ... ... a.c ... ... ... ... ..a>

OSPA-IP3            440         450         460         470         480
[ 2558 ]            ... ... ..t ... .a. ..g ... ... ... ... a.c ... ... ... ... ..a>

OspA-PKO            440         450         460         470         480
[ 2558 ]            ... ... ..t ... .a. ..g ... ... ... ... a.c ... ... ... ... ..a>

OspA-ACAI           440         450         460         470         480
[ 2556 ]            ... ... ..t ... .a. ..g ... ... ... ... a.c ... ... ... ... ..a>

OspA-P-GAU          440         450         460         470         480
[ 2544 ]            ... ... ..t ... .a. ..g ... ... ... ... a.c ... ... ... ... ..a>

490         500         510         520
OspA-B31            GTT TTA AAA GGC TAT CTT CTT GAA GGA ACT CTA ACT GCT GAA AAA ACA
                    CAA AAT TTT CCG ATA GAA GAA CTT CCT TGA GAT TGA CGA CTT TTT TGT

OspA-B31                 490         500         510         520
[ 3298 ]            ... ... ... ... ... ... ... ... ... ... ... ... ... ... ... ...>

OspA-KA                  490         500         510         520
[ 3289 ]            ... ... ... ... ... ... ... ... ... ... ... ... ... ... ... ...>
```

OspA-N40     530         540         550         560         570
[ 3276 ]        ... ... ... ... ... ... ... ... ... ... ... ... ... ... ...>

OspA-ZS7     530         540         550         560         570
[ 3264 ]        ... ... ... ... ... ... ... ... ... ... ... ... ... ... ...>

OspA-25015   530         540         550         560         570
[ 2802 ]        ... ... ... ... ... ... ... ... ... ... ..t ..g c.c ... ...>

OspA-TRO     530         540         550         560         570
[ 2648 ]        ... ... aaa ... .c. ... ..c ... ... gt. ... ... ... c.c ... c..>

OspA-K48                 540         550         560·        570
[ 2584 ]        ... ... aaa ... .c. ... ..c ... ... gt. ... ... ..g ..c ... .t.>

OspA-HB 11               540         550         560         570
[ 2580 ]        ... ... aaa ... .c. ..g ..c ... ... .... ... ... ..g ..c ... ...>

OspA-DK29                540         550         560         570
[ 2566 ]        ... ... aaa ... .c. ... ..c ... ... gt. ... ... ..g ..c ... .t.>

OspA-Ip90                540         550         560         570
[ 2562 ]        ... ..a aaa ... .c. ... ..c ... ... gt. ... ... ... c.c ... ...>

OspA-BO      530         540         550         560         570
[ 2558 ]        ... ... .aa ..a ... ... ... ..c ... ... ... ..t ..g g.a ... g..>

OSPA-IP3     530         540         550         560         570
[ 2558 ]        ... ... .aa ..a ... ... ... ..c ... ... ... ..t ..g g.a ... g..>

OspA-PKO     530         540         550         560         570
[ 2558 ]        ... ... .aa ..a ... ... ... ..c ... ... ... ..t ..g g.a ... g..>

OspA-ACAI    530         540         550         560         570
[ 2556 ]        ... ... .aa ..a ... ... ... ..c ... ... ... ..t ..g g.a ... g..>

OspA-P-GAU   530         540         550         560         570
[ 2544 ]        ... ... .aa ..a ... ... ... ..c ... ... ... ..t ..g g.a ... g..>

580         590         600         610         620
              *           *           *           *           *
OspA-B31     AAA TCT GGG GAA GTT TCA GTT GAA CTT AAT GAC ACT GAC AGT AGT GCT
             TTT AGA CCC CTT CAA AGT CAA CTT GAA TTA CTG TGA CTC TCA TCA CGA

OspA-B31     580         590         600         610         620
[ 3288 ]        ... ... ... ... ... ... ... ... ... ... ... ... ..- ... ...>

OspA-KA      580         590         600         610         620
[ 3288 ]        ... ... ... ... ... ... ... ... ... ... ... ... ..- ... ...>

OspA-N40     580         590         600         610         620
[ 3276 ]        ... ... ... ... ... ... ... ... ... ... ... ... ..- ... ...>

OspA-ZS7     580         590         600         610         620
[ 3264 ]        ... ... ... ... ... ... ... ... ... ... ... ... ..- ... ...>
```

FIG. 17K

```
OspA-25015     580            590         600           610          620
[ 2802 ]       ... ... ..a ... ..a a.. .c. ... ... ... ... ... ... .c. caa>

OspA-TRO       580            590         600           610          620
[ 2648 ]       ..c ... ..a ... a.a a.. ... ..g ... ... ... t.. a... tc. .c. cag>

OspA-K48    580            590            600           610          620
[ 2584 ]       ... ..c ..a ... a.a a.. ... .c. ... g.. ... t.. ... .c. .c. cag>

OspA-HB   11580            590           600           610          620
[ 2580 ]       ... ..c ..a ... a.a a.. ... .c. ... g.. ... ... ... tc. .-- ..g>

OspA-DK29   580            590           600           610          620
[ 2566 ]       ... ..c ..a ... a.a a.. .c. .c. ... g.. ...-t..... .c. .c. cgg>

OspA-Ip90   580            590           600           610          620
[ 2552 ]       ..c ... ..a ... a.a a.. ... ..g ... ... ... t.. ... .c. .c. cag>

OspA-BO        580            590         600           610          620
[ 2558 ]       ... ... ..a ... ..a a.. ... .ct ... ... ... ... a... .c. .c. cag>

OSPA-IP3       580            590         600           610          620
[ 2558 ]       ... ... ..a ... ..a a.. ... .ct ... ... ... ... a... .c. .c. cag>

OspA-PKO       580            590         600           610          620
[ 2558 ]       ... ... ..a ... ..a a.. ... .ct ... ... ... ... a... .c. .c. cag>

OspA-ACAI      580            590         600           610          620
[ 2556 ]       ... ... ..a ... ..a a.. ... .ct ... ... ... ... a... .c. .c. cag>

OspA-P-GAU     580            590         600           610          620
[ 2544 ]       ... ... ..a ... ..a a.. ... .ct ... ... ... ... a... .c. .c. cag>

630            640         650           660          670
OspA-B31       GCT ACT AAA AAA ACT GCA GCT TGG AAT TCA GGC ACT TCA ACT TTA ACA
               CGA TGA TTT TTT TGA CGT CGA ACC TTA AGT CCG TGA AGT TGA AAT TGT

OspA-B31       630            640         650           660          670
[ 3288 ]       ... ... ... ... ... ... ... ... ... ... ... ... ... ... ...>

OspA-KA        630            640         650           660          670
[ 3288 ]       ... ... ... ... ... ... ... ... ... ... ... ... ... ... ...>

OspA-N40       630            640         650           660          670
[ 3276 ]       ... ... ... ... ... ... ... ... ... ... ... ... ... ... ...>

OspA-ZS7       630            640         650           660          670
[ 3264 ]       ... ... ... ... ... ... ... ... ... ... ... ... ... ... ...>

OspA-25015     630            640         650           660          670
[ 2802 ]       ... ... ... ... ... .gg aaa ... g.. g.. ... ... ... ... ...>

OspA-TRO       630            640         650           660          670
[ 2648 ]       ... ... ... ... ... .g. aaa ... g.. ... aat ... ..c ... ...>
```

FIG. 17L

```
OspA-K48      630         640        650        660        670
[ 2584 ]      ... ... ... ... ... .g. aaa ... g.. ... aaa ... ..c ... ... ...>

OspA-HE 11       630         640        650        660        670
[ 2580 ]      ..- .a. ... ... t.c .g. a.a ... g.. ... ..t ... ..t ... ... ...>

OspA-DK29     630         640        650        660        670
[ 2566 ]      ... ... ... ... ... .g. aaa ... g.. ... aag ... ..c ... ... ...>

OspA-Ip90     630         640        650        660        670
[ 2562 ]      ... ... ... ... ... .g. a.a ... g.. ... aag ... ..c ... ... ...>

OspA-BO          630         640        650        660        670
[ 2558 ]      ... ... ... ... ... .gc ..a ... g.. ... aaa ... ..t ... ... ...>

OSPA-IP3         630         640        650        660        670
[ 2558 ]      ... ... ... ... ... .gc ..a ... g.. ... aaa ... ..t ... ... ...>

OspA-PKO         630         640        650        660        670
[ 2558 ]      ... ... ... ... ... .gc ..a ... g.. ... aaa ... ..t ... ... ...>

OspA-ACAI        630         640        650        660        670
[ 2556 ]      ... ... ... ... ... .gc ..a ... g.. ... aaa ... ..t ... ... ...>

OspA-P-GAU       630         640        650        660        670
[ 2544 ]      ... ... ... ... ... .gc ..a ... g.. ... aaa ... ..t ... ... ...>

680          690          700          710          720
                *    *     *     *     *     *     *     *     *     *
OspA-B31      ATT ACT GTA AAC AGT AAA AAA ACT AAA GAC CTT GTG TTT ACA AAA GAA
              TAA TGA CAT TTG TCA TTT TTT TGA TTT CTG GAA CAC AAA TGT TTT CTT

OspA-B31           680          690          700          710          720
[ 3288 ]      ... ... ... ... ... ... ... ... ... ... ... ... ... ... ... ...>

OspA-KA            680          690          700          710          720
[ 3288 ]      ... ... ... ... ... ... ... ... ... ... ... ... ... ... ... ...>

OspA-N40           680          690          700          710          720
[ 3276 ]      ... ... ... ... ... ... ... ... ... ... ... ... ... ... ... ...>

OspA-ZS7           680          690          700          710          720
[ 3264 ]      ... ... ... ... ... ... ... ... ... ... ... ... ... ... ... ...>

OspA-25015         680          690          700          710          720
[ 2802 ]      ... ... ... ... .ac ... ... ... ... .c. ... ..a ... ... ... c..>

OspA-TRO           680          690          700          710          720
[ 2648 ]      ... .g. ..g ..t ..c ... ... ... ... a.. a.. ..a ... ... ... ...>

OspA-K48      680          690          700          710          720
[ 2584 ]      ... .g. ..g ..t ..c c.. ... ..c ... a.. ... ..a ..c ... ... ...>

OspA-HE 11         680          690          700          710          720
[ 2580 ]      ... .g. aa. ... ..a c.. ... ... ... c.a ... ..a ..c ... ... ...>

OspA-DK29     680          690          700          710          720
```

FIG. 17M

```
[ 2566 ]        ...  .g.   ...g  ..t  ..c c..  ...  ...  .c  ...  a..  ...  ...a  ..c  ...  ...  ...>
OspA-Ip90         680         690         700         710         720
[ 2562 ]        ...  .g.   ...g  ..t  ..c cg.  ...  ...  .c  ...  a..  ...  ...a  ..c  ...  ...  ...>
OspA-BO           680         690         700         710         720
[ 2558 ]        ...  .g.   ...t  ...  ..c  ...  ...  ...  .c.  c.a  ...  ...  ...  ..t  ...  c..>
OSPA-IP3          680         690         700         710         720
[ 2558 ]        ...  .g.   ...t  ...  ...  ...  ...  ...  .c.  c.a  ...  ...  ...  ..t  ...  c..>
OspA-PKO          680         690         700         710         720
[ 2558 ]        ...  .g.   ...t  ...  ..c  ...  ...  ...  .c.  c.a  ...  ...  ...  ..t  ...  c..>
OspA-ACAI         680         690         700         710         720
[ 2556 ]        ...  .g.   ...t  ...  ..c  ...  ...  ...  .c.  c.a  ...  ...  ...  ..t  ...  c..>
ospA-P-GAU        680         690         700         710         720
[ 2544 ]        ...  .g.   ...t  ...  ..c  ...  ...  ...  .c.  c.a  ...  ...  ...  ..t  ...  c..>

730         740         750         760
                      *         *         *         *         *
OspA-B31        AAC ACA ATT ACA GTA CAA CAA TAC GAC TCA AAT GGC ACC AAA TTA GAG
                TTG TGT TAA TGT CAT GTT GTT ATG CTG AGT TTA CCG TGG TTT AAT CTC

OspA-B31                   730         740         750         760
[ 3288 ]         ...  ...  ...  ...  ...  ...  ...  ...  ...  ...  ...  ...  ...  ...  ...  ...>
OspA-KA                    730         740         750         760
[ 3288 ]         ...  ...  ...  ...  ...  ...  ...  ...  ...  ...  ...  ...  ...  ...  ...  ...>
OspA-N40                   730         740         750         760
[ 3276 ]         ...  ...  ...  ...  ...  ...  ...  ...  ...  ...  ...  ...  ...  ...  ...  ...>
OspA-ZS7                   730         740         750         760
[ 3264 ]         ...  ...  ...  ...  ...  ...  ...  ...  ...  ...  ...  ...  ...  ...  ...  ...>
OspA-25015                 730         740         750         760
[ 2802 ]         g..  ...  ...  ...  tc.  ...  a..  ...  ...  ...  gca  ..a  ...  ..c  ..g  ..a>
OspA-TRO                   730         740         750         760
[ 2648 ]         g..  ...  ..a  ...  ...  ...  a..  ...  ...  ...  gca  ...  ...  ..t  c..  ..a>
OspA-K48              730         740         750         760         770
[ 2584 ]         g..  ...  ..a  ...  ...  ...  a..  ...  ...  ...  gca  ...  ...  ..t  c..  ..a>
OspA-HE 11            730         740         750         760
[ 2580 ]         g..  ...  ..a  ...  ...  ...  a.c  ...  ...  ...  gca  ...  ...  ..t  c..  ..a>
OspA-DK29             730         740         750         760         770
[ 2566 ]         g..  ...  ..a  ...  ...  ...  ag.  ...  ...  ...  gca  ...  ...  ..t  c..  ..a>
OspA-Ip90             730         740         750         760         770
[ 2562 ]         g..  ...  ..a  ...  ...  ...  a..  ...  ...  ...  gca  ...  ...  ..t  c..  ..a>
OspA-BO                    730         740         750         760
[ 2558 ]         g..  ...  ..a  ..t  ...  ...  a..  ...  ...  ..c  gca  ..t  ...  ..t  ...  ..a>
```

FIG. 17N

```
OSPA-IP3           730          740          750          760
[ 2558 ]      g.. ... ..a ..t ... ... a.. ... ... ..c gca ..t ... ..t ... ..a>

OspA-PKO           730          740          750          760
[ 2558 ]      g.. ... ..a ..t ... ... a.. ... ... ..c gca ..t ......t ... ..a>

OspA-ACAI          730          740          750          760
[ 2556 ]      g.. ... ..a ..t ... ... a.. ... ... ..c gca ..t ... ..t ... ..a> ospA-P-GAU         730          740          750          760
[ 2544 ]      t.. ... ..a ..t ... a.. ... ... ... ..c gca ..t ... ..t. ... ..a>

770         780         790         800         810
               *     *     *     *     *     *     *     *     *     *
OspA-B31      GGG TCA GCA GTT GAA ATT ACA AAA CTT GAT GAA ATT AAA AAC GCT TTA
              CCC AGT CGT CAA CTT TAA TGT TTT GAA CTA CTT TAA TTT TTG CGA AAT

OspA-B31      770         780         790         800         810
[ 3288 ]      ... ... ... ... ... ... ... ... ... ... ... ... ... ... ... ...>

OspA-HA       770         780         790         800         810
[ 3288 ]      ... ... ... ... ... ... ... ... ... ... ... ... ... ... ... ...>

OspA-N40      770         780         790         800         810
[ 3276 ]      ... ... ... ... ... ... ... ... ... ... ... ... ... ... ... ...>

OspA-ZS7      770         780         790         800         810
[ 3264 ]      ... ... ... ... ... ... ... ... ... ... ... ... ... ... ... ...>

OspA-25015    770         780         790         800         810
[ 2802 ]      ..c a.. ... ..c ... ... .a. .c. ... ... ... c.. ... ... ... ...>

OspA-TRO      770         780         790         800         810
[ 2648 ]      ..c aac ... ..c ... ... .a. .c. ... ... ... c.. ... .. ... ...>

OspA-K48                  780         790         800         810
[ 2584 ]      ..c aa. ... ..c ... ... ... .c. ... a.a ... c.. ... ... ... ...>

OspA-HE 11    770         780         790         800         810
[ 2580 ]      ..c aa. ... ..c ... ... .c. ... a.a ... c.. ... ... ... ...>

OspA-DK29                 780         790         800         810
[ 2566 ]      ..c aa. ... ..c ... ... .c. ... a.a ... c.. ... ... -.. ...>

OspA-Ip90                 780         790         800         810
[ 2562 ]      ..c aa. ... ..c ... ... .cg ... a.a ... c.. ... g.t ... ...>

OspA-BO       770         780         790         800         810
[ 2558 ]      ..c a.. ... ..c ... ... .a. .c. ... ... ... c.. ... ... ... ...>

OSPA-IP3      770         780         790         800         810
[ 2558 ]      ..c a.. ... ..c ... ... .a. .c. ... ... ... c.. ... ... ... ...>

OspA-PKO      770         780         790         800         810
[ 2558 ]      ..c a.. ... ..c ... ... .a. .c. ... ... ... c.. ... ... ... ...>
```

FIG. 170

```
OspA-ACAI  770         780         790         800         810
[ 2556 ]    ..c a..  ... ..c ... ...  .a.  .c.  ... ... ...  c..  ... ... ... ...g>

OspA-P-GAU 770         780         790         800         810
[ 2544 ]    ..c a..  ... ..c ... ...  .a.  .c.  ... ... ...  c..  ... ... ... ...>

820
                 *
OspA-B31    AAA TAA
            TTT ATT

OspA-B31       820
[ 3288 ]    ... ...>

OspA-KA        820
[ 3288 ]    ... ...>

OspA-N40       820
[ 3276 ]    ... ...>

OspA-ZS7       820
[ 3264 ]    ... ...>

OspA-25015
[ 2802 ]    .g.>

OspA-TRO       820
[ 2648 ]    ... ..>

OspA-K48   820
[ 2584 ]    ... ...>

OspA-HB 11     820
[ 2580 ]    ... ..>

OspA-DK29  820
[ 2566 ]    ... ...>

OspA-Ip90  820
[ 2562 ]    ... ..>

OspA-BO        820
[ 2558 ]    ... ..>

OSPA-IP3       820
[ 2558 ]    ... ..>

OspA-PKO       820
[ 2558 ]    ... ..>

OspA-ACAI      820
[ 2556 ]    ... ...>

OspA-P-GAU     820
[ 2544 ]    ... ...>
```

FIG. 17P

```
              10             20             30             40
    *     *        *      *        *     *        *     *        *
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT 50             60             70             80             90
    *        *      *        *     *        *     *        *      *
CCA TGT AAG CAA AAT GTT AGC AGC CTT GAT GAA AAA AAT AGC GTT
CGT ACA TTC GTT TTA CAA TCG TCG GAA CTA CTT TTT TTA TCG CAA 100            110            120            130
    *     *        *      *        *     *        *     *        *
TCA GTA GAT TTA CCT GGT GGA ATG ACA GTT CTT GTA AGT AAA GAA
AGT CAT CTA AAT GGA CCA CCT TAC TGT CAA GAA CAT TCA TTT CTT 140            150            160            170            180
    *        *      *        *     *        *     *        *      *
AAA GAC AAA GAC GGT AAA TAC AGT CTA GAG GCA ACA GTA GAC AAG
TTT CTG TTT CTG CCA TTT ATG TCA GAT CTC CGT TGT CAT CTG TTC 190            200            210            220
    *     *        *      *        *     *        *     *        *
CTT GAG CTT AAA GGA ACT TCT GAT AAA AAC AAC GGT TCT GGA ACA
GAA CTC GAA TTT CCT TGA AGA CTA TTT TTG TTG CCA AGA CCT TGT 230            240            250            260            270
    *        *      *        *     *        *     *        *      *
CTT GAA GGT GAA AAA ACT GAC AAA AGT AAA GTA AAA TTA ACA ATT
GAA CTT CCA CTT TTT TGA CTG TTT TCA TTT CAT TTT AAT TGT TAA 280            290            300            310
    *     *        *      *        *     *        *     *        *
GCT GAT GAC CTA AGT CAA ACT AAA TTT GAA ATT TTC AAA GAA GAT
CGA CTA CTG GAT TCA GTT TGA TTT AAA CTT TAA AAG TTT CTT CTA 320            330            340            350            360
    *        *      *        *     *        *     *        *      *
GCC AAA ACA TTA GTA TCA AAA AAA GTA ACC CTT AAA GAC AAG TCA
CGG TTT TGT AAT CAT AGT TTT TTT CAT TGG GAA TTT CTG TTC AGT 370            380            390            400
    *     *        *      *        *     *        *     *        *
TCA ACA GAA GAA AAA TTC AAC GAA AAG GGT GAA ACA TCT GAA AAA
AGT TGT CTT CTT TTT AAG TTG CTT TTC CCA CTT TGT AGA CTT TTT 410            420            430            440            450
    *        *      *        *     *        *     *        *      *
ACA ATA GTA AGA GCA AAT GGA ACC AGA CTT GAA TAC ACA GAC ATA
TGT TAT CAT TCT CGT TTA CCT TGG TCT GAA CTT ATG TGT CTG TAT 460            470            480            490
    *     *        *      *        *     *        *     *        *
AAA AGC GAT GGA TCC GGA AAA GCT AAA GAA GTT TTA AAA GAC TTT
TTT TCG CTA CCT AGG CCT TTT CGA TTT CTT CAA AAT TTT CTG AAA 500            510            520            530            540
    *        *      *        *     *        *     *        *      *
ACT CTT GAA GGA ACT CTA GCT GCT GAC GGC AAA ACA ACA TTC AAA
TGA GAA CTT CCT TGA GAT CGA CGA CTG CCG TTT TGT TGT AAC TTT 550            560            570            580
    *     *        *      *        *     *        *     *        *
GTT ACA GAA GGC ACT GTT GTT TTA ACC AAC AAC ATT TTA AAA TCC
```

Fig. 18A

```
              CAA TGT CTT CCG TGA CAA CAA AAT TCG TTC TTG TAA AAT TTT AGG 590         600         610         620         630
              *       *   *       *       *   *       *       *   *
              GGA GAA ATA ACA GTT GCA CTT GAT GAC TCT GAC ACT ACT CAG GCT
              CCT CTT TAT TGT CAA CGT GAA CTA CTG AGA CTG TGA TGA GTC CGA 640         650         660         670
                *       *       *       *       *       *       *
              ACT AAA AAA ACT GGA AAA TGG GAT TCA AAT ACT TCC ACT TTA ACA
              TGA TTT TTT TGA CCT TTT ACC CTA AGT TTA TGA AGG TGA AAT TGT 680         690         700         710         720
                    *       *       *       *       *       *       *
              ATT AGT GTG AAT AGC AAA AAA ACT AAA AAC ATT GTA TTT ACA AAA
              TAA TCA CAC TTA TCG TTT TTT TGA TTT TTG TAA CAT AAA TGT TTT 730         740         750         760
                *       *       *       *       *       *       *
              GAA GAC ACA ATA ACA GTA CAA AAA TAC GAC TCA GCA GGC ACC AAT
              CTT CTG TGT TAT TGT CAT GTT TTT ATG CTG AGT CGT CCG TGG TTA 770         780         790         800         810
                    *       *       *       *       *       *       *
              CTA GAA GGC AAC GCA GTC GAA ATT AAA ACA CTT GAT GAA CTT AAA
              GAT CTT CCG TTG CGT CAG CTT TAA TTT TGT GAA CTA CTT GAA TTT

820
                      *       *       *
              AAC GCT TTA AAA TAG
              TTG CGA AAT TTT ATC
```

FIG. 18B

```
            10          20          30          40
         *           *           *           *
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT 50          60          70          80          90
         *           *           *           *           *
GCA TGC AAG CAA AAT GTT AGC AGC CTT GAT GAA AAA AAC AGC GCT
CGT ACG TTC GTT TTA CAA TCG TCG GAA CTA CTT TTT TTG TCG CGA 100         110         120         130
         *           *           *           *
TCA GTA GAT TTG CCT GGT GAG ATG AAA GTT CTT GTA AGT AAA GAA
AGT CAT CTA AAC GGA CCA CTC TAC TTT CAA GAA CAT TCA TTT CTT 140         150         160         170         180
         *           *           *           *           *
AAA GAC AAA GAC GGT AAG TAC AGT CTA AAG GCA ACA GTA GAC AAG
TTT CTG TTT CTG CCA TTC ATG TCA GAT TTC CGT TGT CAT CTG TTC 190         200         210         220
         *           *           *           *
ATT GAG CTA AAA GGA ACT TCT GAT AAA GAC AAT GGT TCT GGA GTG
TAA CTC GAT TTT CCT TGA AGA CTA TTT CTG TTA CCA AGA CCT CAC 230         240         250         260         270
         *           *           *           *           *
CTT GAA GGT ACA AAA GAT GAC AAA AGT AAA GCA AAA TTA ACA ATT
GAA CTT CCA TGT TTT CTA CTG TTT TCA TTT CGT TTT AAT TGT TAA 280         290         300         310
         *           *           *           *
GCT GAC GAT CTA AGT AAA ACC ACA TTC GAA CTT TTA AAA GAA GAT
CGA CTG CTA GAT TCA TTT TGG TGT AAG CTT GAA AAT TTT CTT CTA 320         330         340         350         360
         *           *           *           *           *
GGC AAA ACA TTA GTG TCA AGA AAA GTA AGT TCT ACA GAC AAA ACA
CCG TTT TGT AAT CAC AGT TCT TTT CAT TCA AGA TCT CTG TTT TGT 370         380         390         400
         *           *           *           *
TCA ACA GAT GAA ATG TTC AAT GAA AAA GGT GAA TTG TCT GCA AAA
AGT TGT CTA CTT TAC AAG TTA CTT TTT CCA CTT AAC AGA CGT TTT 410         420         430         440         450
         *           *           *           *           *
ACC ATG ACA AGA GAA AAT GGA ACC AAA CTT GAA TAT ACA GAA ATG
TGG TAC TGT TCT CTT TTA CCT TGG TTT GAA CTT ATA TGT CTT TAC 460         470         480         490
         *           *           *           *
AAA AGC GAT GGA ACC GGA AAA GCT AAA GAA GTT TTA AAA AAG TTT
TTT TCG CTA CCT TGG CCT TTT CGA TTT CTT CAA AAT TTT TTC AAA 500         510         520         530         540
         *           *           *           *           *
ACT CTT GAA GGA AAA GTA GCT AAT GAT AAA GTA ACA TTG GAA GTA
TGA GAA CTT CCT TTT CAT CGA TTA CTA TTT CAT TGT AAC CTT CAT 550         560         570         580
         *           *           *           *
AAA GAA GGA ACC GTT ACT TTA AGT AAG GAA ATT GCA AAA TCT GGA
```

FIG. 19A

```
                    TTT CTT CCT TGG CAA TGA AAT TCA TTC CTT TAA CGT TTT AGA CCT 590         600         610         620         630
GAA GTA ACA GTT GCT CTT AAT GAC ACT AAC ACT ACT CAG GCT ACT
CTT CAT TGT CAA CGA GAA TTA CTG TGA TTG TGA TGA GTC CGA TGA 640         650         660         670
AAA AAA ACT GGC GCA TGG GAT TCA AAA ACT TCT ACT TTA ACA ATT
TTT TTT TGA CCG CGT ACC CTA AGT TTT TGA AGA TGA AAT TGT TAA 680         690         700         710         720
AGT GTT AAC AGC AAA AAA ACT ACA CAA CTT GTG TTT ACT AAA CAA
TCA CAA TTG TCG TTT TTT TGA TGT GTT GAA CAC AAA TGA TTT GTT 730         740         750         760
GAC ACA ATA ACT GTA CAA AAA TAC GAC TCC GCA GGT ACC AAT TTA
CTG TGT TAT TGA CAT GTT TTT ATG CTG AGG CGT CCA TGG TTA AAT 770         780         790         800         810
GAA GGC ACA GCA GTC GAA ATT AAA ACA CTT GAT GAA CTT AAA AAC
CTT CCG TGT CGT CAG CTT TAA TTT TGT GAA CTA CTT GAA TTT TTG

820
GCT TTA AAA TAG
CGA AAT TTT ATC
```

FIG. 19B

```
         10          20          30          40
          *           *           *           *
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT 50          60          70          80          90
          *           *           *           *           *
GCA TGT AAG CAA AAT GTT AGC AGC CTT GAC GAG AAA AAC AGC CTT
CGT ACA TTC GTT TTA CAA TCG TCG GAA CTG CTC TTT TTG TCG GAA 100         110         120         130
                *           *           *           *
TCA GTA GAT TTG CCT GGT GAA ATG AAA GTT CTT GTA AGC AAA GAA
AGT CAT CTA AAC GGA CCA CTT TAC TTT CAA GAA CAT TCG TTT CTT 140         150         160         170         180
          *           *           *           *           *
AAA AAC AAA GAC GGC AAG TAC GAT CTA ATT GCA ACA GTA GAC AAG
TTT TTG TTT CTG CCG TTC ATG CTA GAT TAA CGT TGT CAT CTG TTC 190         200         210         220
                *           *           *           *
CTT GAG CTT AAA GGA ACT TCT GAT AAA AAC AAT GGA TCT GGA GTA
GAA CTC GAA TTT CCT TGA AGA CTA TTT TTG TTA CCT AGA CCT CAT 230         240         250         260         270
          *           *           *           *           *
CTT GAA GGC GTA AAA GCT GAC AAA AGT AAA GTA AAA TTA ACA ATT
GAA CTT CCG CAT TTT CGA CTG TTT TCA TTT CAT TTT AAT TGT TAA 280         290         300         310
                *           *           *           *
TCT GAC GAT CTA GGT CAA ACC ACA CTT GAA GTT TTC AAA GAA GAT
AGA CTG CTA GAT CCA GTT TGG TGT GAA CTT CAA AAG TTT CTT CTA 320         330         340         350         360
          *           *           *           *           *
GGC AAA ACA CTA GTA TCA AAA AAA GTA ACT TCC AAA GAC AAG TCA
CCG TTT TGT GAT CAT AGT TTT TTT CAT TGA AGG TTT CTG TTC AGT 370         380         390         400
                *           *           *           *
TCA ACA GAA GAA AAA TTC AAT GAA AAA GGT GAA GTA TCT GAA AAA
AGT TGT CTT CTT TTT AAG TTA CTT TTT CCA CTT CAT AGA CTT TTT 410         420         430         440         450
          *           *           *           *           *
ATA ATA ACA AGA GCA AAT GGA ACC AAA CTT GAA TAT ACA GAA ATG
TAT TAT TGT TCT CGT TTA CCT TGG TTT GAA CTT ATA TGT CTT TAC 460         470         480         490
                *           *           *           *
AAA AGC GAT GGA ACC GGA AAA GCT AAA GAA GTT TTA AAA AAG TTT
TTT TCG CTA CCT TGG CCT TTT CGA TTT CTT CAA AAT TTT TTC AAA 500         510         520         530         540
          *           *           *           *           *
ACT CTT GAA GGA AAA GTA GCT AAT GAT AAA GTA ACA TTG GAA GTA
TGA GAA CTT CCT TTT CAT CGA TTA CTA TTT CAT TGT AAC CTT CAT 550         560         570         580
                *           *           *           *
AAA GAA GGA ACC GTT ACT TTA AGT AAG GAA ATT TCA AAA TCT GGG
```

FIG. 20A

```
TTT CTT CCT TGG CAA TGA AAT TCA TTC CTT TAA AGT TTT AGA CCC 590           600           610           620           630
        *      *      *      *      *      *      *      *      *
GAA GTT TCA GTT CAA CTT AAT GAC ACT GAC AGT AGT GCT GCT ACT
CTT CAA AGT CAA GTT CAA TTA CTG TGA CTG TCA TCA CGA CGA TGA 640           650           660           670
        *      *      *      *      *      *      *      *      *
AAA AAA ACT GCA GCT TGG AAT TCA AAA ACT TCC ACT TTA ACA ATT
TTT TTT TGA CGT CGA ACC TTA AGT TTT TGA AGG TGA AAT TGT TAA 680           690           700           710           720
        *      *      *      *      *      *      *      *      *
AGT GTG AAT AGC CAA AAA ACC AAA AAC CTT GTA TTC ACA AAA GAA
TCA CAC TTA TCG GTT TTT TGG TTT TTG GAA CAT AAG TGT TTT CTT 730           740           750           760
        *      *      *      *      *      *      *      *      *
GAC ACA ATA ACA GTA CAA AAA TAC GAC TCA GCA GGC ACC AAT CTA
CTG TGT TAT TGT CAT GTT TTT ATG CTG AGT CGT CCG TGG TTA GAT 770           780           790           800           810
        *      *      *      *      *      *      *      *      *
GAA GGC AAA GCA GTC GAA ATT ACA ACA CTT AAA GAA CTT AAA AAC
CTT CCG TTT CGT CAG CTT TAA TGT TGT GAA TTT CTT GAA TTT TTG

820
        *      *
GCT TTA AAA TAA
CGA AAT TTT ATT
```

FIG. 20B

```
           10          20          30          40
    *       *     *     *     .     *     *     *     *
ATG AAA AAA TAT TTA TTG GCA ATA GGT CTA ATA TTA GCC TTA ATA
TAC TTT TTT ATA AAT AAC CGT TAT CCA GAT TAT AAT CGG AAT TAT 50          60          70          80          90
    *     *     *     *     *     *     *     *     *     *
GCA TGC AAG CAA AAT GTT AGC AGC CTT GAT GAA AAA AAC AGC GCT
CGT ACG TTC GTT TTA CAA TCG TCG GAA CTA CTT TTT TTG TCG CGA 100         110         120         130
        *     *     *     *     *     *     *     *     *
TCA GTA GAT TTG CCT GGT GAG ATG AAA GTT CTT GTA AGT AAA GAA
AGT CAT CTA AAC GGA CCA CTC TAC TTT CAA GAA CAT TCA TTT CTT 140         150         160         170         180
    *     *     *     *     *     *     *     *     *     *
AAA GAC AAA GAC GGT AAG TAC AGT CTA AAG GCA ACA GTA GAC AAG
TTT CTG TTT CTG CCA TTC ATG TCA GAT TTC CGT TGT CAT CTG TTC 190         200         210         220
        *     *     *     *     *     *     *     *     *
ATT GAG CTA AAA GGA ACT TCT GAT AAA GAC AAT GGT TCT GGA GTG
TAA CTC GAT TTT CCT TGA AGA CTA TTT CTG TTA CCA AGA CCT CAC 230         240         250         260         270
    *     *     *     *     *     *     *     *     *     *
CTT GAA GGT ACA AAA GAT GAC AAA AGT AAA GCA AAA TTA ACA ATT
GAA CTT CCA TGT TTT CTA CTG TTT TCA TTT CGT TTT AAT TGT TAA 280         290         300         310
        *     *     *     *     *     *     *     *     *
GCT GAC GAT CTA AGT AAA ACC ACA TTC GAA CTT TTA AAA GAA GAT
CGA CTG CTA GAT TCA TTT TGG TGT AAG CTT GAA AAT TTT CTT CTA 320         330         340         350         360
    *     *     *     *     *     *     *     *     *     *
GGC AAA ACA TTA GTG TCA AGA AAA GTA AGT TCT ACA GAC AAA ACA
CCG TTT TGT AAT CAC AGT TCT TTT CAT TCA AGA TCT CTG TTT TGT 370         380         390         400
        *     *     *     *     *     *     *     *     *
TCA ACA GAT GAA ATG TTC AAT GAA AAA GGT GAA TTG TCT GCA AAA
AGT TGT CTA CTT TAC AAG TTA CTT TTT CCA CTT AAC AGA CGT TTT 410         420         430         440         450
    *     *     *     *     *     *     *     *     *     *
ACC ATG ACA AGA GAA AAT GGA ACC AAA CTT GAA TAT ACA GAA ATG
TGG TAC TGT TCT CTT TTA CCT TGG TTT GAA CTT ATA TGT CTT TAC 460         470         480         490
        *     *     *     *     *     *     *     *     *
AAA AGC GAT GGA ACC GGA AAA GCT AAA GAA GTT TTA AAA AAG TTT
TTT TCG CTA CCT TGG CCT TTT CGA TTT CTT CAA AAT TTT TTC AAA 500         510         520         530         540
    *     *     *     *     *     *     *     *     *     *
ACT CTT GAA GGA AAA GTA GCT AAT GAT AAA GTA ACA TTG GAA GTA
TGA GAA CTT CCT TTT CAT CGA TTA CTA TTT CAT TGT AAC CTT CAT 550         560         570         580
        *     *     *     *     *     *     *     *     *
AAA GAA GGA ACC GTT ACT TTA AGT AAG GAA ATT TCA AAA TCT GGG
```

FIG. 21A

```
                TTT CTT CCT TGG CAA TGA AAT TCA TTC CTT TAA AGT TTT AGA CCC 590            600            610            620            630
          *     *        *     *        *     *        *     *        *     *
        GAA GTT TCA GTT GAA CTT AAT GAC ACT GAC AGT AGT GCT GCT ACT
        CTT CAA AGT CAA CTT GAA TTA CTG TGA CTG TCA TCA CGA CGA TGA 640            650            660            670
          *     *        *     *        *     *        *     *        *
        AAA AAA ACT GCA GCT TGG AAT TCA AAA ACT TCC ACT TTA ACA ATT
        TTT TTT TGA CGT CGA ACC TTA AGT TTT TGA AGG TGA AAT TGT TAA 680            690            700            710            720
          *     *        *     *        *     *        *     *        *     *
        AGT GTG AAT AGC CAA AAA ACC AAA AAC CTT GTA TTC ACA AAA GAA
        TCA CAC TTA TCG GTT TTT TGG TTT TTG GAA CAT AAG TGT TTT CTT 730            740            750            760
          *     *        *     *        *     *        *     *        *
        GAC ACA ATA ACA GTA CAA AAA TAC GAC TCA GCA GGC ACC AAT CTA
        CTG TGT TAT TGT CAT GTT TTT ATG CTG AGT CGT CCG TGG TTA GAT 770            780            790            800            810
          *     *        *     *        *     *        *     *        *     *
        GAA GGC AAA GCA GTC GAA ATT ACA ACA CTT AAA GAA CTT AAA AAC
        CTT CCG TTT CGT CAG CTT TAA TGT TGT GAA TTT CTT GAA TTT TTG

820
          *     *
        GCT TTA AAA TAA
        CGA AAT TTT ATT
```

FIG. 21B

```
               10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50                  60                  70                  80                  90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150                 160                 170                 180                 190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200                 210                 220                 230                 240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

250                 260                 270                 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290                 300                 310                 320                 330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

340                 350                 360                 370                 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390                 400                 410                 420                 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440                 450                 460                 470                 480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

490                 500                 510                 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 30A

```
     530           540           550           560           570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
 N   S   V   K   E   L   T   S   P   V   V   A   E   S   P   K>

580           590           600           610           620
AAA CCT TCC ATG GCC AAG CAA AAT GTT AGC AGC CTT GAC GAG AAA AAC
TTT GGA AGG TAC CGG TTC GTT TTA CAA TCG TCG GAA CTG CTC TTT TTG
 K   P   S   M   A   K   Q   N   V   S   S   L   D   E   K   N>

630           640           650           660           670
AGC GTT TCA GTA GAT TTG CCT GGT GAA ATG AAA GTT CTT GTA AGC AAA
TCG CAA AGT CAT CTA AAC GGA CCA CTT TAC TTT CAA GAA CAT TCG TTT
 S   V   S   V   D   L   P   G   E   M   K   V   L   V   S   K>

680           690           700           710           720
GAA AAA AAC AAA GAC GGC AAG TAC GAT CTA ATT GCA ACA GTA GAC AAG
CTT TTT TTG TTT CTG CCG TTC ATG CTA GAT TAA CGT TGT CAT CTG TTC
 E   K   N   K   D   G   K   Y   D   L   I   A   T   V   D   K>

730           740           750           760
CTT GAG CTT AAA GGA ACT TCT GAT AAA AAC AAT GGA TCT GGA GTA CTT
GAA CTC GAA TTT CCT TGA AGA CTA TTT TTG TTA CCT AGA CCT CAT GAA
 L   E   L   K   G   T   S   D   K   N   N   G   S   G   V   L>

770           780           790           800           810
GAA GGC GTA AAA GCT GAC AAA AGT AAA GTA AAA TTA ACA ATT TCT GAC
CTT CCG CAT TTT CGA CTG TTT TCA TTT CAT TTT AAT TGT TAA AGA CTG
 E   G   V   K   A   D   K   S   K   V   K   L   T   I   S   D>

820           830           840           850           860
GAT CTA GGT CAA ACC ACA CTT GAA GTT TTC AAA GAA GAT GGC AAA ACA
CTA GAT CCA GTT TGG TGT GAA CTT CAA AAG TTT CTT CTA CCG TTT TGT
 D   L   G   Q   T   T   L   E   V   F   K   E   D   G   K   T>

870           880           890           900           910
CTA GTA TCA AAA AAA GTA ACT TCC AAA GAC AAG TCA TCA ACA GAA GAA
GAT CAT AGT TTT TTT CAT TGA AGG TTT CTG TTC AGT AGT TGT CTT CTT
 L   V   S   K   K   V   T   S   K   D   K   S   S   T   E   E>

920           930           940           950           960
AAA TTC AAT GAA AAA GGT GAA GTA TCT GAA AAA ATA ATA ACA AGA GCA
TTT AAG TTA CTT TTT CCA CTT CAT AGA CTT TTT TAT TAT TGT TCT CGT
 K   F   N   E   K   G   E   V   S   E   K   I   I   T   R   A>

970           980           990           1000
GAC GGA ACC AGA CTT GAA TAC ACA GGA ATT AAA AGC GAT GGA TCT GGA
CTG CCT TGG TCT GAA CTT ATG TGT CCT TAA TTT TCG CTA CCT AGA CCT
 D   G   T   R   L   E   Y   T   G   I   K   S   D   G   S   G>

1010          1020          1030          1040          1050
AAA GCT AAA GAG GTT TTA AAA GGC TAT GTT CTT GAA GGA ACT CTA ACT
TTT CGA TTT CTC CAA AAT TTT CCG ATA CAA GAA CTT CCT TGA GAT TGA
 K   A   K   E   V   L   K   G   Y   V   L   E   G   T   L   T>

1060          1070          1080          1090          1100
GCT GAA AAA ACA ACA TTG GTG GTT AAA GAA GGA ACT GTT ACT TTA AGC
```

FIG. 30B

```
CGA CTT TTT TGT TGT AAC CAC CAA TTT CTT CCT TGA CAA TGA AAT TCG
 A   E   K   T   T   L   V   V   K   E   G   T   V   T   L   S>

1110            1120            1130            1140            1150
AAA AAT ATT TCA AAA TCT GGG GAA GTT TCA GTT GAA CTT AAT GAC ACT
TTT TTA TAA AGT TTT AGA CCC CTT CAA AGT CAA CTT GAA TTA CTG TGA
 K   N   I   S   K   S   G   E   V   S   V   E   L   N   D   T>

1160            1170            1180            1190            1200
GAC AGT AGT GCT GCT ACT AAA AAA ACT GCA GCT TGG AAT TCA GGC ACT
CTG TCA TCA CGA CGA TGA TTT TTT TGA CGT CGA ACC TTA AGT CCG TGA
 D   S   S   A   A   T   K   K   T   A   A   W   N   S   G   T>

1210            1220            1230            1240
TCA ACT TTA ACA ATT ACT GTA AAC AGT AAA AAA ACT AAA GAC CTT GTG
AGT TGA AAT TGT TAA TGA CAT TTG TCA TTT TTT TGA TTT CTG GAA CAC
 S   T   L   T   I   T   V   N   S   K   K   T   K   D   L   V>

1250            1260            1270            1280            1290
TTT ACA AAA GAA AAC ACA ATT ACA GTA CAA CAA TAC GAC TCA AAT GGC
AAA TGT TTT CTT TTG TGT TAA TGT CAT GTT GTT ATG CTG AGT TTA CCG
 F   T   K   E   N   T   I   T   V   Q   Q   Y   D   S   N   G>

1300            1310            1320            1330            1340
ACC AAA TTA GAG GGG TCA GCA GTT GAA ATT ACA AAA CTT GAT GAA ATT
TGG TTT AAT CTC CCC AGT CGT CAA CTT TAA TGT TTT GAA CTA CTT TAA
 T   K   L   E   G   S   A   V   E   I   T   K   L   D   E   I>

1350            1360
AAA AAC GCT TTA AAA TAA
TTT TTG CGA AAT TTT ATT
 K   N   A   L   K   *>
```

FIG. 30C

```
                10             20             30             40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50             60             70             80             90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

100            110            120            130            140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150            160            170            180            190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200            210            220            230            240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

250            260            270            280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290            300            310            320            330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

340            350            360            370            380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390            400            410            420            430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440            450            460            470            480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

490            500            510            520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A >
```

FIG. 31A

```
      530             540             550             560             570
   AAT TCA GTT AAA GAG CTT ACA AGC CCT GTT GTG GCA GAA AGT CCA GCC
   TTA AGT CAA TTT CTC GAA TGT TCG GGA CAA CAC CGT CTT TCA GGT CGG
    N   S   V   K   E   L   T   S   P   V   V   A   E   S   P   A>

580             590             600             610             620
   ATG GCC AAG CAA AAT GTT AGC AGC CTT GAC GAG AAA AAC AGC GTT TCA
   TAC CGG TTC GTT TTA CAA TCG TCG GAA CTG CTC TTT TTG TCG CAA AGT
    M   A   K   Q   N   V   S   S   L   D   E   K   N   S   V   S>

630             640             650             660             670
   GTA GAT TTG CCT GGT GAA ATG AAA GTT CTT GTA AGC AAA GAA AAA AAC
   CAT CTA AAC GGA CCA CTT TAC TTT CAA GAA CAT TCG TTT CTT TTT TTG
    V   D   L   P   G   E   M   K   V   L   V   S   K   E   K   N>

680             690             700             710             720
   AAA GAC GGC AAG TAC GAT CTA ATT GCA ACA GTA GAC AAG CTT GAG CTT
   TTT CTG CCG TTC ATG CTA GAT TAA CGT TGT CAT CTG TTC GAA CTC GAA
    K   D   G   K   Y   D   L   I   A   T   V   D   K   L   E   L>

730             740             750             760
   AAA GGA ACT TCT GAT AAA AAC AAT GGA TCT GGA GTA CTT GAA GGC GTA
   TTT CCT TGA AGA CTA TTT TTG TTA CCT AGA CCT CAT GAA CTT CCG CAT
    K   G   T   S   D   K   N   N   G   S   G   V   L   E   G   V>

770             780             790             800             810
   AAA GCT GAC AAA AGT AAA GTA AAA TTA ACA ATT TCT GAC GAT CTA GGT
   TTT CGA CTG TTT TCA TTT CAT TTT AAT TGT TAA AGA CTG CTA GAT CCA
    K   A   D   K   S   K   V   K   L   T   I   S   D   D   L   G>

820             830             840             850             860
   CAA ACC ACA CTT GAA GTT TTC AAA GAA GAT GGC AAA ACA CTA GTA TCA
   GTT TGG TGT GAA CTT CAA AAG TTT CTT CTA CCG TTT TGT GAT CAT AGT
    Q   T   T   L   E   V   F   K   E   D   G   K   T   L   V   S>

870             880             890             900             910
   AAA AAA GTA ACT TCC AAA GAC AAG TCA TCA ACA GAA GAA AAA TTC AAT
   TTT TTT CAT TGA AGG TTT CTG TTC AGT AGT TGT CTT CTT TTT AAG TTA
    K   K   V   T   S   K   D   K   S   S   T   E   E   K   F   N>

920             930             940             950         960
   GAA AAA GGT GAA GTA TCT GAA AAA ATA ATA ACA AGA GCA GAC GGA ACC
   CTT TTT CCA CTT CAT AGA CTT TTT TAT TAT TGT TCT CGT CTG CCT TGG
    E   K   G   E   V   S   E   K   I   I   T   R   A   D   G   T>

970             980             990             1000
   AGA CTT GAA TAC ACA GGA ATT AAA AGC GAT GGA TCT GGA AAA GCT AAA
   TCT GAA CTT ATG TGT CCT TAA TTT TCG CTA CCT AGA CCT TTT CGA TTT
    R   L   E   Y   T   G   I   K   S   D   G   S   G   K   A   K>

1010            1020            1030            1040            1050
   GAG GTT TTA AAA GGC TAT GTT CTT GAA GGA ACT CTA ACT GCT GAA AAA
   CTC CAA AAT TTT CCG ATA CAA GAA CTT CCT TGA GAT TGA CGA CTT TTT
    E   V   L   K   G   Y   V   L   E   G   T   L   T   A   E   K>

1060            1070            1080            1090            1100
   ACA ACA TTG GTG GTT AAA GAA GGA ACT GTT ACT TTA AGC AAA AAT ATT
```

FIG. 31B

```
         TGT TGT AAC CAC CAA TTT CTT CCT TGA CAA TGA AAT TCG TTT TTA TAA
          T   T   L   V   V   K   E   G   T   V   T   L   S   K   N   I>

1110            1120            1130            1140            1150
         TCA AAA TCT GGG GAA GTT TCA GTT GAA CTT AAT GAC ACT GAC AGT AGT
         AGT TTT AGA CCC CTT CAA AGT CAA CTT GAA TTA CTG TGA CTG TCA TCA
          S   K   S   G   E   V   S   V   E   L   N   D   T   D   S   S>

1160            1170            1180            1190            1200
         GCT GCT ACT AAA AAA ACT GCA GCT TGG AAT TCA GGC ACT TCA ACT TTA
         CGA CGA TGA TTT TTT TGA CGT CGA ACC TTA AGT CCG TGA AGT TGA AAT
          A   A   T   K   K   T   A   A   W   N   S   G   T   S   T   L>

1210            1220            1230            1240
         ACA ATT ACT GTA AAC AGT AAA AAA ACT AAA GAC CTT GTG TTT ACA AAA
         TGT TAA TGA CAT TTG TCA TTT TTT TGA TTT CTG GAA CAC AAA TGT TTT
          T   I   T   V   N   S   K   K   T   K   D   L   V   F   T   K>

1250            1260            1270            1280            1290
         GAA AAC ACA ATT ACA GTA CAA CAA TAC GAC TCA AAT GGC ACC AAA TTA
         CTT TTG TGT TAA TGT CAT GTT GTT ATG CTG AGT TTA CCG TGG TTT AAT
          E   N   T   I   T   V   Q   Q   Y   D   S   N   G   T   K   L>

1300            1310            1320            1330            1340
         GAG GGG TCA GCA GTT GAA ATT ACA AAA CTT GAT GAA ATT AAA AAC GCT
         CTC CCC AGT CGT CAA CTT TAA TGT TTT GAA CTA CTT TAA TTT TTG CGA
          E   G   S   A   V   E   I   T   K   L   D   E   I   K   N   A>

1350
         TTA AAA TAA
         AAT TTT ATT
          L   K   *>
```

FIG. 31C

```
            10              20              30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50              60              70              80              90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
 A   D   E   S   V   K   G   P   N   L   T   E   I   S   K   K>

100             110             120             130             140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150             160             170             180             190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
 L   L   S   S   I   D   E   L   A   K   A   I   G   K   K   I>

200             210             220             230             240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
 K   N   D   G   S   L   D   N   E   A   N   R   N   E   S   L>

250             260             270             280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
 L   A   G   A   Y   T   I   S   T   L   I   T   Q   K   L   S>

290     300             310             320             330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
 K   L   N   G   S   E   G   L   K   E   K   I   A   A   A   K>

340             350             360             370             380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
 K   C   S   E   E   F   S   T   K   L   K   D   N   H   A   Q>

390             400             410             420             430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
 L   G   I   Q   G   V   T   D   E   N   A   K   K   A   I   L>

440             450             460             470             480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
 K   A   N   A   A   G   K   D   K   G   V   E   E   L   E   K>

490             500             510             520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
 L   S   G   S   L   E   S   L   S   K   A   A   K   E   M   L>
```

FIG. 32A

```
     530              540            550             560             570
  GCT AAT TCA GTT AAA GAG CTT ACA AGC CCT GTT GTC CAT GGC AAG CAA
  CGA TTA AGT CAA TTT CTC GAA TGT TCG GGA CAA CAG GTA CCG TTC GTT
   A   N   S   V   K   E   L   T   S   P   V   V   H   G   K   Q>

580              590            600             610             620
  AAT GTT AGC AGC CTT GAC GAG AAA AAC AGC GTT TCA GTA GAT TTG CCT
  TTA CAA TCG TCG GAA CTG CTC TTT TTG TCG CAA AGT CAT CTA AAC GGA
   N   V   S   S   L   D   E   K   N   S   V   S   V   D   L   P>

630              640            650             660             670
  GGT GAA ATG AAA GTT CTT GTA AGC AAA GAA AAA AAC AAA GAC GGC AAG
  CCA CTT TAC TTT CAA GAA CAT TCG TTT CTT TTT TTG TTT CTG CCG TTC
   G   E   M   K   V   L   V   S   K   E   K   N   K   D   G   K>

680              690            700             710             720
  TAC GAT CTA ATT GCA ACA GTA GAC AAG CTT GAG CTT AAA GGA ACT TCT
  ATG CTA GAT TAA CGT TGT CAT CTG TTC GAA CTC GAA TTT CCT TGA AGA
   Y   D   L   I   A   T   V   D   K   L   E   L   K   G   T   S>

730            740             750             760
  GAT AAA AAC AAT GGA TCT GGA GTA CTT GAA GGC GTA AAA GCT GAC AAA
  CTA TTT TTG TTA CCT AGA CCT CAT GAA CTT CCG CAT TTT CGA CTG TTT
   D   K   N   N   G   S   G   V   L   E   G   V   K   A   D   K>

770              780            790             800             810
  AGT AAA GTA AAA TTA ACA ATT TCT GAC GAT CTA GGT CAA ACC ACA CTT
  TCA TTT CAT TTT AAT TGT TAA AGA CTG CTA GAT CCA GTT TGG TGT GAA
   S   K   V   K   L   T   I   S   D   D   L   G   Q   T   T   L>

820              830            840             850             860
  GAA GTT TTC AAA GAA GAT GGC AAA ACA CTA GTA TCA AAA AAA GTA ACT
  CTT CAA AAG TTT CTT CTA CCG TTT TGT GAT CAT AGT TTT TTT CAT TGA
   E   V   F   K   E   D   G   K   T   L   V   S   K   K   V   T>

870              880            890             900             910
  TCC AAA GAC AAG TCA TCA ACA GAA GAA AAA TTC AAT GAA AAA GGT GAA
  AGG TTT CTG TTC AGT AGT TGT CTT CTT TTT AAG TTA CTT TTT CCA CTT
   S   K   D   K   S   S   T   E   E   K   F   N   E   K   G   E>

920              930            940             950             960
  GTA TCT GAA AAA ATA ATA ACA AGA GCA GAC GGA ACC AGA CTT GAA TAC
  CAT AGA CTT TTT TAT TAT TGT TCT CGT CTG CCT TGG TCT GAA CTT ATG
   V   S   E   K   I   I   T   R   A   D   G   T   R   L   E   Y>

970            980             990            1000
  ACA GGA ATT AAA AGC GAT GGA TCT GGA AAA GCT AAA GAG GTT TTA AAA
  TGT CCT TAA TTT TCG CTA CCT AGA CCT TTT CGA TTT CTC CAA AAT TTT
   T   G   I   K   S   D   G   S   G   K   A   K   E   V   L   K>

1010             1020           1030            1040            1050
  GGC TAT GTT CTT GAA GGA ACT CTA ACT GCT GAA AAA ACA ACA TTG GTG
  CCG ATA CAA GAA CTT CCT TGA GAT TGA CGA CTT TTT TGT TGT AAC CAC
   G   Y   V   L   E   G   T   L   T   A   E   K   T   T   L   V>

1060             1070           1080            1090            1100
  GTT AAA GAA GGA ACT GTT ACT TTA AGC AAA AAT ATT TCA AAA TCT GGG
```

FIG. 32B

```
CAA TTT CTT CCT TGA CAA TGA AAT TCG TTT TTA TAA AGT TTT AGA CCC
 V   K   E   G   T   V   T   L   S   K   N   I   S   K   S   G>

1110         1120         1130         1140         1150
GAA GTT TCA GTT GAA CTT AAT GAC ACT GAC AGT AGT GCT GCT ACT AAA
CTT CAA AGT CAA CTT GAA TTA CTG TGA CTG TCA TCA CGA CGA TGA TTT
 E   V   S   V   E   L   N   D   T   D   S   S   A   A   T   K>

1160         1170         1180         1190         1200
AAA ACT GCA GCT TGG AAT TCA GGC ACT TCA ACT TTA ACA ATT ACT GTA
TTT TGA CGT CGA ACC TTA AGT CCG TGA AGT TGA AAT TGT TAA TGA CAT
 K   T   A   A   W   N   S   G   T   S   T   L   T   I   T   V>

1210         1220         1230         1240
AAC AGT AAA AAA ACT AAA GAC CTT GTG TTT ACA AAA GAA AAC ACA ATT
TTG TCA TTT TTT TGA TTT CTG GAA CAC AAA TGT TTT CTT TTG TGT TAA
 N   S   K   K   T   K   D   L   V   F   T   K   E   N   T   I>

1250         1260         1270         1280         1290
ACA GTA CAA CAA TAC GAC TCA AAT GGC ACC AAA TTA GAG GGG TCA GCA
TGT CAT GTT GTT ATG CTG AGT TTA CCG TGG TTT AAT CTC CCC AGT CGT
 T   V   Q   Q   Y   D   S   N   G   T   K   L   E   G   S   A>

1300         1310         1320         1330         1340
GTT GAA ATT ACA AAA CTT GAT GAA ATT AAA AAC GCT TTA AAA TAA
CAA CTT TAA TGT TTT GAA CTA CTT TAA TTT TTG CGA AAT TTT ATT
 V   E   I   T   K   L   D   E   I   K   N   A   L   K   *>
```

FIG. 32C

```
             10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50                  60                  70                  80                  90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150                 160                 170                 180                 190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200                 210                 220                 230                 240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

250                 260                 270                 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290                 300                 310                 320                 330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

340                 350                 360                 370                 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390                 400                 410                 420                 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440                 450                 460                 470                 480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

490                 500                 510                 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 33A

```
530            540            550            560            570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
 N   S   V   K   E   L   T   S   P   V   V   A   E   S   P   K>

580            590            600            610            620
AAA CCT TCC ATG GCC AAG CAA AAT GTT AGC AGC CTT GAC GAG AAA AAC
TTT GGA AGG TAC CGG TTC GTT TTA CAA TCG TCG GAA CTG CTC TTT TTG
 K   P   S   M   A   K   Q   N   V   S   S   L   D   E   K   N>

630            640            650            660            670
AGC GTT TCA GTA GAT TTG CCT GGT GAA ATG AAA GTT CTT GTA AGC AAA
TCG CAA AGT CAT CTA AAC GGA CCA CTT TAC TTT CAA GAA CAT TCG TTT
 S   V   S   V   D   L   P   G   E   M   K   V   L   V   S   K>

680            690            700            710            720
GAA AAA AAC AAA GAC GGC AAG TAC GAT CTA ATT GCA ACA GTA GAC AAG
CTT TTT TTG TTT CTG CCG TTC ATG CTA GAT TAA CGT TGT CAT CTG TTC
 E   K   N   K   D   G   K   Y   D   L   I   A   T   V   D   K>

730            740            750            760
CTT GAG CTT AAA GGA ACT TCT GAT AAA AAC AAT GGA TCT GGA GTA CTT
GAA CTC GAA TTT CCT TGA AGA CTA TTT TTG TTA CCT AGA CCT CAT GAA
 L   E   L   K   G   T   S   D   K   N   N   G   S   G   V   L>

770            780            790            800            810
GAA GGC GTA AAA GCT GAC AAA AGT AAA GTA AAA TTA ACA ATT TCT GAC
CTT CCG CAT TTT CGA CTG TTT TCA TTT CAT TTT AAT TGT TAA AGA CTG
 E   G   V   K   A   D   K   S   K   V   K   L   T   I   S   D>

820            830            840            850            860
GAT CTA GGT CAA ACC ACA CTT GAA GTT TTC AAA GAA GAT GGC AAA ACA
CTA GAT CCA GTT TGG TGT GAA CTT CAA AAG TTT CTT CTA CCG TTT TGT
 D   L   G   Q   T   T   L   E   V   F   K   E   D   G   K   T>

870            880            890            900            910
CTA GTA TCA AAA AAA GTA ACT TCC AAA GAC AAG TCA TCA ACA GAA GAA
GAT CAT AGT TTT TTT CAT TGA AGG TTT CTG TTC AGT AGT TGT CTT CTT
 L   V   S   K   K   V   T   S   K   D   K   S   S   T   E   E>

920            930            940            950            960
AAA TTC AAT GAA AAA GGT GAA GTA TCT GAA AAA ATA ATA ACA AGA GCA
TTT AAG TTA CTT TTT CCA CTT CAT AGA CTT TTT TAT TAT TGT TCT CGT
 K   F   N   E   K   G   E   V   S   E   K   I   I   T   R   A>

970            980            990           1000
GAC GGA ACC AGA CTT GAA TAC ACA GGA ATT AAA AGC GAT GGA TCT GGA
CTG CCT TGG TCT GAA CTT ATG TGT CCT TAA TTT TCG CTA CCT AGA CCT
 D   G   T   R   L   E   Y   T   G   I   K   S   D   G   S   G>

1010           1020           1030           1040           1050
AAA GCT AAA GAG GTT TTA AAA GGC TAT GTT CTT GAA GGA ACT CTA ACT
TTT CGA TTT CTC CAA AAT TTT CCG ATA CAA GAA CTT CCT TGA GAT TGA
 K   A   K   E   V   L   K   G   Y   V   L   E   G   T   L   T>

1060           1070           1080           1090           1100
GCT GAA AAA ACA ACA TTG GTG GTT AAA GAA GGA ACT GTT ACT TTA AGC
```

FIG. 33B

```
CGA CTT TTT TGT TGT AAC CAC CAA TTT CTT CCT TGA CAA TGA AAT TCG
 A   E   K   T   T   L   V   V   K   E   G   T   V   T   L   S>

1110        1120        1130        1140        1150
AAA AAT ATT TCA AAA TCT GGG GAA GTT TCA GTT GAA CTT AAT GAC ACT
TTT TTA TAA AGT TTT AGA CCC CTT CAA AGT CAA CTT GAA TTA CTG TGA
 K   N   I   S   K   S   G   E   V   S   V   E   L   N   D   T>

1160        1170        1180        1190        1200
GAC AGT AGT GCT GCT ACT AAA AAA ACT GCA GCT TGG AAT TCA AAA ACT
CTG TCA TCA CGA CGA TGA TTT TTT TGA CGT CGA ACC TTA AGT TTT TGA
 D   S   S   A   A   T   K   K   T   A   A   W   N   S   K   T>

1210        1220        1230        1240
TCC ACT TTA ACA ATT AGT GTG AAT AGC CAA AAA ACC AAA AAC CTT GTA
AGG TGA AAT TGT TAA TCA CAC TTA TCG GTT TTT TGG TTT TTG GAA CAT
 S   T   L   T   I   S   V   N   S   Q   K   T   K   N   L   V>

1250        1260        1270        1280        1290
TTC ACA AAA GAA GAC ACA ATA ACA GTA CAA AAA TAC GAC TCA GCA GGC
AAG TGT TTT CTT CTG TGT TAT TGT CAT GTT TTT ATG CTG AGT CGT CCG
 F   T   K   E   D   T   I   T   V   Q   K   Y   D   S   A   G>

1300        1310        1320        1330        1340
ACC AAT CTA GAA GGC AAA GCA GTC GAA ATT ACA ACA CTT AAA GAA CTT
TGG TTA GAT CTT CCG TTT CGT CAG CTT TAA TGT TGT GAA TTT CTT GAA
 T   N   L   E   G   K   A   V   E   I   T   T   L   K   E   L>

1350        1360
AAA AAC GCT TTA AAA TAA
TTT TTG CGA AAT TTT ATT
 K   N   A   L   K   *>
```

FIG. 33C

```
           10              20              30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50              60              70              80              90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
 A   D   E   S   V   K   G   P   N   L   T   E   I   S   K   K>

100             110             120             130             140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150             160             170             180             190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
 L   L   S   S   I   D   E   L   A   K   A   I   G   K   K   I>

200             210             220             230             240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
 K   N   D   G   S   L   D   N   E   A   N   R   N   E   S   L>

250             260             270             280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
 L   A   G   A   Y   T   I   S   T   L   I   T   Q   K   L   S>

290             300             310             320             330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
 K   L   N   G   S   E   G   L   K   E   K   I   A   A   A   K>

340             350             360             370             380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
 K   C   S   E   E   F   S   T   K   L   K   D   N   H   A   Q>

390             400             410             420             430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
 L   G   I   Q   G   V   T   D   E   N   A   K   K   A   I   L>

440             450             460             470             480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
 K   A   N   A   A   G   K   D   K   G   V   E   E   L   E   K>

490             500             510             520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
 L   S   G   S   L   E   S   L   S   K   A   A   K   E   M   L>
```

FIG. 34A

```
    530            540             550            560             570
GCT AAT TCA GTT AAA GAG CTT ACA AGC CCT GTT GTC CAT GGC AAG CAA
CGA TTA AGT CAA TTT CTC GAA TGT TCG GGA CAA CAG GTA CCG TTC GTT
 A   N   S   V   K   E   L   T   S   P   V   V   H   G   K   Q>

580            590             600            610             620
AAT GTT AGC AGC CTT GAC GAG AAA AAC AGC GTT TCA GTA GAT TTG CCT
TTA CAA TCG TCG GAA CTG CTC TTT TTG TCG CAA AGT CAT CTA AAC GGA
 N   V   S   S   L   D   E   K   N   S   V   S   V   D   L   P>

630            640             650            660             670
GGT GAA ATG AAA GTT CTT GTA AGC AAA GAA AAA AAC AAA GAC GGC AAG
CCA CTT TAC TTT CAA GAA CAT TCG TTT CTT TTT TTG TTT CTG CCG TTC
 G   E   M   K   V   L   V   S   K   E   K   N   K   D   G   K>

680            690             700            710             720
TAC GAT CTA ATT GCA ACA GTA GAC AAG CTT GAG CTT AAA GGA ACT TCT
ATG CTA GAT TAA CGT TGT CAT CTG TTC GAA CTC GAA TTT CCT TGA AGA
 Y   D   L   I   A   T   V   D   K   L   E   L   K   G   T   S>

730            740             750            760
GAT AAA AAC AAT GGA TCT GGA GTA CTT GAA GGC GTA AAA GCT GAC AAA
CTA TTT TTG TTA CCT AGA CCT CAT GAA CTT CCG CAT TTT CGA CTG TTT
 D   K   N   N   G   S   G   V   L   E   G   V   K   A   D   K>

770            780             790            800             810
AGT AAA GTA AAA TTA ACA ATT TCT GAC GAT CTA GGT CAA ACC ACA CTT
TCA TTT CAT TTT AAT TGT TAA AGA CTG CTA GAT CCA GTT TGG TGT GAA
 S   K   V   K   L   T   I   S   D   D   L   G   Q   T   T   L>

820            830             840            850             860
GAA GTT TTC AAA GAA GAT GGC AAA ACA CTA GTA TCA AAA AAA GTA ACT
CTT CAA AAG TTT CTT CTA CCG TTT TGT GAT CAT AGT TTT TTT CAT TGA
 E   V   F   K   E   D   G   K   T   L   V   S   K   K   V   T>

870            880             890            900             910
TCC AAA GAC AAG TCA TCA ACA GAA GAA AAA TTC AAT GAA AAA GGT GAA
AGG TTT CTG TTC AGT AGT TGT CTT CTT TTT AAG TTA CTT TTT CCA CTT
 S   K   D   K   S   S   T   E   E   K   F   N   E   K   G   E>

920            930             940            950             960
GTA TCT GAA AAA ATA ATA ACA AGA GCA GAC GGA ACC AGA CTT GAA TAC
CAT AGA CTT TTT TAT TAT TGT TCT CGT CTG CCT TGG TCT GAA CTT ATG
 V   S   E   K   I   I   T   R   A   D   G   T   R   L   E   Y>

970            980             990           1000
ACA GGA ATT AAA AGC GAT GGA TCT GGA AAA GCT AAA GAG GTT TTA AAA
TGT CCT TAA TTT TCG CTA CCT AGA CCT TTT CGA TTT CTC CAA AAT TTT
 T   G   I   K   S   D   G   S   G   K   A   K   E   V   L   K>

1010           1020            1030           1040            1050
GGC TAT GTT CTT GAA GGA ACT CTA ACT GCT GAA AAA ACA ACA TTG GTG
CCG ATA CAA GAA CTT CCT TGA GAT TGA CGA CTT TTT TGT TGT AAC CAC
 G   Y   V   L   E   G   T   L   T   A   E   K   T   T   L   V>

1060           1070            1080           1090            1100
GTT AAA GAA GGA ACT GTT ACT TTA AGC AAA AAT ATT TCA AAA TCT GGG
```

FIG. 34B

```
                CAA  TTT  CTT  CCT  TGA  CAA  TGA  AAT  TCG  TTT  TTA  TAA  AGT  TTT  AGA  CCC
                 V    K    E    G    T    V    T    L    S    K    N    I    S    K    S    G>

1110           1120           1130           1140           1150
                GAA  GTT  TCA  GTT  GAA  CTT  AAT  GAC  ACT  GAC  AGT  AGT  GCT  GCT  ACT  AAA
                CTT  CAA  AGT  CAA  CTT  GAA  TTA  CTG  TGA  CTG  TCA  TCA  CGA  CGA  TGA  TTT
                 E    V    S    V    E    L    N    D    T    D    S    S    A    A    T    K>

1160           1170           1180           1190           1200
                AAA  ACT  GCA  GCT  TGG  AAT  TCA  AAA  ACT  TCC  ACT  TTA  ACA  ATT  AGT  GTG
                TTT  TGA  CGT  CGA  ACC  TTA  AGT  TTT  TGA  AGG  TGA  AAT  TGT  TAA  TCA  CAC
                 K    T    A    A    W    N    S    K    T    S    T    L    T    I    S    V>

1210           1220           1230           1240
                AAT  AGC  CAA  AAA  ACC  AAA  AAC  CTT  GTA  TTC  ACA  AAA  GAA  GAC  ACA  ATA
                TTA  TCG  GTT  TTT  TGG  TTT  TTG  GAA  CAT  AAG  TGT  TTT  CTT  CTG  TGT  TAT
                 N    S    Q    K    T    K    N    L    V    F    T    K    E    D    T    I>

1250           1260           1270           1280           1290
                ACA  GTA  CAA  AAA  TAC  GAC  TCA  GCA  GGC  ACC  AAT  CTA  GAA  GGC  AAA  GCA
                TGT  CAT  GTT  TTT  ATG  CTG  AGT  CGT  CCG  TGG  TTA  GAT  CTT  CCG  TTT  CGT
                 T    V    Q    K    Y    D    S    A    G    T    N    L    E    G    K    A>

1300           1310           1320           1330           1340
                GTC  GAA  ATT  ACA  ACA  CTT  AAA  GAA  CTT  AAA  AAC  GCT  TTA  AAA  TAA
                CAG  CTT  TAA  TGT  TGT  GAA  TTT  CTT  GAA  TTT  TTG  CGA  AAT  TTT  ATT
                 V    E    I    T    T    L    K    E    L    K    N    A    L    K    *>
```

FIG. 34C

```
         10              20              30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50              60              70              80              90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

100             110             120             130             140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150             160             170             180             190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200             210             220             230             240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

250             260             270             280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290             300             310             320             330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

340             350             360             370             380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390             400             410             420             430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440             450             460             470             480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

490             500             510             520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 35A

```
530              540              550              560              570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
 N   S   V   K   E   L   T   S   P   V   V   A   E   S   P   K>

580              590              600              610              620
AAA CCT TCC ATG GCC AAG CAA AAT GTT AGC AGC CTT GAC GAG AAA AAC
TTT GGA AGG TAC CGG TTC GTT TTA CAA TCG TCG GAA CTG CTC TTT TTG
 K   P   S   M   A   K   Q   N   V   S   S   L   D   E   K   N>

630              640              650              660              670
AGC GTT TCA GTA GAT TTG CCT GGT GAA ATG AAA GTT CTT GTA AGC AAA
TCG CAA AGT CAT CTA AAC GGA CCA CTT TAC TTT CAA GAA CAT TCG TTT
 S   V   S   V   D   L   P   G   E   M   K   V   L   V   S   K>

680              690              700              710              720
GAA AAA AAC AAA GAC GGC AAG TAC GAT CTA ATT GCA ACA GTA GAC AAG
CTT TTT TTG TTT CTG CCG TTC ATG CTA GAT TAA CGT TGT CAT CTG TTC
 E   K   N   K   D   G   K   Y   D   L   I   A   T   V   D   K>

730              740              750              760
CTT GAG CTT AAA GGA ACT TCT GAT AAA AAC AAT GGA TCT GGA GTA CTT
GAA CTC GAA TTT CCT TGA AGA CTA TTT TTG TTA CCT AGA CCT CAT GAA
 L   E   L   K   G   T   S   D   K   N   N   G   S   G   V   L>

770              780              790              800              810
GAA GGC GTA AAA GCT GAC AAA AGT AAA GTA AAA TTA ACA ATT TCT GAC
CTT CCG CAT TTT CGA CTG TTT TCA TTT CAT TTT AAT TGT TAA AGA CTG
 E   G   V   K   A   D   K   S   K   V   K   L   T   I   S   D>

820              830              840              850              860
GAT CTA GGT CAA ACC ACA CTT GAA GTT TTC AAA GAA GAT GGC AAA ACA
CTA GAT CCA GTT TGG TGT GAA CTT CAA AAG TTT CTT CTA CCG TTT TGT
 D   L   G   Q   T   T   L   E   V   F   K   E   D   G   K   T>

870              880              890              900              910
CTA GTA TCA AAA AAA GTA ACT TCC AAA GAC AAG TCA TCA ACA GAA GAA
GAT CAT AGT TTT TTT CAT TGA AGG TTT CTG TTC AGT AGT TGT CTT CTT
 L   V   S   K   K   V   T   S   K   D   K   S   S   T   E   E>

920              930              940              950              960
AAA TTC AAT GAA AAA GGT GAA GTA TCT GAA AAA ATA ATA ACA AGA GCA
TTT AAG TTA CTT TTT CCA CTT CAT AGA CTT TTT TAT TAT TGT TCT CGT
 K   F   N   E   K   G   E   V   S   E   K   I   I   T   R   A>

970              980              990              1000
GAC GGA ACC AGA CTT GAA TAC ACA GGA ATT AAA AGC GAT GGA TCT GGA
CTG CCT TGG TCT GAA CTT ATG TGT CCT TAA TTT TCG CTA CCT AGA CCT
 D   G   T   R   L   E   Y   T   G   I   K   S   D   G   S   G>

1020             1030             1040             1050
1010 AAA GCT AAA GAG GTT TTA AAA GGC TAT GTT CTT GAA GGA ACT CTA ACT
     TTT CGA TTT CTC CAA AAT TTT CCG ATA CAA GAA CTT CCT TGA GAT TGA
      K   A   K   E   V   L   K   G   Y   V   L   E   G   T   L   T>

1060             1070             1080             1090             1100
GCT GAA AAA ACA ACA TTG GTG GTT AAA GAA GGA ACT GTT ACT TTA AGC
```

FIG. 35B

```
CGA CTT TTT TGT TGT AAC CAC CAA TTT CTT CCT TGA CAA TGA AAT TCG
 A   E   K   T   T   L   V   V   K   E   G   T   V   T   L   S>

1110         1120         1130         1140         1150
AAA AAT ATT TCA AAA TCT GGG GAA GTT TCA GTT GAA CTT AAT GAC ACT
TTT TTA TAA AGT TTT AGA CCC CTT CAA AGT CAA CTT GAA TTA CTG TGA
 K   N   I   S   K   S   G   E   V   S   V   E   L   N   D   T>

1160         1170         1180         1190         1200
GAC AGT AGT GCT GCT ACT AAA AAA ACT GCA GCT TGG AAT TCA AAA ACT
CTG TCA TCA CGA CGA TGA TTT TTT TGA CGT CGA ACC TTA AGT TTT TGA
 D   S   S   A   A   T   K   K   T   A   A   W   N   S   K   T>

1210         1220         1230         1240
TCT ACT TTA ACA ATT AGT GTT AAC AGC AAA AAA ACT ACA CAA CTT GTG
AGA TGA AAT TGT TAA TCA CAA TTG TCG TTT TTT TGA TGT GTT GAA CAC
 S   T   L   T   I   S   V   N   S   K   K   T   T   Q   L   V>

250          1260         1270         1280         1290
TTT ACT AAA CAA GAC ACA ATA ACT GTA CAA AAA TAC GAC TCC GCA GGT
AAA TGA TTT GTT CTG TGT TAT TGA CAT GTT TTT ATG CTG AGG CGT CCA
 F   T   K   Q   D   T   I   T   V   Q   K   Y   D   S   A   G>

1300         1310         1320         1330         1340
ACC AAT TTA GAA GGC ACA GCA GTC GAA ATT AAA ACA CTT GAT GAA CTT
TGG TTA AAT CTT CCG TGT CGT CAG CTT TAA TTT TGT GAA CTA CTT GAA
 T   N   L   E   G   T   A   V   E   I   K   T   L   D   E   L>

1350         1360
AAA AAC GCT TTA AAA TAA
TTT TTG CGA AAT TTT ATT
 K   N   A   L   K   *>
```

FIG. 35C

```
                10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50                  60                  70                  80                  90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
 A   D   E   S   V   K   G   P   N   L   T   E   I   S   K   K>

100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150                 160                 170                 180                 190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
 L   L   S   S   I   D   E   L   A   K   A   I   G   K   K   I>

200                 210                 220                 230                 240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
 K   N   D   G   S   L   D   N   E   A   N   R   N   E   S   L>

250                 260                 270                 280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
 L   A   G   A   Y   T   I   S   T   L   I   T   Q   K   L   S>

290                 300                 310                 320                 330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
 K   L   N   G   S   E   G   L   K   E   K   I   A   A   A   K>

340                 350                 360                 370                 380
AAA TGC TCT GAA GAG TTT AGT ACT AAA CTA AAA GAT AAT CAT GCA CAG
TTT ACG AGA CTT CTC AAA TCA TGA TTT GAT TTA CTA TTA GTA CGT GTC
 K   C   S   E   E   F   S   T   K   L   K   D   N   H   A   Q>

390                 400                 410                 420                 430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
 L   G   I   Q   G   V   T   D   E   N   A   K   K   A   I   L>

440                 450                 460                 470                 480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
 K   A   N   A   A   G   K   D   K   G   V   E   E   L   E   K>

490                 500                 510                 520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
 L   S   G   S   L   E   S   L   S   K   A   A   K   E   M   L>
```

FIG. 36A

```
   530             540             550             560             570
GCT AAT TCA GTT AAA GAG CTT ACA AGC CCT GTT GTC CAT GGC AAG CAA
CGA TTA AGT CAA TTT CTC GAA TGT TCG GGA CAA CAG GTA CCG TTC GTT
 A   N   S   V   K   E   L   T   S   P   V   V   H   G   K   Q>

580             590             600             610             620
AAT GTT AGC AGC CTT GAC GAG AAA AAC AGC GTT TCA GTA GAT TTG CCT
TTA CAA TCG TCG GAA CTG CTC TTT TTG TCG CAA AGT CAT CTA AAC GGA
 N   V   S   S   L   D   E   K   N   S   V   S   V   D   L   P>

630             640             650             660             670
GGT GAA ATG AAA GTT CTT GTA AGC AAA GAA AAA AAC AAA GAC GGC AAG
CCA CTT TAC TTT CAA GAA CAT TCG TTT CTT TTT TTG TTT CTG CCG TTC
 G   E   M   K   V   L   V   S   K   E   K   N   K   D   G   K>

680             690             700             710             720
TAC GAT CTA ATT GCA ACA GTA GAC AAG CTT GAG CTT AAA GGA ACT TCT
ATG CTA GAT TAA CGT TGT CAT CTG TTC GAA CTC GAA TTT CCT TGA AGA
 Y   D   L   I   A   T   V   D   K   L   E   L   K   G   T   S>

730             740             750             760
GAT AAA AAC AAT GGA TCT GGA GTA CTT GAA GGC GTA AAA GCT GAC AAA
CTA TTT TTG TTA CCT AGA CCT CAT GAA CTT CCG CAT TTT CGA CTG TTT
 D   K   N   N   G   S   G   V   L   E   G   V   K   A   D   K>

770             780             790             800             810
AGT AAA GTA AAA TTA ACA ATT TCT GAC GAT CTA GGT CAA ACC ACA CTT
TCA TTT CAT TTT AAT TGT TAA AGA CTG CTA GAT CCA GTT TGG TGT GAA
 S   K   V   K   L   T   I   S   D   D   L   G   Q   T   T   L>

820             830             840             850             860
GAA GTT TTC AAA GAA GAT GGC AAA ACA CTA GTA TCA AAA AAA GTA ACT
CTT CAA AAG TTT CTT CTA CCG TTT TGT GAT CAT AGT TTT TTT CAT TGA
 E   V   F   K   E   D   G   K   T   L   V   S   K   K   V   T>

870             880             890             900             910
TCC AAA GAC AAG TCA TCA ACA GAA GAA AAA TTC AAT GAA AAA GGT GAA
AGG TTT CTG TTC AGT AGT TGT CTT CTT TTT AAG TTA CTT TTT CCA CTT
 S   K   D   K   S   S   T   E   E   K   F   N   E   K   G   E>

920             930             940             950             960
GTA TCT GAA AAA ATA ATA ACA AGA GCA GAC GGA ACC AGA CTT GAA TAC
CAT AGA CTT TTT TAT TAT TGT TCT CGT CTG CCT TGG TCT GAA CTT ATG
 V   S   E   K   I   I   T   R   A   D   G   T   R   L   E   Y>

970             980             990            1000
ACA GGA ATT AAA AGC GAT GGA TCT GGA AAA GCT AAA GAG GTT TTA AAA
TGT CCT TAA TTT TCG CTA CCT AGA CCT TTT CGA TTT CTC CAA AAT TTT
 T   G   I   K   S   D   G   S   G   K   A   K   E   V   L   K>

1010            1020            1030            1040            1050
GGC TAT GTT CTT GAA GGA ACT CTA ACT GCT GAA AAA ACA ACA TTG GTG
CCG ATA CAA GAA CTT CCT TGA GAT TGA CGA CTT TTT TGT TGT AAC CAC
 G   Y   V   L   E   G   T   L   T   A   E   K   T   T   L   V>

1060            1070            1080            1090            1100
GTT AAA GAA GGA ACT GTT ACT TTA AGC AAA AAT ATT TCA AAA TCT GGG
```

FIG. 36B

```
CAA TTT CTT CCT TGA CAA TGA AAT TCG TTT TTA TAA AGT TTT AGA CCC
V   K   E   G   T   V   T   L   S   K   N   I   S   K   S   G>

1110            1120            1130            1140            1150
GAA GTT TCA GTT GAA CTT AAT GAC ACT GAC AGT AGT GCT GCT ACT AAA
CTT CAA AGT CAA CTT GAA TTA CTG TGA CTG TCA TCA CGA CGA TGA TTT
E   V   S   V   E   L   N   D   T   D   S   S   A   A   T   K>

1160            1170            1180            1190            1200
AAA ACT GCA GCT TGG AAT TCA AAA ACT TCT ACT TTA ACA ATT AGT GTT
TTT TGA CGT CGA ACC TTA AGT TTT TGA AGA TGA AAT TGT TAA TCA CAA
K   T   A   A   W   N   S   K   T   S   T   L   T   I   S   V>

1210            1220            1230            1240
AAC AGC AAA AAA ACT ACA CAA CTT GTG TTT ACT AAA CAA TAC ACA ATA
TTG TCG TTT TTT TGA TGT GTT GAA CAC AAA TGA TTT GTT ATG TGT TAT
N   S   K   K   T   T   Q   L   V   F   T   K   Q   Y   T   I>

1250        1260            1270            1280            1290
ACT GTA AAA CAA TAC GAC TCC GCA GGT ACC AAT TTA GAA GGC ACA GCA
TGA CAT TTT GTT ATG CTG AGG CGT CCA TGG TTA AAT CTT CCG TGT CGT
T   V   K   Q   Y   D   S   A   G   T   N   L   E   G   T   A>

1300            1310            1320            1330            1340
GTC GAA ATT AAA ACA CTT GAT GAA CTT AAA AAC GCT TTA AAA TAA
CAG CTT TAA TTT TGT GAA CTA CTT GAA TTT TTG CGA AAT TTT ATT
V   E   I   K   T   L   D   E   L   K   N   A   L   K   *>
```

FIG. 36C

```
          10              20              30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50              60              70              80              90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
 A   D   E   S   V   K   G   P   N   L   T   E   I   S   K   K>

100             110             120             130             140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150             160             170             180             190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200             210             220             230         240
ATA CAC CAA AAT AAT GGT TTG GAT ACC GAA TAT AAT CAC AAT GGA TCA
TAT GTG GTT TTA TTA CCA AAC CTA TGG CTT ATA TTA GTG TTA CCT AGT
 I   H   Q   N   N   G   L   D   T   E   Y   N   H   N   G   S>

250             260             270             280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290             300             310             320             330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

340             350             360             370             380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390             400             410             420         430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440             450             460             470     480
AAA ACA AAT GGT ACT AAA ACT AAA GGT GCT GAA GAA CTT GGA AAA TTA
TTT TGT TTA CCA TGA TTT TGA TTT CCA CGA CTT CTT GAA CCT TTT AAT
 K   T   N   G   T   K   T   K   G   A   E   E   L   G   K   L>

490             500             510             520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 37A

```
530             540             550             560             570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
 N   S   V   K   E   L   T   S   P   V   V   A   E   S   P   K>

580             590             600             610             620
AAA CCT TCC ATG GCC AAG CAA AAT GTT AGC AGC CTT GAT GAA AAA AAT
TTT GGA AGG TAC CGG TTC GTT TTA CAA TCG TCG GAA CTA CTT TTT TTA
 K   P   S   M   A   K   Q   N   V   S   S   L   D   E   K   N>

630             640             650             660             670
AGC GTT TCA GTA GAT TTA CCT GGT GGA ATG ACA GTT CTT GTA AGT AAA
TCG CAA AGT CAT CTA AAT GGA CCA CCT TAC TGT CAA GAA CAT TCA TTT
 S   V   S   V   D   L   P   G   G   M   T   V   L   V   S   K>

680             690             700             710             720
GAA AAA GAC AAA GAC GGT AAA TAC AGT CTA GAG GCA ACA GTA GAC AAG
CTT TTT CTG TTT CTG CCA TTT ATG TCA GAT CTC CGT TGT CAT CTG TTC
 E   K   D   K   D   G   K   Y   S   L   E   A   T   V   D   K>

730             740             750             760
CTT GAG CTT AAA GGA ACT TCT GAT AAA AAC AAC GGT TCT GGA ACA CTT
GAA CTC GAA TTT CCT TGA AGA CTA TTT TTG TTG CCA AGA CCT TGT GAA
 L   E   L   K   G   T   S   D   K   N   N   G   S   G   T   L>

770             780             790             800             810
GAA GGT GAA AAA ACT GAC AAA AGT AAA GTA AAA TTA ACA ATT GCT GAT
CTT CCA CTT TTT TGA CTG TTT TCA TTT CAT TTT AAT TGT TAA CGA CTA
 E   G   E   K   T   D   K   S   K   V   K   L   T   I   A   D>

820             830             840             850             860
GAC CTA AGT CAA ACT AAA TTT GAA ATT TTC AAA GAA GAT GCC AAA ACA
CTG GAT TCA GTT TGA TTT AAA CTT TAA AAG TTT CTT CTA CGG TTT TGT
 D   L   S   Q   T   K   F   E   I   F   K   E   D   A   K   T>

870             880             890             900             910
TTA GTA TCA AAA AAA GTA ACC CTT AAA GAC AAG TCA TCA ACA GAA GAA
AAT CAT AGT TTT TTT CAT TGG GAA TTT CTG TTC AGT AGT TGT CTT CTT
 L   V   S   K   K   V   T   L   K   D   K   S   S   T   E   E>

920             930             940             950             960
AAA TTC AAC GAA AAG GGT GAA ACA TCT GAA AAA ACA ATA GTA AGA GCA
TTT AAG TTG CTT TTC CCA CTT TGT AGA CTT TTT TGT TAT CAT TCT CGT
 K   F   N   E   K   G   E   T   S   E   K   T   I   V   R   A>

970             980             990             1000
AAT GGA ACC AGA CTT GAA TAC ACA GAC ATA AAA AGC GAT GGA TCC GGA
TTA CCT TGG TCT GAA CTT ATG TGT CTG TAT TTT TCG CTA CCT AGG CCT
 N   G   T   R   L   E   Y   T   D   I   K   S   D   G   S   G>

1010            1020            1030            1040            1050
AAA GCT AAA GAA GTT TTA AAA GAC TTT ACT CTT GAA GGA ACT CTA GCT
TTT CGA TTT CTT CAA AAT TTT CTG AAA TGA GAA CTT CCT TGA GAT CGA
 K   A   K   E   V   L   K   D   F   T   L   E   G   T   L   A>

1060            1070            1080            1090            1100
GCT GAC GGC AAA ACA ACA TTG AAA GTT ACA GAA GGC ACT GTT GTT TTA
```

FIG. 37B

```
              CGA CTG CCG TTT TGT TGT AAC TTT CAA TGT CTT CCG TGA CAA CAA AAT
               A   D   G   K   T   T   L   K   V   T   E   G   T   V   V   L>

1110        1120        1130        1140        1150
              AGC AAG AAC ATT TTA AAA TCC GGA GAA ATA ACA GTT GCA CTT GAT GAC
              TCG TTC TTG TAA AAT TTT AGG CCT CTT TAT TGT CAA CGT GAA CTA CTG
               S   K   N   I   L   K   S   G   E   I   T   V   A   L   D   D>

1160        1170        1180        1190        1200
              TCT GAC ACT ACT CAG GCT ACT AAA AAA ACT GGA AAA TGG GAT TCA AAT
              AGA CTG TGA TGA GTC CGA TGA TTT TTT TGA CCT TTT ACC CTA AGT TTA
               S   D   T   T   Q   A   T   K   K   T   G   K   W   D   S   N>

1210        1220        1230        1240
              ACT TCC ACT TTA ACA ATT AGT GTG AAT AGC AAA AAA ACT AAA AAC ATT
              TGA AGG TGA AAT TGT TAA TCA CAC TTA TCG TTT TTT TGA TTT TTG TAA
               T   S   T   L   T   I   S   V   N   S   K   K   T   K   N   I>

1250        1260        1270        1280        1290
           GTA TTT ACA AAA GAA GAC ACA ATA ACA GTA CAA AAA TAC GAC TCA GCA
           CAT AAA TGT TTT CTT CTG TGT TAT TGT CAT GTT TTT ATG CTG AGT CGT
            V   F   T   K   E   D   T   I   T   V   Q   K   Y   D   S   A>

1300        1310        1320        1330        1340
              GGC ACC AAT CTA GAA GGC AAC GCA GTC GAA ATT AAA ACA CTT GAT GAA
              CCG TGG TTA GAT CTT CCG TTG CGT CAG CTT TAA TTT TGT GAA CTA CTT
               G   T   N   L   E   G   N   A   V   E   I   K   T   L   D   E>

1350        1360
              CTT AAA AAC GCT TTA AAA TAG
              GAA TTT TTG CGA AAT TTT ATC
               L   K   N   A   L   K   *>
```

FIG. 37C

```
                10                  20                  30                  40
    ATG GCT TGT AAT AAT TCA GGG AAA GAT GGG AAT ACA TCT GCA AAT TCT
    TAC CGA ACA TTA TTA AGT CCC TTT CTA CCC TTA TGT AGA CGT TTA AGA
     M   A   C   N   N   S   G   K   D   G   N   T   S   A   N   S>

50                  60                  70                  80                  90
    GCT GAT GAG TCT GTT AAA GGG CCT AAT CTT ACA GAA ATA AGT AAA AAA
    CGA CTA CTC AGA CAA TTT CCC GGA TTA GAA TGT CTT TAT TCA TTT TTT
     A   D   E   S   V   K   G   P   N   L   T   E   I   S   K   K>

100                 110                 120                 130                 140
    ATT ACG GAT TCT AAT GCG GTT TTA CTT GCT GTG AAA GAG GTT GAA GCG
    TAA TGC CTA AGA TTA CGC CAA AAT GAA CGA CAC TTT CTC CAA CTT CGC
     I   T   D   S   N   A   V   L   L   A   V   K   E   V   E   A>

150                 160                 170                 180                 190
    TTG CTG TCA TCT ATA GAT GAG CTT GCT AAA GCT ATT GGT AAA AAA ATA
    AAC GAC AGT AGA TAT CTA CTC GAA CGA TTT CGA TAA CCA TTT TTT TAT
     L   L   S   S   I   D   E   L   A   K   A   I   G   K   K   I>

200                 210                 220                 230                 240
    AAA AAC GAT GGT AGT TTA GAT AAT GAA GCA AAT CGC AAC GAG TCA TTG
    TTT TTG CTA CCA TCA AAT CTA TTA CTT CGT TTA GCG TTG CTC AGT AAC
     K   N   D   G   S   L   D   N   E   A   N   R   N   E   S   L>

250                 260                 270                 280
    TTA GCA GGA GCT TAT ACA ATA TCA ACC TTA ATA ACA CAA AAA TTA AGT
    AAT CGT CCT CGA ATA TGT TAT AGT TGG AAT TAT TGT GTT TTT AAT TCA
     L   A   G   A   Y   T   I   S   T   L   I   T   Q   K   L   S>

290                 300                 310                 320                 330
    AAA TTA AAC GGA TCA GAA GGT TTA AAG GAA AAG ATT GCC GCA GCT AAG
    TTT AAT TTG CCT AGT CTT CCA AAT TTC CTT TTC TAA CGG CGT CGA TTC
     K   L   N   G   S   E   G   L   K   E   K   I   A   A   A   K>

340                 350                 360                 370                 380
    AAA TGC TCT GAA GAG TTT AGT ACT AAA CTA AAA GAT AAT CAT GCA CAG
    TTT ACG AGA CTT CTC AAA TCA TGA TTT GAT TTT CTA TTA GTA CGT GTC
     K   C   S   E   E   F   S   T   K   L   K   D   N   H   A   Q>

390                 400                 410                 420                 430
    CTT GGT ATA CAG GGC GTT ACT GAT GAA AAT GCA AAA AAA GCT ATT TTA
    GAA CCA TAT GTC CCG CAA TGA CTA CTT TTA CGT TTT TTT CGA TAA AAT
     L   G   I   Q   G   V   T   D   E   N   A   K   K   A   I   L>

440                 450                 460                 470                 480
    AAA GCA AAT GCA GCG GGT AAA GAT AAG GGC GTT GAA GAA CTT GAA AAG
    TTT CGT TTA CGT CGC CCA TTT CTA TTC CCG CAA CTT CTT GAA CTT TTC
     K   A   N   A   A   G   K   D   K   G   V   E   E   L   E   K>

490                 500                 510                 520
    TTG TCC GGA TCA TTA GAA AGC TTA TCA AAA GCA GCT AAA GAG ATG CTT
    AAC AGG CCT AGT AAT CTT TCG AAT AGT TTT CGT CGA TTT CTC TAC GAA
     L   S   G   S   L   E   S   L   S   K   A   A   K   E   M   L>
```

FIG. 38A

```
    530         540         550         560         570
GCT AAT TCA GTT AAA GAG CTT ACA AGC CCT GTT GTC CAT GGC AAG CAA
CGA TTA AGT CAA TTT CTC GAA TGT TCG GGA CAA CAG GTA CCG TTC GTT
 A   N   S   V   K   E   L   T   S   P   V   V   H   G   K   Q>

580         590         600         610         620
AAT GTT AGC AGC CTT GAT GAA AAA AAT AGC GTT TCA GTA GAT TTA CCT
TTA CAA TCG TCG GAA CTA CTT TTT TTA TCG CAA AGT CAT CTA AAT GGA
 N   V   S   S   L   D   E   K   N   S   V   S   V   D   L   P>

630         640         650         660         670
GGT GGA ATG ACA GTT CTT GTA AGT AAA GAA AAA GAC AAA GAC GGT AAA
CCA CCT TAC TGT CAA GAA CAT TCA TTT CTT TTT CTG TTT CTG CCA TTT
 G   G   M   T   V   L   V   S   K   E   K   D   K   D   G   K>

680         690         700         710         720
TAC AGT CTA GAG GCA ACA GTA GAC AAG CTT GAG CTT AAA GGA ACT TCT
ATG TCA GAT CTC CGT TGT CAT CTG TTC GAA CTC GAA TTT CCT TGA AGA
 Y   S   L   E   A   T   V   D   K   L   E   L   K   G   T   S>

730         740         750         760
GAT AAA AAC AAC GGT TCT GGA ACA CTT GAA GGT GAA AAA ACT GAC AAA
CTA TTT TTG TTG CCA AGA CCT TGT GAA CTT CCA CTT TTT TGA CTG TTT
 D   K   N   N   G   S   G   T   L   E   G   E   K   T   D   K>

770         780         790         800         810
AGT AAA GTA AAA TTA ACA ATT GCT GAT GAC CTA AGT CAA ACT AAA TTT
TCA TTT CAT TTT AAT TGT TAA CGA CTA CTG GAT TCA GTT TGA TTT AAA
 S   K   V   K   L   T   I   A   D   D   L   S   Q   T   K   F>

820         830         840         850         860
GAA ATT TTC AAA GAA GAT GCC AAA ACA TTA GTA TCA AAA AAA GTA ACC
CTT TAA AAG TTT CTT CTA CGG TTT TGT AAT CAT AGT TTT TTT CAT TGG
 E   I   F   K   E   D   A   K   T   L   V   S   K   K   V   T>

870         880         890         900         910
CTT AAA GAC AAG TCA TCA ACA GAA GAA AAA TTC AAC GAA AAG GGT GAA
GAA TTT CTG TTC AGT AGT TGT CTT CTT TTT AAG TTG CTT TTC CCA CTT
 L   K   D   K   S   S   T   E   E   K   F   N   E   K   G   E>

920         930         940         950         960
ACA TCT GAA AAA ACA ATA GTA AGA GCA AAT GGA ACC AGA CTT GAA TAC
TGT AGA CTT TTT TGT TAT CAT TCT CGT TTA CCT TGG TCT GAA CTT ATG
 T   S   E   K   T   I   V   R   A   N   G   T   R   L   E   Y>

970         980         990         1000
ACA GAC ATA AAA AGC GAT GGA TCC GGA AAA GCT AAA GAA GTT TTA AAA
TGT CTG TAT TTT TCG CTA CCT AGG CCT TTT CGA TTT CTT CAA AAT TTT
 T   D   I   K   S   D   G   S   G   K   A   K   E   V   L   K>

1010        1020        1030        1040        1050
    GAC TTT ACT CTT GAA GGA ACT CTA GCT GCT GAC GGC AAA ACA ACA TTG
    CTG AAA TGA GAA CTT CCT TGA GAT CGA CGA CTG CCG TTT TGT TGT AAC
     D   F   T   L   E   G   T   L   A   A   D   G   K   T   T   L>

1060        1070        1080        1090        1100
AAA GTT ACA GAA GGC ACT GTT GTT TTA AGC AAG AAC ATT TTA AAA TCC
```

FIG. 38B

```
TTT CAA TGT CTT CCG TGA CAA CAA AAT TCG TTC TTG TAA AAT TTT AGG
 K   V   T   E   G   T   V   V   L   S   K   N   I   L   K   S>

1110        1120        1130        1140        1150
GGA GAA ATA ACA GTT GCA CTT GAT GAC TCT GAC ACT ACT CAG GCT ACT
CCT CTT TAT TGT CAA CGT GAA CTA CTG AGA CTG TGA TGA GTC CGA TGA
 G   E   I   T   V   A   L   D   D   S   D   T   T   Q   A   T>

1160        1170        1180        1190        1200
AAA AAA ACT GGA AAA TGG GAT TCA AAT ACT TCC ACT TTA ACA ATT AGT
TTT TTT TGA CCT TTT ACC CTA AGT TTA TGA AGG TGA AAT TGT TAA TCA
 K   K   T   G   K   W   D   S   N   T   S   T   L   T   I   S>

1210        1220        1230        1240
   GTG AAT AGC AAA AAA ACT AAA AAC ATT GTA TTT ACA AAA GAA GAC ACA
   CAC TTA TCG TTT TTT TGA TTT TTG TAA CAT AAA TGT TTT CTT CTG TGT
    V   N   S   K   K   T   K   N   I   V   F   T   K   E   D   T>

1250        1260        1270        1280        1290
ATA ACA GTA CAA AAA TAC GAC TCA GCA GGC ACC AAT CTA GAA GGC AAC
TAT TGT CAT GTT TTT ATG CTG AGT CGT CCG TGG TTA GAT CTT CCG TTG
 I   T   V   Q   K   Y   D   S   A   G   T   N   L   E   G   N>

1300        1310        1320        1330        1340
 GCA GTC GAA ATT AAA ACA CTT GAT GAA CTT AAA AAC GCT TTA AAA TAG
 CGT CAG CTT TAA TTT TGT GAA CTA CTT GAA TTT TTG CGA AAT TTT ATC
  A   V   E   I   K   T   L   D   E   L   K   N   A   L   K   *>
```

FIG. 38C

```
         10              20              30              40
ATG GCT TGT AAT AAT TCA GGA AAA GAT GGG AAT ACA TCT GCA AAT TCT
TAC CGA ACA TTA TTA AGT CCT TTT CTA CCC TTA TGT AGA CGT TTA AGA
 M   A   C   N   N   S   G   K   D   G   N   T   S   A   N   S>

50              60              70              80              90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
 A   D   E   S   V   K   G   P   N   L   T   E   I   S   K   K>

100             110             120             130             140
ATT ACA GAA TCT AAC GCA GTT GTT CTG GCT GTG AAA GAA ATT GAA ACT
TAA TGT CTT AGA TTG CGT CAA CAA GAC CGA CAC TTT CTT TAA CTT TGA
 I   T   E   S   N   A   V   V   L   A   V   K   E   I   E   T>

150             160             170             180             190
TTG CTT GCA TCT ATA GAT GAA CTT GCT ACT AAA GCT ATT GGT AAA AAA
AAC GAA CGT AGA TAT CTA CTT GAA CGA TGA TTT CGA TAA CCA TTT TTT
 L   L   A   S   I   D   E   L   A   T   K   A   I   G   K   K>

200             210             220             230             240
ATA CAA CAA AAT GGT GGT TTA GCT GTC GAA GCG GGG CAT AAT GGA ACA
TAT GTT GTT TTA CCA CCA AAT CGA CAG CTT CGC CCC GTA TTA CCT TGT
 I   Q   Q   N   G   G   L   A   V   E   A   G   H   N   G   T>

250             260             270             280
TTG TTA GCA GGT GCT TAT ACA ATA TCA AAA CTA ATA ACA CAA AAA TTA
AAC AAT CGT CCA CGA ATA TGT TAT AGT TTT GAT TAT TGT GTT TTT AAT
 L   L   A   G   A   Y   T   I   S   K   L   I   T   Q   K   L>

290             300             310             320             330
GAT GGA TTG AAA AAT TCA GAA AAA TTA AAG GAA AAA ATT GAA AAT GCT
CTA CCT AAC TTT TTA AGT CTT TTT AAT TTC CTT TTT TAA CTT TTA CGA
 D   G   L   K   N   S   E   K   L   K   E   K   I   E   N   A>

340             350             360             370             380
AAG AAA TGT TCT GAA GAT TTT ACT AAA AAA CTA GAA GGA GAA CAT GCG
TTC TTT ACA AGA CTT CTA AAA TGA TTT TTT GAT CTT CCT CTT GTA CGC
 K   K   C   S   E   D   F   T   K   K   L   E   G   E   H   A>

390             400             410             420             430
CAA CTT GGA ATT GAA AAT GTT ACT GAT GAG AAT GCA AAA AAA GCT ATT
GTT GAA CCT TAA CTT TTA CAA TGA CTA CTC TTA CGT TTT TTT CGA TAA
 Q   L   G   I   E   N   V   T   D   E   N   A   K   K   A   I>

440             450             460             470             480
TTA ATA ACA GAT GCA GCT AAA GAT AAG GGC GCT GCA GAG CTT GAA AAG
AAT TAT TGT CTA CGT CGA TTT CTA TTC CCG CGA CGT CTC GAA CTT TTC
 L   I   T   D   A   A   K   D   K   G   A   A   E   L   E   K>

490             500             510             520
CTA TTT AAA GCA GTA GAA AAC TTG GCA AAA GCA GCT AAA GAG ATG CTT
GAT AAA TTT CGT CAT CTT TTG AAC CGT TTT CGT CGA TTT CTC TAC GAA
 L   F   K   A   V   E   N   L   A   K   A   A   K   E   M   L>
```

FIG. 39A

```
      530         540         550         560         570
GCT AAT TCA GTT AAA GAG CTT ACA AGT CCT ATT GTG CAT GGC GTT TCA
CGA TTA AGT CAA TTT CTC GAA TGT TCA GGA TAA CAC GTA CCG CAA AGT
 A   N   S   V   K   E   L   T   S   P   I   V   H   G   V   S>

580         590         600         610         620
GTA GAT TTG CCT GGT GAA ATG AAA GTT CTT GTA AGC AAA GAA AAA AAC
CAT CTA AAC GGA CCA CTT TAC TTT CAA GAA CAT TCG TTT CTT TTT TTG
 V   D   L   P   G   E   M   K   V   L   V   S   K   E   K   N>

630         640         650         660         670
AAA GAC GGC AAG TAC GAT CTA ATT GCA ACA GTA GAC AAG CTT GAG CTT
TTT CTG CCG TTC ATG CTA GAT TAA CGT TGT CAT CTG TTC GAA CTC GAA
 K   D   G   K   Y   D   L   I   A   T   V   D   K   L   E   L>

680         690         700         710         720
AAA GGA ACT TCT GAT AAA AAC AAT GGA TCT GGA GTA CTT GAA GGC GTA
TTT CCT TGA AGA CTA TTT TTG TTA CCT AGA CCT CAT GAA CTT CCG CAT
 K   G   T   S   D   K   N   N   G   S   G   V   L   E   G   V>

730         740         750         760
      AAA GCT GAC AAA AGT AAA GTA AAA TTA ACA ATT TCT GAC GAT CTA GGT
      TTT CGA CTG TTT TCA TTT CAT TTT AAT TGT TAA AGA CTG CTA GAT CCA
       K   A   D   K   S   K   V   K   L   T   I   S   D   D   L   G>

770         780         790         800         810
CAA ACC ACA CTT GAA GTT TTC AAA GAA GAT GGC AAA ACA CTA GTA TCA
GTT TGG TGT GAA CTT CAA AAG TTT CTT CTA CCG TTT TGT GAT CAT AGT
 Q   T   T   L   E   V   F   K   E   D   G   K   T   L   V   S>

820         830         840         850         860
AAA AAA GTA ACT TCC AAA GAC AAG TCA TCA ACA GAA GAA AAA TTC AAT
TTT TTT CAT TGA AGG TTT CTG TTC AGT AGT TGT CTT CTT TTT AAG TTA
 K   K   V   T   S   K   D   K   S   S   T   E   E   K   F   N>

870         880         890         900         910
GAA AAA GGT GAA GTA TCT GAA AAA ATA ATA ACA AGA GCA GAC GGA ACC
CTT TTT CCA CTT CAT AGA CTT TTT TAT TAT TGT TCT CGT CTG CCT TGG
 E   K   G   E   V   S   E   K   I   I   T   R   A   D   G   T>

920         930         940         950         960
AGA CTT GAA TAC ACA GGA ATT AAA AGC GAT GGA TCT GGA AAA GCT AAA
TCT GAA CTT ATG TGT CCT TAA TTT TCG CTA CCT AGA CCT TTT CGA TTT
 R   L   E   Y   T   G   I   K   S   D   G   S   G   K   A   K>

970         980         990         1000
GAG GTT TTA AAA AAA TTT ACT CTT GAA GGA AAA GTA GCT AAT GAT AAA
CTC CAA AAT TTT TTT AAA TGA GAA CTT CCT TTT CAT CGA TTA CTA TTT
 E   V   L   K   K   F   T   L   E   G   K   V   A   N   D   K>

1010        1020        1030        1040        1050
GTA ACA TTG GAA GTA AAA GAA GGA ACC GTT ACT TTA AGT AAG AAC ATT
CAT TGT AAC CTT CAT TTT CTT CCT TGG CAA TGA AAT TCA TTC TTG TAA
 V   T   L   E   V   K   E   G   T   V   T   L   S   K   N   I>

1060        1070        1080        1090        1100
TCA AAA TCT GGG GAA GTT TCA GTT GAA CTT AAT GAC ACT GAC AGT AGT
```

FIG. 39B

```
AGT TTT AGA CCC CTT CAA AGT CAA CTT GAA TTA CTG TGA CTG TCA TCA
 S   K   S   G   E   V   S   V   E   L   N   D   T   D   S   S>

1110        1120        1130        1140        1150
GCT GCT ACT AAA AAA ACT GCA GCT TGG AAT TCA GGC ACT TCA ACT TTA
CGA CGA TGA TTT TTT TGA CGT CGA ACC TTA AGT CCG TGA AGT TGA AAT
 A   A   T   K   K   T   A   A   W   N   S   G   T   S   T   L>

1160        1170        1180        1190        1200
ACA ATT ACT GTA AAC AGT AAA AAA ACT AAA GAC CTT GTG TTT ACA AAA
TGT TAA TGA CAT TTG TCA TTT TTT TGA TTT CTG GAA CAC AAA TGT TTT
 T   I   T   V   N   S   K   K   T   K   D   L   V   F   T   K>

1210        1220        1230        1240
GAA AAC ACA ATT ACA GTA CAA CAA TAC GAC TCA AAT GGC ACC AAA TTA
CTT TTG TGT TAA TGT CAT GTT GTT ATG CTG AGT TTA CCG TGG TTT AAT
 E   N   T   I   T   V   Q   Q   Y   D   S   N   G   T   K   L>

1250        1260        1270        1280        1290
GAG GGG TCA GCA GTT GAA ATT ACA AAA CTT GAT GAA ATT AAA AAC GCT
CTC CCC AGT CGT CAA CTT TAA TGT TTT GAA CTA CTT TAA TTT TTG CGA
 E   G   S   A   V   E   I   T   K   L   D   E   I   K   N   A>

1300
TTA AAA TAA
AAT TTT ATT
 L   K   *>
```

FIG. 39C

```
            10           20           30           40
ATG GCT TGT AGT AAT TCA GGG AAA GGT GGG GAT TCT GCA TCT ACT AAT
TAC CGA ACA TCA TTA AGT CCC TTT CCA CCC CTA AGA CGT AGA TGA TTA
 M   A   C   S   N   S   G   K   G   G   D   S   A   S   T   N>

50           60           70           80           90
CCT GCT GAC GAG TCT GCG AAA GGG CCT AAT CTT ACA GAA ATA AGC AAA
GGA CGA CTG CTC AGA CGC TTT CCC GGA TTA GAA TGT CTT TAT TCG TTT
 P   A   D   E   S   A   K   G   P   N   L   T   E   I   S   K>

100          110          120          130          140
AAA ATT ACA GAT TCT AAT GCA TTT GTA CTT GCT GTT AAA GAA GTT GAG
TTT TAA TGT CTA AGA TTA CGT AAA CAT GAA CGA CAA TTT CTT CAA CTC
 K   I   T   D   S   N   A   F   V   L   A   V   K   E   V   E>

150          160          170          180          190
ACT TTG GTT TTA TCT ATA GAT GAA CTT GCT AAG AAA GCT ATT GGT CAA
TGA AAC CAA AAT AGA TAT CTA CTT GAA CGA TTC TTT CGA TAA CCA GTT
 T   L   V   L   S   I   D   E   L   A   K   K   A   I   G   Q>

200          210          220          230          240
AAA ATA GAC AAT AAT AAT GGT TTA GCT GCT TTA AAT AAT CAG AAT GGA
TTT TAT CTG TTA TTA TTA CCA AAT CGA CGA AAT TTA TTA GTC TTA CCT
 K   I   D   N   N   N   G   L   A   A   L   N   N   Q   N   G>

250          260          270          280
TCG TTG TTA GCA GGA GCC TAT GCA ATA TCA ACC CTA ATA ACA GAA AAA
AGC AAC AAT CGT CCT CGG ATA CGT TAT AGT TGG GAT TAT TGT CTT TTT
 S   L   L   A   G   A   Y   A   I   S   T   L   I   T   E   K>

290          300          310          320          330
TTG AGT AAA TTG AAA AAT TTA GAA GAA TTA AAG ACA GAA ATT GCA AAG
AAC TCA TTT AAC TTT TTA AAT CTT CTT AAT TTC TGT CTT TAA CGT TTC
 L   S   K   L   K   N   L   E   E   L   K   T   E   I   A   K>

340          350          360          370          380
GCT AAG AAA TGT TCC GAA GAA TTT ACT AAT AAA CTA AAA AGT GGT CAT
CGA TTC TTT ACA AGG CTT CTT AAA TGA TTA TTT GAT TTT TCA CCA GTA
 A   K   K   C   S   E   E   F   T   N   K   L   K   S   G   H>

390          400          410          420          430
GCA GAT CTT GGC AAA CAG GAT GCT ACC GAT GAT CAT GCA AAA GCA GCT
CGT CTA GAA CCG TTT GTC CTA CGA TGG CTA CTA GTA CGT TTT CGT CGA
 A   D   L   G   K   Q   D   A   T   D   D   H   A   K   A   A>

440          450          460          470          480
ATT TTA AAA ACA CAT GCA ACT ACC GAT AAA GGT GCT AAA GAA TTT AAA
TAA AAT TTT TGT GTA CGT TGA TGG CTA TTT CCA CGA TTT CTT AAA TTT
 I   L   K   T   H   A   T   T   D   K   G   A   K   E   F   K>

490          500          510          520
GAT TTA TTT GAA TCA GTA GAA GGT TTG TTA AAA GCA GCT CAA GTA GCA
CTA AAT AAA CTT AGT CAT CTT CCA AAC AAT TTT CGT CGA GTT CAT CGT
 D   L   F   E   S   V   E   G   L   L   K   A   A   Q   V   A>
```

FIG. 40A

```
     530         540         550         560         570
  CTA ACT AAT TCA GTT AAA GAA CTT ACA AGT CCT GTT GTA GCA GAA AGT
  GAT TGA TTA AGT CAA TTT CTT GAA TGT TCA GGA CAA CAT CGT CTT TCA
   L   T   N   S   V   K   E   L   T   S   P   V   V   A   E   S>

580         590         600         610         620
  CCA AAA AAA CCT TCC ATG GCC GTT TCA GTA GAT TTG CCT GGT GAA ATG
  GGT TTT TTT GGA AGG TAC CGG CAA AGT CAT CTA AAC GGA CCA CTT TAC
   P   K   K   P   S   M   A   V   S   V   D   L   P   G   E   M>

630         640         650         660         670
  AAA GTT CTT GTA AGC AAA GAA AAA AAC AAA GAC GGC AAG TAC GAT CTA
  TTT CAA GAA CAT TCG TTT CTT TTT TTG TTT CTG CCG TTC ATG CTA GAT
   K   V   L   V   S   K   E   N   K   D   G   K   Y   D   L>

680         690         700         710         720
  ATT GCA ACA GTA GAC AAG CTT GAG CTT AAA GGA ACT TCT GAT AAA AAC
  TAA CGT TGT CAT CTG TTC GAA CTC GAA TTT CCT TGA AGA CTA TTT TTG
   I   A   T   V   D   K   L   E   L   K   G   T   S   D   K   N>

730         740         750         760
  AAT GGA TCT GGA GTA CTT GAA GGC GTA AAA GCT GAC AAA AGT AAA GTA
  TTA CCT AGA CCT CAT GAA CTT CCG CAT TTT CGA CTG TTT TCA TTT CAT
   N   G   S   G   V   L   E   G   V   K   A   D   K   S   K   V>

770         780         790         800         810
  AAA TTA ACA ATT TCT GAC GAT CTA GGT CAA ACC ACA CTT GAA GTT TTC
  TTT AAT TGT TAA AGA CTG CTA GAT CCA GTT TGG TGT GAA CTT CAA AAG
   K   L   T   I   S   D   D   L   G   Q   T   T   L   E   V   F>

820         830         840         850         860
  AAA GAA GAT GGC AAA ACA CTA GTA TCA AAA AAA GTA ACT TCC AAA GAC
  TTT CTT CTA CCG TTT TGT GAT CAT AGT TTT TTT CAT TGA AGG TTT CTG
   K   E   D   G   K   T   L   V   S   K   K   V   T   S   K   D>

870         880         890         900         910
  AAG TCA TCA ACA GAA GAA AAA TTC AAT GAA AAA GGT GAA GTA TCT GAA
  TTC AGT AGT TGT CTT CTT TTT AAG TTA CTT TTT CCA CTT CAT AGA CTT
   K   S   S   T   E   E   K   F   N   E   K   G   E   V   S   E>

920         930         940         950         960
  AAA ATA ATA ACA AGA GCA GAC GGA ACC AGA CTT GAA TAC ACA GGA ATT
  TTT TAT TAT TGT TCT CGT CTG CCT TGG TCT GAA CTT ATG TGT CCT TAA
   K   I   I   T   R   A   D   G   T   R   L   E   Y   T   G   I>

970         980         990        1000
  AAA AGC GAT GGA TCT GGA AAA GCT AAA GAG GTT TTA AAA AAA TTT ACT
  TTT TCG CTA CCT AGA CCT TTT CGA TTT CTC CAA AAT TTT TTT AAA TGA
   K   S   D   G   S   G   K   A   K   E   V   L   K   K   F   T>

1010        1020        1030        1040        1050
  CTT GAA GGA AAA GTA GCT AAT GAT AAA GTA ACA TTG GAA GTA AAA GAA
  GAA CTT CCT TTT CAT CGA TTA CTA TTT CAT TGT AAC CTT CAT TTT CTT
   L   E   G   K   V   A   N   D   K   V   T   L   E   V   K   E>

1060        1070        1080        1090        1100
  GGA ACC GTT ACT TTA AGT AAG AAT ATT TCA AAA TCT GGG GAA GTT TCA
```

FIG. 40B

```
              CCT TGG CAA TGA AAT TCA TTC TTA TAA AGT TTT AGA CCC CTT CAA AGT
              G   T   V   T   L   S   K   N   I   S   K   S   G   E   V   S>

1110            1120            1130            1140            1150
              GTT GAA CTT AAT GAC ACT GAC AGT AGT GCT GCT ACT AAA AAA ACT GCA
              CAA CTT GAA TTA CTG TGA CTG TCA TCA CGA CGA TGA TTT TTT TGA CGT
              V   E   L   N   D   T   D   S   S   A   A   T   K   K   T   A>

1160            1170            1180            1190            1200
              GCT TGG AAT TCA AAA ACT TCC ACT TTA ACA ATT AGT GTG AAT AGC CAA
              CGA ACC TTA AGT TTT TGA AGG TGA AAT TGT TAA TCA CAC TTA TCG GTT
              A   W   N   S   K   T   S   T   L   T   I   S   V   N   S   Q>

1210            1220            1230            1240
              AAA ACC AAA AAC CTT GTA TTC ACA AAA GAA GAC ACA ATA ACA GTA CAA
              TTT TGG TTT TTG GAA CAT AAG TGT TTT CTT CTG TGT TAT TGT CAT GTT
              K   T   K   N   L   V   F   T   K   E   D   T   I   T   V   Q>

1250            1260            1270            1280            1290
              AAA TAC GAC TCA GCA GGC ACC AAT CTA GAA GGC AAA GCA GTC GAA ATT
              TTT ATG CTG AGT CGT CCG TGG TTA GAT CTT CCG TTT CGT CAG CTT TAA
              K   Y   D   S   A   G   T   N   L   E   G   K   A   V   E   I>

1300            1310            1320            1330
              ACA ACA CTT AAA GAA CTT AAA AAC GCT TTA AAA TAA
              TGT TGT GAA TTT CTT GAA TTT TTG CGA AAT TTT ATT
              T   T   L   K   E   L   K   N   A   L   K   *>
```

FIG. 40C

```
         10              20              30              40
ATG GCT TGT AAT AAT TCA GGT GGG GAT TCT GCA TCT ACT AAT CCT GAT
TAC CGA ACA TTA TTA AGT CCA CCC CTA AGA CGT AGA TGA TTA GGA CTA
 M   A   C   N   N   S   G   G   D   S   A   S   T   N   P   D>

50              60              70              80              90
GAG TCT GCA AAA GGA CCT AAT CTT ACC GTA ATA AGC AAA AAA ATT ACA
CTC AGA CGT TTT CCT GGA TTA GAA TGG CAT TAT TCG TTT TTT TAA TGT
 E   S   A   K   G   P   N   L   T   V   I   S   K   K   I   T>

100             110             120             130             140
GAT TCT AAT GCA TTT TTA CTG GCT GTG AAA GAA GTT GAG GCT TTG CTT
CTA AGA TTA CGT AAA AAT GAC CGA CAC TTT CTT CAA CTC CGA AAC GAA
 D   S   N   A   F   L   L   A   V   K   E   V   E   A   L   L>

150             160             170             180             190
TCA TCT ATA GAT GAA CTT TCT AAA GCT ATT GGT AAA AAA ATA AAA AAT
AGT AGA TAT CTA CTT GAA AGA TTT CGA TAA CCA TTT TTT TAT TTT TTA
 S   S   I   D   E   L   S   K   A   I   G   K   K   I   K   N>

200             210             220             230             240
GAT GGT ACT TTA GAT AAC GAA GCA AAT CGA AAC GAA TCA TTG ATA GCA
CTA CCA TGA AAT CTA TTG CTT CGT TTA GCT TTG CTT AGT AAC TAT CGT
 D   G   T   L   D   N   E   A   N   R   N   E   S   L   I   A>

250             260             270             280
GGA GCT TAT GAA ATA TCA AAA CTA ATA ACA CAA AAA TTA AGT GTA TTG
CCT CGA ATA CTT TAT AGT TTT GAT TAT TGT GTT TTT AAT TCA CAT AAC
 G   A   Y   E   I   S   K   L   I   T   Q   K   L   S   V   L>

290             300             310             320             330
AAT TCA GAA GAA TTA AAG GAA AAA ATT AAA GAG GCT AAG GAT TGT TCC
TTA AGT CTT CTT AAT TTC CTT TTT TAA TTT CTC CGA TTC CTA ACA AGG
 N   S   E   E   L   K   E   K   I   K   E   A   K   D   C   S>

340             350             360             370             380
GAA AAA TTT ACT ACT AAG CTA AAA GAT AGT CAT GCA GAG CTT GGT ATA
CTT TTT AAA TGA TGA TTC GAT TTT CTA TCA GTA CGT CTC GAA CCA TAT
 E   K   F   T   T   K   L   K   D   S   H   A   E   L   G   I>

390             400             410             420             430
CAA AGC GTT CAG GAT GAT AAT GCA AAA AAA GCT ATT TTA AAA ACA CAT
GTT TCG CAA GTC CTA CTA TTA CGT TTT TTT CGA TAA AAT TTT TGT GTA
 Q   S   V   Q   D   D   N   A   K   K   A   I   L   K   T   H>

440             450             460             470             480
GGA ACT AAA GAC AAG GGT GCT AAA GAA CTT GAA GAG TTA TTT AAA TCA
CCT TGA TTT CTG TTC CCA CGA TTT CTT GAA CTT CTC AAT AAA TTT AGT
 G   T   K   D   K   G   A   K   E   L   E   E   L   F   K   S>

490             500             510             520
CTA GAA AGC TTG TCA AAA GCA GCG CAA GCA GCA TTA ACT AAT TCA GTT
GAT CTT TCG AAC AGT TTT CGT CGC GTT CGT CGT AAT TGA TTA AGT CAA
 L   E   S   L   S   K   A   A   Q   A   A   L   T   N   S   V>
```

FIG. 41A

```
        530         540         550         560         570
    AAA GAG CTT ACA AAT CCT GTT GTG GCA GAA AGT CCA AAA AAA CCT TCC
    TTT CTC GAA TGT TTA GGA CAA CAC CGT CTT TCA GGT TTT TTT GGA AGG
     K   E   L   T   N   P   V   V   A   E   S   P   K   K   P   S>

580         590         600         610         620
    ATG GCC GTT TCA GTA GAT TTG CCT GGT GAA ATG AAA GTT CTT GTA AGC
    TAC CGG CAA AGT CAT CTA AAC GGA CCA CTT TAC TTT CAA GAA CAT TCG
     M   A   V   S   V   D   L   P   G   E   M   K   V   L   V   S>

630         640         650         660         670
    AAA GAA AAA AAC AAA GAC GGC AAG TAC GAT CTA ATT GCA ACA GTA GAC
    TTT CTT TTT TTG TTT CTG CCG TTC ATG CTA GAT TAA CGT TGT CAT CTG
     K   E   K   N   K   D   G   K   Y   D   L   I   A   T   V   D>

680         690         700         710         720
    AAG CTT GAG CTT AAA GGA ACT TCT GAT AAA AAC AAT GGA TCT GGA GTA
    TTC GAA CTC GAA TTT CCT TGA AGA CTA TTT TTG TTA CCT AGA CCT CAT
     K   L   E   L   K   G   T   S   D   K   N   N   G   S   G   V>

730         740         750         760
    CTT GAA GGC GTA AAA GCT GAC AAA AGT AAA GTA AAA TTA ACA ATT TCT
    GAA CTT CCG CAT TTT CGA CTG TTT TCA TTT CAT TTT AAT TGT TAA AGA
     L   E   G   V   K   A   D   K   S   K   V   K   L   T   I   S>

770         780         790         800         810
    GAC GAT CTA GGT CAA ACC ACA CTT GAA GTT TTC AAA GAA GAT GGC AAA
    CTG CTA GAT CCA GTT TGG TGT GAA CTT CAA AAG TTT CTT CTA CCG TTT
     D   D   L   G   Q   T   T   L   E   V   F   K   E   D   G   K>

820         830         840         850         860
    ACA CTA GTA TCA AAA AAA GTA ACT TCC AAA GAC AAG TCA TCA ACA GAA
    TGT GAT CAT AGT TTT TTT CAT TGA AGG TTT CTG TTC AGT AGT TGT CTT
     T   L   V   S   K   K   V   T   S   K   D   K   S   S   T   E>

870         880         890         900         910
    GAA AAA TTC AAT GAA AAA GGT GAA GTA TCT GAA AAA ATA ATA ACA AGA
    CTT TTT AAG TTA CTT TTT CCA CTT CAT AGA CTT TTT TAT TAT TGT TCT
     E   K   F   N   E   K   G   E   V   S   E   K   I   I   T   R>

920         930         940         950         960
    GCA GAC GGA ACC AGA CTT GAA TAC ACA GGA ATT AAA AGC GAT GGA TCT
    CGT CTG CCT TGG TCT GAA CTT ATG TGT CCT TAA TTT TCG CTA CCT AGA
     A   D   G   T   R   L   E   Y   T   G   I   K   S   D   G   S>

970         980         990         1000
    GGA AAA GCT AAA GAG GTT TTA AAA AAA TTT ACT CTT GAA GGA AAA GTA
    CCT TTT CGA TTT CTC CAA AAT TTT TTT AAA TGA GAA CTT CCT TTT CAT
     G   K   A   K   E   V   L   K   K   F   T   L   E   G   K   V>

1010        1020        1030        1040        1050
    GCT AAT GAT AAA GTA ACA TTG GAA GTA AAA GAA GGA ACC GTT ACT TTA
    CGA TTA CTA TTT CAT TGT AAC CTT CAT TTT CTT CCT TGG CAA TGA AAT
     A   N   D   K   V   T   L   E   V   K   E   G   T   V   T   L>

1060        1070        1080        1090        1100
    AGT AAG AAC ATT TCA AAA TCT GGG GAA GTT TCA GTT GAA CTT AAT GAC
```

FIG. 41B

```
              TCA TTC TTG TAA AGT TTT AGA CCC CTT CAA AGT CAA CTT GAA TTA CTG
               S   K   N   I   S   K   S   G   E   V   S   V   E   L   N   D>

1110        1120        1130        1140        1150
              ACT GAC AGT AGT GCT GCT ACT AAA AAA ACT GCA GCT TGG AAT TCA AAA
              TGA CTG TCA TCA CGA CGA TGA TTT TTT TGA CGT CGA ACC TTA AGT TTT
               T   D   S   S   A   A   T   K   K   T   A   A   W   N   S   K>

1160        1170        1180        1190        1200
              ACT TCT ACT TTA ACA ATT AGT GTT AAC AGC AAA AAA ACT ACA CAA CTT
              TGA AGA TGA AAT TGT TAA TCA CAA TTG TCG TTT TTT TGA TGT GTT GAA
               T   S   T   L   T   I   S   V   N   S   K   K   T   T   Q   L>

1210        1220        1230        1240
              GTG TTT ACT AAA CAA GAC ACA ATA ACT GTA CAA AAA TAC GAC TCC GCA
              CAC AAA TGA TTT GTT CTG TGT TAT TGA CAT GTT TTT ATG CTG AGG CGT
               V   F   T   K   Q   D   T   I   T   V   Q   K   Y   D   S   A>

1250        1260        1270        1280        1290
              GGT ACC AAT TTA GAA GGC ACA GCA GTC GAA ATT AAA ACA CTT GAT GAA
              CCA TGG TTA AAT CTT CCG TGT CGT CAG CTT TAA TTT TGT GAA CTA CTT
               G   T   N   L   E   G   T   A   V   E   I   K   T   L   D   E>

1300        1310
      CTT AAA AAC GCT TTA AAA TAA
      GAA TTT TTG CGA AAT TTT ATT
       L   K   N   A   L   K   *>
```

FIG. 41C

```
          10              20              30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50              60              70              80              90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

100             110             120             130             140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150             160             170             180             190
TTG CTG TCA TCT ATA GAT GAA ATT GCT GCT AAA GCT ATT GCT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200             210             220             230             240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

250             260             270             280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290             300             310             320             330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

340             350             360             370             380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390             400             410             420             430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440             450             460             470             480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

490             500             510             520
TTT GAA TCA GTA GAG GTC TTG TCA AAA GCA GCT AAA CAG ATG CTT GCT
AAA CTT AGT CAT CTC CAG AAC AGT TTT CGT CGA TTT GTC TAC GAA CGA
 F   E   S   V   E   V   L   S   K   A   A   K   E   M   L   A>
```

FIG. 42A

```
      530           540           550           560           570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
 N   S   V   K   E   L   T   S   P   V   V   A   E   S   P   K>

580           590           600           610           620
AAA CCT TCC ATG GCC AAG CAA AAT GTT TCT GAA AAA ATA ATA ACA AGA
TTT GGA AGG TAC CGG TTC GTT TTA CAA AGA CTT TTT TAT TAT TGT TCT
 K   P   S   M   A   K   Q   N   V   S   E   K   I   I   T   R>

630           640           650           660           670
GCA GAC GGA ACC AGA CTT GAA TAC ACA GGA ATT AAA AGC GAT GGA TCT
CGT CTG CCT TGG TCT GAA CTT ATG TGT CCT TAA TTT TCG CTA CCT AGA
 A   D   G   T   R   L   E   Y   T   G   I   K   S   D   G   S>

680           690           700           710       720
    GGA AAA GCT AAA GAG GTT TTA AAA GGC TAT GTT CTT GAA GGA ACT CTA
    CCT TTT CGA TTT CTC CAA AAT TTT CCG ATA CAA GAA CTT CCT TGA GAT
     G   K   A   K   E   V   L   K   G   Y   V   L   E   G   T   L>

730           740           750           760
ACT GCT GAA AAA ACA ACA TTG GTG GTT AAA GAA GGA ACT GTT ACT TTA
TGA CGA CTT TTT TGT TGT AAC CAC CAA TTT CTT CCT TGA CAA TGA AAT
 T   A   E   K   T   T   L   V   V   K   E   G   T   V   T   L>

770           780           790           800           810
AGC AAA AAT ATT TCA AAA TCT GGG GAA GTT TCA GTT GAA CTT AAT GAC
TCG TTT TTA TAA AGT TTT AGA CCC CTT CAA AGT CAA CTT GAA TTA CTG
 S   K   N   I   S   K   S   G   E   V   S   V   E   L   N   D>

820           830           840           850           860
ACT GAC AGT AGT GCT GCT ACT AAA AAA ACT GCA GCT TGG AAT TCA GGC
TGA CTG TCA TCA CGA CGA TGA TTT TTT TGA CGT CGA ACC TTA AGT CCG
 T   D   S   S   A   A   T   K   K   T   A   A   W   N   S   G>

870           880           890           900           910
ACT TCA ACT TTA ACA ATT ACT GTA AAC AGT AAA AAA ACT AAA GAC CTT
TGA AGT TGA AAT TGT TAA TGA CAT TTG TCA TTT TTT TGA TTT CTG GAA
 T   S   T   L   T   I   T   V   N   S   K   K   T   K   D   L>

920           930           940           950           960
GTG TTT ACA AAA GAA AAC ACA ATT ACA GTA CAA CAA TAC GAC TCA AAT
CAC AAA TGT TTT CTT TTG TGT TAA TGT CAT GTT GTT ATG CTG AGT TTA
 V   F   T   K   E   N   T   I   T   V   Q   Q   Y   D   S   N>

970           980           990           1000
GGC ACC AAA TTA GAG GGG TCA GCA GTT GAA ATT ACA AAA CTT GAT GAA
CCG TGG TTT AAT CTC CCC AGT CGT CAA CTT TAA TGT TTT GAA CTA CTT
 G   T   K   L   E   G   S   A   V   E   I   T   K   L   D   E>

1010          1020
ATT AAA AAC GCT TTA AAA TAA
TAA TTT TTG CGA AAT TTT ATT
 I   K   N   A   L   K   *>
```

FIG. 42B

```
            10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50                  60                  70                  80                  90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150                 160                 170                 180                 190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200                 210                 220                 230                 240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

250                 260                 270                 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K - L>

290                 300                 310                 320                 330
GAT GGA TTG AAA AAT GAA GGA TTA AAG GAA AAA ATT GAT GCG GCT AA G
CTA CCT AAC TTT TTA CTT CCT AAT TTC CTT TTT TAA CTA CGC CGA TT C
 D   G   L   K   N   E   G   L   K   E   K   I   D   A   A   K>

340                 350                 360                 370                 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390                 400                 410                 420                 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440                 450                 460                 470                 480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

490                 500                 510                 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 43A

```
530             540             550             560             570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
 N   S   V   K   E   L   T   S   P   V   V   A   E   S   P   K>

580             590             600             610             620
AAA CCT TCC ATG GCC AAG CAA AAT GTA TCT GAA AAA ATA ATA ACA AGA
TTT GGA AGG TAC CGG TTC GTT TTA CAT AGA CTT TTT TAT TAT TGT TCT
 K   P   S   M   A   K   Q   N   V   S   E   K   I   I   T   R>

630             640             650             660             670
GCA GAC GGA ACC AGA CTT GAA TAC ACA GGA ATT AAA AGC GAT GGA TCT
CGT CTG CCT TGG TCT GAA CTT ATG TGT CCT TAA TTT TCG CTA CCT AGA
 A   D   G   T   R   L   E   Y   T   G   I   K   S   D   G   S>

680             690             700             710             720
GGA AAA GCT AAA GAG GTT TTA AAA GGC TAT GTT CTT GAA GGA ACT CTA
CCT TTT CGA TTT CTC CAA AAT TTT CCG ATA CAA GAA CTT CCT TGA GAT
 G   K   A   K   E   V   L   K   G   Y   V   L   E   G   T   L>

730             740             750             760
ACT GCT GAA AAA ACA ACA TTG GTG GTT AAA GAA GGA ACT GTT ACT TTA
TGA CGA CTT TTT TGT TGT AAC CAC CAA TTT CTT CCT TGA CAA TGA AAT
 T   A   E   K   T   T   L   V   V   K   E   G   T   V   T   L>

770             780             790             800             810
AGC AAA AAT ATT TCA AAA TCT GGG GAA GTT TCA GTT GAA CTT AAT GAC
TCG TTT TTA TAA AGT TTT AGA CCC CTT CAA AGT CAA CTT GAA TTA CTG
 S   K   N   I   S   K   S   G   E   V   S   V   E   L   N   D>

820             830             840             850             860
ACT GAC AGT AGT GCT GCT ACT AAA AAA ACT GCA GCT TGG AAT TCA AAA
TGA CTG TCA TCA CGA CGA TGA TTT TTT TGA CGT CGA ACC TTA AGT TTT
 T   D   S   S   A   A   T   K   K   T   A   A   W   N   S   K>

870             880             890             900             910
ACT TCC ACT TTA ACA ATT AGT GTG AAT AGC CAA AAA ACC AAA AAC CTT
TGA AGG TGA AAT TGT TAA TCA CAC TTA TCG GTT TTT TGG TTT TTG GAA
 T   S   T   L   T   I   S   V   N   S   Q   K   T   K   N   L>

920             930             940             950             960
GTA TTC ACA AAA GAA GAC ACA ATA ACA GTA CAA AAA TAC GAC TCA GCA
CAT AAG TGT TTT CTT CTG TGT TAT TGT CAT GTT TTT ATG CTG AGT CGT
 V   F   T   K   E   D   T   I   T   V   Q   K   Y   D   S   A>

970             980             990             1000
GGC ACC AAT CTA GAA GGC AAA GCA GTC GAA ATT ACA ACA CTT AAA GAA
CCG TGG TTA GAT CTT CCG TTT CGT CAG CTT TAA TGT TGT GAA TTT CTT
 G   T   N   L   E   G   K   A   V   E   I   T   T   L   K   E>

?10             1020
CTT AAA AAC GCT TTA AAA TAA
GAA TTT TTG CGA AAT TTT ATT
 L   K   N   A   L   K   *>
```

FIG. 43B

```
         10                 20                 30                 40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50                 60                 70                 80                 90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

100                110                120                130                140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150                160                170                180                190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200                210                220                230                240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

250                260                270                280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290                300                310                320                330
GAT GGA TTG AAA AAT GAA GGA TTA AAG GAA AAA ATT GAT GCG CCT AAG
CTA CCT AAC TTT TTA CTT CCT AAT TTC CTT TTT TAA CTA CGC GGA TTC
 D   G   L   K   N   E   G   L   K   E   K   I   D   A   A   K>

340                350                360                370                380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390                400                410                420                430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440                450                460                470                480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

490                500                510                520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 44A

```
      530           540           550           560           570
     AAT TCA GTT AAA GAG CTT ACA AGC CCT GTT GTG GCA GAA AGT CCA AAA
     TTA AGT CAA TTT CTC GAA TGT TCG GGA CAA CAC CGT CTT TCA GGT TTT
      N   S   V   K   E   L   T   S   P   V   V   A   E   S   P   K>

580           590           600           610           620
     AAA CCT TCC ATG GCC AAG CAA AAT GTA TCT GAA AAA ATA ATA ACA AGA
     TTT GGA AGG TAC CGG TTC GTT TTA CAT AGA CTT TTT TAT TAT TGT TCT
      K   P   S   M   A   K   Q   N   V   S   E   K   I   I   T   R>

630           640           650           660           670
     GCA GAC GGA ACC AGA CTT GAA TAC ACA GGA ATT AAA AGC GAT GGA TCT
     CGT CTG CCT TGG TCT GAA CTT ATG TGT CCT TAA TTT TCG CTA CCT AGA
      A   D   G   T   R   L   E   Y   T   G   I   K   S   D   G   S>

680           690           700           710           720
     GGA AAA GCT AAA GAG GTT TTA AAA GGC TAT GTT CTT GAA GGA ACT CTA
     CCT TTT CGA TTT CTC CAA AAT TTT CCG ATA CAA GAA CTT CCT TGA GAT
      G   K   A   K   E   V   L   K   G   Y   V   L   E   G   T   L>

730           740           750           760
     ACT GCT GAA AAA ACA ACA TTG GTG GTT AAA GAA GGA ACT GTT ACT TTA
     TGA CGA CTT TTT TGT TGT AAC CAC CAA TTT CTT CCT TGA CAA TGA AAT
      T   A   E   K   T   T   L   V   V   K   E   G   T   V   T   L>

770           780           790           800           810
     AGC AAA AAT ATT TCA AAA TCT GGG GAA GTT TCA GTT GAA CTT AAT GAC
     TCG TTT TTA TAA AGT TTT AGA CCC CTT CAA AGT CAA CTT GAA TTA CTG
      S   K   N   I   S   K   S   G   E   V   S   V   E   L   N   D>

820           830           840           850           860
     ACT GAC AGT AGT GCT GCT ACT AAA AAA ACT GCA GCT TGG AAT TCA AAA
     TGA CTG TCA TCA CGA CGA TGA TTT TTT TGA CGT CGA ACC TTA AGT TTT
      T   D   S   S   A   A   T   K   K   T   A   A   W   N   S   K>

870           880           890           900           910
     ACT TCT ACT TTA ACA ATT AGT GTT AAC AGC AAA AAA ACT ACA CAA CTT
     TGA AGA TGA AAT TGT TAA TCA CAA TTG TCG TTT TTT TGA TGT GTT GAA
      T   S   T   L   T   I   S   V   N   S   K   K   T   T   Q   L>

920           930           940           950           960
     GTG TTT ACT AAA CAA GAC ACA ATA ACT GTA CAA AAA TAC GAC TCC GCA
     CAC AAA TGA TTT GTT CTG TGT TAT TGA CAT GTT TTT ATG CTG AGG CGT
      V   F   T   K   Q   D   T   I   T   V   Q   K   Y   D   S   A>

970           980           990           1000
     GGT ACC AAT TTA GAA GGC ACA GCA GTC GAA ATT AAA ACA CTT GAT GAA
     CCA TGG TTA AAT CTT CCG TGT CGT CAG CTT TAA TTT TGT GAA CTA CTT
      G   T   N   L   E   G   T   A   V   E   I   K   T   L   D   E>

1010          1020
     CTT AAA AAC GCT TTA AAA TAA
     GAA TTT TTG CGA AAT TTT ATT
      L   K   N   A   L   K   *>
```

FIG. 44B

```
              10               20              30              40
   ATG GCT TGT AAT AAT TCA GGG AAA GAT GGG AAT ACA TCT GCA AAT TCT
   TAC CGA ACA TTA TTA AGT CCC TTT CTA CCC TTA TGT AGA CGT TTA AGA
    M   A   C   N   N   S   G   K   D   G   N   T   S   A   N   S>

50              60              70              80              90
   GCT GAT GAG TCT GTT AAA GGG CCT AAT CTT ACA GAA ATA AGT AAA AAA
   CGA CTA CTC AGA CAA TTT CCC GGA TTA GAA TGT CTT TAT TCA TTT TTT
    A   D   E   S   V   K   G   P   N   L   T   E   I   S   K   K>

100             110             120             130             140
   ATT ACG GAT TCT AAT GCG GTT TTA CTT GCT GTG AAA GAG GTT GAA GCG
   TAA TGC CTA AGA TTA CGC CAA AAT GAA CGA CAC TTT CTC CAA CTT CGC
    I   T   D   S   N   A   V   L   L   A   V   K   E   V   E   A>

150             160             170             180             190
   TTG CTG TCA TCT ATA GAT GAA ATT GCT GCT AAA GCT ATT GGT AAA AAA
   AAC GAC AGT AGA TAT CTA CTT TAA CGA CGA TTT CGA TAA CCA TTT TTT
    L   L   S   S   I   D   E   I   A   A   K   A   I   G   K   K>

200             210             220             230             240
   ATA CAC CAA AAT AAT GGT TTG GAT ACC GAA TAT AAT CAC AAT GGA TCA
   TAT GTG GTT TTA TTA CCA AAC CTA TGG CTT ATA TTA GTG TTA CCT AGT
    I   H   Q   N   N   G   L   D   T   E   Y   N   H   N   G   S>

250             260             270             280
   TTG TTA GCG GGA GCT TAT GCA ATA TCA ACC CTA ATA AAA CAA AAA TTA
   AAC AAT CGC CCT CGA ATA CGT TAT AGT TGG GAT TAT TTT GTT TTT AAT
    L   L   A   G   A   Y   A   I   S   T   L   I   K   Q   K   L>

290             300             310             320             330
   GAT GGA TTG AAA AAT GAA GGA TTA AAG GAA AAA ATT GAT GCG GCT AAG
   CTA CCT AAC TTT TTA CTT CCT AAT TTC CTT TTT TAA CTA CGC CGA TTC
    D   G   L   K   N   E   G   L   K   E   K   I   D   A   A   K>

340             350             360             370             380
   AAA TGT TCT GAA ACA TTT ACT AAT AAA TTA AAA GAA AAA CAC ACA GAT
   TTT ACA AGA CTT TGT AAA TGA TTA TTT AAT TTT CTT TTT GTG TGT CTA
    K   C   S   E   T   F   T   N   K   L   K   E   K   H   T   D>

390             400             410             420             430
   CTT GGT AAA GAA GGT GTT ACT GAT GCT GAT GCA AAA GAA GCC ATT TTA
   GAA CCA TTT CTT CCA CAA TGA CTA CGA CTA CGT TTT CTT CGG TAA AAT
    L   G   K   E   G   V   T   D   A   D   A   K   E   A   I   L>

440             450             460             470             480
   AAA ACA AAT GGT ACT AAA ACT AAA GGT GCT GAA GAA CTT GGA AAA TTA
   TTT TGT TTA CCA TGA TTT TGA TTT CCA CGA CTT CTT GAA CCT TTT AAT
    K   T   N   G   T   K   T   K   G   A   E   E   L   G   K   L>

490             500             510             520
   TTT GAA TCA GTA GAG GTC TTG TCA AAA GCA GCT AAA GAG ATG CTT GCT
   AAA CTT AGT CAT CTC CAG AAC AGT TTT CGT CGA TTT CTC TAC GAA CGA
    F   E   S   V   E   V   L   S   K   A   A   K   E   M   L   A>
```

FIG. 45A

```
       530           540           550           560           570
    AAT TCA GTT AAA GAG CTT ACA AGC CCT GTT GTG GCA GAA AGT CCA AAA
    TTA AGT CAA TTT CTC GAA TGT TCG GGA CAA CAC CGT CTT TCA GGT TTT
     N   S   V   K   E   L   T   S   P   V   V   A   E   S   P   K>

580           590           600           610           620
    AAA CCT TCC ATG GCC AAG CAA AAT GTT ACA TCT GAA AAA ACA ATA GTA
    TTT GGA AGG TAC CGG TTC GTT TTA CAA TGT AGA CTT TTT TGT TAT CAT
     K   P   S   M   A   K   Q   N   V   T   S   E   K   T   I   V>

630           640           650           660           670
    AGA GCA AAT GGA ACC AGA CTT GAA TAC ACA GAC ATA AAA AGC GAT GGA
    TCT CGT TTA CCT TGG TCT GAA CTT ATG TGT CTG TAT TTT TCG CTA CCT
     R   A   N   G   T   R   L   E   Y   T   D   I   K   S   D   G>

680           690           700           710           720
    TCC GGA AAA GCT AAA GAA GTT TTA AAA GAC TTT ACT CTT GAA GGA ACT
    AGG CCT TTT CGA TTT CTT CAA AAT TTT CTG AAA TGA GAA CTT CCT TGA
     S   G   K   A   K   E   V   L   K   D   F   T   L   E   G   T>

730           740           750           760
    CTA GCT GCT GAC GGC AAA ACA ACA TTG AAA GTT ACA GAA GGC ACT GTT
    GAT CGA CGA CTG CCG TTT TGT TGT AAC TTT CAA TGT CTT CCG TGA CAA
     L   A   A   D   G   K   T   T   L   K   V   T   E   G   T   V>

770           780           790           800           810
    GTT TTA AGC AAG AAC ATT TTA AAA TCC GGA GAA ATA ACA GTT GCA CTT
    CAA AAT TCG TTC TTG TAA AAT TTT AGG CCT CTT TAT TGT CAA CGT GAA
     V   L   S   K   N   I   L   K   S   G   E   I   T   V   A   L>

820           830           840           850           860
    GAT GAC TCT GAC ACT ACT CAG GCT ACT AAA AAA ACT GGA AAA TGG GAT
    CTA CTG AGA CTG TGA TGA GTC CGA TGA TTT TTT TGA CCT TTT ACC CTA
     D   D   S   D   T   T   Q   A   T   K   K   T   G   K   W   D>

870           880           890           900           910
    TCA AAT ACT TCC ACT TTA ACA ATT AGT GTG AAT AGC AAA AAA ACT AAA
    AGT TTA TGA AGG TGA AAT TGT TAA TCA CAC TTA TCG TTT TTT TGA TTT
     S   N   T   S   T   L   T   I   S   V   N   S   K   K   T   K>

920           930           940           950           960
    AAC ATT GTA TTT ACA AAA GAA GAC ACA ATA ACA GTA CAA AAA TAC GAC
    TTG TAA CAT AAA TGT TTT CTT CTG TGT TAT TGT CAT GTT TTT ATG CTG
     N   I   V   F   T   K   E   D   T   I   T   V   Q   K   Y   D>

970           980           990           1000
    TCA GCA GGC ACC AAT CTA GAA GGC AAC GCA GTC GAA ATT AAA ACA CTT
    AGT CGT CCG TGG TTA GAT CTT CCG TTG CGT CAG CTT TAA TTT TGT GAA
     S   A   G   T   N   L   E   G   N   A   V   E   I   K   T   L>

1010          1020          1030
    GAT GAA CTT AAA AAC GCT TTA AAA TAG
    CTA CTT GAA TTT TTG CGA AAT TTT ATC
     D   E   L   K   N   A   L   K   *>
```

FIG. 45B

```
              10                  20                  30                  40
 ATG GCT TGT AAT AAT TCA GGG AAA GAT GGG AAT ACA TCT GCA AAT TCT
 TAC CGA ACA TTA TTA AGT CCC TTT CTA CCC TTA TGT AGA CGT TTA AGA
  M   A   C   N   N   S   G   K   D   G   N   T   S   A   N   S>

50                  60                  70                  80                  90
 GCT GAT GAG TCT GTT AAA GGG CCT AAT CTT ACA GAA ATA AAT AAA AAA
 CGA CTA CTC AGA CAA TTT CCC GGA TTA GAA TGT CTT TAT TTA TTT TTT
  A   D   E   S   V   K   G   P   N   L   T   E   I   N   K   K>

100                 110                 120                 130                 140
 ATT ACG GAT TCT AAT GCG GTT TTA CTT GCT GTG AAA GAG GTT GAA GCG
 TAA TGC CTA AGA TTA CGC CAA AAT GAA CGA CAC TTT CTC CAA CTT CGC
  I   T   D   S   N   A   V   L   L   A   V   K   E   V   E   A>

150                 160                 170                 180                 190
 TTG CTG TCA TCT ATA GAT GAA ATT GCT GCT AAA GCT ATT GGT AAA AAA
 AAC GAC AGT AGA TAT CTA CTT TAA CGA CGA TTT CGA TAA CCA TTT TTT
  L   L   S   S   I   D   E   I   A   A   K   A   I   G   K   K>

200                 210                 220                 230                 240
 ATA CAC CAA AAT AAT GGT TTG GAT ACC GAA AAT AAT CAC AAT GGA TCA
 TAT GTG GTT TTA TTA CCA AAC CTA TGG CTT TTA TTA GTG TTA CCT AGT
  I   H   Q   N   N   G   L   D   T   E   N   N   H   N   G   S>

250                 260                 270                 280
 TTG TTA GCG GGA GCT TAT GCA ATA TCA ACC CTA ATA AAA CAA AAA TTA
 AAC AAT CGC CCT CGA ATA CGT TAT AGT TGG GAT TAT TTT GTT TTT AAT
  L   L   A   G   A   Y   A   I   S   T   L   I   K   Q   K   L>

290                 300                 310                 320                 330
 GAT GGA TTG AAA AAT GAA GGA TTA AAG GAA AAA ATT GAT GCG GCT AAG
 CTA CCT AAC TTT TTA CTT CCT AAT TTC CTT TTT TAA CTA CGC CGA TTC
  D   G   L   K   N   E   G   L   K   E   K   I   D   A   A   K>

340                 350                 360                 370                 380
 AAA TGT TCT GAA ACA TTT ACT AAT AAA TTA AAA GAA AAA CAC ACA GAT
 TTT ACA AGA CTT TGT AAA TGA TTA TTT AAT TTT CTT TTT GTG TGT CTA
  K   C   S   E   T   F   T   N   K   L   K   E   K   H   T   D>

390                 400                 410                 420                 430
 CTT GGT AAA GAA GGT GTT ACT GAT GCT GAT GCA AAA GAA GCC ATT TTA
 GAA CCA TTT CTT CCA CAA TGA CTA CGA CTA CGT TTT CTT CGG TAA AAT
  L   G   K   E   G   V   T   D   A   D   A   K   E   A   I   L>

440                 450                 460                 470                 480
 AAA GCA AAT GGT ACT AAA ACT AAA GGT GCT GAA GAA CTT GGA AAA TTA
 TTT CGT TTA CCA TGA TTT TGA TTT CCA CGA CTT CTT GAA CCT TTT AAT
  K   A   N   G   T   K   T   K   G   A   E   E   L   G   K   L>

490                 500                 510                 520
 TTT GAA TCA GTA GAG GTC TTG TCA AAA GCA GCT AAA GAG ATG CTT GCT
 AAA CTT AGT CAT CTC CAG AAC AGT TTT CGT CGA TTT CTC TAC GAA CGA
  F   E   S   V   E   V   L   S   K   A   A   K   E   M   L   A>
```

FIG. 46A

```
      530           540           550           560           570
     AAT TCA GTT AAA GAG CTT ACA AGC CCT GTT GTG GCA GAA AGT CCA AAA
     TTA AGT CAA TTT CTC GAA TGT TCG GGA CAA CAC CGT CTT TCA GGT TTT
      N   S   V   K   E   L   T   S   P   V   V   A   E   S   P   K>

580           590           600           610           620
     AAA CCT TCC ATG GCC GTT TCA GTA GAT TTG CCT GGT GAA ATG AAA GTT
     TTT GGA AGG TAC CGG CAA AGT CAT CTA AAC GGA CCA CTT TAC TTT CAA
      K   P   S   M   A   V   S   V   D   L   P   G   E   M   K   V>

630           640           650           660           670
     CTT GTA AGC AAA GAA AAA AAC AAA GAC GGC AAG TAC GAT CTA ATT GCA
     GAA CAT TCG TTT CTT TTT TTG TTT CTG CCG TTC ATG CTA GAT TAA CGT
      L   V   S   K   E   K   N   K   D   G   K   Y   D   L   I   A>

680           690           700           710           720
     ACA GTA GAC AAG CTT GAG CTT AAA GGA ACT TCT GAT AAA AAC AAT GGA
     TGT CAT CTG TTC GAA CTC GAA TTT CCT TGA AGA CTA TTT TTG TTA CCT
      T   V   D   K   L   E   L   K   G   T   S   D   K   N   N   G>

730           740           750           760
     TCT GGA GTA CTT GAA GGC GTA AAA GCT GAC AAA AGT AAA GTA AAA TTA
     AGA CCT CAT GAA CTT CCG CAT TTT CGA CTG TTT TCA TTT CAT TTT AAT
      S   G   V   L   E   G   V   K   A   D   K   S   K   V   K   L>

770           780           790           800           810
ACA ATT TCT GAC GAT CTA GGT CAA ACC ACA CTT GAA GTT TTC AAA GAA
TGT TAA AGA CTG CTA GAT CCA GTT TGG TGT GAA CTT CAA AAG TTT CTT
 T   I   S   D   D   L   G   Q   T   T   L   E   V   F   K   E>

820           830           840           850           860
     GAT GGC AAA ACA CTA GTA TCA AAA AAA GTA ACT TCC AAA GAC AAG TCA
     CTA CCG TTT TGT GAT CAT AGT TTT TTT CAT TGA AGG TTT CTG TTC AGT
      D   G   K   T   L   V   S   K   K   V   T   S   K   D   K   S>

870           880           890           900           910
     TCA ACA GAA GAA AAA TTC AAT GAA AAA GGT GAA GTA TCT GAA AAA ATA
     AGT TGT CTT CTT TTT AAG TTA CTT TTT CCA CTT CAT AGA CTT TTT TAT
      S   T   E   E   K   F   N   E   K   G   E   V   S   E   K   I>

920           930           940           950           960
     ATA ACA AGA GCA GAC GGA ACC AGA CTT GAA TAC ACA GGA ATT AAA AGC
     TAT TGT TCT CGT CTG CCT TGG TCT GAA CTT ATG TGT CCT TAA TTT TCG
      I   T   R   A   D   G   T   R   L   E   Y   T   G   I   K   S>

970           980           990           1000
     GAT GGA TCT GGA AAA GCT AAA GAG GTT TTA AAA GGC TTT ACT CTT GAA
     CTA CCT AGA CCT TTT CGA TTT CTC CAA AAT TTT CCG AAA TGA GAA CTT
      D   G   S   G   K   A   K   E   V   L   K   G   F   T   L   E>

1010          1020          1030          1040          1050
     GGA AAA GTA GCT AAT GAT AAA GTA ACA TTG GAA GTA AAA GAA GGA ACC
     CCT TTT CAT CGA TTA CTA TTT CAT TGT AAC CTT CAT TTT CTT CCT TGG
      G   K   V   A   N   D   K   V   T   L   E   V   K   E   G   T>

1060          1070          1080          1090          1100
     GTT ACT TTA AGT AAG ATT TCA AAA TCT GGG GAA GTT TCA GTT GAA CTT
```

FIG. 46B

```
                    CAA TGA AAT TCA TTC TAA AGT TTT AGA CCC CTT CAA AGT CAA CTT GAA
                     V   T   L   S   K   I   S   K   S   G   E   V   S   V   E   L>

1110           1120           1130           1140           1150
        AAT GAC ACT GAC AGT AGT GCT GCT ACT AAA AAA ACT GCA GCT TGG AAT
        TTA CTG TGA CTG TCA TCA CGA CGA TGA TTT TTT TGA CGT CGA ACC TTA
         N   D   T   D   S   S   A   A   T   K   K   T   A   A   W   N>

1160           1170           1180           1190           1200
        TCA AAA ACT TCT ACT TTA ACA ATT AGT GTT AAC AGC AAA AAA ACT ACA
        AGT TTT TGA AGA TGA AAT TGT TAA TCA CAA TTG TCG TTT TTT TGA TGT
         S   K   T   S   T   L   T   I   S   V   N   S   K   K   T   T>

1210           1220           1230           1240
        CAA CTT GTG TTT ACT AAA CAA GAC ACA ATA ACT GTA CAA AAA TAC GAC
        GTT GAA CAC AAA TGA TTT GTT CTG TGT TAT TGA CAT GTT TTT ATG CTG
         Q   L   V   F   T   K   Q   D   T   I   T   V   Q   K   Y   D>

1250           1260           1270           1280           1290
        TCC GCA GGT ACC AAT TTA GAA GGC ACA GCA GTC GAA ATT AAA ACA CTT
        AGG CGT CCA TGG TTA AAT CTT CCG TGT CGT CAG CTT TAA TTT TGT GAA
         S   A   G   T   N   L   E   G   T   A   V   E   I   K   T   L>

1300           1310           1320
        GAT GAA CTT AAA AAC GCT TTA AAA TAA
        CTA CTT GAA TTT TTG CGA AAT TTT ATT
         D   E   L   K   N   A   L   K   *>
```

FIG. 46C

```
                10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50                  60                  70                  80                  90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
 A   D   E   S   V   K   G   P   N   L   T   E   I   S   K   K>

100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150                 160                 170                 180                 190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
 L   L   S   S   I   D   E   L   A   K   A   I   G   K   K   I>

200                 210                 220                 230                 240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
 K   N   D   G   S   L   D   N   E   A   N   R   N   E   S   L>

250                 260                 270                 280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
 L   A   G   A   Y   T   I   S   T   L   I   T   Q   K   L   S>

290                 300                 310                 320                 330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
 K   L   N   G   S   E   G   L   K   E   K   I   A   A   A   K>

340                 350                 360                 370                 380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
 K   C   S   E   E   F   S   T   K   L   K   D   N   H   A   Q>

390                 400                 410                 420                 430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
 L   G   I   Q   G   V   T   D   E   N   A   K   K   A   I   L>

440                 450                 460                 470                 480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
 K   A   N   A   A   G   K   D   K   G   V   E   E   L   E   K>

490                 500                 510                 520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
 L   S   G   S   L   E   S   L   S   K   A   A   K   E   M   L>
```

FIG. 47A

```
    530             540             550             560             570
GCT AAT TCA GTT AAA GAG CTT ACA AGC CCT GTT GTC CAT GGC GTT TCA
CGA TTA AGT CAA TTT CTC GAA TGT TCG GGA CAA CAG GTA CCG CAA AGT
 A   N   S   V   K   E   L   T   S   P   V   V   H   G   V   S>

580             590             600             610             620
GTA GAT TTG CCT GGT GAA ATG AAA GTT CTT GTA AGC AAA GAA AAA AAC
CAT CTA AAC GGA CCA CTT TAC TTT CAA GAA CAT TCG TTT CTT TTT TTG
 V   D   L   P   G   E   M   K   V   L   V   S   K   E   K   N>

630             640             650             660             670
AAA GAC GGC AAG TAC GAT CTA ATT GCA ACA GTA GAC AAG CTT GAG CTT
TTT CTG CCG TTC ATG CTA GAT TAA CGT TGT CAT CTG TTC GAA CTC GAA
 K   D   G   K   Y   D   L   I   A   T   V   D   K   L   E   L>

680             690             700             710             720
AAA GGA ACT TCT GAT AAA AAC AAT GGA TCT GGA GTA CTT GAA GGC GTA
TTT CCT TGA AGA CTA TTT TTG TTA CCT AGA CCT CAT GAA CTT CCG CAT
 K   G   T   S   D   K   N   N   G   S   G   V   L   E   G   V>

730             740             750             760
AAA GCT GAC AAA AGT AAA GTA AAA TTA ACA ATT TCT GAC GAT CTA GGT
TTT CGA CTG TTT TCA TTT CAT TTT AAT TGT TAA AGA CTG CTA GAT CCA
 K   A   D   K   S   K   V   K   L   T   I   S   D   D   L   G>

770             780             790             800             810
CAA ACC ACA CTT GAA GTT TTC AAA GAA GAT GGC AAA ACA CTA GTA TCA
GTT TGG TGT GAA CTT CAA AAG TTT CTT CTA CCG TTT TGT GAT CAT AGT
 Q   T   T   L   E   V   F   K   E   D   G   K   T   L   V   S>

820             830             840             850             860
AAA AAA GTA ACT TCC AAA GAC AAG TCA TCA ACA GAA GAA AAA TTC AAT
TTT TTT CAT TGA AGG TTT CTG TTC AGT AGT TGT CTT CTT TTT AAG TTA
 K   K   V   T   S   K   D   K   S   S   T   E   E   K   F   N>

870             880             890             900             910
GAA AAA GGT GAA GTA TCT GAA AAA ATA ATA ACA AGA GCA GAC GGA ACC
CTT TTT CCA CTT CAT AGA CTT TTT TAT TAT TGT TCT CGT CTG CCT TGG
 E   K   G   E   V   S   E   K   I   I   T   R   A   D   G   T>

920             930             940             950             960
AGA CTT GAA TAC ACA GGA ATT AAA AGC GAT GGA TCT GGA AAA GCT AAA
TCT GAA CTT ATG TGT CCT TAA TTT TCG CTA CCT AGA CCT TTT CGA TTT
 R   L   E   Y   T   G   I   K   S   D   G   S   G   K   A   K>

970             980             990             1000
GAG GTT TTA AAA GGC TTT ACT CTT GAA GGA AAA GTA GCT AAT GAT AAA
CTC CAA AAT TTT CCG AAA TGA GAA CTT CCT TTT CAT CGA TTA CTA TTT
 E   V   L   K   G   F   T   L   E   G   K   V   A   N   D   K>

1010            1020            1030            1040            1050
GTA ACA TTG GAA GTA AAA GAA GGA ACC GTT ACT TTA AGT AAG ATT TCA
CAT TGT AAC CTT CAT TTT CTT CCT TGG CAA TGA AAT TCA TTC TAA AGT
 V   T   L   E   V   K   E   G   T   V   T   L   S   K   I   S>

1060            1070            1080            1090            1100
AAA TCT GGG GAA GTT TCA GTT GAA CTT AAT GAC ACT GAC AGT AGT   GCT
```

FIG. 47B

```
TTT AGA CCC CTT CAA AGT CAA CTT GAA TTA CTG TGA CTG TCA TCA CGA
 K   S   G   E   V   S   V   E   L   N   D   T   D   S   S   A>

1110        1120        1130        1140        1150
GCT ACT AAA AAA ACT GCA GCT TGG AAT TCA AAA ACT TCT ACT TTA ACA
CGA TGA TTT TTT TGA CGT CGA ACC TTA AGT TTT TGA AGA TGA AAT TGT
 A   T   K   K   T   A   A   W   N   S   K   T   S   T   L   T>

1160        1170        1180        1190        1200
ATT AGT GTT AAC AGC AAA AAA ACT ACA CAA CTT GTG TTT ACT AAA CAA
TAA TCA CAA TTG TCG TTT TTT TGA TGT GTT GAA CAC AAA TGA TTT GTT
 I   S   V   N   S   K   K   T   T   Q   L   V   F   T   K   Q>

1210        1220        1230        1240
GAC ACA ATA ACT GTA CAA AAA TAC GAC TCC GCA GGT ACC AAT TTA GAA
CTG TGT TAT TGA CAT GTT TTT ATG CTG AGG CGT CCA TGG TTA AAT CTT
 D   T   I   T   V   Q   K   Y   D   S   A   G   T   N   L   E>

1250        1260        1270        1280        1290
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
 G   T   A   V   E   I   K   T   L   D   E   L   K   N   A   L>

1300
AAA TAA
TTT ATT
 K   *>
```

FIG. 47C

```
              10              20              30              40
               *               *               *               *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50              60              70              80              90
        *               *               *               *               *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100             110             120             130             140
        *               *               *               *               *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150             160             170             180             190
        *               *               *               *               *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200             210             220             230             240
        *               *               *               *               *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250             260             270             280
        *               *               *               *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290             300             310             320             330
  *               *               *               *               *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys >

340             350             360             370             380
        *               *               *               *               *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 48A

```
          390            400           410           420          430
           .              .             .             .            .
AAA GGT GAA GTA TCT GAA AAA ATA ATA ACA ATG GCA GAC GGA ACC AGA
TTT CCA CTT CAT AGA CTT TTT TAT TAT TGT TAC CGT CTG CCT TGG TCT
Lys Gly Glu Val Ser Glu Lys Ile Ile Thr Met Ala Asp Gly Thr Arg>

440            450           460           470          480
           .              .             .             .            .
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490            500           510           520
           .              .             .             .
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530            540           550           560          570
   .              .             .             .            .
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580            590           600           610          620
           .              .             .             .            .
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630            640           650           660          670
           .              .             .             .            .
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

680            690           700           710          720
           .              .             .             .            .
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

730            740           750           760
           .              .             .             .
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770            780           790           800          810
   .              .             .             .            .
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

820
 *
AAA TAA
TTT ATT
Lys ***>
```

FIG. 48B

```
              10            20            30            40
     .    .    .    .    .    .    .    .    .
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50            60            70            80            90
     .    .    .    .    .    .    .    .    .    .
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100           110           120           130           140
     .    .    .    .    .    .    .    .    .    .
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150           160           170           180           190
     .    .    .    .    .    .    .    .    .    .
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200           210           220           230           240
     .    .    .    .    .    .    .    .    .    .
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250           260           270           280
     .    .    .    .    .    .    .    .
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290           300           310           320           330
     .    .    .    .    .    .    .    .    .    .
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys >

340           350           360           370           380
     .    .    .    .    .    .    .    .    .    .
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 49A

```
           390              400              410              420              430
            .                .                .                .                .
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

440              450              460              470              480
            .                .                .                .                .
CTT GAA TAC ACA GGA ATT AAA AGC GAT GGA TCT GGA AAA GCT AAA TAT
GAA CTT ATG TGT CCT TAA TTT TCG CTA CCT AGA CCT TTT CGA TTT ATA
Leu Glu Tyr Thr Gly Ile Lys Ser Asp Gly Ser Gly Lys Ala Lys Tyr 490              500              510              520
            .                .                .                .
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530              540              550              560              570
   .                .                .                .                .
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser >

580              590              600              610              620
            .                .                .                .                .
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630              640              650              660              670
            .                .                .                .                .
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr >

680              690              700              710              720
            .                .                .                .                .
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

730              740              750              760
            .                .                .                .
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770              780              790              800              810
   .                .                .                .                .
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

820
   *
AAA TAA
TTT ATT
Lys ***>                    FIG. 49B
```

```
              10              20              30              40
         *         *      *         *    *         *    *         *    *
    ATG AAA AAA TAT TTA TTG GGA ATA GGT CTA ATA TTA GCC TTA ATA GCA
    TAC TTT TTT ATA AAT AAC CCT TAT CCA GAT TAT AAT CGG AAT TAT CGT
    Met Lys Lys Tyr Leu Leu Gly Ile Gly Leu Ile Leu Ala Leu Ile Ala>

50              60              70              80              90
      *      *         *      *         *      *         *      *      *
    TGT AAG CAA AAT GTT AGC AGC CTT GAC GAG AAA AAC AGC GTT TCA GTA
    ACA TTC GTT TTA CAA TCG TCG GAA CTG CTC TTT TTG TCG CAA AGT CAT
    Cys Lys Gln Asn Val Ser Ser Leu Asp Glu Lys Asn Ser Val Ser Val>

100             110             120             130             140
         *         *      *         *      *         *      *         *
    GAT TTG CCT GGT GAA ATG AAA GTT CTT GTA AGC AAA GAA AAA AAC AAA
    CTA AAC GGA CCA CTT TAC TTT CAA GAA CAT TCG TTT CTT TTT TTG TTT
    Asp Leu Pro Gly Glu Met Lys Val Leu Val Ser Lys Glu Lys Asn Lys>

150             160             170             180             190
      *         *      *         *      *         *      *         *      *
    GAC GGC AAG TAC GAT CTA ATT GCA ACA GTA GAC AAG CTT GAG CTT AAA
    CTG CCG TTC ATG CTA GAT TAA CGT TGT CAT CTG TTC GAA CTC GAA TTT
    Asp Gly Lys Tyr Asp Leu Ile Ala Thr Val Asp Lys Leu Glu Leu Lys>

200             210             220             230             240
         *         *      *         *      *         *      *         *
    GGA ACT TCT GAT AAA AAC AAT GGA TCT GGA GTA CTT GAA GGC GTA AAA
    CCT TGA AGA CTA TTT TTG TTA CCT AGA CCT CAT GAA CTT CCG CAT TTT
    Gly Thr Ser Asp Lys Asn Asn Gly Ser Gly Val Leu Glu Gly Val Lys>

250             260             270             280
       *         *      *         *      *         *      *         *
    GCT GAC AAA AGT AAA GTA AAA TTA ACA ATT TCT GAC GAT CTA GGT CAA
    CGA CTG TTT TCA TTT CAT TTT AAT TGT TAA AGA CTG CTA GAT CCA GTT
    Ala Asp Lys Ser Lys Val Lys Leu Thr Ile Ser Asp Asp Leu Gly Gln>

290             300             310             320             330
      *         *      *         *      *         *      *         *    *
    ACC ACA CTT GAA GTT TTC AAA GAA GAT GGC AAA ACA CTA GTA TCA AAA
    TGG TGT GAA CTT CAA AAG TTT CTT CTA CCG TTT TGT GAT CAT AGT TTT
    Thr Thr Leu Glu Val Phe Lys Glu Asp Gly Lys Thr Leu Val Ser Lys >

340             350             360             370             380
         *         *      *         *      *         *      *         *
    AAA GTA ACT TCC AAA GAC AAG TCA TCA ACA GAA GAA AAA TTC AAT GAA
    TTT CAT TGA AGG TTT CTG TTC AGT AGT TGT CTT CTT TTT AAG TTA CTT
    Lys Val Thr Ser Lys Asp Lys Ser Ser Thr Glu Glu Lys Phe Asn Glu>

FIG. 50A
```

```
        390           400           410           420           430
    *         *         *         *         *         *         *         *         *
AAA GGT GAA GTA TCT GAA AAA ATA ATA ACA ATG GCA GAC GGA ACC AGA
TTT CCA CTT CAT AGA CTT TTT TAT TAT TGT TAC CGT CTG CCT TGG TCT
Lys Gly Glu Val Ser Glu Lys Ile Ile Thr Met Ala Asp Gly Thr Arg>

440           450           460           470           480
    *         *         *         *         *         *         *         *         *         *
CTT GAA TAC ACA GGA ATT AAA AGC GAT GGA TCT GGA AAA GCT AAA TAT
GAA CTT ATG TGT CCT TAA TTT TCG CTA CCT AGA CCT TTT CGA TTT ATA
Leu Glu Tyr Thr Gly Ile Lys Ser Asp Gly Ser Gly Lys Ala Lys Tyr>

490           500           510           520
    *         *         *         *         *         *         *         *         *
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530           540           550           560           570
    *         *         *         *         *         *         *         *         *         *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580           590           600           610           620
    *         *         *         *         *         *         *         *         *         *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630           640           650           660           670
    *         *         *         *         *         *         *         *         *         *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

680           690           700           710           720
    *         *         *         *         *         *         *         *         *         *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

730           740           750           760
    *         *         *         *         *         *         *         *         *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770           780           790           800           810
    *         *         *         *         *         *         *         *         *         *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

820
    *
AAA TAA
TTT ATT
Lys ***>
```

FIG. 50B

```
         10             20             30             40
   .    *    .     *    .    *    .    *    .    *    .
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50             60             70             80             90
    .    *    .    *    .    *    .    *    .    *    .
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100            110            120            130            140
    *    .    *    .    *    .    *    .    *    .    *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150            160            170            180            190
   .    *    .    *    .    *    .    *    .    *    .
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200            210            220            230            240
    *    .    *    .    *    .    *    .    *    .    *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250            260            270            280
    *    .    *    .    *    .    *    .    *    .    *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290            300            310            320            330
    *    .    *    .    *    .    *    .    *    .    *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340            350            360            370            380
    *    .    *    .    *    .    *    .    *    .    *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 51A

```
             390            400            410            420           430
              .              .              .              .             .
      .       *      .       *      .       *      .       *      .      *
     AAA GGT GAA GTA TCT GAA AAA ATA ATA ACA AGA GCA GAC GGA ACC  AGA
     TTT CCA CTT CAT AGA CTT TTT TAT TAT TGT TCT CGT CTG CCT TGG  TCT
     Lys Gly Glu Val Ser Glu Lys Ile Ile Thr Arg Ala Asp Gly Thr  Arg>

440            450            460            470           480
              .              .              .              .             .
      .       *      .       *      .       *      .       *      .      *
     CTT GAA TAC ACA GGA ATT AAA AGC GAT GGA TCT GGA AAA GCT AAA  TAT
     GAA CTT ATG TGT CCT TAA TTT TCG CTA CCT AGA CCT TTT CGA TTT  ATA
     Leu Glu Tyr Thr Gly Ile Lys Ser Asp Gly Ser Gly Lys Ala Lys  Tyr 490            500            510            520
                   .              .              .              .
      .       *      .       *      .       *      .       *      .       .
     GTT TTA AAA GGC TAT GTT CTT GAA GGA ACT CTA ACT GCT GAA AAA  ACA
     CAA AAT TTT CCG ATA CAA GAA CTT CCT TGA GAT TGA CGA CTT TTT  TGT
     Val Leu Lys Gly Tyr Val Leu Glu Gly Thr Leu Thr Ala Glu Lys  Thr>

530            540            550            560            570
     .              .              .              .              .
      .       *      .       *      .       *      .       *      .       -
     ACA TTG GTG GTT AAA GAA GGA ACT GTT ACT TTA AGC AAA AAT ATT  TCA
     TGT AAC CAC CAA TTT CTT CCT TGA CAA TGA AAT TCG TTT TTA TAA  AGT
     Thr Leu Val Val Lys Glu Gly Thr Val Thr Leu Ser Lys Asn Ile  Ser>

580            590            600            610            620
     .              .              .              .              .
      .       *      .       *      .       *      .       *      .       -
     AAA TCT GGG GAA GTT TCA GTT GAA CTT AAT GAC ACT GAC AGT AGT  GCT
     TTT AGA CCC CTT CAA AGT CAA CTT GAA TTA CTG TGA CTG TCA TCA  CGA
     Lys Ser Gly Glu Val Ser Val Glu Leu Asn Asp Thr Asp Ser Ser  Ala>

630            640            650            660            670
             .              .              .              .              .
      .       *      .       *      .       *      .       *      .       -
     GCT ACT AAA AAA ACT GCA GCT TGG AAT TCA GGC ACT TCA ACT TTA  ACA
     CGA TGA TTT TTT TGA CGT CGA ACC TTA AGT CCG TGA AGT TGA AAT  TGT
     Ala Thr Lys Lys Thr Ala Ala Trp Asn Ser Gly Thr Ser Thr Leu  Thr>

680            690            700            710           720
              .              .              .              .             .
      .       *      .       *      .       *      .       *      .      *
     ATT ACT GTA AAC AGT AAA AAA ACT AAA GAC CTT GTG TTT ACA AAA  GAA
     TAA TGA CAT TTG TCA TTT TTT TGA TTT CTG GAA CAC AAA TGT TTT  CTT
     Ile Thr Val Asn Ser Lys Lys Thr Lys Asp Leu Val Phe Thr Lys  Glu>

730            740            750            760
                   .              .              .              .
      .       *      .       *      .       *      .       *      .       .
     AAC ACA ATT ACA GTA CAA CAA TAC GAC TCA AAT GGC ACC AAA TTA  GAG
     TTG TGT TAA TGT CAT GTT GTT ATG CTG AGT TTA CCG TGG TTT AAT  CTC
     Asn Thr Ile Thr Val Gln Gln Tyr Asp Ser Asn Gly Thr Lys Leu  Glu>

770            780            790            800            810
     .              .              .              .              .
      .       *      .       *      .       *      .       *      .       -
     GGG TCA GCA GTT GAA ATT ACA AAA CTT GAT GAA ATT AAA AAC GCT  TTA
     CCC AGT CGT CAA CTT TAA TGT TTT GAA CTA CTT TAA TTT TTG CGA  AAT
     Gly Ser Ala Val Glu Ile Thr Lys Leu Asp Glu Ile Lys Asn Ala  Leu>

820
     *
    AAA TAA
    TTT ATT
    Lys ***>                 FIG. 51B
```

```
           10              20              30              40
            .               .               .               .
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50              60              70              80              90
      .               .               .               .               .
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100             110             120             130             140
          .               .               .               .               .
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150             160             170             180             190
          .               .               .               .               .
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200             210             220             230             240
          .               .               .               .               .
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250             260             270             280
          .               .               .               .
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290             300             310             320             330
     .               .               .               .               .
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys >

340             350             360             370             380
          .               .               .               .               .
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 52A

```
         390           400           410           420           430
  .   *    .    *    .    *    .    *    .    *    .
AAA GGT GAA GTA TCT GAA AAA ATA ATA ACA ATG GCA GAC GGA ACC AGA
TTT CCA CTT CAT AGA CTT TTT TAT TAT TGT TAC CGT CTG CCT TGG TCT
Lys Gly Glu Val Ser Glu Lys Ile Ile Thr Met Ala Asp Gly Thr Arg>

440           450           460           470           480
  .   *    .    *    .    *    .    *    .    *    .
CTT GAA TAC ACA GGA ATT AAA AGC GAT GGA TCT GGA AAA GCT AAA TAT
GAA CTT ATG TGT CCT TAA TTT TCG CTA CCT AGA CCT TTT CGA TTT ATA
Leu Glu Tyr Thr Gly Ile Lys Ser Asp Gly Ser Gly Lys Ala Lys Tyr 490           500           510           520
  .   *    .    *    .    *    .    *    .    *    .
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530           540           550           560           570
  .    *    .    *    .    *    .    *    .    *    .
ACA TTG GTG GTT AAA GAA GGA ACT GTT ACT TTA AGC ATG AAT ATT TCA
TGT AAC CAC CAA TTT CTT CCT TGA CAA TGA AAT TCG TAC TTA TAA AGT
Thr Leu Val Val Lys Glu Gly Thr Val Thr Leu Ser Met Asn Ile Ser>

580           590           600           610           620
  .   *    .    *    .    *    .    *    .    *    .
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630           640           650           660           670
  .   *    .    *    .    *    .    *    .    *    .
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr >

680           690           700           710           720
  .   *    .    *    .    *    .    *    .    *    .
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

730           740           750           760
  .   *    .    *    .    *    .    *    .    *    .
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770           780           790           800           810
  .    *    .    *    .    *    .    *    .    *    .
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

820
 *
AAA TAA
TTT ATT
Lys ***>              FIG. 52B
```

```
          10              20              30              40
     .    *     *    *    .    v    .    f    .    .    *    .
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50              60              70              80              90
     *    *    *    *    .    .    *    f    .    *    .    *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100             110             120             130             140
     *    *    *    *    *    *    *    *    *    *    *    *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150             160             170             180             190
     *    *    *    *    *    *    *    *    *    *    *    *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200             210             220             230             240
     *    *    *    *    *    *    *    *    *    *    *    *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250             260             270             280
     *    *    *    *    *    *    *    *    *    *    *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290             300             310             320             330
     *    *    *    *    *    *    *    *    *    *    *    *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys >

340             350             360             370             380
     *    *    *    *    *    *    *    *    *    *    *    *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 53A

```
        390             400             410             420             430
  .       .       .       .       .       .       .       .       .       .
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

440             450             460             470             480
  .       .       .       .       .       .       .       .       .       .
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490             500             510             520
  .       .       .       .       .       .       .       .       .
GTT TTA AAA GGC TTT GTT CTT GAA GGA ACT CTA ACT GCT GAA AAA ACA
CAA AAT TTT CCG AAA CAA GAA CTT CCT TGA GAT TGA CGA CTT TTT TGT
Val Leu Lys Gly Phe Val Leu Glu Gly Thr Leu Thr Ala Glu Lys Thr>

530             540             550             560             570
  .       .       .       .       .       .       .       .       .       .
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580             590             600             610             620
  .       .       .       .       .       .       .       .       .       .
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630             640             650             660             670
  .       .       .       .       .       .       .       .       .       .
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

680             690             700             710             720
  .       .       .       .       .       .       .       .       .       .
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

730             740             750             760
  .       .       .       .       .       .       .       .       .
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770             780             790             800             810
  .       .       .       .       .       .       .       .       .       .
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

820
  *
AAA TAA
TTT ATT
Lys ***>            FIG. 53B
```

```
                10              20              30              40
         *       *       *       *       *       *       *       *       *
       ATG AAA AAA TAT TTA TTG GGA ATA GGT CTA ATA TTA GCC TTA ATA GCA
       TAC TTT TTT ATA AAT AAC CCT TAT CCA GAT TAT AAT CGG AAT TAT CGT
       Met Lys Lys Tyr Leu Leu Gly Ile Gly Leu Ile Leu Ala Leu Ile Ala>

50              60              70              80              90
         *       *       *       *       *       *       *       *       *
       TGT AAG CAA AAT GTT AGC AGC CTT GAC GAG AAA AAC AGC GTT TCA GTA
       ACA TTC GTT TTA CAA TCG TCG GAA CTG CTC TTT TTG TCG CAA AGT CAT
       Cys Lys Gln Asn Val Ser Ser Leu Asp Glu Lys Asn Ser Val Ser Val>

100             110             120             130             140
         *       *       *       *       *       *       *       *       *
       GAT TTG CCT GGT GAA ATG AAA GTT CTT GTA AGC AAA GAA AAA AAC AAA
       CTA AAC GGA CCA CTT TAC TTT CAA GAA CAT TCG TTT CTT TTT TTG TTT
       Asp Leu Pro Gly Glu Met Lys Val Leu Val Ser Lys Glu Lys Asn Lys>

150             160             170             180             190
         *       *       *       *       *       *       *       *       *
       GAC GGC AAG TAC GAT CTA ATT GCA ACA GTA GAC AAG CTT GAG CTT AAA
       CTG CCG TTC ATG CTA GAT TAA CGT TGT CAT CTG TTC GAA CTC GAA TTT
       Asp Gly Lys Tyr Asp Leu Ile Ala Thr Val Asp Lys Leu Glu Leu Lys>

200             210             220             230             240
         *       *       *       *       *       *       *       *       *
       GGA ACT TCT GAT AAA AAC AAT GGA TCT GGA GTA CTT GAA GGC GTA AAA
       CCT TGA AGA CTA TTT TTG TTA CCT AGA CCT CAT GAA CTT CCG CAT TTT
       Gly Thr Ser Asp Lys Asn Asn Gly Ser Gly Val Leu Glu Gly Val Lys>

250             260             270             280
         *       *       *       *       *       *       *       *       *
       GCT GAC AAA AGT AAA GTA AAA TTA ACA ATT TCT GAC GAT CTA GGT CAA
       CGA CTG TTT TCA TTT CAT TTT AAT TGT TAA AGA CTG CTA GAT CCA GTT
       Ala Asp Lys Ser Lys Val Lys Leu Thr Ile Ser Asp Asp Leu Gly Gln>

290             300             310             320             330
         *       *       *       *       *       *       *       *       *
       ACC ACA CTT GAA GTT TTC AAA GAA GAT GGC AAA ACA CTA GTA TCA AAA
       TGG TGT GAA CTT CAA AAG TTT CTT CTA CCG TTT TGT GAT CAT AGT TTT
       Thr Thr Leu Glu Val Phe Lys Glu Asp Gly Lys Thr Leu Val Ser Lys >

340             350             360             370             380
         *       *       *       *       *       *       *       *       *
       AAA GTA ACT TCC AAA GAC AAG TCA TCA ACA GAA GAA AAA TTC AAT GAA
       TTT CAT TGA AGG TTT CTG TTC AGT AGT TGT CTT CTT TTT AAG TTA CTT
       Lys Val Thr Ser Lys Asp Lys Ser Ser Thr Glu Glu Lys Phe Asn Glu>
```

FIG. 54A

```
          390             400             410             420             430
      *       *       *       *       *       *       *       *       *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

440             450             460             470             480
          *       *       *       *       *       *       *       *       *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490             500             510             520
          *       *       *       *       *       *       *       *       *
GTT TTA AAA GGC TTT ACT CTT GAA GGA ACT CTA ACT GCT GAA AAA ACA
CAA AAT TTT CCG AAA TGA GAA CTT CCT TGA GAT TGA CGA CTT TTT TGT
Val Leu Lys Gly Phe Thr Leu Glu Gly Thr Leu Thr Ala Glu Lys Thr>

530             540             550             560             570
      *       *       *       *       *       *       *       *       *       *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580             590             600             610             620
          *       *       *       *       *       *       *       *       *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630             640             650             660             670
          *       *       *       *       *       *       *       *       *       *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

680             690             700             710             720
          *       *       *       *       *       *       *       *       *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

730             740             750             760
          *       *       *       *       *       *       *       *       *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770             780             790             800             810
      *       *       *       *       *       *       *       *       *       *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

820
          *
AAA TAA
TTT ATT
Lys ***>
```

FIG. 54B

```
            10           20           30           40
       .    .    .    .    .    .    .    .    .    .
ATG  AAA  AAA  TAT  TTA  TTG  GGA  ATA  GGT  CTA  ATA  TTA  GCC  TTA  ATA  GCA
TAC  TTT  TTT  ATA  AAT  AAC  CCT  TAT  CCA  GAT  TAT  AAT  CGG  AAT  TAT  CGT
Met  Lys  Lys  Tyr  Leu  Leu  Gly  Ile  Gly  Leu  Ile  Leu  Ala  Leu  Ile  Ala>

50           60           70           80           90
   .    .    .    .    .    .    .    .    .    .    .
TGT  AAG  CAA  AAT  GTT  AGC  AGC  CTT  GAC  GAG  AAA  AAC  AGC  GTT  TCA  GTA
ACA  TTC  GTT  TTA  CAA  TCG  TCG  GAA  CTG  CTC  TTT  TTG  TCG  CAA  AGT  CAT
Cys  Lys  Gln  Asn  Val  Ser  Ser  Leu  Asp  Glu  Lys  Asn  Ser  Val  Ser  Val>

100          110          120          130          140
        .    .    .    .    .    .    .    .    .    .
GAT  TTG  CCT  GGT  GAA  ATG  AAA  GTT  CTT  GTA  AGC  AAA  GAA  AAA  AAC  AAA
CTA  AAC  GGA  CCA  CTT  TAC  TTT  CAA  GAA  CAT  TCG  TTT  CTT  TTT  TTG  TTT
Asp  Leu  Pro  Gly  Glu  Met  Lys  Val  Leu  Val  Ser  Lys  Glu  Lys  Asn  Lys>

150          160          170          180          190
        .    .    .    .    .    .    .    .    .    .
GAC  GGC  AAG  TAC  GAT  CTA  ATT  GCA  ACA  GTA  GAC  AAG  CTT  GAG  CTT  AAA
CTG  CCG  TTC  ATG  CTA  GAT  TAA  CGT  TGT  CAT  CTG  TTC  GAA  CTC  GAA  TTT
Asp  Gly  Lys  Tyr  Asp  Leu  Ile  Ala  Thr  Val  Asp  Lys  Leu  Glu  Leu  Lys>

200          210          220          230          240
        .    .    .    .    .    .    .    .    .    .
GGA  ACT  TCT  GAT  AAA  AAC  AAT  GGA  TCT  GGA  GTA  CTT  GAA  GGC  GTA  AAA
CCT  TGA  AGA  CTA  TTT  TTG  TTA  CCT  AGA  CCT  CAT  GAA  CTT  CCG  CAT  TTT
Gly  Thr  Ser  Asp  Lys  Asn  Asn  Gly  Ser  Gly  Val  Leu  Glu  Gly  Val  Lys>

250          260          270          280
        .    .    .    .    .    .    .    .
GCT  GAC  AAA  AGT  AAA  GTA  AAA  TTA  ACA  ATT  TCT  GAC  GAT  CTA  GGT  CAA
CGA  CTG  TTT  TCA  TTT  CAT  TTT  AAT  TGT  TAA  AGA  CTG  CTA  GAT  CCA  GTT
Ala  Asp  Lys  Ser  Lys  Val  Lys  Leu  Thr  Ile  Ser  Asp  Asp  Leu  Gly  Gln>

290          300          310          320          330
 .    .    .    .    .    .    .    .    .    .
ACC  ACA  CTT  GAA  GTT  TTC  AAA  GAA  GAT  GGC  AAA  ACA  CTA  GTA  TCA  AAA
TGG  TGT  GAA  CTT  CAA  AAG  TTT  CTT  CTA  CCG  TTT  TGT  GAT  CAT  AGT  TTT
Thr  Thr  Leu  Glu  Val  Phe  Lys  Glu  Asp  Gly  Lys  Thr  Leu  Val  Ser  Lys >

340          350          360          370          380
        .    .    .    .    .    .    .    .    .    .
AAA  GTA  ACT  TCC  AAA  GAC  AAG  TCA  TCA  ACA  GAA  GAA  AAA  TTC  AAT  GAA
TTT  CAT  TGA  AGG  TTT  CTG  TTC  AGT  AGT  TGT  CTT  CTT  TTT  AAG  TTA  CTT
Lys  Val  Thr  Ser  Lys  Asp  Lys  Ser  Ser  Thr  Glu  Glu  Lys  Phe  Asn  Glu>
```

FIG. 55A

```
            390             400             410             420             430
     *       *       *       *       *       *       *       *       *       *
    AAA     GGT     GAA     GTA     TCT     GAA     AAA     ATA     ATA     ACA     AGA     GCA     GAC     GGA     ACC     AGA
    TTT     CCA     CTT     CAT     AGA     CTT     TTT     TAT     TAT     TGT     TCT     CGT     CTG     CCT     TGG     TCT
    Lys     Gly     Glu     Val     Ser     Glu     Lys     Ile     Ile     Thr     Arg     Ala     Asp     Gly     Thr     Arg>

440             450             460             470             480
     *       *       *       *       *       *       *       *       *       *
    CTT     GAA     TAC     ACA     GGA     ATT     AAA     AGC     GAT     GGA     TCT     GGA     AAA     GCT     AAA     GAG
    GAA     CTT     ATG     TGT     CCT     TAA     TTT     TCG     CTA     CCT     AGA     CCT     TTT     CGA     TTT     CTC
    Leu     Glu     Tyr     Thr     Gly     Ile     Lys     Ser     Asp     Gly     Ser     Gly     Lys     Ala     Lys     Glu>

490             500             510             520
             *       *       *       *       *       *       *       *       *
            GTT     TTA     AAA     GGC     TAT     ACT     CTT     GAA     GGA     ACT     CTA     ACT     GCT     GAA     AAA     ACA
            CAA     AAT     TTT     CCG     ATA     TGA     GAA     CTT     CCT     TGA     GAT     TGA     CGA     CTT     TTT     TGT
            Val     Leu     Lys     Gly     Tyr     Thr     Leu     Glu     Gly     Thr     Leu     Thr     Ala     Glu     Lys     Thr>

530             540             550             560             570
     *       *       *       *       *       *       *       *       *       *
    ACA     TTG     GTG     GTT     AAA     GAA     GGA     ACT     GTT     ACT     TTA     AGC     AAA     AAT     ATT     TCA
    TGT     AAC     CAC     CAA     TTT     CTT     CCT     TGA     CAA     TGA     AAT     TCG     TTT     TTA     TAA     AGT
    Thr     Leu     Val     Val     Lys     Glu     Gly     Thr     Val     Thr     Leu     Ser     Lys     Asn     Ile     Ser>

580             590             600             610             620
     *       *       *       *       *       *       *       *       *
    AAA     TCT     GGG     GAA     GTT     TCA     GTT     GAA     CTT     AAT     GAC     ACT     GAC     AGT     AGT     GCT
    TTT     AGA     CCC     CTT     CAA     AGT     CAA     CTT     GAA     TTA     CTG     TGA     CTG     TCA     TCA     CGA
    Lys     Ser     Gly     Glu     Val     Ser     Val     Glu     Leu     Asn     Asp     Thr     Asp     Ser     Ser     Ala>

630             640             650             660             670
     *       *       *       *       *       *       *       *       *       *
    GCT     ACT     AAA     AAA     ACT     GCA     GCT     TGG     AAT     TCA     GGC     ACT     TCA     ACT     TTA     ACA
    CGA     TGA     TTT     TTT     TGA     CGT     CGA     ACC     TTA     AGT     CCG     TGA     AGT     TGA     AAT     TGT
    Ala     Thr     Lys     Lys     Thr     Ala     Ala     Trp     Asn     Ser     Gly     Thr     Ser     Thr     Leu     Thr>

680             690             700             710             720
     *       *       *       *       *       *       *       *       *       *
    ATT     ACT     GTA     AAC     AGT     AAA     AAA     ACT     AAA     GAC     CTT     GTG     TTT     ACA     AAA     GAA
    TAA     TGA     CAT     TTG     TCA     TTT     TTT     TGA     TTT     CTG     GAA     CAC     AAA     TGT     TTT     CTT
    Ile     Thr     Val     Asn     Ser     Lys     Lys     Thr     Lys     Asp     Leu     Val     Phe     Thr     Lys     Glu>

730             740             750             760
     *       *       *       *       *       *       *       *       *
    AAC     ACA     ATT     ACA     GTA     CAA     CAA     TAC     GAC     TCA     AAT     GGC     ACC     AAA     TTA     GAG
    TTG     TGT     TAA     TGT     CAT     GTT     GTT     ATG     CTG     AGT     TTA     CCG     TGG     TTT     AAT     CTC
    Asn     Thr     Ile     Thr     Val     Gln     Gln     Tyr     Asp     Ser     Asn     Gly     Thr     Lys     Leu     Glu>

770             780             790             800             810
     *       *       *       *       *       *       *       *       *       *
    GGG     TCA     GCA     GTT     GAA     ATT     ACA     AAA     CTT     GAT     GAA     ATT     AAA     AAC     GCT     TTA
    CCC     AGT     CGT     CAA     CTT     TAA     TGT     TTT     GAA     CTA     CTT     TAA     TTT     TTG     CGA     AAT
    Gly     Ser     Ala     Val     Glu     Ile     Thr     Lys     Leu     Asp     Glu     Ile     Lys     Asn     Ala     Leu>

820
     *
    AAA     TAA
    TTT     ATT
    Lys     ***>
```

FIG. 55B

```
          10            20            30            40
           *             *             *             *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50            60            70            80            90
     *             *             *             *             *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100           110           120           130           140
      *             *             *             *             *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150           160           170           180           190
      *             *             *             *             *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200           210           220           230           240
      *             *             *             *             *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250           260           270           280
      *             *             *             *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290           300           310           320           330
 *             *             *             *             *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys >

340           350           360           370           380
      *             *             *             *             *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 56A

```
         390         400         410         420         430
  *       *       *       *       *       *       *       *       *       *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

440         450         460         470         480
  *       *       *       *       *       *       *       *       *       *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490         500         510         520
  *       *       *       *       *       *       *       *       *
GTT TTA AAA GGC TAT ACT CTT GAA GGA AAG CTA ACT GCT GAA AAA ACA
CAA AAT TTT CCG ATA TGA GAA CTT CCT TTC GAT TGA CGA CTT TTT TGT
Val Leu Lys Gly Tyr Thr Leu Glu Gly Lys Leu Thr Ala Glu Lys Thr>

530         540         550         560         570
  *       *       *       *       *       *       *       *       *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580         590         600         610         620
  *       *       *       *       *       *       *       *       *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630         640         650         660         670
  *       *       *       *       *       *       *       *       *       *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gl       er Thr Leu Thr>

680         690         700         710         720
  *       *       *       *       *       *       *       *       *       *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

730         740         750         760
  *       *       *       *       *       *       *       *       *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770         780         790         800         810
  *       *       *       *       *       *       *       *       *       *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

820
      *
AAA TAA
TTT ATT
Lys ***>
```

FIG. 56B

```
                10                  20                  30                  40
                 .                   .                   .                   .
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50                  60                  70                  80                  90
         .                   .                   .                   .                   .
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100                 110                 120                 130                 140
                 .                   .                   .                   .                   .
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150                 160                 170                 180                 190
             .                   .                   .                   .                   .
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200                 210                 220                 230                 240
                 .                   .                   .                   .                   .
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250                 260                 270                 280
                     .                   .                   .                   .
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290                 300                 310                 320                 330
 .                   .                   .                   .                   .
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys >

340                 350                 360                 370                 380
         .                   .                   .                   .                   .
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 57A

```
        390           400           410           420           430
   *      *       *      *       *      *       *      *       *      *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

440           450           460           470           480
       *       *      *       *      *       *      *       *      *      *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490           500           510           520
       *       *      *       *      *       *      *       *      *
GTT TTA AAA GGC TTT ACT CTT GAA GGA AAG CTA ACT GCT GAA AAA ACA
CAA AAT TTT CCG AAA TGA GAA CTT CCT TTG GAT TGA CGA CTT TTT TGT
Val Leu Lys Gly Phe Thr Leu Glu Gly Lys Leu Thr Ala Glu Lys Thr>

530           540           550           560           570
   *       *      *       *      *       *      *       *      *      *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580           590           600           610           620
   *       *       *      *       *      *       *      *       *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630           640           650           660           670
   *       *       *       *       *       *      *       *      *       *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

680           690           700           710           720
       *       *      *       *      *       *      *       *      *      *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

730           740           750           760
       *       *      *       *      *       *      *       *      *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770           780           790           800           810
   *       *       *      *       *      *       *      *       *      *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

820
       *
AAA TAA
TTT ATT
Lys ***>
```

FIG. 57B

```
            10           20           30           40
             *            *            *            *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50           60           70           80           90
       *            *            *            *            *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100          110          120          130          140
       *            *            *            *            *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150          160          170          180          190
       *            *            *            *            *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200          210          220          230          240
       *            *            *            *            *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250          260          270          280
       *            *            *            *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290          300          310          320          330
 *            *            *            *            *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340          350          360          370          380
       *            *            *            *            *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 58A

```
            390             400             410             420             430
      *       *       *       *       *       *       *       *       *       *
    AAA GGT GAA GTA TCT GAA AAA ATA ATA ACA ATG GCA GAC GGA ACC AGA
    TTT CCA CTT CAT AGA CTT TTT TAT TAT TGT TAC CGT CTG CCT TGG TCT
    Lys Gly Glu Val Ser Glu Lys Ile Ile Thr Met Ala Asp Gly Thr Arg>

440             450             460             470             480
          *       *       *       *       *       *       *       *       *       *
    CTT GAA TAC ACA GGA ATT AAA AGC GAT GGA TCT GGA AAA GCT AAA TAT
    GAA CTT ATG TGT CCT TAA TTT TCG CTA CCT AGA CCT TTT CGA TTT ATA
    Leu Glu Tyr Thr Gly Ile Lys Ser Asp Gly Ser Gly Lys Ala Lys Tyr>

490             500             510             520
          *       *       *       *       *       *       *       *       *
    GTT TTA AAA GGC TTT ACT CTT GAA GGA AAG CTA ACT GCT GAA AAA ACA
    CAA AAT TTT CCG AAA TGA GAA CTT CCT TTG GAT TGA CGA CTT TTT TGT
    Val Leu Lys Gly Phe Thr Leu Glu Gly Lys Leu Thr Ala Glu Lys Thr>

530             540             550             560             570
      *       *       *       *       *       *       *       *       *       *
    ACA TTG GTG GTT AAA GAA GGA ACT GTT ACT TTA AGC ATG AAT ATT TCA
    TGT AAC CAC CAA TTT CTT CCT TGA CAA TGA AAT TCG TAC TTA TAA AGT
    Thr Leu Val Val Lys Glu Gly Thr Val Thr Leu Ser Met Asn Ile Ser>

580             590             600             610             620
          *       *       *       *       *       *       *       *       *
    AAA TCT GGG GAA GTT TCA GTT GAA CTT AAT GAC ACT GAC AGT AGT GCT
    TTT AGA CCC CTT CAA AGT CAA CTT GAA TTA CTG TGA CTG TCA TCA CGA
    Lys Ser Gly Glu Val Ser Val Glu Leu Asn Asp Thr Asp Ser Ser Ala>

630             640             650             660             670
          *       *       *       *       *       *       *       *       *       *
    GCT ACT AAA AAA ACT GCA GCT TGG AAT TCA GGC ACT TCA ACT TTA ACA
    CGA TGA TTT TTT TGA CGT CGA ACC TTA AGT CCG TGA AGT TGA AAT TGT
    Ala Thr Lys Lys Thr Ala Ala Trp Asn Ser Gly Thr Ser Thr Leu Thr>

680             690             700             710             720
          *       *       *       *       *       *       *       *       *       *
    ATT ACT GTA AAC AGT AAA AAA ACT AAA GAC CTT GTG TTT ACA AAA GAA
    TAA TGA CAT TTG TCA TTT TTT TGA TTT CTG GAA CAC AAA TGT TTT CTT
    Ile Thr Val Asn Ser Lys Lys Thr Lys Asp Leu Val Phe Thr Lys Glu>

730             740             750             760
          *       *       *       *       *       *       *       *
    AAC ACA ATT ACA GTA CAA CAA TAC GAC TCA AAT GGC ACC AAA TTA GAG
    TTG TGT TAA TGT CAT GTT GTT ATG CTG AGT TTA CCG TGG TTT AAT CTC
    Asn Thr Ile Thr Val Gln Gln Tyr Asp Ser Asn Gly Thr Lys Leu Glu>

770             780             790             800             810
      *       *       *       *       *       *       *       *       *       *
    GGG TCA GCA GTT GAA ATT ACA AAA CTT GAT GAA ATT AAA AAC GCT TTA
    CCC AGT CGT CAA CTT TAA TGT TTT GAA CTA CTT TAA TTT TTG CGA AAT
    Gly Ser Ala Val Glu Ile Thr Lys Leu Asp Glu Ile Lys Asn Ala Leu>

820
          *
    AAA TAA
    TTT ATT
    Lys ***>
```

FIG. 58B

ALTERED OSPA OF *BORRELIA BURGDORFERI*

RELATED APPLICATIONS

This application is a continuation of U.S. application Ser. No. 10/369,339, filed Feb. 18, 2003, now abandoned, which is a continuation of International Application No. PCT/US01/25852, which designated the United States, was published in English and was filed on Aug. 17, 2001, which claims the benefit of U.S. Provisional Application No. 60/226,484, filed on Aug. 18, 2000. The entire teachings of these applications are incorporated herein by reference.

GOVERNMENT SUPPORT

The invention was supported, in whole or in part, by Grant 2R01AI37256-05A1 from the National Institute of Allergy and Infectious Diseases and Grant NIH GM057215 from the National Institutes of Health. The Government has certain rights in the invention.

BACKGROUND OF THE INVENTION

Lyme disease (Lyme borreliosis) is the most common tick-borne infectious disease in North America and Europe, and has been found in Russia, Japan, China and Australia. Lyme disease begins at the site of a tick bite, producing a primary infection with spread of the organism to secondary sites occurring during the course of infection. The causative bacterial agent of this disease is the spirochete *Borrelia burgdorferi*, which was first isolated and cultivated in 1982 (Burgdorferi, W. A. et al., *Science* 216: 1317-1319 (1982); Steere, A. R. et al., *N. Engl. J. Med.*, 308:733-740 (1983)).

Three pathogenic genospecies of *Borrelia*, *B. burgdorferi* sensu stricto (*B. burgdorferi* or B.b.s.s.), *B. afzelei* and *B. garinii* have been described (Baranton, G., et al., *Int. J. Syst. Bacteriol.*, 42:378-383 (1992)). These are members of a species complex, *B. burgdorferi* sensu lato, which consists of at least 10 different genospecies (Piken, R. N. et al., *J. Invest. Dermatol.*, 110:211-214 (1998); Postic, D. et al., *Int. J. Syst. Bacteriol.*, 44:743-752 (1994); Valsangiacomo, C. T. et al., *Int. J. Syst. Bacteriol.*, 47:1-10 (1997)). The three genospecies, *B. burgdorferi* sensu stricto, *B. afzelii* and *B. garinii*, are all thought to be pathogenic and all are found in Europe.

*B. burgdorferi* has an outer membrane whose major protein constituents are the outer surface proteins A and B (OspA and OspB). OspA is a basic lipoprotein of approximately 31 kd, which is encoded on a large linear plasmid along with OspB, a basic lipoprotein of approximately 34 kd (Szczepanski, A., and J. L. Benach, *Microbiol. Rev.*, 55:21 (1991)). The immune response to these outer surface proteins tends to occur late in the disease, if at all (Craft, J. E. et al., *J. Clin Invest.* 78:934-939 (1986); Dattwyler, R. J. and B. J. Luft, *Rheum. Clin. North Am.*, 15:727-734 (1989)). Furthermore, patients acutely and chronically infected with *B. burgdorferi* respond variably to the different antigens, including OspA, OspB, OspC, OspD, p39, p41 and p93.

Currently, Lyme Disease is treated with a range of antibiotics, e.g., tetracyclines, penicillin and cephalosporins. However, such treatment is not always successful in clearing the infection. Treatment is often delayed due to improper diagnosis with the deleterious effect that the infection proceeds to a chronic condition, where treatment with antibiotics is often not useful. One of the factors contributing to delayed treatment is the lack of effective diagnostic tools.

Vaccines against Lyme borreliosis have been attempted. However, a vaccine that consists of recombinant OspA may require frequent booster immunizations. An additional concern of OspA-based vaccines is the recent identification of a putative autoreactive OspA domain with a high degree of similarity to a region of human leukocyte function-associated antigen-1 (hLFA-1) (Gross, D. M. et al., *Science*, 281: 703-706 (1998)).

Therefore, it should be advantageous to develop modified OspA proteins having decreased cross-reactivity to hLFA-1 in order to reduce potential side effects of an OspA vaccine. Development of OspA proteins with decreased hLFA-1 cross-reactivity that maintain or have increased immunoreactivity to more than one member of the *Borrelia* complex would also be desirable. To be useful as vaccines, the conformations of these modified proteins must be sufficiently stable to retain certain OspA structural features that are required to elicit a protective immune response. OspA proteins with these features would allow for improvements in diagnosis and/or vaccination against all, or most, of the *Borrelia* that cause Lyme Disease.

Analysis of the immune status of OspA immunized individuals revealed that the overall quantitative response is not predictive of protection, but rather the reactivity with a specific epitope of the OspA lipoprotein directly correlates to protective immunity. The anti-OspA monoclonal antibody, LA-2 (Kramer et al., 1990) defines an epitope of the lipoprotein that is apparently necessary for protective immunity after OspA vaccination. For instance, passive immunization of mice with this antibody leads to protection against infection with the spirochete (Schaible et al., 1993). In addition, immunization of mice and canines with OspA resulting in significant titers of LA-2 equivalent serum antibody accurately predicts protection from tick transmission of infection (Golde, 1997). Insufficient levels of LA-2 equivalent antibody result in a lack of protection in the face of high serum antibody titers to OspA (Johnson et al., 1995).

SUMMARY OF THE INVENTION

The present invention is drawn to altered forms of OspA from *Borrelia burgdorferi* that have increased conformational stability while maintaining at least some of the antigenicity of wild type OspA. In some embodiments, the altered OspA polypeptide has decreased cross-reactivity with hLFA-1, as compared to the corresponding unaltered OspA polypeptide. The altered OspA polypeptides can comprise almost all or only a portion of the native OspA polypeptide. In some embodiments, the altered OspA polypeptide can be part of a cocktail which includes one or more other proteins, such as, for example, other *Borrelia burgdorferi* polypeptides including OspA, OspB, OspC, OspD, p93 and p41. In other embodiments, the altered OspA polypeptide can be part of a chimeric protein, such as those described in U.S. Pat. No. 6,248,562, the entire teachings of which are incorporated herein by reference.

In one embodiment, the altered OspA polypeptides of the present invention comprise an amino acid sequence of OspA protein from *Borrelia burgdorferi* from about residue 139 to about residue 273, wherein the sequence includes at least one alteration selected from the group consisting of: residue 139 changed to methionine, residue 160 changed to tyrosine, residue 189 changed to methionine and combinations thereof. In other embodiments, the altered OspA polypeptides of the present invention comprise an amino acid sequence of OspA protein from *Borrelia burgdorferi* from about residue 131 to about residue 273 or from about residue 17 to about residue 273. The OspA polypeptides of the present invention can comprise longer or shorter fragments of OspA protein. The numbering of the residues corresponds to the numbering of SEQ ID NO:7 (OspA from B31).

In another embodiment, the OspA polypeptides of the present invention comprise an amino acid sequence of OspA protein from *Borrelia burgdorferi* from about residue 160 to about residue 170, wherein the sequence includes at least two alterations selected from the group consisting of: residue 165 changed to phenylalanine, residue 166 changed to threonine and residue 170 changed to lysine. In yet another embodiment, the OspA polypeptides of the present invention comprise an amino acid sequence of OspA protein from a sensu stricto strain of *Borrelia burgdorferi* from about residue 160 to about residue 170, wherein the sequence includes at least one alteration selected from the group consisting of: residue 165 changed to phenylalanine, residue 166 changed to threonine, residue 170 changed to lysine and combinations thereof. In other embodiments, the altered OspA polypeptides of the present invention comprise an amino acid sequence of OspA protein from *Borrelia burgdorferi* from about residue 150 to about residue 180 or from about residue 17 to about residue 273. The OspA polypeptides of the present invention can comprise longer, or shorter fragments of OspA protein. The numbering of the residues corresponds to the numbering of SEQ ID NO:7.

The polypeptides of the present invention include polypeptides selected from the group consisting of: SEQ ID NO:96, 98, 100, 102, 104, 106, 108, 110, 112, 114 and 116.

The present invention is also drawn to polynucleotides encoding the amino acid sequences described herein, such as polynucleotides encoding OspA polypeptides from *Borrelia burgdorferi* from about residue 131 to about residue 273, wherein the sequence encodes at least one alteration selected from the group consisting of: codon 139 encoding methionine, codon 160 encoding tyrosine, codon 189 encoding methionine and combinations thereof. The polynucleotide encoding OspA polypeptides of the present invention can encode longer or shorter fragments of OspA protein. The numbering of the residues corresponds to the numbering of SEQ ID NO:7.

In another embodiment, the polynucleotide encodes an amino acid sequence of an OspA polypeptide from *Borrelia burgdorferi* from about residue 160 to about residue 170, wherein the sequence encodes at least one alteration selected from the group consisting of: codon 165 encoding phenylalanine, codon 166 encoding threonine, codon 170 encoding lysine and combinations thereof. The polynucleotides which encode OspA polypeptides of the present invention can encode longer or shorter fragments of OspA protein. The numbering of the residues corresponds to the numbering of SEQ ID NO:7.

The polynucleotides of the present invention include a polynucleotide selected from the group consisting of: SEQ ID NO:95, 97, 99, 101, 103, 105, 107, 109, 111, 113 and 115.

The present invention is also drawn to a method of generating an altered *Borrelia burgdorferi* OspA polypeptide with increased conformational stability, as compared to the corresponding unaltered *Borrelia burgdorferi* OspA polypeptide. The method comprises selecting a polynucleotide encoding a *Borrelia burgdorferi* OspA polypeptide that includes at least one of residues 139, 160 and 189, wherein the numbering corresponds to the numbering of SEQ ID NO:7. The polynucleotide is altered such that at least one of the following alterations is present: residue 139 is changed to methionine, residue 160 is changed to tyrosine and residue 189 is changed to methionine or a combination thereof. In one embodiment, both the alteration at residue 160 and the alteration at 189 is made. In another embodiment, the alterations at all three residues are made. The altered polynucleotide is expressed, thereby generating an altered *Borrelia burgdorferi* OspA polypeptide with increased conformational stability, as compared to the corresponding unaltered *Borrelia burgdorferi* OspA polypeptide.

In another embodiment, the present invention is drawn to a method of generating an altered *Borrelia burgdorferi* OspA polypeptide with reduced cross-reactivity with an hLFA-1 molecule, as compared to the corresponding unaltered *Borrelia burgdorferi* OspA polypeptide. The method comprises selecting a polynucleotide encoding an OspA polypeptide from *Borrelia burgdorferi* that includes at least one of residues 165, 166 and 170, wherein the numbering corresponds to the numbering of SEQ ID NO:7. The polynucleotide is altered such that at least one alteration from the following list is present: residue 165 is changed to phenylalanine, residue 166 is changed to threonine and residue 170 is changed to lysine or combination thereof. The altered polynucleotide is expressed, thereby generating an altered *Borrelia burgdorferi* OspA polypeptide with reduced cross-reactivity with the hLFA-1 molecule, as compared to the corresponding unaltered *Borrelia burgdorferi* OspA polypeptide.

The present invention is also drawn to an expression vector which comprises an isolated DNA encoding an altered *Borrelia* OspA protein. The present invention also encompasses a host cell which comprises a recombinant nucleic acid that encodes an altered OspA protein as described herein.

The present invention is also drawn to a method of delivering the altered *Borrelia* OspA polypeptides described herein. In one embodiment, the method comprises administering the altered OspA polypeptide in a physiologically-acceptable carrier to an individual. As a result of the administration of the altered OspA protein, the individual develops at least some immune response to the protein. As an example, the individual generates a humoral immune response, wherein antibodies that recognize at least a portion of said polypeptide are produced by the individual. In a preferred embodiment, the individual generates an immunoprotective response, for example, by generating antibodies that recognize the LA-2 epitope.

The present invention is also drawn to a method of delivering a nucleic acid which encodes an altered OspA polypeptide described herein. In one embodiment, the method comprises administering the nucleic acid in a physiologically-acceptable carrier to an individual. As a result of the administration of the nucleic acid, the altered OspA polypeptide is at least transiently expressed and the individual develops at least some immune response, preferably an immunoprotective response to the altered OspA protein encoded by the nucleic acid. As an example, the individual generates a humoral immune response, wherein antibodies that recognize at least a portion of the altered OspA polypeptide produced from the nucleic acid are produced by the individual. In a preferred embodiment, the individual generates an immunoprotective response, for example, by generating antibodies that recognize the LA-2 epitope.

The invention also encompasses methods of using the proteins described herein in diagnostic assays. In one embodiment, the method can be used to detect the presence of OspA specific antibodies in a host sample of interest. The method comprises contacting a host sample of interest with the altered protein, under conditions wherein antibodies, if present in the host sample, bind to the altered protein, forming antigen-antibody complexes. The antigen-antibody complexes are then detected using standard methods known in the art.

The present invention is also drawn to a diagnostic kit comprising the altered polypeptides described herein. The kit comprises an altered *Borrelia burgdorferi* OspA protein as described herein. The kit also includes reagents for detecting antibody-antigen complexes that are formed between the OspA altered protein and antibodies that are present in the user-supplied host sample.

As a result of the present invention, OspA proteins, or fragments thereof, having either increased conformational stability while maintaining at least some antigenicity, or having reduced cross-reactivity to hLFA-1, are available for use in research, vaccines and/or diagnostic assays. Furthermore, as a result of the present invention, nucleic acids encoding OspA polypeptides having reduced cross-reactivity with hLFA-1 are available for research and vaccines. The altered OspA polypeptides of the present invention are expected to allow for improved vaccines having fewer side effects.

For a better understanding of the present invention together with other and further objects, reference is made to the following description, taken together with the accompanying drawings.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 2A-2D depict is a comparison of the antigenic domains depicted in FIG. 1, for OspA in nine strains of *B. burgdorferi*. FIG. 2A, Domain 1: B-31 (SEQ ID NO: 131); TRo (SEQ ID NO:132); K48 (SEQ ID NO:133); DK29 (SEQ ID NO:134); P-Gau (SEQ ID NO:135); PKo (SEQ ID NO:136); IP3 (SEQ ID NO:137); IP90 (SEQ ID NO:138); and 25015 (SEQ ID NO:139). FIG. 2B, Domain 2: B-31 (SEQ ID NO: 140); TRo (SEQ ID NO:141); K48 (SEQ ID NO:142); DK29 (SEQ ID NO:143); P-Gau (SEQ ID NO:144); PKo (SEQ ID NO:145); IP3 (SEQ ID NO:146); IP90 (SEQ ID NO:147); and 25015 (SEQ ID NO:148). FIG. 2C, Domain 3: B-31 (SEQ ID NO: 149); TRo (SEQ ID NO:150); K48 (SEQ ID NO:151); DK29 (SEQ ID NO:152); P-Gau (SEQ ID NO:153); PKo (SEQ ID NO:154); IP3 (SEQ ID NO:155); IP90 (SEQ ID NO:156); and 25015 (SEQ ID NO:157). FIG. 2D, Domain 4: B-31 (SEQ ID NO: 158); TRo (SEQ ID NO:159); K48 (SEQ ID NO:160); DK29 (SEQ ID NO:161); P-Gau (SEQ ID NO:162); PKo (SEQ ID NO:163); IP3 (SEQ ID NO:164); IP90 (SEQ ID NO:165); and 25015 (SEQ ID NO:166).

FIG. 4 depicts the amino acid alignment of residues 200 through 220 for OspAs from strains B31 (SEQ ID NO:167) and K48 (SEQ ID NO:168) as well as for the site-directed mutants 613 (SEQ ID NO:169), 625 (SEQ ID NO:170), 640 (SEQ ID NO:171), 613/625 (SEQ ID NO:172), and 613/640 (SEQ ID NO:173). Arrow indicates Trp216. Amino acid changes are underlined.

FIGS. 6A and 6B depict the nucleic acid sequence of OspA-B31 (SEQ ID NO:6), and the encoded protein sequence (SEQ ID NO:7).

FIGS. 7A, 7B and 7C depict the nucleic acid sequence of OspA-K48 (SEQ ID NO:8), and the encoded protein sequence (SEQ ID NO:9).

FIGS. 8A, 8B and 8C depict the nucleic acid sequence of OspA-PGau (SEQ ID NO:10), and the encoded protein sequence (SEQ ID NO:11).

FIGS. 9A and 9B depict the nucleic acid sequence of an OspA gene (SEQ ID NO:127 and its encoded protein sequence (SEQ ID NO:128).

FIGS. 10A, 10B and 10C depict the nucleic acid sequence of the OspA-K48/OspA-PGau chimer (SEQ ID NO:28) and the encoded chimeric protein sequence (SEQ ID NO:29).

FIGS. 11A, 11B and 11C depict the nucleic acid sequence of the OspA-B31/OspA-PGau chimer (SEQ ID NO:30) and the encoded chimeric protein sequence (SEQ ID NO:31).

FIGS. 12A and 12B depict the nucleic acid sequence of the OspA-B31/OspA-K48 chimer (SEQ ID NO:32) and the encoded chimeric protein sequence (SEQ ID NO:33).

FIGS. 13A, 13B and 13C depict the nucleic acid sequence of the OspA-B31/OspA-25015 chimer (SEQ ID NO:34) and the encoded chimeric protein sequence (SEQ ID NO:35).

FIGS. 14A, 14B and 14C depict the nucleic acid sequence of the OspA-K48/OspA-B31/OspA-K48 chimer (SEQ ID NO:36) and the encoded chimeric protein sequence (SEQ ID NO:37).

FIGS. 15A, 15B and 15C depict the nucleic acid sequence of the OspA-B31/OspA-K48/OspA-B31/OspA-K48 chimer (SEQ ID NO:38) and the encoded chimeric protein sequence (SEQ ID NO:39).

FIGS. 16A, 16B and 16C depict the nucleic acid sequence of the OspA-B31/OspB-B31 chimer (SEQ ID NO:40) and the encoded chimeric protein sequence (SEQ ID NO:41).

FIGS. 17A, 17B, 17C, 17D, 17E, 17F, 17G, 17H, 17I, 17J, 17K, 17L, 17M, 17N, 17O, and 17P, depict an alignment of the nucleic acid sequences for OspA-B31 (SEQ ID NO:6), OspA-pKa1 (SEQ ID NO:42), OspA-N40 (SEQ ID NO:43), OspA-ZS7 (SEQ ID NO:44), OspA-25015 (SEQ ID NO:12), OspA-pTrob (SEQ ID NO:45), OspA-K48 (SEQ ID NO:8), OspA-Hei (SEQ ID NO:46), OspA-DK29 (SEQ ID NO:21), OspA-Ip90 (SEQ ID NO:22), OspA-pBo (SEQ ID NO:23), OspA-Ip3 (SEQ ID NO:24), OspA-Pko (SEQ ID NO:25), OspA-ACAI (SEQ ID NO:26), and OspA-PGau (SEQ ID NO:10). Nucleic acids which are identical to those in the lead nucleic acid sequence (here, OspA-B31) are represented by a period (.); differing nucleic acids are shown in lower case letters.

FIGS. 18A and 18B depict the nucleic acid sequence of the OspA-Tro/OspA-Bo chimer (SEQ ID NO:47) and the encoded chimeric protein sequence (SEQ ID NO:48).

FIGS. 19A and 19B depict the nucleic acid sequence of the OspA-PGau/OspA-Bo chimer (SEQ ID NO:49) and the encoded chimeric protein sequence (SEQ ID NO:50).

FIGS. 20A and 20B depict the nucleic acid sequence of the OspA-B31/OspA-PGau/OspA-B31/OspA-K48 chimer (SEQ ID NO:53) and the encoded chimeric protein sequence (SEQ ID NO:54).

FIGS. 21A and 21B depict the nucleic acid sequence of the OspA-PGau/OspA-B31/OspA-K48 chimer (SEQ ID NO:51) and the encoded chimeric protein sequence (SEQ ID NO:52).

FIGS. 30A, 30B and 30C depict the nucleic acid sequence of the OspC-B31 (bp 55-633)/OspA-B31 (bp 52-822) chimer (SEQ ID NO:55) and the encoded chimeric protein sequence (SEQ ID NO:56).

FIGS. 31A, 31B and 31C depict the nucleic acid sequence of the OspC-B31 (bp 55-624)/OspA-B31 (bp 52-822) chimer (SEQ ID NO:57) and the encoded chimeric protein sequence (SEQ ID NO:58).

FIGS. 32A, 32B and 32C depict the nucleic acid sequence of the OspC-C2 (bp 55-612)/OspA-B31 (bp 52-822) chimer (SEQ ID NO:59) and the encoded chimeric protein sequence (SEQ ID NO:60).

FIGS. 33A, 33B, and 33C depict the nucleic acid sequence of the OspC-B31 (bp 55-633)/OspA-B31 (bp 52-651)/OspA-K48 (bp 652-820) chimer (SEQ ID NO:61) and the encoded chimeric protein sequence (SEQ ID NO:62).

FIGS. 34A, 34B and 34C depict the nucleic acid sequence of the OspC-C2 (bp 55-612)/OspA-B31 (bp 52-651)/OspA-K48 (bp 652-820) chimer (SEQ ID NO:63) and the encoded chimeric protein sequence (SEQ ID NO:64).

FIGS. 35A, 35B and 35C depict the nucleic acid sequence of the OspC-B31 (bp 55-633)/OspA-B31 (bp 52-651)/OspA-Pko (bp 652-820) chimer (SEQ ID NO:65) and the encoded chimeric protein sequence (SEQ ID NO:66).

FIGS. 36A, 36B and 36C depict the nucleic acid sequence of the OspC-C2 (bp 55-612)/OspA-B31 (bp 52-651)/OspA-Pko (bp 652-820) chimer (SEQ ID NO:67) and the encoded chimeric protein sequence (SEQ ID NO:68).

FIGS. 37A, 37B and 37C depict the nucleic acid sequence of the OspC-B31 (bp 55-633)/OspA-K48 (bp 52-654)/OspA-Tro (bp 655-819) chimer (SEQ ID NO:69) and the encoded chimeric protein sequence (SEQ ID NO:70).

FIGS. 38A, 38B and 38C depict the nucleic acid sequence of the OspC-C2 (bp 55-612)/OspA-K48 (bp 52-654)/OspA-Tro (bp 655-819) chimer (SEQ ID NO:71) and the encoded chimeric protein sequence (SEQ ID NO:72).

FIGS. 39A, 39B, 39C depict the nucleic acid sequence of the OspC-C12 (bp 55-612)/OspA-B31 (bp 88-450)/OspA-Pko (bp 451-537)/OspA-B31 (bp 538-822) chimer (SEQ ID NO:73) and the encoded chimeric protein sequence (SEQ ID NO:74).

FIGS. 40A, 40B and 40C depict the nucleic acid sequence of the OspC-Pko (bp 55-639)/OspA-B31 (bp 88-450)/OspA-Pko (bp 451-537)/OspA-B31 (bp 538-651)/OspA-K48 (bp 652-825) chimer (SEQ ID NO:75) and the encoded chimeric protein sequence (SEQ ID NO:76).

FIGS. 41A, 41B and 41C depict the nucleic acid sequence of the OspC-Tro (bp 55-624)/OspA-B31 (bp 88-450)/OspA-Pko (bp 451-537)/OspA-B31 (bp 538-651)/OspA-Pko (bp 652-822) chimer (SEQ ID NO:77) and the encoded chimeric protein sequence (SEQ ID NO:78).

FIGS. 42A and 42B depict the nucleic acid sequence of the OspC-B31 (bp 55-633)/OspA-B31 (bp 394-820) chimer (SEQ ID NO:79) and the encoded chimeric protein sequence (SEQ ID NO:80).

FIGS. 43A and 43B depict the nucleic acid sequence of the OspC-B31 (bp 55-631)/OspA-B31 (bp 394-651)/OspA-K48 (bp 652-820) chimer (SEQ ID NO:81) and the encoded chimeric protein sequence (SEQ ID NO:82).

FIGS. 44A and 44B depict the nucleic acid sequence of the OspC-B31 (bp 55-633)/OspA-B31 (bp 394-651)/OspA-Pko (bp 652-820) chimer (SEQ ID NO:83) and the encoded chimeric protein sequence (SEQ ID NO:84).

FIGS. 45A and 45B depict the nucleic acid sequence of the OspC-B31 (bp 55-633)/OspA-K48 (bp 394-654)/OspA-Tro (bp 655-819) chimer (SEQ ID NO:85) and the encoded chimeric protein sequence (SEQ ID NO:86).

FIGS. 46A, 46B and 46C depict the nucleic acid sequence of the OspC-B31 (bp 55-633)/OspA-B31 (bp 88-450)/OspA-Pko (bp 451-537)/OspA-B31 (bp 541-651)/OspA-Pko (bp 652-822) chimer (SEQ ID NO:87) and the encoded chimeric protein sequence (SEQ ID NO:88).

FIGS. 47A, 47B, and 47C depict the nucleic acid sequence of the OspC-C2 (bp 55-612)/OspA-B31 (bp 88-450)/OspA-Pko (bp 451-537)/OspA-B31 (bp 541-651)/OspA-Pko (bp 652-822) chimer (SEQ ID NO:89) and the encoded chimeric protein sequence (SEQ ID NO:90).

FIGS. 48A and 48B depict the nucleic acid and encoded protein sequence of an R139M altered OspA (SEQ ID NO:95 and 96).

FIGS. 49A and 49B depict the nucleic acid and encoded protein sequence of an E160Y altered OspA (SEQ ID NO:97 and 98).

FIGS. 50A and 50B depict the nucleic acid and encoded protein sequence of an R139M, E160Y altered OspA (SEQ ID NO:99 and 100).

FIGS. 51A and 51B depict the nucleic acid and encoded protein sequence of an E160Y altered OspA (SEQ ID NO:101 and 102).

FIGS. 52A and 52B depict the nucleic acid and encoded protein sequence of an R139M, E160Y, K189M altered OspA (SEQ ID NO:103 and 104).

FIGS. 53A and 53B depict the nucleic acid and encoded protein sequence of an Y165F altered OspA (SEQ ID NO:105 and 106).

FIGS. 54A and 54B depict the nucleic acid and encoded protein sequence of an Y165F, V166T altered OspA (SEQ ID NO:107 and 108).

FIGS. 55A and 55B depict the nucleic acid and encoded protein sequence of a V166T altered OspA (SEQ ID NO:109 and 110).

FIGS. 56A and 56B depict the nucleic acid and encoded protein sequence of a V166T, T170K altered OspA (SEQ ID NO:111 and 112).

FIGS. 57A and 57B depict the nucleic acid and encoded protein sequence of an Y165F, V166T, T170K altered OspA (SEQ ID NO:113 and 114).

FIGS. 58A and 58B depict the nucleic acid and encoded protein sequence of an R139M, E160Y, K189M, Y165F, V166T, T170K altered OspA (SEQ ID NO:115 and 116).

DETAILED DESCRIPTION OF THE INVENTION

Figure 1:
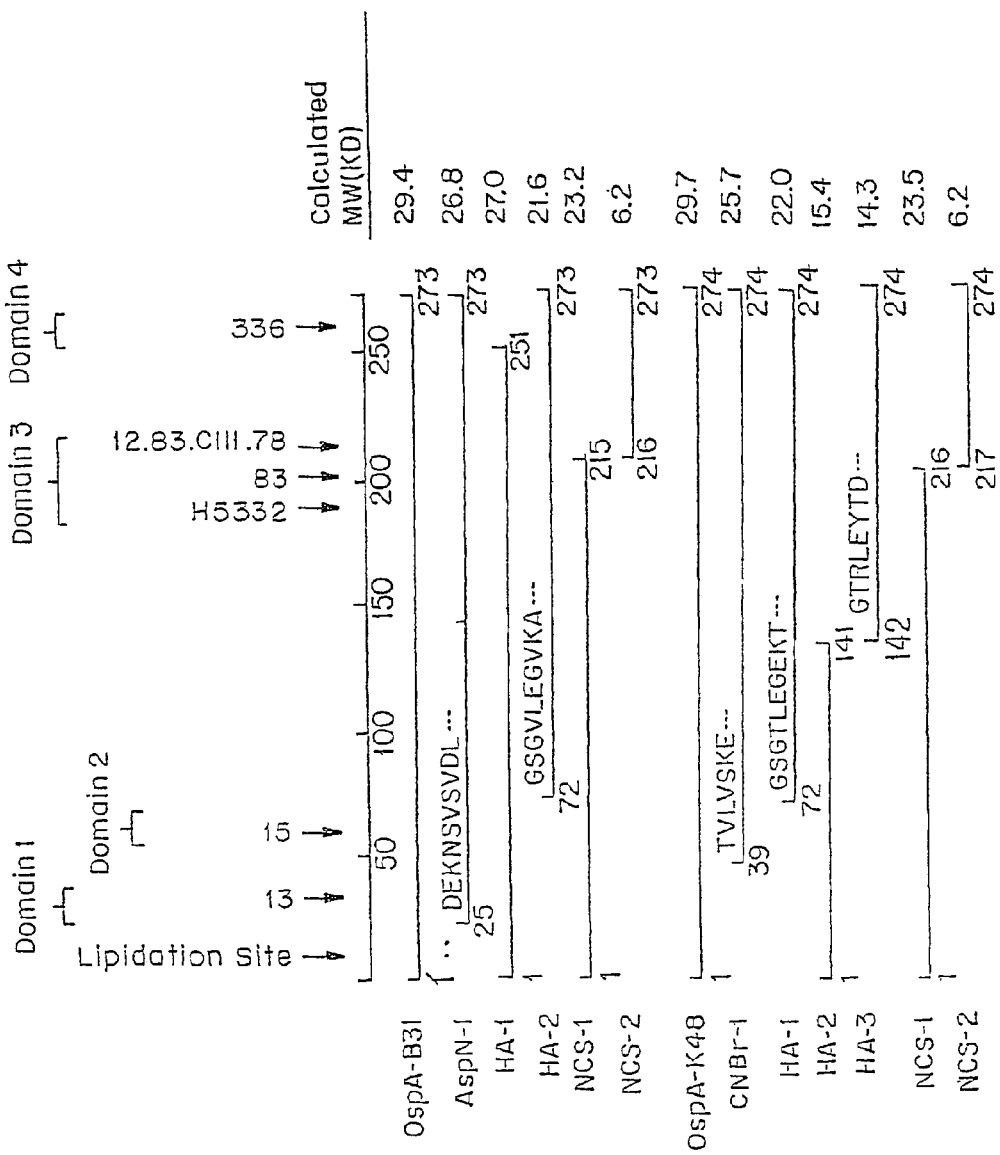
FIG. 1 summarizes peptides and antigenic domains localized by proteolytic and chemical fragmentation of OspA.
Figure 3:
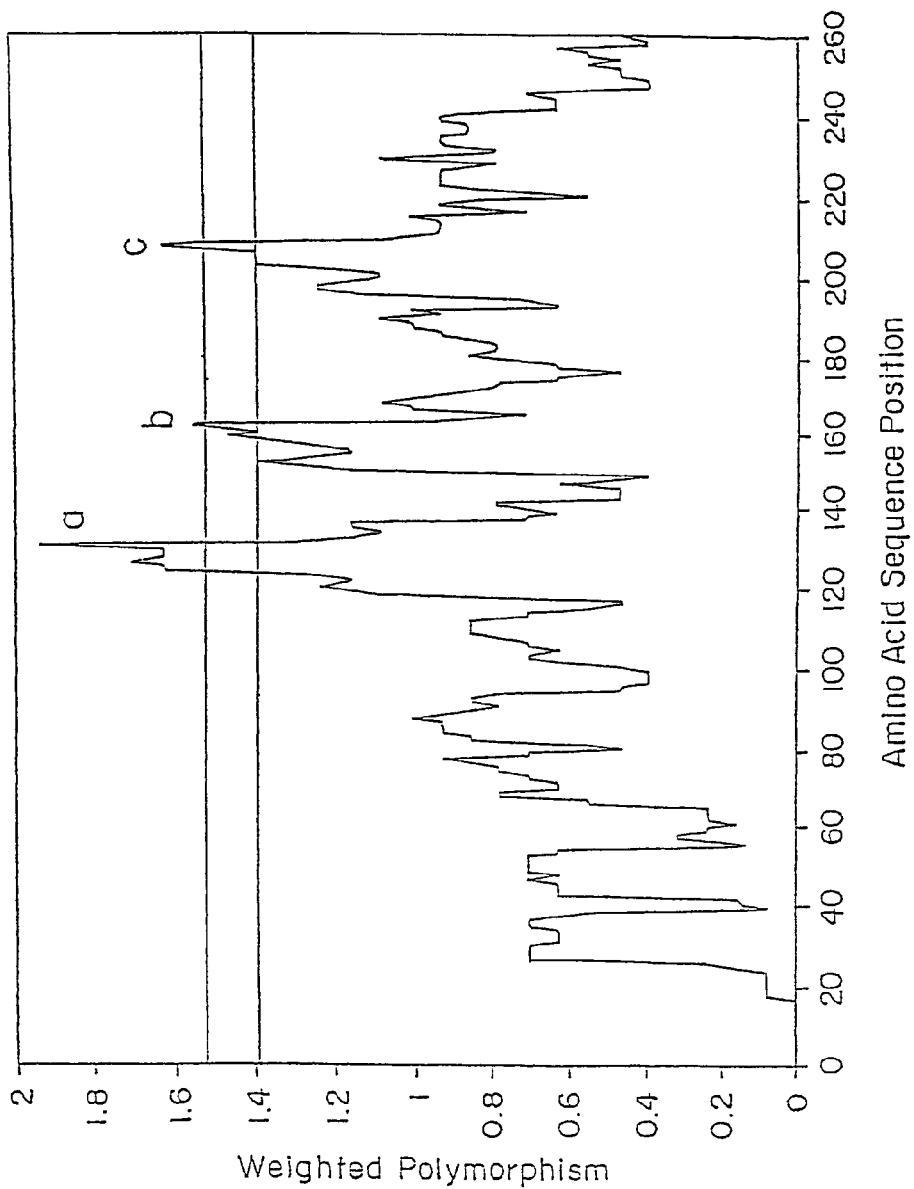
FIG. 3 is a graph depicting a plot of weighted polymorphism versus amino acid position among 14 OspA variants. The marked peaks are: a) amino acids 132-145; b) amino acids 163-177; c) amino acids 208-221. The lower dotted line at polymorphism value 1.395 demarcates statistically significant excesses of polymorphism at p=0.05. The upper dotted line at 1.520 is the same, except that the first 29 amino acids at the monomorphic-terminus have been removed from the original analysis.
Figure 5:
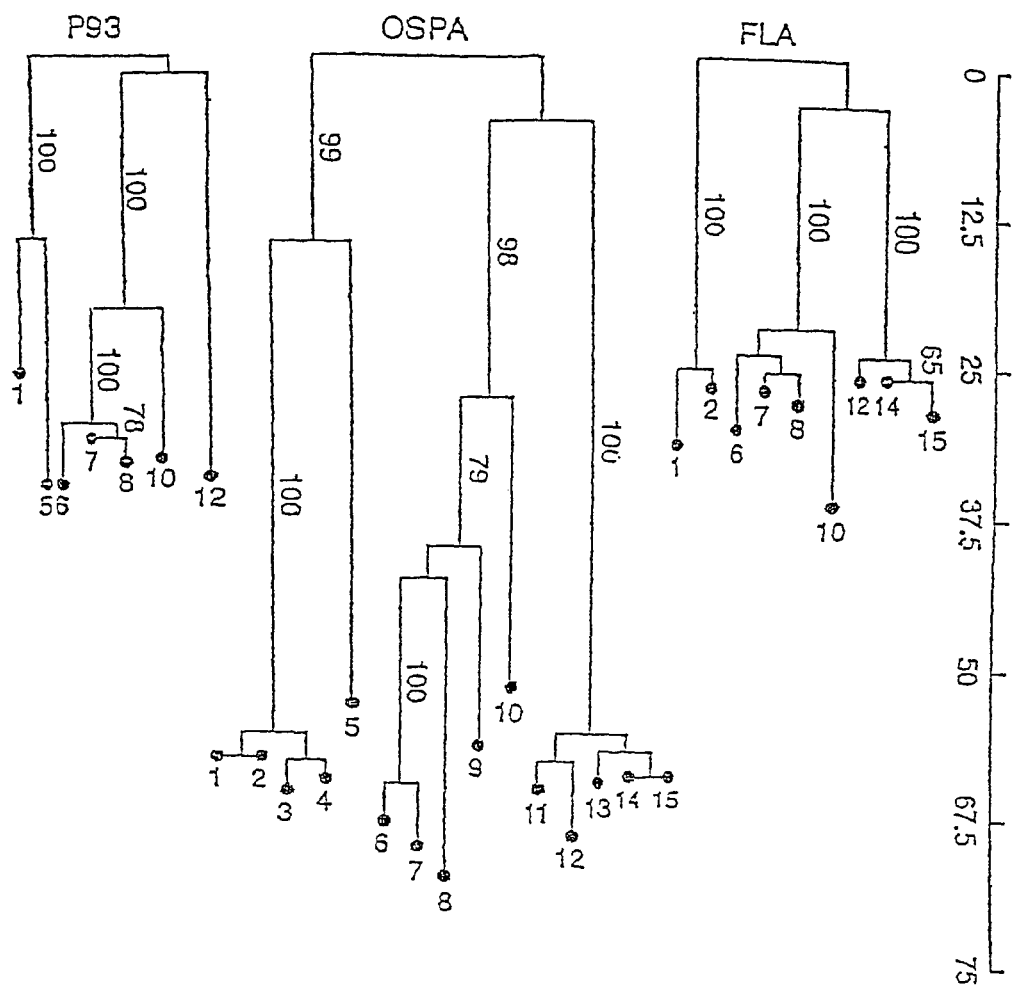
FIG. 5 depicts a phylogenetic tree for strains of *Borrelia* described in Table I. The strains are as follows: 1=B31; 2=Pka1; 3=ZS7; 4=N40; 5=25015; 6=K48; 7=DK29; 8=PHei; 9=Ip90; 10=PTrob; 11=ACAI; 12=PGau; 13=Ip3; 14=PBo; 15=Pko.

A description of preferred embodiments of the invention follows.

The present invention is drawn to altered forms of OspA from *Borrelia burgdorferi* that have increased conformational stability while maintaining antigenicity, as indicated, for example, by the ability to be bound by the LA-2 monoclonal antibody. In some embodiments, the altered OspA polypeptides also have decreased cross-reactivity with hLFA-1. The altered OspA polypeptides can comprise all (with the exception of the alterations described herein) or a portion, such as the C-terminal portion, of a wild type OspA polypeptide. Applicants have found that some forms of the OspA protein, such as truncated versions of OspA, do not elicit a strong immunoprotective response when administered to an animal even when the OspA polypeptide has the immunoprotective LA-2 epitope sequence.

The structure for recombinant OspA has been determined to 1.95□ resolution in a binary complex with the Fab fragment of the nonprotective mouse mAb184.1, which is reactive with the OspA-terminus (Li et al., *Proc. Natl. Acad. Sci. U.S.A.* 94:3584-3589 (1997)). The OspA polypeptide folds into 21 consecutive antiparallel β-strands followed by a C-terminal α-helix. The structure is conveniently described as two discrete folded domains, an N-terminal sandwich domain and a C-terminal barrel domain, connected by a long central β-sheet. One set of altered polypeptides described herein is designed to remove buried charges and/or salt bridges in the OspA C-terminal portion and replace them with residues that promote hydrophobic interactions.

Accordingly, in one embodiment, the altered OspA polypeptides of the present invention comprise altered OspA protein or polypeptides from *Borrelia burgdorferi* from about residue 139 to about residue 273, wherein the sequence includes at least one alteration selected from the group consisting of: residue 139 changed to methionine, residue 160 changed to tyrosine, residue 189 changed to methionine and combinations thereof. The numbering of the residues corresponds to the numbering of SEQ ID NO:7. In one embodiment, the altered OspA polypeptide has a tyrosine at residue position 160 and a methionine at residue position 189. These alterations have been found to stabilize the conformation of the immunoprotective LA-2 epitope in LA-2-containing OspA polypeptides. In another embodiment, the altered OspA polypeptide has a methionine at residue position 139, a tyrosine at residue position 160 and a methionine at residue position 189. In other embodiments, the altered OspA polypeptides have both increased conformational stability and reduced cross-reactivity to the hLFA-1 protein.

For the alterations at positions 139, 160 and 189, the altered OspA sequence can be from any Lyme borreliosis strain of *Borrelia burgdorferi*, such as strains from *Borrelia burgdorferi* sensu stricto, *Borrelia afzelii* and *Borrelia garinii*. Strains of *Borrelia burgdorferi* are well known to those of skill in the art. For example, strains of *Borrelia burgdorferi* sensu stricto include B31, strains of *Borrelia* afzelii include Pgau and Pko and strains of *Borrelia garinii* include K48.

In one embodiment, the OspA polypeptides of the present invention comprise an amino acid sequence of OspA protein from *Borrelia burgdorferi* from about residue 160 to about residue 170, wherein the sequence includes at least two alterations selected from the group consisting of: residue 165 changed to phenylalanine, residue 166 changed to threonine and residue 170 changed to lysine, wherein the numbering of the residues corresponds to the numbering of SEQ ID NO:7. In another embodiment, the OspA polypeptides of the present invention comprise an amino acid sequence of OspA protein from a sensu stricto strain of *Borrelia burgdorferi* from about residue 160 to about residue 170, wherein the sequence includes at least one alteration selected from the group consisting of: residue 165 changed to phenylalanine, residue 166 changed to threonine, residue 170 changed to lysine and combinations thereof. The numbering of the residues corresponds to the numbering of SEQ ID NO:7. In another embodiment, the altered OspA polypeptide has a phenylalanine at residue position 165 and a threonine at residue position 166. In still another embodiment, the altered OspA polypeptide has a phenylalanine at residue position 165, a threonine at residue position 166 and a lysine at residue position 170. In yet another embodiment, the altered OspA polypeptide includes all of the alterations described herein. In this embodiment, the altered OspA polypeptide has a methionine at residue position 139, a tyrosine at residue position 160, a methionine at residue position 189, a phenylalanine at residue position 165, a threonine at residue position 166 and a lysine at residue position 170.

This invention also pertains to polypeptides comprising SEQ ID NO:96, 98, 100, 102, 104, 106, 108, 110, 112, 114, or 116. The altered OspA polypeptides of the invention can be partially or substantially purified (e.g., purified to homogeneity), and/or substantially free of other proteins.

The present invention is also drawn to polynucleotides encoding the amino acid sequences described herein. As defined herein, the term "polynucleotide" refers to a nucleotide multimer or oligomer which is composed of deoxyribonucleotides or ribonucleotides, or a combination thereof, having from a few, e.g., 2-20, to many, e.g., 20 to several thousand or more, nucleotides. As such, polynucleotides include nucleic acids of any length and further encompass both naturally-occurring and synthetic oligonucleotides and polynucleotides.

The polynucleotides of the present invention include polynucleotides encoding OspA polypeptides from Borrelia burgdorferi from about residue 139 to about residue 189, wherein the sequence encodes at least one alteration selected from the group consisting of: codon 139 encoding methionine, codon 160 encoding tyrosine, codon 189 encoding methionine and combinations thereof. The numbering of the residues corresponds to the numbering of SEQ ID NO:7. As described above for the polypeptides, in the case of alterations at positions 139, 160 and 189, the polynucleotide encoding the altered OspA sequence can be from any Lyme borreliosis strain of Borrelia burgdorferi.

In another embodiment, the polynucleotide encodes an amino acid sequence of an OspA polypeptide from Borrelia burgdorferi from about residue 160 to about residue 170, wherein the sequence encodes at least one alteration selected from the group consisting of: codon 165 encoding phenylalanine, codon 166 encoding threonine, codon 170 encoding lysine and combinations thereof. The numbering of the residues corresponds to the numbering of SEQ ID NO:7.

The polynucleotides of the present invention include polynucleotides selected from the group consisting of: SEQ ID NO:95, 97, 99, 101, 103, 105, 107, 109, 111, 113 and 115.

The altered OspA polypeptides of the present invention can be derived from OspA molecules comprising fragments, derivatives, analogs, variants and mutants of the OspA protein (modified OspA) or can be fragmented, derivatized, or otherwise altered after having the alterations described herein inserted. These modified OspA molecules possess OspA antigenic activity.

The present invention is also drawn to a method of generating an altered Borrelia burgdorferi OspA polypeptide with increased conformational stability, as compared to the corresponding unaltered Borrelia burgdorferi OspA polypeptide. The method comprises selecting a polynucleotide encoding a Borrelia burgdorferi OspA polypeptide that includes residues 139, 160 and 189, wherein the numbering corresponds to the numbering of SEQ ID NO:7. The polynucleotide is altered such that residue 139 is methionine, residue 160 is tyrosine or residue 189 is methionine or combination thereof. The altered polynucleotide is expressed, thereby generating an altered Borrelia burgdorferi OspA polypeptide with increased conformational stability compared to the corresponding unaltered Borrelia burgdorferi OspA polypeptide. Methods of altering a polynucleotide are described below and in the Exemplification and are well known to those of skill in the art. Methods of expressing the altered polypeptides of the invention are also described below and in the Exemplification and are well known to those of skill in the art.

Residues 165-173 on β-strand 13 of OspA have been implicated in induction of Lyme-related arthritis (Gross D. M. et al., Science 281:703-706 (1998)). This region has homology to residues 332-340 of hLFA-1, suggesting that this protein has a cross-reactive T cell epitope (YVLEGTLTA-B31 (SEQ ID NO:129 and YVIEGTSKQ-hLFA-1 (SEQ ID NO:130), respectively). Although B. burgdorferi sensu stricto is generally believed to be more arthritogenic that other Borrelia strains, a recent study of ospA alleles in synovial fluid of patients with Lyme arthritis indicates that B. garinii and B. afzelii may also cause arthritis (Eiffert, L. F. et al., Scand. J. Infect. Dis. 30:265-268 (1998)).

One way to eliminate the cross-reactive sequence is to replace the α-13 region of OspA-B31 (YVLEGTLTA (SEQ ID NO:129)) with an analogous region from a strain that does not possess the same sequence, such as that from a B. Afzelii strain, e.g., Pgau or Pko (U.S. patent application entitled "Recombinant Constructs of Borrelia burgdorferi" by Luft et al., filed on Aug. 7, 2001, the entire teachings of which are incorporated herein by reference).

Accordingly, in another embodiment, the present invention is drawn to a method of generating an altered Borrelia burgdorferi OspA polypeptide with reduced cross-reactivity with the hLFA-1 molecule, as compared to the corresponding unaltered Borrelia burgdorferi OspA polypeptide. The method comprises selecting a polynucleotide encoding an OspA polypeptide from Borrelia burgdorferi that includes residues 165, 166 and 170, wherein the numbering corresponds to the numbering of SEQ ID NO:7. The polynucleotide is altered such that residue 165 is changed to phenylalanine, residue 166 is changed to threonine or residue 170 is changed to lysine or combination thereof. The altered polynucleotide is expressed, thereby generating an altered Borrelia burgdorferi OspA polypeptide with reduced cross-reactivity with the hLFA-1 molecule compared to the corresponding unaltered Borrelia burgdorferi OspA polypeptide. In another embodiment, an altered OspA polypeptide having reduced cross-reactivity to hLFA-1 while retaining the ability to be bound by LA-2 is generated. In that embodiment, for example, residue 130 is methionine, residue 160 is tyrosine, residue 165 is phenylalanine, residue 166 is threonine, residue 170 is lysine and residue 189 is methionine. Polynucleotides encoding Borrelia burgdorferi OspA polypeptides can be selected as described herein.

In one embodiment, the altered OspA polypeptide includes the minimal sequence that includes the positions of the alterations. For example, the altered polypeptide can comprise OspA from about residue 139 to about residue 189, wherein the numbering corresponds to SEQ ID NO:7. In another embodiment, the altered polypeptide can comprise OspA from about residue 165 to about residue 170, wherein the numbering corresponds to SEQ ID NO:7. The altered OspA polypeptides of the present invention also include larger fragments of OspA. For example, the altered OspA polypeptides include, but are not limited to, altered OspA polypeptides which comprise OspA from about residue 160 to about residue 170, OspA from about residue 150 to 180, OspA from about residue 131 to 273 or OspA from about residue 17 to 273. Methods of generating and expressing varying-sized fragments of OspA which incorporate one or more of the alterations described herein are described below and are well known to those of skill in the art.

As described herein, the OspA sequence used to generate the altered OspA polypeptide can itself be a chimeric OspA polypeptide, having two or more segments derived from OspA proteins from different genospecies or strains of Borrelia. The size of the altered OspA polypeptide can vary depending on the method used to generate the altered polypeptide and/or the purpose for which it is generated, and such altered OspA chimeric polypeptides can include fragments of OspA. The altered polypeptide can be part of a larger polypeptide, including additional OspA sequences on the N-terminus, the C-terminus or both termini. A fragment of OspA protein can encompass polypeptides that are only a part of the full-length OspA protein. Such OspA fragments typically include at least one of the altered residues described herein and possess at least some of the antigenicity of wild type OspA. OspA fragments can be produced by amino and/or carboxyl terminal deletions, as well as internal deletions. Fragments can also be produced by enzymatic digestion. Such modified OspA molecules can be tested for antigenic activity as described herein or using methods known in the art.

In some embodiments, the altered OspA polypeptide can be part of a cocktail with one or more other proteins, such as other *Borrelia burgdorferi* polypeptides, including but not limited to, OspA, OspB, OspC, OspD, p93 and p41. In other embodiments, the altered OspA polypeptide can be part of a larger molecule, such as a chimeric polypeptide, for example, as described in U.S. Pat. No. 6,248,562 and U.S. patent application entitled "Recombinant Constructs of *Borrelia burgdorferi*", by Luft et al., filed on Aug. 7, 2001. Such larger polypeptides can include amino acid sequences from other proteins including but not limited to, other *Borrelia burgdorferi* proteins and/or other proteins useful in generating fusion proteins for vaccine and/or immunodiagnostic methods. Additional components, for example, labels (a radioisotope, an epitope label (tag)(e.g., a hemagglutinin (HA) epitope, a hexahistidine tag), an affinity label (e.g., biotin, avidin), a spin label, an enzyme label, a fluorescent group, a chemiluminescent group) can be incorporated into the altered OspA polypeptides of the invention to assist in the isolation and/or purification of the polypeptide. For example, a hexahistidine tag would permit ready purification by nickel chromatography. These and other components can also be incorporated in the altered OspA polypeptides of the invention in order to extend the half life of the polypeptides. Methods of incorporating such components into the polypeptides of the invention are well known to those of skill in the art.

In one embodiment, the altered OspA polypeptide of the invention is a chimeric polypeptide. In a particular embodiment, the altered OspA polypeptide comprises the following: a) an amino acid sequence of a first OspA polypeptide from about residue 1 to about residue 164 from a first strain of *Borrelia burgdorferi*; b) an amino acid sequence of a second OspA polypeptide from about residue 165 to about residue 179 from a second strain of *Borrelia burgdorferi*, wherein said second strain is a different strain from said first strain; c) an amino acid sequence of a third OspA polypeptide from about residue 180 to about residue 216 from a third strain of *Borrelia burgdorferi*, wherein said third strain is a different strain from said second strain; d) an amino acid sequence of a fourth OspA polypeptide from about residue 217 to about residue 273 from a fourth strain of *Borrelia burgdorferi*, wherein said fourth strain is a different strain from said third strain; wherein the sequence includes at least one alteration selected from the group consisting of: residue 139 being methionine, residue 160 being tyrosine, residue 189 being methionine and combinations thereof, wherein the numbering corresponds to the numbering of SEQ ID NO:7.

Polypeptides described herein can be isolated from naturally-occurring sources, chemically synthesized or recombinantly produced. The altered OspA polypeptides of the present invention can be derived from naturally-occurring OspA molecules or from nucleic acids which encode such molecules The OspA polypeptides of the present invention can comprise fragments, derivatives, analogs, variants and mutants of an OspA protein (modified OspA) and/or can be fragmented, derivatized or otherwise altered after having the alterations described herein inserted (also referred to as modified OspA). Such modified OspA molecules possess at least some OspA antigenic activity. According to the invention, the amino acid sequence of the altered OspA polypeptides of the invention can be that of a naturally-occurring protein or can comprise additional modifications. Such additional modifications include conservative and/or non-conservative amino acid substitutions, additions of one or more amino acids, and/or deletions of one or more amino acids. Such additional modifications should also preserve at least some activity of the encoded protein or polypeptide. For example, the further modified polypeptide or protein should have similar or improved conformational stability, similar or improved immunoprotective activity or reduced cross-reactivity to hLFA-1, as compared to the corresponding altered OspA polypeptide (i.e., the OspA polypeptide comprising one or more of the alterations described herein but not comprising the further modification(s)).

For example, the further modification(s) preferably preserve the three-dimensional configuration of an antibody binding site of the native protein such as the LA-2 binding site. The presence or absence of biological activity or activities can be determined by various functional assays as described herein or using methods that are known in the art, e.g., recognition using an ELISA assay, elicitation of an immune response (e.g., an immunoprotective response) in an animal. Appropriate amino acid alterations that fall within the scope of the invention can be made on the basis of several criteria, including hydrophobicity, basic or acidic character, charge, polarity, size, the presence or absence of a functional group (e.g., —SH or a glycosylation site), and aromatic character, provided that the resulting molecule has at least one of the alterations described herein and maintains increased conformational stability and/or reduced cross-reactivity to hLFA-1. Assignment of various amino acids to similar groups based on the properties above will be readily apparent to the skilled artisan; further appropriate amino acid changes can also be found in Bowie (*Science,* 247:1306-1310 (1990)).

"Variants" and "mutants" of OspA can be produced using in vitro and/or in vivo techniques well-known to those of skill in the art, for example, site-specific mutagenesis, and oligonucleotide mutagenesis. Manipulations of the OspA polypeptide sequence can be made at the protein level as well. Chemical modifications can be carried out using known techniques including but not limited to, specific chemical cleavage using cyanogen bromide, trypsin and/or papain. OspA can also be structurally modified and/or denatured, for example, using heat. In general, mutations can be conservative or non-conservative amino acid substitutions, amino acid insertions or amino acid deletions.

For example, a nucleic acid (e.g., DNA) encoding a modified OspA polypeptide can be prepared by site-directed mutagenesis of the nucleic acid (e.g., DNA) that encodes a wild type OspA. Site-directed (site-specific) mutagenesis allows the production of OspA variants through the use of specific oligonucleotide sequences that encode the DNA sequence of the desired mutation (e.g., alteration, deletion, insertion), as well as a sufficient number of adjacent nucleotides, to provide a primer sequence of sufficient size and sequence complexity to form a stable duplex on both sides of the desired mutation. Typically, a primer of about 20 to 25 nucleotides in length is preferred, with about 5 to 10 complementary residues on both sides of the mutation of the sequence being altered. In general, the techniques of site-specific mutagenesis are well known in the art, as exemplified by publications such as Edelman et al., DNA, 2:183, 1983. For example, a site-specific mutagenesis technique can employ a phage vector that exists in both a single-stranded and double-stranded form. Typical vectors useful in site-directed mutagenesis include vectors such as the M13 phage, for example, as disclosed by Messing et al., Third Cleveland Symposium on Macromolecules and Recombinant DNA, A. Walton, ed., Elsevier, Amsterdam, 1981. This and other phage vectors are commercially available and their use is well known to those skilled in the art. A versatile and efficient procedure for the construction of oligonucleotide directed site-specific mutations in DNA fragments using M13-derived vectors was published by Zoller, M. J. and Smith, M., *Nucleic Acids Res.*, 10:6487-6500, 1982. In addition, plasmid vectors that contain a single-stranded phage origin of replication can be employed to obtain single-stranded DNA (see for example, Veira et al., *Meth Enzymol.*, 153:3, (1987)).

Alternatively, nucleotide substitutions can be introduced by synthesizing the appropriate DNA fragment in vitro, and amplifying it using PCR procedures known in the art.

In general, site-specific mutagenesis can be performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc Natl Acad Sci USA.*, 75:5765, 1978. This primer can then be annealed with the single-stranded protein sequence-containing vector, and subjected to DNA polymerizing enzymes, e.g., *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector can then be used to transform appropriate host cells such as JM 101 cells, and clones can be selected that include recombinant vectors bearing the mutated sequence arrangement. Thereafter, the mutated region can be removed and placed in an appropriate expression vector for protein production.

The PCR technique can be used in creating amino acid sequence variants of OspA. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers can be designed to overlap the position of the mutation and to contain the mutation; the sequence of the other primer is preferably identical to a stretch of sequence of the opposite strand of the plasmid, but this sequence can be located anywhere along the plasmid DNA. It is preferred, however, that the sequence of the second primer be located within 500 nucleotides from that of the first, such that in the end the entire amplified region of DNA bounded by the primers can be easily sequenced. PCR amplification using a primer pair like the one just described results in a population of DNA fragments that differ at the end position of the mutation specified by the primer.

The DNA fragments produced bearing the desired mutation can be used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more) part ligation.

An additional method for preparing variants, cassette mutagenesis, is based on the technique described by Wells et al., *Gene*, 34:315, 1985. The starting material can be the plasmid (or vector) comprising the OspA DNA to be mutated. The codon(s) within the OspA to be mutated are identified. There must be unique restriction endonuclease sites on each side of the identified mutation site(s). If such restriction sites do not exist, they can be generated using the above-described oligonucleotide-mediated mutagenesis method to introduce them at appropriate locations in the OspA DNA or they can be generated using PCR and the desired primers as described in the Exemplification. After the restriction sites have been introduced into the plasmid, the plasmid is cut at these sites to linearize it. A double stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. The plasmid now contains the mutated OspA DNA sequence, and can be subcloned and/or expressed to produce the modified OspA polypeptide or protein.

The OspA encoding nucleic acid molecules (e.g., polynucleotides) of the present invention have at least one of the alterations described herein and generally hybridize under high stringency hybridization conditions to a polynucleotide-encoding OspA nucleic acid or fragment thereof from a sensu stricto strain of *Borrelia burgdorferi*, e.g., SEQ ID NO:7. In one embodiment, the OspA-encoding nucleic acid molecules (e.g., polynucleotides) of the present invention hybridize under high stringency hybridization conditions to a polynucleotide encoding OspA or fragment thereof from *Borrelia afzelii*, e.g., SEQ ID NO:10. In another embodiment, the OspA-encoding nucleic acid molecules (e.g., polynucleotides) of the present invention hybridize under high stringency hybridization conditions to a polynucleotide encoding OspA or fragment thereof from *Borrelia garinii*, e.g., SEQ ID NO:8. Thus, the polynucleotides and polypeptides of the present invention include modified versions of OspA as described herein.

Appropriate selective stringency conditions are known to those skilled in the art or can be found in standard texts such as *Current Protocols in Molecular Biology*, John Wiley & Sons, N.Y. (1989), 6.3.1-6.3.6. For example, stringent hybridization conditions include a sodium ion concentration of no more than 1 M and a temperature of at least 25° C. In one embodiment, conditions of 5×SSPE (750 mM NaCl, 50 mM NaPhosphate, 5 mM EDTA, pH 7.4) and a temperature of 25-30° C., or equivalent conditions, are suitable for specific hybridization. Equivalent conditions can be determined by varying one or more of the parameters, as is known in the art, while maintaining a similar degree of identity or similarity between the target nucleic acid molecule and the primer or probe used. Hybridizable nucleic acid molecules are useful as probes and primers for diagnostic applications.

Accordingly, the invention pertains to nucleic acid molecules which have a substantial identity with the nucleic acid molecules encoding the altered OspA polypeptides described herein wherein the nucleic acid encodes for one or more of the alterations described herein; particularly preferred are nucleic acid molecules which have at least about 90%, more preferably at least about 95% and most preferably at least about 98% identity with nucleic acid molecules described herein, wherein the nucleic acid encodes for at least one of the alterations described herein. Sequence identity can be determined using publicly or commercially available sequence alignment algorithms, using, for example, default parameters.

Thus, DNA molecules which comprise a sequence which is different from the naturally-occurring nucleic acid molecule but which, due to the degeneracy of the genetic code, encode the same protein or polypeptide are encompassed by the present invention. The invention also encompasses variations of the nucleic acid molecules of the invention, such as those encoding portions, analogues or derivatives of the encoded protein or polypeptide. Such variations can be naturally-occurring, such as in the case of allelic variation, or non-naturally-occurring, such as those induced by various mutagens and mutagenic processes, so long as the nucleic acid molecule encodes at least one of the alterations described herein and the encoded protein has either increased conformational stability and/or decreased cross-reactivity to hLFA-1 (as compared to the corresponding unaltered protein) that is conferred by the alterations described herein. Intended variations include, but are not limited to, addition, deletion and/or substitution of one or more nucleotides which can result in conservative or non-conservative amino acid changes, including additions and deletions. Preferably, such nucleotide or amino acid variations are silent; that is, they do not alter one or more characteristics or activity of the encoded altered OspA protein or polypeptide. As used herein, activities of the encoded protein or polypeptide include, but are not limited to, binding function, antigenic function and conformational stability.

The invention also provides expression vectors containing a nucleic acid sequence described herein, operably linked to at least one regulatory sequence. Many such vectors are commercially available, and other suitable vectors can be readily prepared by the skilled artisan. "Operably linked" is intended to mean that the nucleic acid molecule is linked to a regulatory sequence in a manner which allows expression of the nucleic acid sequence. Regulatory sequences are art-recognized and are selected to produce the encoded polypeptide or protein. Accordingly, the term "regulatory sequence" includes promoters, enhancers, and other expression control elements which are described in Goeddel, *Gene Expression Technology. Methods in Enzymology* 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the type of protein desired to be expressed. For instance, the polypeptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al., (Cold Spring Harbor Laboratory Press, 1989) Chapters 16 and 17). Typically, expression constructs will contain one or more selectable markers, including but not limited to, the gene that encodes dihydrofolate reductase and the genes that confer resistance to neomycin, tetracycline, ampicillin, chloramphenicol, kanamycin or streptomycin.

Prokaryotic and eukaryotic host cells transfected by the described vectors are also provided by this invention. For instance, cells which can be transfected with the vectors of the present invention include, but are not limited to, bacterial cells such as *E. coli* (e.g., *E. coli* K12, BL21, DH5a strains), *Streptomyces, Pseudomonas, Serratia marcescens* and *Salmonella typhimurium*, insect cells (baculovirus) including *Drosophila*, fungal cells, such as yeast cells, plant cells and mammalian cells, such as thymocytes, Chinese hamster ovary cells (CHO) and COS cells.

Thus, a nucleic acid molecule comprising, for example SEQ ID NO:6 with at least one of the specific alterations described herein, or a nucleic acid molecule which encodes, for example SEQ ID NO:7 with at least one of the specific alterations described herein, can be used to produce a recombinant form of the protein via microbial or eukaryotic cellular processes. Ligating the nucleic acid molecule (e.g., polynucleotide) into a gene construct, such as an expression vector, and transforming or transfecting into hosts, either eukaryotic (yeast, avian, insect, plant or mammalian) or prokaryotic (bacterial cells), are standard procedures used in producing other well known proteins. Similar procedures, or modifications thereof, can be employed to prepare recombinant proteins according to the present invention by microbial means or tissue-culture technology. Accordingly, the invention pertains to the production of encoded proteins or polypeptides by recombinant technology.

The proteins and polypeptides of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

The present invention also pertains to pharmaceutical compositions comprising polypeptides and other compounds described herein. For instance, a polypeptide or protein of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to well known procedures, and will depend on the ultimate pharmaceutical formulation desired. Methods of introduction of exogenous polypeptides at the site of treatment include, but are not limited to, intradermal, intramuscular, intraperitoneal, intravenous, subcutaneous, oral and intranasal. Other suitable methods of introduction can also include gene therapy, rechargeable or biodegradable devices and slow release polymeric devices. The pharmaceutical compositions of this invention can also be administered as part of a combinatorial therapy with other agents.

The altered OspA proteins described herein can be produced so that they are highly soluble, hyper-produced in *E. coli*, and non-lipidated. In addition, the altered OspA proteins can be designed to begin or end in a suitable affinity tag (e.g., a His-tag) to facilitate purification. The recombinant proteins described herein have been constructed to maintain high levels of antigenicity and improved conformational stability.

The altered OspA proteins of the current invention are advantageous in that they retain at least some specific reactivity to monoclonal and/or polyclonal antibodies against wild-type *Borrelia* proteins, are immunogenic, and inhibit the growth or induce lysis of *Borrelia* in vitro. The proteins are particularly useful in immunodiagnostic assays. For example, proteins of the present invention can be used as reagents in assays to detect the presence of antibodies to native *Borrelia* in potentially infected individuals. These proteins can also be used as immunodiagnostic reagents, such as in dot blots, Western blots, enzyme-linked immunosorbent assays, or agglutination assays. The altered OspA proteins of the present invention can be produced by known techniques, such as by recombinant methodology, polymerase chain reaction, or mutagenesis.

Furthermore, the proteins of the current invention are useful as vaccine immunogens against *Borrelia* infection. One or more of the altered proteins can be combined with a physiologically acceptable carrier and administered to a vertebrate animal through standard methods (e.g., intravenously or intramuscularly, for example).

The altered forms of the OspA proteins described herein were bioengineered such that at least one immunoprotective domain of the protein was maintained. As described herein, antigenic refers to the ability of a compound to bind products of an immune response, such as antibodies, T-cell receptors or both. Such responses can be measured using standard antibody detection assays, such as ELISA or standard T-cell activation assays. In a preferred embodiment, the altered forms of OspA described herein elicit an immunoprotective response, for example, by eliciting antibodies that recognize the LA-2 epitope.

It is understood that the nucleic acids that encode the polypeptides that comprise the altered OspA protein can include extra nucleotides or fewer nucleotides in order to simplify the construction of the gene encoding the chimeric polypeptide, e.g., to allow for the use of convenient restriction endonuclease sites, or to allow the ligation of the gene fragments such that a contiguous coding region is created. Based on the guidance provided herein, one of ordinary skill in the art would readily be able to add or remove nucleotides from the termini of the gene fragments encoding the polypeptides of the OspA protein in order to generate the altered OspA proteins of the present invention with no experimentation or using only routine experimentation. The altered OspA polypeptides of the present invention can be lipidated or non-lipidated.

To test the antigenicity of the altered OspA polypeptides, mice can be immunized with OspA polypeptides or proteins containing the polypeptide sequences in aluminum hydroxide. Mice are then bled and tested for antibody responses against OspA derived from various strains of *Borrelia*. In additional experiments, these immunized mice can be challenged with ticks infected with *Borrelia burgdorferi* and transmission of infection can be assessed as described in the Exemplification which use OspA, OspC and OspC/OspA chimeric molecules. The results of such a tick challenge reveals whether the animal has developed a protective immune response. For example, an immunized animal that does not seroconvert in response to subsequent tick challenge has likely generated an immunoprotective response to the immunization.

The immunogenic compositions of the present invention can be used to immunize animals including humans. Immunization is understood to elicit specific immunogenic responses, preferably immunoprotective responses, as described above. As described herein, an immunogenic response includes responses that result in at least some level of immune response in the treated animal, where the animal was previously treated with a composition comprising at least one altered OspA polypeptide of the present invention.

Immunity, as described herein, is understood to mean the ability of the treated animal to resist infection, to resist systemic infection, or to overcome infection such as systemic infection more easily or more quickly when compared to non-immunized or non-treated individuals. Immunity can also include an improved ability of the treated individual to sustain an infection with reduced or no clinical symptoms of systemic infection. The individual may be treated with the altered OspA proteins of the present invention either proactively, e.g., once a year or, alternatively, after sustaining a tick bite.

In one embodiment, the altered OspA protein of the present invention, together with suitable excipients and/or adjuvants, is administered to an animal such that the animal develops an immune response to the OspA polypeptide of the composition. The pharmaceutical composition can also be administered with other components suitable for in vitro and/or in vivo use. These additional components include buffers, carrier proteins, adjuvants, preservatives and combinations thereof. In a preferred embodiment, the individual generates an immunoprotective response, for example, by generating antibodies that recognize the LA-2 epitope.

The present invention is also drawn to a physiological composition comprising an altered OspA protein. The composition is useful to administer to an animal in order to generate an immune response or in the diagnostic methods described herein.

For use as a vaccine, the composition of the present invention can include suitable adjuvants, well known in the art, to enhance immunogenicity, potency or half-life of the chimeric proteins in the treated animal. Adjuvants and their use are well known in the art (see for example PCT Publication WO 96/40290, the entire teachings of which are incorporated herein by reference). The composition can be prepared by known methods of preparing vaccines. For example, the altered OspA polypeptides described herein can be isolated and/or purified using known techniques, such as by size exclusion chromatography, ion exchange chromatography, affinity chromatography, preparative electrophoresis, selective precipitation or combinations thereof. The prepared proteins can be mixed with suitable other reagents as described above, wherein the protein is at a suitable concentration. The dosage of the protein will vary and depends upon the age, weight and/or physical condition of the animal to be treated. The optimal dosage can be determined by routine optimization techniques, using suitable animal models.

The composition to be used as a vaccine can be administered by any suitable technique. In one embodiment, administration is by injection, e.g., subcutaneous, intramuscular, intravenous, or intra peritoneal injection. In another embodiment, the composition is administered to mucosa, e.g., by exposing nasal mucosa to nose drops containing the proteins of chimeric proteins of the present invention. In another embodiment, the immunogenic composition is administered by oral administration. In another embodiment of the present invention the chimeric proteins are administered by DNA immunization using nucleic acids encoding an altered OspA polypeptide.

The present invention is also drawn to a diagnostic kit comprising the altered OspA polypeptides described herein. The kit also includes reagents for detecting antibody-antigen complexes that are formed between the OspA protein and antibodies that are present in an sample, e.g., a user-supplied host sample.

The present invention is also drawn to methods of detecting an immune response to Lyme Disease-causing *Borrelia* in a host sample. The method comprises contacting a host sample with an OspA altered protein, such that anti-OspA antibodies, if present in said sample, bind to said OspA protein. The quantity of antibodies that have bound said OspA protein are measured, thereby detecting an immune response to Lyme disease-causing *Borrelia*.

EXEMPLIFICATION

Example 1

Purification of *Borrelia burgdorferi* Outer Surface Protein A and Analysis of Antibody Binding Domains This example details a method for the purification of large amounts of native outer surface protein A (OspA) to homogeneity, and describes mapping of the antigenic specificities of several anti-OspA MAbs. OspA was purified to homogeneity by exploiting its resistance to trypsin digestion. Intrinsic labeling with $^{14}$C-palmitic acid confirmed that OspA was lipidated, and partial digestion established lipidation at the amino-terminal cysteine of the molecule.

The reactivity of seven anti-OspA murine monoclonal antibodies to nine different *Borrelia* isolates was ascertained by Western blot analysis. The reactivity of the altered OspA polypeptides described herein was tested using similar methods. Intact, lipidated or non-lipidated OspA and altered OspA can also be tested using similar methods. Purified OspA was fragmented by enzymatic or chemical cleavage, and the monoclonal antibodies were able to define four distinct immunogenic domains (see FIG. 1). Domain 3, which included residues 190-220 of OspA, was reactive with protective antibodies known to agglutinate the organism in vitro, and included distinct specificities, some of which were not restricted to a genotype of *B. burgdorferi*.

A. Purification of Native OspA

Detergent solubilization of *B. burgdorferi* strips the outer surface proteins and yields partially-purified preparations containing both OspA and outer surface protein B (OspB) (Barbour, A. G. et al., *Infect. Immun.*, 52(5):549-554 (1986); Coleman, J. L. et al., *J Infect. Dis.*, 155 (4):756-765 (1987); Cunningham, T. M. et al., *Ann. NY Acad. Sci.*, 539:376-378 (1988); Brandt, M. E. et al., *Infect. Immun.*, 58: 983-991 (1990); Sambri, V. and R. Cevenini, *Microbiol*, 14:307-314 (1991)). Although both OspA and OspB are sensitive to proteinase K digestion, in contrast to OspB, OspA is resistant to cleavage by trypsin (Dunn, J. et al., *Prot. Exp. Purif.*, 1:159-168 (1990); Barbour, A. G. et al., *Infect. Immun.*, 45:94-100 (1984)). The relative insensitivity to trypsin is surprising in view of the fact that OspA has a high (16% for B31) lysine content, and may relate to the relative configuration of OspA and B in the outer membrane.

Intrinsic Radiolabeling of *Borrelia*

Labeling for lipoproteins was performed as described by Brandt et al. (Brandt et al., *Infect. Immun.*, 58:983-991 (1990)). $^{14}$C-palmitic acid (ICN, Irvine, Calif.) was added to the BSK II media to a final concentration of 0.5 µCi per milliliter (ml). Organisms were cultured at 34° C. in this medium until a density of $10^8$ cells per ml was achieved.

Purification of OspA Protein from *Borrelia* Strain B31

*Borrelia burgdorferi*, either $^{14}$C-palmitic acid-labeled or unlabeled, were harvested and washed as described (Brandt, M. E. et al., *Infect. Immun.*, 58:983-991 (1990)). Whole organisms were trypsinized according to the protocol of Barbour et al., (*Infect. Immun.*, 45:94-100 (1984)) with some modifications. The pellet was suspended in phosphate buffered saline (PBS, 10 mM, pH 7.2), containing 0.8% tosyl-L-phenylalanine chloromethyl ketone (TPCK)-treated trypsin (Sigma, St. Louis, Mo.), the latter at a ratio of 1 µg per $10^8$ cells. Reaction was carried out at 25° C. for 1 hour, following which the cells were centrifuged. The pellet was washed in PBS with 100 µg/ml phenylmethylsulfonyl fluoride (PMSF). Triton X-114 partitioning of the pellet was carried out as described by Brandt et al., (Brandt et al., *Infect. Immun.*, 58:983-991 (1990)). Following trypsin treatment, cells were resuspended in ice-cold 2% (v/v) Triton X-114 in PBS at $10^9$ cells per ml. The suspension was rotated overnight at 4° C., and the insoluble fraction removed as a pellet after centrifugation at 10,000×g for 15 minutes at 4° C. The supernatant (soluble fraction) was incubated at 37° C. for 15 minutes and centrifuged at room temperature at 1000×g for 15 minutes to separate the aqueous and detergent phases. The aqueous phase was decanted, and ice cold PBS added to the lower Triton phase, mixed, warmed to 37° C., and again centrifuged at 1000×g for 15 minutes. Washing was repeated twice more. Finally, detergent was removed from the preparation using a spin column of Bio-beads SM2 (BioRad, Melville, N.Y.) as described (Holloway, P. W., *Anal. Biochem.*, 53:304-308 (1973)).

Ion exchange chromatography was carried out as described by Dunn et al., (Dunn et al., *Prot. Exp. Purif*, 1:159-168 (1990)) with minor modifications. Crude OspA was dissolved in buffer A (1% Triton X-100, 10 mM phosphate buffer (pH 5.0)) and loaded onto a SP Sepharose resin (Pharmacia, Piscataway, N.J.), pre-equilibrated with buffer A at 25° C. After washing the column with 10 bed-volumes of buffer A, the bound OspA was eluted with buffer B (1% Triton X-100, 10 mM phosphate buffer (pH 8.0)). OspA fractions were detected by protein assay using the BCA method (Pierce, Rockford, Ill.), or as radioactivity when intrinsically labeled material was fractionated. Triton X-100 was removed using a spin column of Bio-beads SM2.

This method purifies OspA from an outer surface membrane preparation. In the absence of trypsin-treatment, OspA and B were the major components of the soluble fraction obtained after Triton partitioning of strain B31. In contrast, when Triton extraction was carried out after trypsin-treatment, the OspB band is not seen. Further purification of OspA-B31 on a SP Sepharose column resulted in a single band by SDS-PAGE. The yield following removal of detergent was approximately 2 mg per liter of culture. This method of purification of OspA, as described herein for strain B31, can be used for other isolates of *Borrelia* as well. For strains such as strain K48, which lack OspB, trypsin treatment can be omitted.

Lipidation Site of OspA-B31

$^{14}$C-palmitic acid labeled OspA from strain B31 was purified as described above and partially digested with endoproteinase Asp-N. Following digestion, a new band of lower molecular weight was apparent by SDS-PAGE, found by direct amino-terminal sequencing to begin at $Asp_{25}$. This band had no trace of radioactivity by autoradiography. OspA and B contain a signal sequence (L-X-Y-C) similar to the consensus described for lipoproteins of *E. coli*, and it has been predicted that the lipidation site of OspA and B should be the amino-terminal cysteine (Brandt, M. E. et al., *Infect. Immun*, 58:983-991 (1990)). The results presented herein support this prediction.

B. Comparison of OspA Antibody Binding Regions in Nine Strains of *Borrelia burgdorferi*

The availability of the amino acid sequenced for OspA from a number of different isolates, combined with peptide mapping and Western blot analysis, permitted the identification of the antigenic domains recognized by monoclonal antibodies (MAbs) and allowed inference of the key amino acid residues responsible for specific antibody reactivity.

Strains of *Borrelia burgdorferi*

Nine strains of *Borrelia*, including seven European strains and two North American strains, were used in this study of antibody binding domains of several proteins. Information concerning the strains is summarized in Table I, below.

TABLE I

Representative *Borrelia* Strains

| Strain | Location and Source | Reference for Strain |
| --- | --- | --- |
| K48 | Czechoslovakia, *Ixodes ricinus* | none |
| PGau | Germany, human ACA | Wilske, B. et al., J. Clin. Microbiol. 32: 340-350 (1993) |
| DK29 | Denmark, human EM | Wilske, B. et al. |
| Pko | Germany, human EM | Wilske, B. et al. |
| PTrob | Germany, human skin | Wilske, B. et al. |
| Ip3 | Khabarovsk, Russia, *I. persulcatus* | Asbrink, E. et al., Acta Derm. Venereol., 64: 506-512 (1984) |
| Ip90 | Khabarovsk, Russia, *I. persulcatus* | Asbrink, E. et al. |
| 25015 | Millbrook, NY, *I. persulcatus* | Barbour, A. G. et al., Curr. Microbiol., 8: 123-126 (1983) |
| B31 | Shelter Island, NY, *I. scapularis* | Luft, B. J. et al., Infect. Immun, 60: 4309-4321 (1992); ATCC 35210 |
| PKa1 | Germany, human CSF | Wilske, B. et al. |
| ZS7 | Freiburg, Germany, *I. ricinus* | Wallich, R. et al., Nucl. Acids Res, 17: 8864 (1989) |
| N40 | Westchester Co., NY | Fikrig, E. et al., Science, 250: 553-556 (1990) |
| PHei | Germany, human CSF | Wilske, B. et al. |
| ACAI | Sweden, human ACA | Luft, B. J. et al., FEMS Microbiol. Lett. 93: 73-68 (1992) |
| PBo | Germany, human CSF | Wilske, B. et al. |

ACA = patient with acrodermatitis chronica atrophicans; EM = patient with erythema migrans; CSF = cerebrospinal fluid of patient with Lyme disease.

Strains K48, PGau and DK29 were supplied by R. Johnson, University of Minnesota; Pko and pTrob were provided by B. Wilske and V. Preac-Mursic of the Pettenkhofer Institute, Munich, Germany; and Ip3 and Ip90 were supplied by L. Mayer of the Center for Disease Control, Atlanta, Ga. The North American strains included strain 25015, provided by J. Anderson of the Connecticut Department of Agriculture; and strain B31 (ATCC 35210).

Monoclonal Antibodies

Seven monoclonal antibodies (MAbs) were utilized in this study. Five of the MAbs (12, 13, 15, 83 and 336) were produced from hybridomas cloned and subcloned as previously described (Schubach, W. H., et al., *Infect. Immun.*, 59(6): 1911-1915 (1991)). MAb H5332 (Barbour, A. G. et al., *Infect. Immun.*, 41: 795-804 (1983)) was a gift from Drs. Alan Barbour, University of Texas, and MAb CIII.78 (Sears, J. E. et al., *J. Immunol.*, 147(6):1995-2000 (1991)) was a gift from Richard A. Flavell, Yale University. MAbs 12 and 15 were raised against whole sonicated B3; MAb 336 was produced against whole PGau; and MAbs 13 and 83 were raised to a truncated form of OspA cloned from the K48 strain and expressed in *E. coli* using the T7 RNA polymerase system (McGrath, B. C. et al., *Vaccines*, Cold Spring Harbor Laboratory Press, Plainview, N.Y., pp. 365-370 (1993)). All MAbs were typed as being Immunoglobulin G (IgG).

Methods of Protein Cleavage, Western Blotting and Amino-Terminal Sequencing

Prediction of the various cleavage sites was achieved by knowledge of the primary amino acid sequence derived from the full nucleotide sequences of OspA, many of which are currently available (see Table II, below). Cleavage sites can also be predicted based on the peptide sequence of OspA, which can be determined by standard techniques after isolation and purification of OspA by the method described above. Cleavage of several OspA isolates was conducted to determine the localization of monoclonal antibody binding of the proteins.

Hydroxylamine-HCl (HA), N-chlorosuccinimide (NCS), and cyanogen bromide cleavage of OspA followed the methods described by Bornstein (*Biochem.* 9 (12):2408-2421 (1970)), Shechter et al., (*Biochem.*, 15 (23):5071-5075 (1976)), and Gross (in Hirs, C. H. W. (ed): *Methods in Enzymology*, (N.Y. Acad. Press), 11:238-255 (1967)) respectively. Protease cleavage by endoproteinase, Asp-N (Boehringer Mannheim, Indianapolis, Ind.), was performed as described by Cleveland D. W. et al., (*J. Biol. Chem.*, 252:1102-1106 (1977)). Ten micrograms of OspA were used for each reaction. The ratio of enzyme to OspA was approximately 1 to 10 (w/w).

Proteins and peptides generated by cleavage were separated by SDS-polyacrylamide gel electrophoresis (SDS-PAGE) (Laemmli, U. K., *Nature* (London) 227:680-685 (1970)), and electroblotted onto immobilon Polyvinylidine Difluoride (PVDF) membranes (Ploskal, M. G. et al., *Biotechniques*, 4:272-283 (1986)). They were detected by amido black staining or by immunostaining with murine MAbs, followed by alkaline phosphatase-conjugated goat anti-mouse IgG. Specific binding was detected using a 5-bromo-4-chloro-3-indolylphosphate (BCIP)/nitroblue tetrazolium (NBT) developer system (KPL Inc., Gaithersburg, Md.).

In addition, amino-terminal amino acid sequence analysis was carried out on several cleavage products, as described by Luft et al., (*Infect. Immun.*, 57:3637-3645 (1989)). Amido black stained bands were excised from PVDF blots and sequenced by Edman degradation using a Biosystems model 475A sequenator with model 120A PTH analyzer and model 900A control/data analyzer.

Cleavage Products of Outer Surface Protein a Isolates

Purified OspA-B31, labeled with $^{14}$C-palmitic acid, was fragmented with hydroxylamine-HCl (HA) into two peptides, designated HA1 and HA2 (data not shown). The HA1 band migrated at 27 kd and retained its radioactivity, indicating that the peptide included the lipidation site at the N-terminus of the molecule (data not shown). From the predicted cleavage point, HA1 should correspond to residues 1 to 251 of OspA-B31. HA2 had a MW of 21.6 kd by SDS-PAGE, with amino-terminal sequence analysis showing it to begin at Gly72, i.e. residues 72 to 273 of OspA-B31. By contrast, HA cleaved OspA-K48 into three peptides, designated HA1, HA2, and HA3 with apparent MWs of 22 kd, 16 kd and 12 kd, respectively. Amino-terminal sequencing showed HA1 to start at Gly72, and HA3 at Gly142. HA2 was found to have a blocked amino-terminus, as was observed for the full-length OspA protein. HA1, 2 and 3 of OspA-K48 were predicted to be residues 72-274, 1 to 141 and 142 to 274, respectively.

N-Chlorosuccinimide (NCS) cleaves tryptophan (W), which is at residue 216 of OspA-B31 or residue 217 of OspA-K48 (data not shown). NCS cleaved OspA-B31 into 2 fragments, NCS1, with MW of 23 kd, residues 1-216 of the protein, and NCS2 with a MW of 6.2 kd, residues 217 to 273 (data not shown). Similarly, K48 OspA was divided into 2 pieces, NCS 1 residues 1-217, and NCS2 residues 218 to 274 (data not shown).

Cleavage of OspA by cyanogen bromide (CNBr) occurs at the carboxy side of methionine, residue 39. The major fragment, CNBr1, has a MW of 25.7 kd, residues 39-274 by amino-terminal amino acid sequence analysis (data not shown). CNBr2 (about 4 kd) could not be visualized by amido black staining; instead, lightly stained bands of about 20 kd MW were seen. These bands reacted with anti-OspA MAbs, and most likely were degradation products due to cleavage by formic acid.

Determination of Antibody Binding Domains for Anti-OspA Monoclonal Antibodies

The cleavage products of OspA-B31 and OspA-K48 were analyzed by Western blot to assess their ability to bind to the six different MAbs. Preliminary Western blot analysis of the cleavage products demonstrated that strains K48 and DK29 have similar patterns of reactivity, as do IP3, PGau and Pko. The OspA of strain PTrob was immunologically distinct from the others, being recognized only by MAb 336. MAb 12 recognized only the two North American strains, B31 and 25015. When the isolates were separated into genogroups, it was remarkable that all the MAbs, except MAb 12, crossed over to react with multiple genogroups.

MAb12, specific for OspA-B31, bound to both HA1 and HA2 of OspA-B31. However, cleavage of OspA-B31 by NCS at residue Trp216 created fragments which did not react with MAb12, suggesting that the relevant domain is near or is structurally dependent upon the integrity of this residue (data not shown). MAb 13 bound only to OspA-K48, and to peptides containing the amino-terminus of that molecule (e.g. HA2; NCS1). It did not bind to CNBr1 residues 39 to 274. Thus the domain recognized by MAb13 is in the amino-terminal end of OspA-K48, near Met38.

MAb15 reacts with the OspA of both the B31 and K48 strains, and to peptides containing the N-terminus of OspA, such as HA1 of OspA-B31 and NCS1, but not to peptides HA2 of OspA-B31 and HA1 of OspA-K48 (data not shown). Both peptides include residue 72 to the C-terminus of the molecules. MAb15 bound to CNBr1 of OspA-K48, indicating the domain for this antibody to be residues 39 to 72, specifically near Gly72 (data not shown).

MAb83 binds to OspA-K48, and to peptides containing the C-terminal portion of the molecule, such as HA1. They do not bind to HA2 of OspA-K48, most likely because the C-terminus of HA2 of OspA-K48 ends at 141. Similar to MAb12 and OspA-B31, binding of MAbs 83 and CIII.78 is eliminated by cleavage of OspA at the tryptophan residue. Thus binding of MAbs 12, 83 and CIII.78 to OspA depends on the structural integrity of the Trp$_{216}$ residue, which appears to be critical for antigenicity. Also apparent is that, although these MAbs bind to a common antigenic domain, the precise epitopes which they recognize are distinct from one another given the varying degrees of cross-reactivity to these MAbs among strains.

Although there is similar loss of binding activity of MAb336 with cleavage at Trp$_{216}$, this MAb does not bind to HA1 of OspA-B31, suggesting the domain for this antibody includes the carboxy-terminal end of the molecule, inclusive of residues 251 to 273. Low MW peptides, such as HA3 (10 kd) and NCS2 (6 kd), of OspA-K48 do not bind this MAb on Western blots. In order to confirm this observation, we tested binding of the 6 MAbs with a recombinant fusion construct p3A/EC that contains a trpE leader protein fused with residues 217 to 273 of OspA-B31 (Schubach, W. H. et al., *Infect. Immun.*, 59(6):1911-1915 (1991)). Only MAb336 reacted with this construct (data not shown). Peptides and antigenic domains localized by fragmentation of OspA are summarized in FIG. 1.

Example 2

Site-Directed Mutagenesis within Hypervariable Domains A., (Residues 120-140), B., (Residues 150-180) and C., (Residues 200-216 or 217)

Site-directed mutagenesis was performed to convert residues within the 204-219 domain of the recombinant B31 OspA to the analogous residues of a European OspA variant, K48. In the region of OspA between residues 204 and 219, there are seven amino acid differences between OspA-B31 and OspA-K48. Three oligonucleotides were generated, each containing nucleotide changes which would incorporate K48 amino acids at their analogous positions in the B31 OspA protein. The oligonucleotides used to create the site-directed mutants were:
5'-CTTAATGACTCTGACACTAGTGC-3' (#613, which converts threonine at position 204 to serine, and serine at 206 to threonine (Thr204-Ser, Thr206-Ser)) (SEQ ID NO:1);
5'-GCTACTAAAAAAACCGGGAAATGGAATTCA-3' (#625, which converts alanine at 214 to glycine, and alanine at 215 to lysine (Ala214-Gly, Ala215-Lys)) (SEQ ID NO:2); and
5'-GCAGCTTGGGATTCAAAAACATCCACTTTAACA-3' (#640, which converts asparagine at 217 to aspartate, and glycine at 219 to lysine (Asn217-Asp, Gly219-Lys)) (SEQ ID NO:3).

Site-directed mutagenesis was carried out by performing mutagenesis with pairs of the above oligonucleotides. Three site-directed mutants were created, each with two changes: OspA 613 (Thr204-Ser, Thr206-Ser), OspA 625 (Ala214-Gly, Ala215-Lys), and 640 (Asn217-Asp, Gly219-Lys). There were also two proteins with four changes: OspA 613/625 (Thr204-Ser, Thr206-Ser, Ala214-Gly, Ala215-Lys) and OspA 613/640 (Thr204-Ser, Thr206-Ser, Asn217-Asp, Gly219-Lys).

Specificity of Antibody Binding to Epitopes of the Non-Mutated Hypervariable Region Monoclonal antibodies that agglutinate spirochetes, including several which are neutralizing in vitro, recognize epitopes that map to the hypervariable region around Trp216 (Barbour, A. G. et al., *Infect. and Immun.*, 41:759 (1983); Schubach, W. H. et al., *Infect. and Immun.*, 59:1911 (1991)). Western Blot analysis demonstrated that chemical cleavage of OspA from the B31 strain at Trp 216 abolishes reactivity of the protein with the agglutinating MAB 105, a monoclonal raised against B31 spirochetes. The reagent, n-chlorosuccinimide (NCS), cleaves OspA at the Trp 216, forming a 23.2 kd fragment and a 6.2 kd peptide which is not retained on the Imobilon-P membrane after transfer. The uncleaved material binds MAb 105; however, the 23.2 kd fragment is unreactive. Similar Western blots with a TrpE-OspA fusion protein containing the carboxy-terminal portion of the OspA protein demonstrated that the small 6.2 kd piece also fails to bind MAb 105 (Schubach, W. H. et al., *Infect. and Immun.*, 59:1911 (1991)).

Monoclonal antibodies H5332 and H3TS (Barbour, A. G. et al., *Infect. and Immun.*, 41:759 (1983)) have been shown by immunofluorescence to decorate the surface of fixed spirochetes (Wilske, B. et al., *World J. Microbiol.*, 7:130 (1991)). These monoclonal antibodies also inhibit the growth of the organism in culture. Epitope mapping with fusion proteins has confirmed that the epitopes which bind these MAbs are conformationally determined and reside in the carboxy half of the protein. MAb H5332 is cross-reactive among all of the known phylogenetic groups, whereas MAb H3TS and MAb 105 seem to be specific to the B31 strain to which they were raised. Like MAb 105, the reactivities of H5332 and H3TS to OspA are abrogated by fragmentation of the protein at Trp216. MAb 336 was raised to whole spirochetes of the strain PGau. It cross-reacts to OspA from group 1 (the group to which B31 belongs) but not to group 2 (of which K48 is a member). Previous studies using fusion proteins and chemical cleavage have indicated that this antibody recognizes a domain of OspA in the region between residues 217 and 273. All of these MAbs agglutinate the B31 spirochete.

Western Blot Analysis of Antibody Binding to Mutated Hyper-Variable Regions

MAbs were used for Western Blot analysis of the site-directed OspA mutants induced in *E. coli* using the T7 expression system (Dunn, J. J. et al., *Protein Expression and Purification*, 1:159 (1990)). *E. coli* cells carrying pET9c plasmids having a site-directed OspA mutant insert were induced at mid-log phase growth with IPTG for four hours at 37° C. Cell lysates were made by boiling an aliquot of the induced cultures in SDS gel loading dye, and this material was then loaded onto a 12% SDS gel (BioRad mini-Protean II), and subjected to electrophoresis. The proteins were then transferred to Imobilon-P membranes (Millipore) 70V, 2 hour at 4° C. using the BioRad mini transfer system. Western analysis was carried out as described by Schubach et al., (*Infect. Immun.*, 59:1911 (1991)).

Western Blot analysis indicated that only the 625 mutant (Ala214-Gly and Ala215-Lys) retained binding to the agglutinating monoclonal H3TS. However, the 613/625 mutant which has additional alterations to the amino terminus of Trp216 (Ser204-Thr and Thr206-Ser) did not bind this monoclonal. Both 640 and 613/640 OspAs which have the Asn217-Asp and Gly219-Lys changes on the carboxy-terminal side of Trp216 also failed to bind MAb H3TS. This indicated that the epitope of the B31 OspA which binds H3TS is comprised of amino acid side-chains on both sides of Trp216.

The 613/625 mutant failed to bind MAbs 105 and H5332, while the other mutants retained their ability to bind these MAbs. This is important in light of the data using fusion proteins that indicate that MAb 105 behaves more like MAb H3TS in terms of its serotype specificity and binding to OspA (Wilske, B. et al., *Med. Microbiol. Immunol.*, 181:191 (1992)). The 613/625 protein has, in addition to the differences at residues Thr204 and Ser206, changes immediately amino-terminal to Trp216 (Ala214-Gly and Ala215-Lys). The abrogation of reactivity of MAbs 105 and H5332 to this protein indicated that the epitopes of OspA which bind these monoclonal antibodies are comprised of residues on the amino-terminal side of Trp216.

The two proteins carrying the Asn217-Asp and Gly219-Lys replacements on the carboxy-terminal side of Trp216 (OspAs 640 and 613/640) retained binding to MAbs 105 and H5332; however, they failed to react with MAb 336, a monoclonal which has been mapped with TrpE-OspA fusion proteins and by chemical cleavage to a more carboxy-terminal domain. This result may explain why MAb 336 failed to recognize the K48-type of OspA (Group 2).

It is clear that amino acids Ser204 and Thr206 play an important part in the agglutinating epitopes in the region of the B31 OspA flanking Trp216. Replacement of these two residues altered the epitopes of OspA that bind MAbs 105, H3TS and H5332. The ability of the 640 changes alone to abolish reactivity of MAb 336 indicated that Thr204 and Ser206 are not involved in direct interaction with MAb 336.

The results indicated that the epitopes of OspA which are available to MAbs that agglutinate spirochetes are comprised at least in part by amino acids in the immediate vicinity of Trp216. Since circular dichroism analysis indicated that the structures of B31 and K48 OspA differ very little within this domain, it is unlikely that the changes made by mutation have radically altered the overall structure of the OspA protein (France, L. L. et al., *Biochem. Biophys. Acta*, 1120:59 (1992); and France et al., *Biochem. Biophys Acta*, submitted (1993)). This hypothesis is supported by the finding that the recombinant, mutant OspAs exhibit the same high solubility and purification properties as the parent B31 protein (data not shown).

In summary, amino acid side-chains at Ser204 and Thr206 are important for many of the agglutinating epitopes. However, a limited set of conservative changes at these sites were not sufficient to abolish binding of all of the agglutinating MAbs. These results suggested that the agglutinating epitopes of OspA are distinct, yet may have some overlap. The results also supported the hypothesis that the surface-exposed epitope around Trp216 which is thought to be important for immune recognition and neutralization is a conformationally-determined and complex domain of OspA.

Example 3

*Borrelia* Strains and Proteins

A. Genes Encoding *Borrelia* Proteins

The altered OspA polypeptides of the current invention can be part of a cocktail with other proteins or can be joined to other proteins to form a chimeric protein. The other polypeptides of the cocktail or chimeric can be derived from any *Borrelia*. Representative proteins include OspA, OspB, OspC, OspD, p12, p39, p41 (fla), p66, and p93. Nucleic acid sequences encoding several *Borrelia* proteins are available (see Table II for examples); alternatively, nucleic acid sequences encoding *Borrelia* proteins can be isolated and characterized using methods such as those described below.

TABLE II

References for Nucleic Acid Sequences for Several Proteins of Various *Borrelia* Strains

| Strain | OspA |
|---|---|
| K48 | X62624 (SID 8) |
| PGau | X62387 (SID 10) |
| DK29 | X63412 (SID 21) |
| Pko | X65599 (SID 25) |
| PTrob | X65598 (SID 45) |
| Ip3 | X70365 (SID 24) |
| Ip90 | Kryuchechnikov, V. N. et al., J. Microbiol. Epid. Immunobiol. 12: 41-44 (1988) (SID 22) |
| 25015 | Fikrig, E. S. et al., J. Immunol. 7: 2256-2260 (1992) (SID 12) |
| B31 | Bergstrom, S. et al., Mol. Microbiol. 3: 479-486 (1989) (SID 6) |
| PKal | X69606 (SID 42) |
| ZS7 | Jonsson, M. et al., Infect. Immun. 60: 1845-1853 (1992) (SID 44) |
| N40 | Kryuchechnikov, V. N. et al. (SID 43) |
| PHei | X65600 (SID 46) |
| ACAI | Kryuchechnikov, V. N. et al. (SID 26) |
| PBo | X65605 (SID 23) |

Numbers with an "X" prefix are GenBank data base accession numbers.
SID = SEQ ID NO.

B. Isolation of *Borrelia* Genes

Nucleic acid sequences encoding full length, lipidated proteins from known *Borrelia* strains were isolated using the polymerase chain reaction (PCR) as described below. In addition, nucleic acid sequences were generated which encoded truncated proteins (proteins in which the lipidation signal has been removed, such as by eliminating the nucleic acid sequence encoding the first 18 amino acids, resulting in non-lipidated proteins). Other proteins were generated which encoded polypeptides of a particular gene (i.e., encoding a segment of the protein which has a different number of amino acids than the protein does in nature). Using similar methods as those described below, primers can be generated from known nucleic acid sequences encoding *Borrelia* proteins and used to isolate other genes encoding *Borrelia* proteins. Primers can be designed to amplify all of a gene, as well as to amplify a nucleic acid sequence encoding truncated protein sequences, such as described below for OspC, or nucleic acid sequences encoding a polypeptide derived from a *Borrelia* protein. Primers can also be designed to incorporate unique restriction enzyme cleavage sites into the amplified nucleic acid sequences. Sequence analysis of the amplified nucleic acid sequences can then be performed using standard techniques.

Cloning and Sequencing of OspA Genes and Relevant Nucleic Acid Sequences

*Borrelia* OspA sequences were isolated in the following manner: 100 μl reaction mixtures containing 50 mM KCl, 10 mM TRIS-HCl (pH 8.3), 1.5 mM $MgCl_2$, 200 μM each NTP 2.5 units of TaqI DNA polymerase (Amplitaq, Perkin-Elmer/Cetus) and 100 pmol each of the 5' and 3' primers (described below) were used. Amplification was performed in a Perkin-Elmer/Cetus thermal cycler as described (Schubach, W. H. et al., *Infect. Immun.*, 59:1811-1915 (1991)). The amplicon was visualized on an agarose gel by ethidium bromide staining. Twenty nanograms of the chloroform-extracted PCR product were cloned directly into the PC-TA vector (Invitrogen) by following the manufacturer's instructions. Recombinant colonies containing the amplified fragment were selected, the plasmids were prepared, and the nucleic acid sequence of each OspA was determined by the dideoxy chain-termination technique using the Sequenase kit (United States Biochemical). Directed sequencing was performed with M13 primers followed by OspA-specific primers derived from sequences, previously obtained with M13 primers.

Because the 5' and 3' ends of the OspA gene are highly conserved (Fikrig, E. S. et al., *J. Immunol.*, 7:2256-2260 (1992); Bergstrom, S. et al., *Mol. Microbiol.* 3:479-486 (1989); Zumstein, G. et al., *Med. Microbiol. Immunol.*, 181: 57-70 (1992)), the 5' and 3' primers for cloning can be based upon any known OspA sequences. For example, the following primers based upon the OspA nucleic acid sequence from strain B31 were used:

5'-GGAGAATATATTATGAAA-3' (−12 to +6) (SEQ ID NO:4); and
5'-CTCCTTATTTTAAAGCG-3' (+826 to +809) (SEQ ID NO:5). (Schubach, W. H. et al., *Infect. Immun*, 59:1811-1915 (1991)).

OspA genes isolated in this manner include those for strains B31, K48, PGau, and 25015; the nucleic acid sequences are depicted in the sequence listing as SEQ ID NO:6 (OspA-B31), SEQ ID NO:8 (OspA-K48), SEQ ID NO:10 (OspA-PGau), and SEQ ID NO:12 (OspA-25015). An alignment of these and other OspA nucleic acid sequences is shown in FIG. 17. The amino acid sequences of the proteins encoded by these nucleic acid sequences are represented as SEQ ID NO:7 (OspA-B31), SEQ ID NO:9 (OspA-K48), SEQ ID NO:11 (OspA-PGau), and SEQ ID NO:13 (OspA-25015).

The following primers were used to generate specific nucleic acid sequences of the OspA gene:

```
                                           (SEQ ID NO: 14)
5'-GTCTGCAAAAACCATGACAAG-3'
(plus strand primer #369);
```

```
                                           (SEQ ID NO: 15)
5'-GTCATCAACAGAAGAAAAATTC-3'
(plus strand primer #357);
```

```
                                           (SEQ ID NO: 16)
5'-CCGGATCCATATGAAAAAATATTTATTGGG-3'
(plus strand primer #607);
```

```
                                           (SEQ ID NO: 17)
5'-CCGGGATCCATATGGCTAAGCAAAATGTTAGC-3'
(plus strand primer #584);
```

```
                                           (SEQ ID NO: 18)
5'-GCGTTCAAGTACTCCAGA-3'
(minus strand primer #200);
```

```
                                           (SEQ ID NO: 19)
5'-GATATCTAGATCTTATTTTAAAGCGTT-3'
(minus strand primer #586);
and
```

```
                                           (SEQ ID NO: 20)
5'-GGATCCGGTGACCTTTTAAAGCGTTTTTAAT-3'
(minus strand primer #1169).
```

C. Expression of Proteins from *Borrelia* Genes

The nucleic acid sequences described above can be incorporated into expression plasmids, using standard techniques, and transfected into compatible host cells in order to express the proteins encoded by the nucleic acid sequences. As an example, the expression of the p12 gene and the isolation of p12 protein is set forth.

Amplification of the p12 nucleic acid sequence was conducted with primers that included a NdeI restriction site into the nucleic acid sequence. The PCR product was extracted with phenol/chloroform and precipitated with ethanol. The precipitated product was digested and ligated into an expression plasmid as follows: 15 μl (approximately 1 μg) of PCR DNA was combined with 2 μl 10× restriction buffer for NdeI (Gibco/BRL), 1 μl NdeI (Gibco/BRL), and 2 μl distilled water, and incubated overnight at 37° C. This mixture was subsequently combined with 3 μl 10× buffer (buffer 3, New England BioLabs), 1 μl BamHI (NEB), and 6 μl distilled water, and incubated at 37° for two hours. The resultant material was purified by preparative gel electrophoresis using low melting point agarose, and the band was visualized under long wave ultraviolet light and excised from the gel. The gel slice was treated with Gelase using conditions recommended by the manufacturer (Epicentre Technologies). The resulting DNA pellet was resuspended in 25-50 μl of 10 mM TRIS-CL (pH 8.0) and 1 mM EDTA (TE). An aliquot of this material was ligated into the pET9c expression vector (Dunn, J. J. et al., *Protein Expression and Purification*, 1:159 (1990)).

To ligate the material into the pET9c expression vector, 20-50 ng of p12 nucleic acid sequences cut and purified as described above was combined with 5 μl 10 One-Phor-All (OPA) buffer (Pharmacia), 30-60 ng pET9c cut with NdeI and BamHI, 2.5 μl 20 mM ATP, 2 μl T4 DNA ligase (Pharmacia) diluted 1:5 in 1×OPA buffer, and sufficient distilled water to bring the final volume to 50 μl. The mixture was incubated at 12° C. overnight.

The resultant ligations were transformed into competent DH5-alpha cells and plated on nutrient agar plates containing 50 μg/ml kanamycin and incubated overnight at 37° C. DH5-alpha is used as a "storage strain" for T7 expression clones, because it is RecA deficient, so that recombination and concatenation are not problematic, and because it lacks the T7 RNA polymerase gene necessary to express the cloned gene. The use of this strain allows for cloning of potentially toxic gene products while minimizing the chance of deletion and/or rearrangement of the desired genes. Other cell lines having similar properties may also be used.

Kanamycin resistant colonies were single-colony purified on nutrient agar plates supplemented with kanamycin at 50 µg/ml. A colony from each isolate was inoculated into 3-5 ml of liquid medium containing 50 µg/ml kanamycin, and incubated at 37° C. without agitation. Plasmid DNA was obtained from 1 ml of each isolate using a hot alkaline lysis procedure (Maniatis, T. et al., *Molecular Cloning: A Laboratory Manual*, Cold Spring Harbor Laboratory, Cold Spring Harbor, N.Y. (1982)).

Plasmid DNA was digested with EcoRI and BglII in the following manner: 15 µl plasmid DNA was combined with 2 µl 10× buffer 3 (NEB), 1 µl EcoRI (NEB), 1 µl BglII (NEB) and 1 µl distilled water, and incubated for two hours at 37° C. The entire reaction mixture was subjected to electrophoresis on an analytical agarose gel. Plasmids carrying the p12 insert were identified by the presence of a band corresponding to 925 base-pairs (full length p12) or 875 base-pairs (nonlipidated p12). One or two plasmid DNAs from the full length and nonlipidated p12 clones in pET9c were used to transform BL21 DE3 pLysS to kanamycin resistance as described by Studier et al., (*Methods in Enzymology*, Goeddel, D. (Ed.), Academic Press, 185: 60-89 (1990)). One or two transformants of the full length and nonlipidated clones were single-colony purified on nutrient plates containing 25 µg/ml chloramphenicol (to maintain pLysS) and 50 µg/ml kanamycin at 37° C. One colony of each isolate was inoculated into liquid medium supplemented with chloramphenicol and kanamycin and incubated overnight at 37° C. The overnight culture was subcultured the following morning into 500 ml of liquid broth with chloramphenicol (25 µg/ml) and kanamycin (50 µg/ml) and grown with aeration at 37° C. in an orbital air-shaker until the absorbance at 600 nm reached 0.4-0.7. Isopropyl-thio-galactoside (IPTG) was added to a final concentration of 0.5 mM, for induction, and the culture was incubated for 3-4 hours at 37° C. as before. The induced cells were pelleted by centrifugation and resuspended in 25 ml of 20 mM $NaPO_4$ (pH 7.7). A small aliquot was removed for analysis by gel electrophoresis. Expressing clones produced proteins which migrated at the 12 kd position.

A crude cell lysate was prepared from the culture as described for recombinant OspA by Dunn, J. J. et al., (*Protein Expression and Purification*, 1:159 (1990)). The crude lysate was first passed over a Q-sepharose column (Pharmacia) which had been pre-equilibrated in Buffer A: 10 mM $NaPO_4$ (pH 7.7), 10 mM NaCl, 0.5 mM PMSF. The column was washed with 10 mM $NaPO_4$, 50 mM NaCl and 0.5 mM PMSF and then p12 was eluted in 10 mM $NaPO_4$, 0.5 mM PMSF with a NaCl gradient from 50-400 mM. p12 eluted approximately halfway through the gradient between 100 and 200 mM NaCl. The peak fractions were pooled and dialyzed against 10 mM NaPO4 (pH 7.7), 10 mM NaCl, 0.5 mM PMSF. The protein was then concentrated and applied to a Sephadex G50 gel filtration column of approximately 50 ml bed volume (Pharmacia), in 10 mM $NaPO_4$, 200 mM NaCl, 0.5 mM PMSF. p12 would typically elute shortly after the excluded volume marker. Peak fractions were determined by running small aliquots of all fractions on a gel. The p12 peak was pooled and stored in small aliquots at −20° C.

Example 4

Generation of Chimeric Nucleic Acid Sequences and Chimeric Proteins

A. General Protocol for Creation of Chimeric Nucleic Acid Sequences

The megaprimer method of site directed mutagenesis and a modification were used to generate chimeric nucleic acid sequences (Sarkar and Sommer, *Biotechniques*, 8(4): 404-407 (1990); Aiyar, A. and J. Leis, *Biotechniques*, 14(3): 366-369 (1993)). A 5' primer for the first genomic template and a 3' fusion oligo are used to amplify the desired region. The fusion primer consists of a 3' end of the first template (DNA that encodes the amino-proximal polypeptide of the fusion protein), coupled to a 5' end of the second template (DNA that encodes the carboxy-proximal polypeptide of the fusion protein).

The PCR amplifications are performed using Taq DNA polymerase, 10×PCR buffer, and $MgCl_2$ (Promega Corp., Madison, Wis.), and Ultrapure dNTPs (Pharmacia, Piscataway, N.J.). One µg of genomic template 1, 5 µl of 10 µM 5' oligo and 5 µl of 10 µM fusion oligo are combined with the following reagents at indicated final concentrations: 10× Buffer-Mg FREE (1×), $MgCl_2$ (2 mM), dNTP mix (200 µM each dNTP), Taq DNA polymerase (2.5 units), water to bring final volume to 100 µl. A Thermal Cycler (Perkin Elmer Cetus, Norwalk, Conn.) is used to amplify under the following conditions: 35 cycles at 95° C. for one minute, 55° C. for two minutes, and 72° for three minutes. This procedure results in a "megaprimer".

The resulting megaprimer is run on a 1×TAE, 4% low-melt agarose gel. The megaprimer band is cut from the gel and purified using the Promega Magic PCR Preps DNA purification system. Purified megaprimer is then used in a second PCR step. One µg of genomic template 2, approximately 0.5 µg of the megaprimer, and 5 µl of 10 µM 3' oligo are added to a cocktail of 10× buffer, $MgCl_2$, dNTPs and Taq at the same final concentrations as noted above, and brought to 100 µl with water. PCR conditions are the same as above. The fusion product resulting from this amplification is also purified using the Promega Magic PCR Preps DNA purification system.

The fusion product is then ligated into TA vector and transformed into *E. coli* using the Invitrogen (San Diego, Calif.) TA Cloning Kit. Approximately 50 ng of PCR fusion product is ligated to 50 ng of pCRII vector with 1× Ligation Buffer, 4 units of T4 ligase, and brought to 10 µl with water. This ligated product mixture is incubated at 12° C. overnight (approximately 14 hours). Two µl of the ligation product mixture is added to 50 µl competent INC F' cells and 2 µl beta mercaptoethanol. The cells are then incubated for 30 minutes, followed by heat shock treatment at 42° C. for 60 seconds, and an ice quenching for two minutes. 450 µl of warmed SOC media is then added to the cells, resulting in a transformed cell culture which is incubated at 37° C. for one hour with slight shaking. 50 µl of the transformed cell culture is plated on LB+50 µg/µl ampicillin plates and incubated overnight at 37° C. Single white colonies are picked and added to individual overnight cultures containing 3 ml LB with ampicillin (50 µg/µl).

The individual overnight cultures are prepared using Promega's Magic Miniprep DNA purification system. A small amount of the resulting DNA is cut using a restriction digest as a check. DNA sequencing is then performed to check the sequence of the fusion nucleic acid sequence, using the United States Biochemical (Cleveland, Ohio) Sequenase Version 2.0 DNA sequencing kit. Three to five µg of plasmid DNA is used per reaction. 2 µl 2M NaOH/2 mM EDTA are added to the DNA, and the volume is brought to 20 µl with water. The mixture is then incubated at room temperature for five minutes. 7 µl water, 3 µl 3M NaAc, 75 µl ethanol are added. The resultant mixture is mixed by vortex and incubated for ten minutes at −70° C., and then subjected to microcentrifugation. After microcentrifugating for ten minutes, the supernatant is aspirated off, and the pellet is dried in the speed vac for 30 second. 6 µl water, 2 µl annealing buffer, and 2 µl of 10 μM of the appropriate oligo is then added. This mixture is incubated for 10 minutes at 37° C. and then allowed to stand at room temperature for 10 minutes. Subsequently, 5.5 μl of label cocktail (described above) is added to each sample of the mixture, which are incubated at room temperature for an additional five minutes. 3.5 μl labeled DNA is then added to each sample which is then incubated for five minutes at 37° C. 4 μl stop solution is added to each well. The DNA is denatured at 95° for two minutes, and then placed on ice.

Clones with the desired fusion nucleic acid sequences are then recloned in frame in the pET expression system in the lipidated (full length) and non-lipidated (truncated, i.e., without first 17 amino acids) forms. The product is amplified using restriction sites contained in the PCR primers. The vector and product are cut with the same enzymes and ligated together with T4 ligase. The resultant plasmid is transformed into competent E. coli using standard transformation techniques. Colonies are screened as described earlier and positive clones are transformed into expression cells, such as E. coli BL21, for protein expression with IPTG for induction. The expressed protein in its bacterial culture lysate form and/or purified form is then injected in mice for antibody production. The mice are bled, and the sera collected for agglutination, in vitro growth inhibition, and complement-dependent and -independent lysis tests.

A specific example of chimeric OspA is as follows. Other OspA chimeras can be made using the same method with suitable primers.

OspA-K48/OspA-PGau

A chimer of OspA from strain K48 (OspA-K48) and OspA from strain PGau (OspA-PGau) was generated using the method described above. This chimeric nucleic acid sequence included bp 1-654 from OspA-K48, followed by bp 655-820 from OspA-PGau. Primers used included: the amino-terminal sequence of OspA primer #607 (SEQ ID NO:16); the fusion primer, 5'-AAAGTAGAAGTTTTTGAATC-CCATTTTCCAGTTTTTTT-3' (minus strand primer #668-654) (SEQ ID NO:27); the carboxy-terminal sequence of OspA primer #586 (SEQ ID NO:19); and the sequence primers #369 (SEQ ID NO:14) and #357 (SEQ ID NO:15). The chimeric nucleic acid sequence is presented as SEQ ID NO:28; the chimeric protein encoded by this chimeric nucleic acid sequence is presented as SEQ ID NO:29.

C. Purification of Proteins Generated by Chimeric Nucleic Acid Sequences

The chimeric nucleic acid sequences described above, as well as chimeric nucleic acid sequences produced by the methods described above, are used to produce chimeric proteins encoded by the nucleic acid sequences. Standard methods, such as those described above in Example 3, concerning the expression of proteins from Borrelia genes, can be used to express the proteins in a compatible host organism. The chimeric proteins can then be isolated and purified using standard techniques.

Nucleic acid encoding altered versions of OspA can be used to generate OspA chimeras. In addition, nucleic acid encoding OspA chimeras can be used to generate the altered OspA polypeptides of the present invention.

If the chimeric protein is soluble, it can be purified on a Sepharose column. Insoluble proteins can be solubilized in guanidine and purified on a $Ni^{2+}$ column; alternatively, they can be solubilized in 10 mM $NaPO_4$ with 0.1-1% TRIXON X 114, and subsequently purified over an S column (Pharmacia). Lipidated proteins were generally purified by the latter method. Solubility was determined by separating both soluble and insoluble fractions of cell lysate on a 12% PAGE gel, and checking for the localization of the protein by Coomassie staining, or by Western blotting with monoclonal antibodies directed to an antigenic polypeptide of the chimeric protein.

Example 5

Generation of OspC/OspA Chimeric Nucleic Acids and Chimeric Proteins

A. General Protocol for Creation of Chimeric Nucleic Acid Sequences

A large number of chimeric nucleic acid sequences encoding proteins comprising at least a first and a second polypeptide from Borrelia burgdorferi were generated. These chimeric nucleic acid sequences were produced such that the encoded chimeric protein comprised a Borrelia burgdorferi OspC polypeptide upstream of (or N-terminal to) a Borrelia burgdorferi OspA polypeptide. The chimeric nucleic acid sequences were also produced such that the nucleic acid encoding one polypeptide was in the same reading frame as the nucleic acid sequence encoding the next polypeptide in the chimeric protein.

The general cloning strategy used to construct the chimeric nucleic acid sequences was as follows. The desired fragment of OspC was amplified using a 5' primer containing a restriction site suitable for cloning the resultant product into a vector of interest and a 3' primer containing a restriction site suitable for ligating the OspC fragment to the OspA fragment. The OspC product was cloned into a suitable vector. For the OspA portion of the chimeric nucleic acid, the desired OspA fragment was amplified using a 5' primer containing a restriction site for ligating the resultant OspA fragment to the OspC fragment and a 3' primer containing a restriction site suitable for cloning the resultant OspA product into the vector with the OspC product. The use of a restriction site to allow ligation of the OspC and OspA fragments results in the insertion of 0 to about 3 amino acids between the OspC and OspA fragments.

A specific example of such a construction follows. It is understood that other suitable restriction sites could be used with no or only routine experimentation. The resultant OspC/OspA Chimer could have, therefore, the addition of 0 to about 3 amino acids or more between the OspC and OspA fragments, depending on the restriction site used.

For the OspC portions of the chimeric nucleic acids, desired fragments of OspC genes from various strains or genospecies were PCR amplified using a 5' primer containing an NdeI site and a 3' primer containing a NcoI site and a BamHI site. The amplified OspC product was then cloned into the NdeI and BamHI sites of the T7 promoter driven expression vector, pET9c. For the OspA portion of the chimeric nucleic acid, desired fragments of OspA genes from a strain of interest or genospecies of interest were PCR amplified using a 5' primer containing an NcoI site and a 3' primer containing a BamHI site. This OspA portion could then be directly cloned into the NcoI and BamHI sites of the pET9c vector containing the desired OspC sequence, thereby producing the desired OspC-OspA construct. By including the sequence for the NcoI restriction site in the primers, a nine nucleotide linker sequence encoding the amino acids Ser-Met-Ala was produced at the junction between the N-terminal OspC sequence and the C-terminal OspA sequence. The use of the NcoI restriction enzyme (CCATGG) in this cloning strategy was a suitable choice as Borrelia is an AT-rich organism which possesses only a few NcoI sites in its genome. One of ordinary skill in the art would know that different restriction sites wold be utilized and would know how to generate the chimeric OspC/A constructs for use in subsequent alterations described herein with no or only routine experimentation.

As an example, OspC-OspA chimeric nucleic acids which contain nonlipidated OspC B31 were generated using the following primers:

(5'OspC-NdeI):
(SEQ ID NO: 91)
5'-GT CAT ATG GCT TGT AAT AAT TCA GGG AAA GA-3';
and (3'OspC-NcoI):
(SEQ ID NO: 92)
5'-T TTC CAT GGA AGG TTT TTT TGG ACT TTC TG-3'.

For OspC-OspA chimeric nucleic acids which contain nonlipidated OspA B31, the following primers were used:

(5'OspA-NcoI:)
(SEQ ID NO: 93)
5'-TT TCC ATG GCC AAG CAA AAT GTT AGC AGC C-3';
and (3'OspA-BamHI):
(SEQ ID NO: 94)
5'-TAA GGA TCC TTA TTT TAA AGC GTT TTT-3'.

Lipidated versions of the OspC/OspA chimeras can be constructed by designing primers to amplify the a portion of the template that includes the lipidation signal sequence or by generating a nucleic acid construct with a suitable lipidation signal sequence. The leader sequence comprising a lipidation signal can be, for example, from a gene encoding the OspA, OspB or OspC polypeptides.

B. Protein Expression

As described in the previous examples, it is possible to express and purify Borrelia proteins or polypeptides, for example, OspA polypeptides, OspC polypeptides, chimeric OspC/OspA polypeptides and polypeptides comprising the OspA alterations described herein. This is accomplished by incorporating the desired nucleic acid sequence, which encodes the protein of choice, into an expression plasmid, for example, using standard techniques. This expression plasmid can then be transfected into a compatible host cell in order to express the desired protein.

For example, the purified OspA, OspC or OspC/OspA chimeric proteins that were used to immunize mice and in the ELISA tests described below, were generated and purified by cloning either OspA, OspC or OspC/OspA chimeric nucleic acid sequences, in frame, into the pET expression plasmid. The expression plasmid was then transfected into the compatible expression cell line *Escherichia coli* strain BL21 (pLysS) or strain B834 (DE3). The BL21 or B834 cells were grown in 10 mL LB media (5 g/L NaCl, 10 g/L tryptone, 5 g/L yeast extract, 25 mg/L chloramphenicol and 50 mg/L ampicillin) at 37° C., with shaking. When the optical density at 600λ reached 0.3-0.4 units, recombinant protein expression was induced by adding IPTG (isopropyl B-D-thiogalactopyranoside) to a final concentration of 0.5 mM and the cells were grown for an additional three hours. The cultures were harvested by centrifugation at 3800×g for five minutes. The cells were resuspended in 20 mM $NaPO_4$, pH 7.7, and stored at −20° C. overnight. Once thawed, the crude extracts were incubated with DNase (2 μg/mL) in the presence of 2.5 mM $MgCl_2$ at room temperature for thirty minutes and then spun at 14,000 rpm (Eppendorf 5417C) for five minutes.

To purify the OspC proteins described below, the crude extracts from the OspC-expressing cells were loaded onto an anion exchange column (Q Sepharose Fast Flow, 2.2×10 cm, Pharmacia) which had been pre-equilibrated with 20 mM Tris-Cl, pH 9.3. The column was washed in the same buffer (20 mM Tris-Cl, pH 9.3) which eluted the OspC protein. The wash fractions that contained OspC were concentrated using Amicon 10K and then were dialyzed with a solution containing 20 mM $NaPO_4$, pH 8.0, and 250 mM NaCl. The partially purified OspC was then passed over a $Ni^{2+}$ metal affinity column (Chelating Sepharose Fast Flow 2.2×10 cm, Pharmacia) equilibrated with 20 mM $NaPO_4$, pH 8.0, and 250 mM NaCl. The column was washed using a decreasing pH gradient of 20 mM sodium acetic acid and 250 mM NaCl and the bound OspC eluted around pH 5.7. The OspC fractions were then concentrated by ultrafiltration and stored at −70° C.

For purification of OspA proteins, the same procedure was followed, except that the dialysis step, after the Amicon 10K cutoff, was done in 20 mM $NaPO_4$, pH 6.0. The partially purified OspA was then applied to a cation exchange column (S Sepharose Fast Flow 2.2×10 cm, Pharmacia) equilibrated with 20 nM $NaPO_4$, pH 6.0. The column was washed using an increasing NaCl gradient from 0 to 100 mM. The OspA-containing fractions were concentrated by ultrafiltration and stored at −70° C.

As previously indicated, both lipidated and non-lipidated (e.g., truncated, lacking the first 17 amino acids) forms of OspC, OspA and OspC/OspA chimeric proteins were generated.

The above-described techniques were also used to express proteins comprising the altered OspA polypeptides of the present invention.

C. Immunization of Mice and Serologic Characterization Using ELISA (Enzyme-Linked Immunosorbent Assay)

Immunization of Mice

Mice, either C3H-J or ICR, were immunized with 3 mg of lipidated OspC/OspA chimeric protein or 6 mg of non-lipidated OspC/OspA chimer in 100 mL of aluminum hydroxide adjuvant (concentration of 1.8 mg/mL) by (SC) subcutaneous injection. As a negative control, mice were immunized with 100 mL of aluminum hydroxide adjuvant only. All mice received a total of three injections which were given at two week intervals. One week after the final immunization, blood was drawn from each mouse (including negative control mice) and the serum was tested for IgG reactivity using the ELISA method described below, for the presence of anti-OspA antibodies to three different purified OspA proteins (*Borrelia burgdorferi* sensu stricto (B31), *Borrelia garinii* (K48) and *Borrelia afzelii* (PGau). The sera was tested at a dilution of 1:1000.

Mice were immunized with the chimeric proteins described in Table III.

TABLE III

Chimeric Proteins Used to Immunize Mice

| Name | Description (amino acid) | SEQ ID NO: (nucleic acid) | SEQ ID NO: (polypeptide) | Fig. No: |
|---|---|---|---|---|
| OspA | OspA-B31(18-273) | 6 | 7 | 22, 23 |
| OspC | OspC-B31(19-211) | * | * | 22, 23 |
| OspC2-OspA | OspC-C2(19-204)/ OspA-B31(18-273) | 59 | 60 | 22, 23 |

TABLE III-continued Chimeric Proteins Used to Immunize Mice

| Name | Description (amino acid) | SEQ ID NO: (nucleic acid) | SEQ ID NO: (polypeptide) | Fig. No: |
|---|---|---|---|---|
| [1]lipOspAP/Bo | OspA-PGau(1-217)/ OspA-Bo(218-273) | 49 | 50 | 24, 25 |
| [1]lipOspAB/P | OspA-B31(1-216)/ OspA-Pko(217-273) | * | * | 24, 25 |
| OspC-OspAB/P | OspC-B31(19-211)/ OspA-B31 (18-216)/ OspA-Pko(217-273) | 65 | 66 | 24, 25, 27, 28, 29 |
| OspCB31-OspAB31 | OspC-B31(19-211)/ OspA-B31(18-273) | 55 | 56 | 26, 27, 28, 29 |
| OspC2-OspAB31 | OspC-C2(19-204)/ OspA-B31(18-273) | 59 | 60 | 26, 27 |
| [1]lip OspA K/T | OspA-K48(1-217)/ OspA-Tro(218-273) | * | * | 27 |
| [1]lip OspC-B31 | OspC-B31(1-211) | * | * | 26 |
| OspCB31-OspABPBP | OspC-B31(19-211)/ OspA-B31(30-150)/ OspA-Pko(151-179)/ OspA-B31(180-216) (190 N deletion)/ OspA-Pko(217-273) B31/B31/Pko | 87 | 88 | 28, 29 |

[1]"lip" means the chimeric protein contains its native N-terminal lipidation signal
Serologic Characterization Using ELISA (Enzyme-Linked Immunosorbent Assay)

Immobilization of antigen onto ELISA Plates

A solution of purified recombinant OspC or OspA protein from each of the *Borrelia burgdorferi* strains B31 (*Borrelia burgdorferi* sensu stricto), K48 (*Borrelia garinii*) and PGau (*Borrelia afzelii*) was added to sodium phosphate buffer, pH 9.0, and was used to coat a commercial microwell plate (MaxiSorp®, Nunc). The coating procedure was as follows: 100 µl of a solution containing the appropriate OspA or, OspC protein (made up at a concentration of 250 ng/ml in the following coating buffer: 100 mM Bis-Tris propane, pH 9.7) was added to each well of a microtiter plate which was incubated for one hour at 37° C. The antigen solution was removed from the wells, the plate was washed three times with phosphate buffered saline (PBS) pH 9.0, and 300 µl of blocking buffer solution was added (3% dry milk, 0.1% polyoxyethylenesorbitan (referred to herein as Tween 20™), 0.02% NaN₃ in 100 nM Bis-Tris propane, pH 9.7). Following a one hour incubation at 37° C., the plates were washed four times with TBS-Tween 20™ wash buffer (20 mM Tris-Cl, pH 7.5, 136 mM NaCl, 0.1% Tween 20™ and 0.02% NaN₃) and then were allowed to dry. The plates were then wrapped in plastic and stored at 4° C. until they were used.

ELISA (Enzyme-Linked Immunosorbent Assay) Tests

The standard procedure for the ELISA tests was as follows: mouse serum was diluted 1:1000 in sample dilution buffer (1% dry milk, 136 mM NaCl, 0.1% Tween 20™, 0.02% NaN₃ in 20 mM Tris-Cl, pH 7.5) and 100 µl of the diluted serum was added to the ELISA microtiter plate wells that had been coated with antigen as described above. Following incubation for 1 hour at 37° C., the samples were removed and the plates were washed four times in TBS-Tween™ (20 mM Tris-Cl, pH 7.5; 136 mM NaCl; 0.1% Tween 20™ and 0.02% NaN₃). For the secondary antibody, goat anti-mouse antisera conjugated to alkaline phosphatase-specific for either IgM (Fc) or IgG (Fab), (Jackson Immuno Research Laboratories) was diluted 1:750 in sample dilution buffer (1% dry milk, 136 mM NaCl, 0.1% Tween 20™, 0.02% NaN₃ in 20 mM Tris-Cl, pH 7.5) and 100 µl of the diluted secondary antibody was added to each well. Following incubation for thirty minutes at 37° C., the plates were washed three times with TBS-Tween™ and 100 µl of Phosphatase Substrate solution (5 mg of p-nitrophenylphosphate tablets dissolved in IX diethanolamine substrate buffer to yield a 2 mg/ml solution—Kirkegaard Perry Laboratory) was added to each well. The plates were incubated for thirty minutes at 37° C. and 100 µl of stop solution (5% EDTA) was added to each well. The absorbance at 405 nm was read on a microplate reader (Dynatech). A sample was considered positive if it produced an average absorbance greater than the mean of the negative controls plus three standard deviations.

Previous work has demonstrated that it is the carboxy-terminal region of OspA that contains the antigenic sites that provide the immunoprotective response. Thus, in addition to the ELISA test described above, a modified ELISA was performed (herein referred to as the Protective ELISA Test), wherein the purified N-terminal region of B31 OspA (amino acids 18-139) was used in excess to block any antibodies present in the mouse serum that had specificity to this N-terminal OspA region. These protective ELISA tests were performed as above, except that 80 µg/ml of a purified B31 OspA fragment (amino acids 18-139) was added to the diluted mouse serum prior to adding the sera to the antigen-coated ELISA microtiter plate wells.

Results of ELISA Tests

Figure 22:
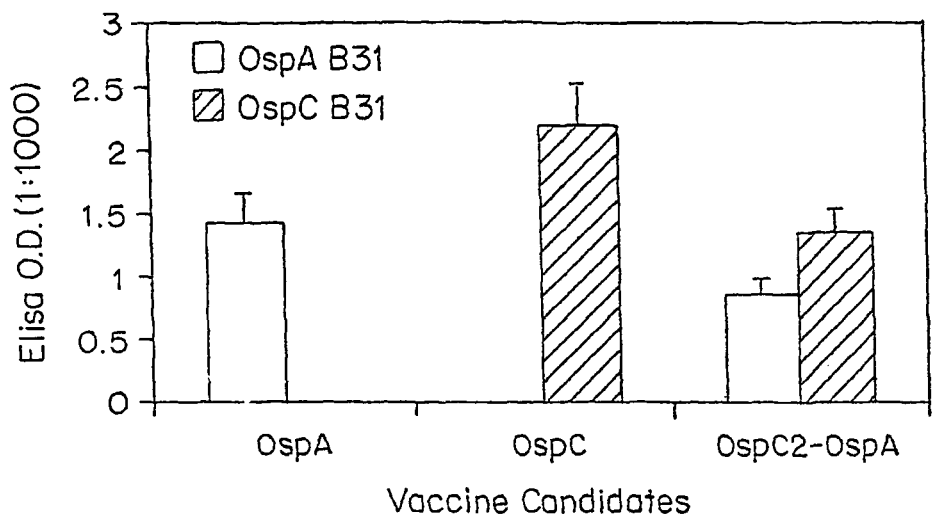
FIG. 22 is a bar graph showing the reactivity (as measured by ELISA) of sera from mice immunized with the indicated *Borrelia* protein (OspA or OspC) or recombinant chimeric protein (OspC2-OspA)(X-axis) against the indicated OspA or OspC antigens (legend) from the strain B31 (*Borrelia burgdorferi* sensu stricto).

Using the above-described ELISA tests, it was demonstrated that mice immunized with a non-lipidated OspC/OspA chimeric protein (OspC2-OspA-composed of OspC (a.a. 19-204 from strain C2)/OspA (a.a. 18-273 from strain B31) (SEQ ID NO:60) produced an immune response both to OspA and OspC that was comparable to the immune response generated to non-lipidated OspA (OspA-a.a. 18-273 from strain B31) and non-lipidated OspC (OspC-a.a. 19-211 from strain B31) control proteins (FIG. 22). As indicated in FIG. 22 and described above, mice were immunized with OspA, OspC or OspC2-OspA proteins and immune responses of the sera were measured against B31 OspA antigen (stippled bars) and B31 OspC antigen (solid bars).

Figure 23:
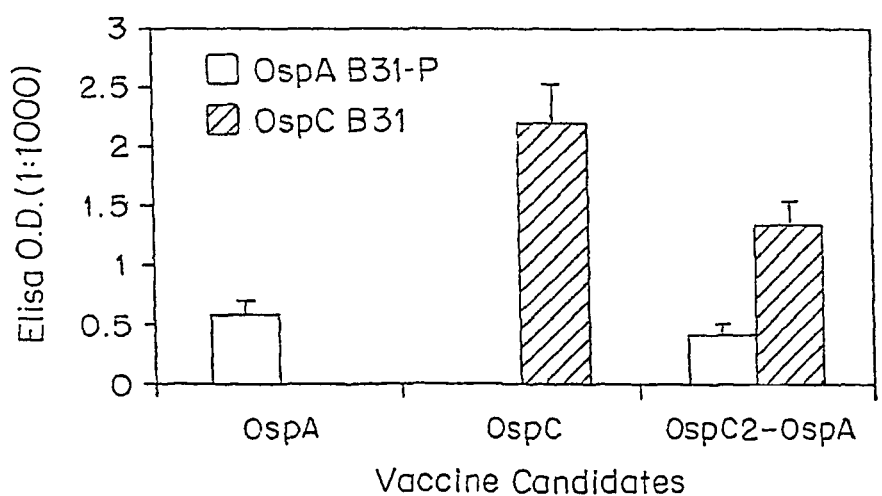
FIG. 23 is a bar graph showing the reactivity (as measured by ELISA) of sera from mice immunized with the indicated *Borrelia* protein (OspA or OspC) or recombinant chimeric protein (OspC2-OspA)(X-axis) against the indicated OspA or OspC antigens (legend) from the strain B31 (*Borrelia burgdorferi* sensu stricto). For the ELISA results to the B31 OspA antigen, a purified fragment of B31 OspA (amino acids 18-139) was added in excess to the sera so that the detected immune response was specific for the C-terminal region of OspA.

Using the above-described Protective ELISA Test, it was also shown that mice immunized with the same non-lipidated OspC/OspA chimeric protein (OspC2-OspA-composed of OspC (a.a. 19-204 from strain C2)/OspA (a.a. 18-273 from strain B31) (SEQ ID NO:60) produced an immune response to the C-terminal portion of OspA that was comparable to the immune response generated to the C-terminal portion of a non-lipidated OspA (OspA-a.a. 18-273 from strain B31) control protein (FIG. 23). As indicated in FIG. 23, mice were immunized with OspA, OspC or OspC2-OspA proteins and immune responses of the sera were measured against B31 OspA antigen. The protective antibody response to B31 OspA antigen is indicated in the stippled bars.

Thus, these results clearly demonstrate that non-lipidated chimeric OspC/OspA proteins are able to induce immune responses in mice that are comparable to the immune response generated against non-lipidated OspC and OspA control proteins.

Figure 24:
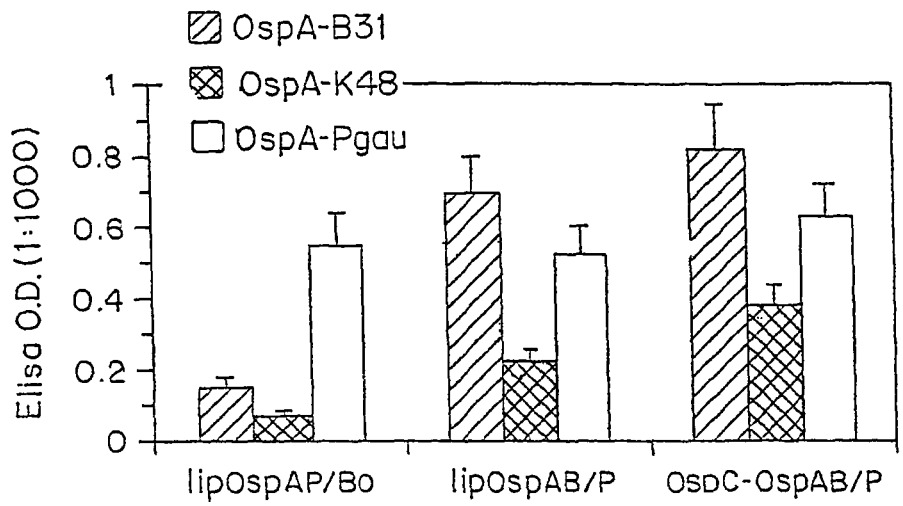
FIG. 24 is a bar graph showing the reactivity of sera from mice immunized with the indicated *Borrelia* chimeric protein (lipOspA/Bo, lipOspAB/P or OspC-OspAB/P)(X-axis) against the indicated OspA antigens (legend) from strains B31 (*Borrelia burgdorferi* sensu stricto), K48 (*Borrelia garinii*) and Pgau (*Borrelia afzelii*).

It had been previously thought that the lipidation signals that are present on *Borrelia burgdorferi* outer surface proteins were required for immunogenicity and that OspC and OspA proteins that lacked this lipidation signal would be less or non-immunogenic. To test this idea, mice were immunized with a non-lipidated OspC/OspA chimeric protein (OspC-OspAB/P-composed of OspC (a.a. 19-211 from strain B31)/OspA (a.a. 18-216 from strain B31)/OspA (a.a. 217-273 from strain Pko) (SEQ ID NO:66) as well as two lipidated OspA proteins, lipOspAP/Bo (composed of OspA (a.a. 1-217 from strain PGau)/OspA (a.a. 218-273 from strain Bo)) and lipOspAB/P (composed of OspA (a.a. 1-216 from strain B31)/OspA (a.a. 217-273 from strain Pko)) and were subjected ELISA tests. Mice immunized with the non-lipidated OspC/OspA chimeric protein (OspC-OspAB/P) produced an immune response to OspA from each of the *Borrelia burgdorferi* strains B31 (*Borrelia burgdorferi* sensu stricto), K48 (*Borrelia garinii*) and PGau (*Borrelia afzelei*), that was equivalent or greater than the immune response generated to the two lipidated OspA control proteins (lipOspAP/Bo and lipOspAb/P) (FIG. 24).

Figure 25:
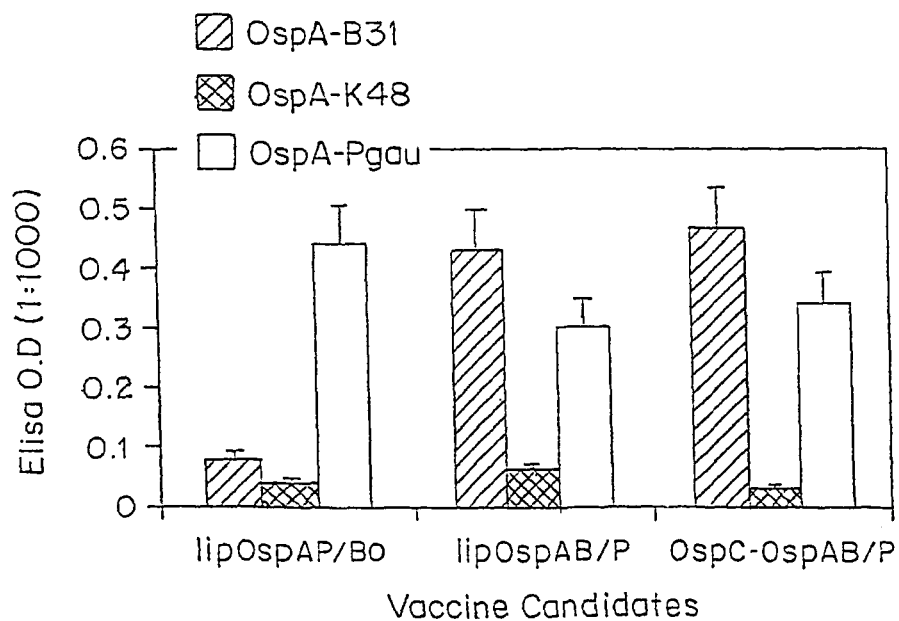
FIG. 25 is a bar graph showing the reactivity of sera from mice immunized with the indicated *Borrelia* chimeric protein (lipOspAP/Bo, lipOspAB/P or OspC-OspAB/P)(X-axis) against the indicated OspA (legend) from strains B31 (*Borrelia burgdorferi* sensu stricto), K48 (*Borrelia garinii*) and Pgau (*Borrelia afzelii*). In all cases, a purified fragment of B31 OspA (amino acids 18-139) was added in excess to the sera so that the detected immune response is specific for the C-terminal region of OspA.

Similar results to these were obtained using the Protective ELISA Test described above. Mice immunized with the non-lipidated OspC/OspA chimeric protein (OspC-OspAB/P) produced an immune response to the C-terminal region of OspA from each of the *Borrelia burgdorferi* strains B31 (*Borrelia burgdorferi* sensu stricto), K48 (*Borrelia garinii*) and PGau (*Borrelia afzelii*), that was equivalent or greater than the immune response generated to the C-terminal region of OspA from the two lipidated OspA control proteins (lipOspAP/Bo and lipOspAb/P) (FIG. 25).

Figure 26:
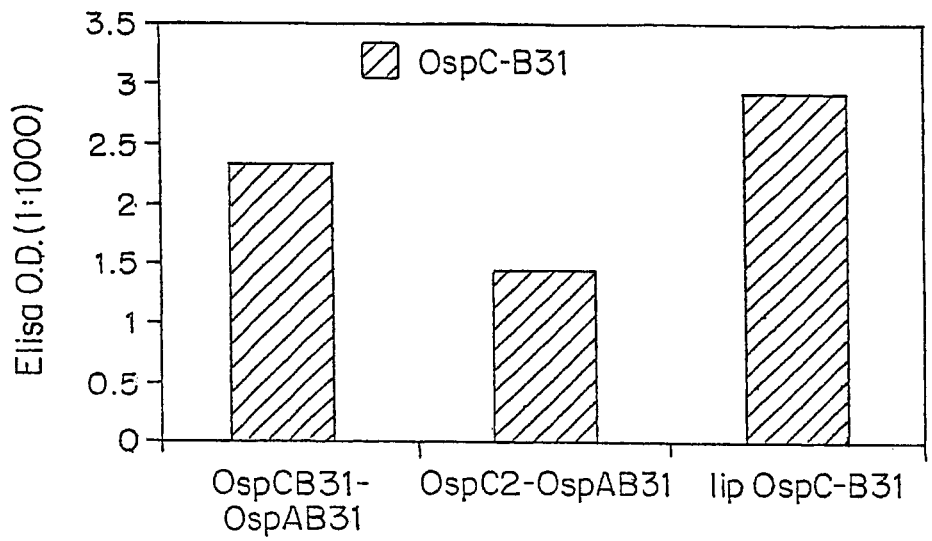
FIG. 26 is a bar graph showing the reactivity of sera from mice immunized with the indicated *Borrelia* chimeric protein (OspCB31-OspAB31, OspC2-OspAB31 or lip OspC-B31)(X-axis) against the indicated OspC antigen (legend) from the strain B31 (*Borrelia burgdorferi* sensu stricto).

In addition to the comparisons between non-lipidated OspC/OspA chimeric proteins and lipidated OspA control proteins, experiments were also performed to compare non-lipidated OspC/OspA chimeric proteins with a lipidated OspC control protein (FIG. 26). Mice that were immunized with either the non-lipidated OspC/OspA chimeric protein OspCB31-OspAB31 (composed of OspC (a.a. 19-211 from strain B31)/OspA (a.a. 18-273 from strain B31) (SEQ ID NO:56) or the non-lipidated OspC/OspA chimeric protein OspC2-OspAB31 (composed of OspC (a.a. 19-204 from strain C2)/OspA (a.a. 18-273 from strain B31) (SEQ ID NO:60) produced an immune response to OspC derived from the *Borrelia burgdorferi* strain B31 that was comparable to the immune response produced by a lipidated OspC control protein (lip OspC-B31-composed of OspC (a.a. 1-211 from strain B31)) (FIG. 26).

Thus, these results clearly demonstrate that non-lipidated chimeric OspC/OspA proteins are able to induce immune responses against OspA and OspC that are comparable to the immune response generated against OspA and OspC using lipidated OspA or OspC control proteins. The use of unlipidated forms of these proteins as vaccine immunogens or diagnostic antigens is highly desirable because the product yield is much greater and the proteins are much easier to purify. For these reasons, the production of these proteins is less expensive.

Figure 27:
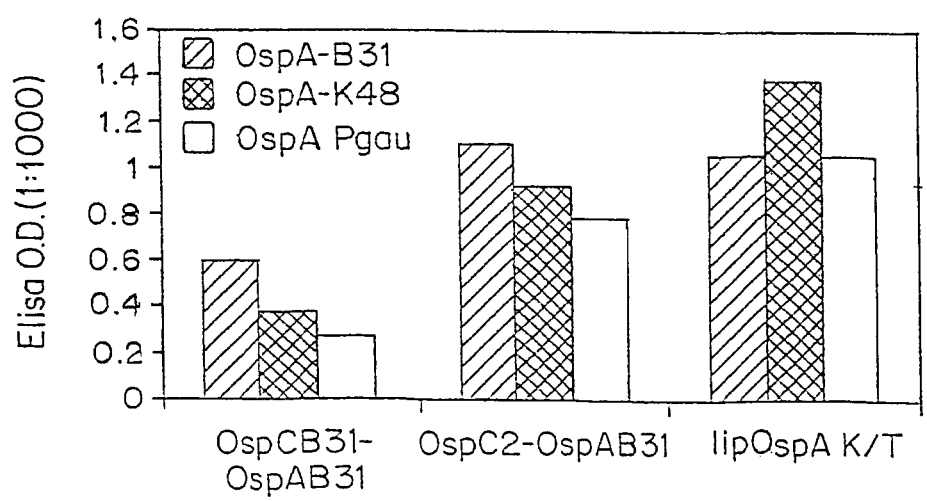
FIG. 27 is a bar graph showing the reactivity of sera from mice immunized with the indicated *Borrelia* chimeric protein (OspCB31-OspAB31, OspC2-OspAB31 or Lip OspA K/T)(X-axis) against the indicated OspA antigens (legend) from strains B31 (*Borrelia burgdorferi* sensu stricto), K48 (*Borrelia garinii*) and Pgau (*Borrelia afzelii*).

The OspC/OspA chimeric proteins of the present invention are also able to generate immune responses against OspA proteins that are derived from strains that are not represented in the chimeric protein. Mice immunized with the OspC/OspA chimeric proteins, OspCB3'-OspAB31 (SEQ ID NO:56) and OspC2-OspAB31 (SEQ ID NO:60), are not only able to generate immune responses that recognize OspA derived from strain B31 (*Borrelia burgdorferi* sensu stricto), but also recognize OspA derived from strain K48 (*Borrelia garinii*) and strain PGau (*Borrelia afzelii*) (FIG. 27). For comparison, mice were also immunized with the lipidated OspA chimeric protein, Lip OspA K/T (composed of OspA (a.a. 1-217 from strain K48)/OspA (a.a. 218-273 from strain Tro)) (FIG. 27).

Figure 28:
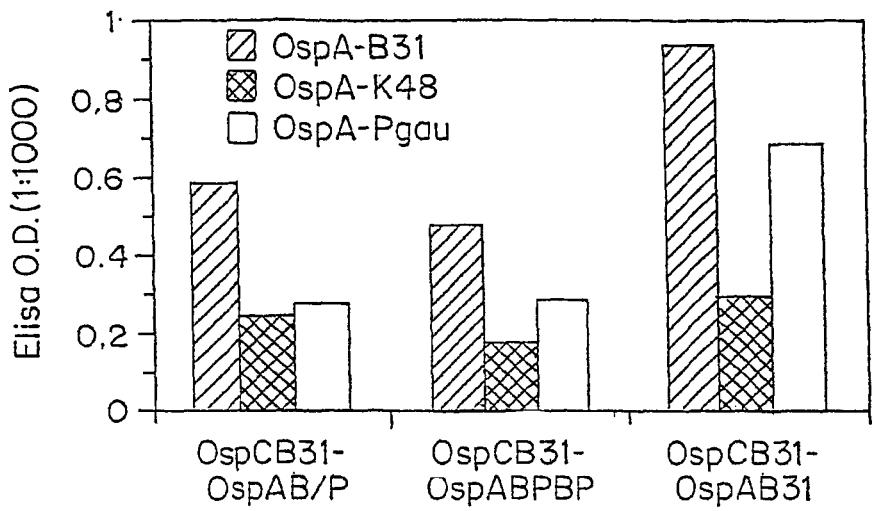
FIG. 28 is a bar graph showing the reactivity of sera from mice immunized with the indicated *Borrelia* chimeric protein (OspCB31-OspAB/P, OspCB31-OspABPBP or OspCB31-OspAB31)(X-axis) against the indicated OspA antigens (legend) from strains B31 (*Borrelia burgdorferi* sensu stricto), K48 (*Borrelia garinii*) and Pgau (*Borrelia afzelii*).
Figure 29:
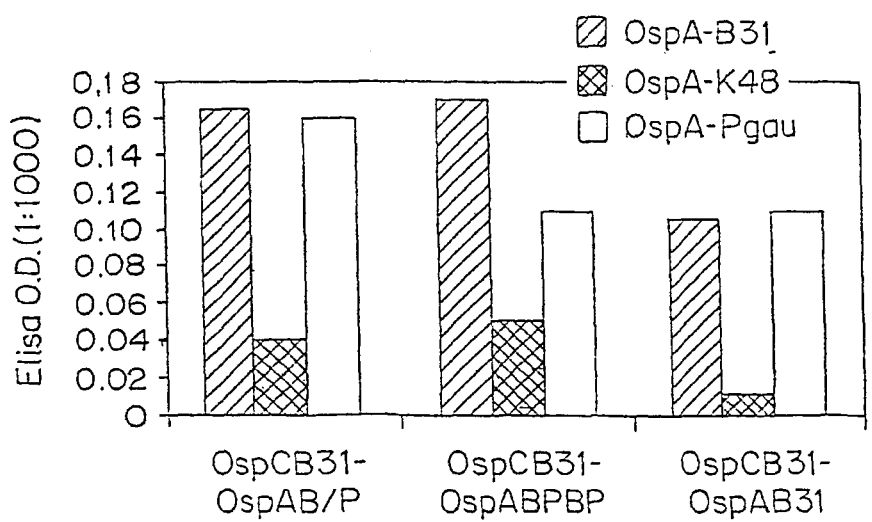
FIG. 29 is a bar graph showing the reactivity of sera from mice immunized with the indicated *Borrelia* chimeric protein (OspCB31-OspAB/P, OspCB31-OspABPBP or OspCB31-OspAB31)(X-axis) against the indicated OspA (legend) from strains B31 (*Borrelia burgdorferi* sensu stricto), K48 (*Borrelia garinii*) and Pgau (*Borrelia afzelii*). In all cases, a purified fragment of B31 OspA (amino acids 18-139) was added in excess to the sera so that the detected immune response is specific for the C-terminal region of OspA.

Additional antibody responses to OspA derived from strain B31 (*Borrelia burgdorferi* sensu stricto), strain K48 (*Borrelia garinii*) and strain PGau (*Borrelia afzelii*) are also presented for sera from mice immunized with other OspC/OspA chimeric proteins. Thus, FIG. 28 presents the ELISA results from mice immunized with either OspCB31-OspAB/P (SEQ ID NO:66), OspCB31-OspABPBP (SEQ ID NO:88) or OspCB31-OspAB31 (SEQ ID NO:56). In each case, sera from the immunized mice was tested against OspA derived from each of strain B31 (*Borrelia burgdorferi* sensu stricto), K48 (*Borrelia garinii*) and PGau (*Borrelia afzelii*). In all cases, a strong immune response was generated (FIG. 28). As with the previously described OspC/OspA chimeric proteins, the three OspC/OspA chimeric proteins used to immunize the mice in FIG. 27 also elicited a strong immune response to the C-terminal region of OspA when examined using the Protective ELISA Test described above (FIG. 29).

The above-described techniques are also used to immunize mice and to serologically characterize the immune response against the proteins comprising the altered OspA polypeptides of the present invention.

Tick Challenge of Immunized Mice

Mice, either C3H-J or JCR, that had been immunized as described above, were also challenged with either laboratory-infected nympha or field nympha. The immunized mice were placed in isolation cages and each mouse received 5-10 nymphs. All of the nymphs were collected at counted after 6 days. Four week after challenge, the mice were bled and sera was tested using commercially-available Western blot strips to *Borrelia burgdorferi* sensu stricto strain B31 (MarDx strips) and/or *Borrelia garinii* (MRL strips). Eight weeks after challenge, the mice were bled, sera was tested again by Western blot and ear punch and bladder samples were cultured. As a positive control, mice which had been immunized with only aluminum hydroxide adjuvant, as described above, were subjected to the same challenge.

The results of the tick challenge studies (Table IV) demonstrate that while immunization with lipidated OspC protein was unable to protect the mice, as evidenced by a positive Western blot signal (in 4 out of 5 mice), immunization with two different OspC/OspA chimeric proteins (SEQ ID NO:56 and SEQ ID NO:62) did provide protection, as indicated by the absence of Western blot signal (in 0 out of 8 mice and 0 out of 3 mice) (Table IV). The sham positive control showed that the challenge by the ticks was successful in all cases, as evidenced by 100% positive signal in Western blots (Table IV). Results from the tick challenge experiments are shown in Table IV.

TABLE IV

Effect of Vaccination on Transmission of *Borrelia* from Ticks

| Vaccine Candidate | Mouse | Tick-nymph | Seroconversion (Western Blots) Vaccinated | Seroconversion (Western Blots) Sham |
|---|---|---|---|---|
| OspC1-OspAB31 | C3H-J | Long Island | 0+/8 | 8+/8 |
| OspC2-OspAB31 | C3H-J | Long Island | 0+/3 | 4+/4 |
| Lip OspC12 | ICR | Long Island | 4+/5 | 5+/5 |

The above-described techniques are also used to measure the ability of mice immunized with proteins comprising the altered OspA polypeptides of the present invention to resist or respond to transmission of *Borrelia* from ticks.

Example 6

Generation of OspA M1, M2, M3, J1, J2 and J3 Constructs Using Site Directed Mutagenesis and PCR All constructs were made using Stratagene's QuikChange site-directed mutagenesis kit. Site-directed mutagenesis was performed using Pfu Turbo DNA polymerase II and a thermal temperature cycler. Pfu Turbo DNA polymerase replicates both plasmid strands with high fidelity and without displacing the mutant oligonucleotide primers. The basic procedure used a supercoiled double-stranded DNA vector (pET 9c for all constructs) with an insert of interest and two synthetic oligonucleotide primers containing the desired mutation(s). The oligonucleotide primers, each complementary to opposite strands of the vector, were extended during the temperature cycling by the Pfu Turbo DNA polymerase. Incorporation of the oligonucleotide primers created a mutated plasmid which contained staggered nicks. Following temperature cycling, the linear product was treated with the restriction enzyme Dpn I, which is specific for methylated DNA. DNA isolated from most *E. coli* strains is dam methylated and therefore is susceptible to Dpn I digestion. Digestion with Dpn I therefore destroyed the original template DNA leaving only the nicked plasmid DNA (which was not methylated) containing the desired mutation(s). This nicked vector DNA (containing the desired mutation(s)) was then transformed into competent *E. coli* which were plated on antibiotic-containing plates. Colonies containing the plasmid (which encodes for antibiotic resistance in addition to the altered OspA polypeptide) were grown and plasmids were purified and sequenced to confirm that they possessed the desired mutation(s).

1) M1, M2 and M3 Mutants

The mutations described herein are made using nucleic acids (e.g., polynucleotides) encoding OspA polypeptides or fragments from any strain of Lyme Disease-causing *Borrelia*, such as *Borrelia burgdorferi* sensu stricto, *Borrelia afzelii* or *Borrelia garinii*. As an example, the generation of the M3 mutations in an OspA chimera, called "BPBP", is described below. The creation of the construct OspA BPBP M3 was as follows. BPBP is a chimeric OspA polypeptide, wherein residues 1-164 are from OspA of B31, residues 165-179 are from OspA of Pko or PGau, residues 180-216 are from OspA of B31 and residues 217-273 are from OspA of Pko (wherein the numbering is as shown in SEQ ID NO:7).

The first step in creating this construct was to make the construct BPBP M1. The M1 mutation consists of a mutation of codon 139 (aga) of OspA from the amino acid arginine to the amino acid methionine (codon atg). A PCR reaction was set up as described above containing a polynucleotide encoding BPBP as the template DNA and the following oligonucleotide primers:

a) 5' R139M:
(SEQ ID NO: 117)
5' gaa aaa ata ata aca atg gca gac gga acc 3'.

b) 3' R139M:
(SEQ ID NO: 118)
5' ggt tcc gtc tgc cat tgt tat tat ttt tc 3'

The PCR reaction also contained reaction buffer, 10 ng of the BPBP DNA template, 125 ng of each oligonucleotide primer, and the dNTP mix. The parameters for the PCR were as outlined in Table V.

TABLE V

Parameters for PCR

| Segment | cycles | temp | time |
|---|---|---|---|
| 1 | 1 | 95° C. | 30 sec. |
| 2 | 18 | 95° C. | 30 sec. |
| 3 | | 50° C. | 1 min. |
| 4 | | 68° C. | 12 min |

Following PCR, the product was transformed into competent *E. coli* XL1-Blue cells. Colonies formed on the selective agar plates (containing kanamycin) were grown and plasmids were purified and sequenced to confirm that they possessed the desired mutation. The construct BPBP M1 was then used as template to make the plasmid BPBP M2, which in addition to the R139M mutation, also contains a mutation that changes the glutamic acid codon (gag) at position 160 to the codon (tat) which encodes for tyrosine. The oligonucleotide primers used to generate this plasmid were:

a) 5' E160Y
(SEQ ID NO: 119)
5' gga aaa gct aaa tat gtt tta aaa ggc 3' b) 3' E160Y
(SEQ ID NO: 120)
5' gcc ttt taa aac ata ttt agc ttt tcc 3'

The parameters for the PCR were as outlined in Table VII. The final mutation, M3, which alters a lysine residue at position 189 to a methionine residue was performed using BPBP M2 as a DNA template. The oligonucleotide primers used to generate this plasmid were:

a) 5' K189M
(SEQ ID NO: 121)
5' gtt act tta agc atg aat att tca aaa tc 3' b) 3' K189M
(SEQ ID NO: 122)
5' ga ttt tga aat att cat gct taa agt aac 3'

This final mutation yielded the desired construct, BPBP M3.

2) J1, J2 and J3 Mutants

J1, J2 and J3 mutants were made using the same protocol described for the generation of the M1, M2 and M3 mutants. Such mutants can be made using nucleic acids (e.g., polynucleotides) encoding OspA polypeptides fragments from any strain of Lyme Disease-causing *Borrelia*, such as *Borrelia burgdorferi* sensu stricto, *Borrelia afzelii* or *Borrelia garinii*.

The oligonucleotide primers which were used to generate the J1 mutation (which contains a Y165F mutation (codon tat to ttt) and a VI 66T mutation (codon gtt to act)) were as follows:

a) 5' B31 YV-FT
(SEQ ID NO: 123)
5' gag gtt tta aaa ggc ttt act ctt gaa gga act c 3' b) 3' B31 YV-FT
(SEQ ID NO: 124)
5' gag ttc ctt caa gag taa agc ctt tta aaa cct g 3'

The oligonucleotide primers which were used to generate the J2 mutation (which contains a T170K mutation (codon act to aag)) were as follows:

a) 5' B31 T-K
(SEQ ID NO: 125)
5' tct tga agg aaa gct aac tgc tg 3' b) 3' B31 T-K
(SEQ ID NO: 126)
5' cag cag tta gct ttc ctt caa ga 3'

To generate the J3 mutant (which contains a Y165F mutation (codon tat to ttt), a VI 66T mutation (codon gtt to act) and a T170K mutation (codon act to aag)), the template containing the J1 mutations was used with the oligonucleotide primers for generating the J2 mutation (5' B31 T-K (SEQ ID NO:125) and 3' B31 T-K (SEQ ID NO:126)).

The altered OspA polypeptides described herein are expressed, used to immunize mice and characterized using ELISA as described in the Experiments above.

While this invention has been particularly shown and described with references to preferred embodiments thereof, it will be understood by those skilled in the art that various changes in form and details may be made therein without departing from the scope of the invention encompassed by the appended claims.

---

SEQUENCE LISTING

<160> NUMBER OF SEQ ID NOS: 173

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 1
cttaatgact ctgacactag tgc                                                23

<210> SEQ ID NO 2
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 2
gctactaaaa aaaccgggaa atggaattca                                         30

<210> SEQ ID NO 3
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 3
gcagcttggg attcaaaaac atccacttta aca                                     33

<210> SEQ ID NO 4
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 4
ggagaatata ttatgaaa                                                      18

<210> SEQ ID NO 5
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 5
ctccttattt taaagcg                                                    17

<210> SEQ ID NO 6
<211> LENGTH: 822
<212> TYPE: DNA
<213> ORGANISM: Borrelia burgdorferi
<220> FEATURE:
<221> NAME/KEY: CDS
<222> LOCATION: (1)...(822)

<400> SEQUENCE: 6

```
atg aaa aaa tat tta ttg gga ata ggt cta ata tta gcc tta ata gca      48
Met Lys Lys Tyr Leu Leu Gly Ile Gly Leu Ile Leu Ala Leu Ile Ala
1               5                   10                  15 tgt aag caa aat gtt agc agc ctt gac gag aaa aac agc gtt tca gta      96
Cys Lys Gln Asn Val Ser Ser Leu Asp Glu Lys Asn Ser Val Ser Val
            20                  25                  30 gat ttg cct ggt gaa atg aaa gtt ctt gta agc aaa gaa aaa aac aaa     144
Asp Leu Pro Gly Glu Met Lys Val Leu Val Ser Lys Glu Lys Asn Lys
        35                  40                  45 gac ggc aag tac gat cta att gca aca gta gac aag ctt gag ctt aaa     192
Asp Gly Lys Tyr Asp Leu Ile Ala Thr Val Asp Lys Leu Glu Leu Lys
    50                  55                  60 gga act tct gat aaa aac aat gga tct gga gta ctt gaa ggc gta aaa     240
Gly Thr Ser Asp Lys Asn Asn Gly Ser Gly Val Leu Glu Gly Val Lys
65                  70                  75                  80 gct gac aaa agt aaa gta aaa tta aca att tct gac gat cta ggt caa     288
Ala Asp Lys Ser Lys Val Lys Leu Thr Ile Ser Asp Asp Leu Gly Gln
                85                  90                  95 acc aca ctt gaa gtt ttc aaa gaa gat ggc aaa aca cta gta tca aaa     336
Thr Thr Leu Glu Val Phe Lys Glu Asp Gly Lys Thr Leu Val Ser Lys
            100                 105                 110 aaa gta act tcc aaa gac aag tca tca aca gaa gaa aaa ttc aat gaa     384
Lys Val Thr Ser Lys Asp Lys Ser Ser Thr Glu Glu Lys Phe Asn Glu
        115                 120                 125 aaa ggt gaa gta tct gaa aaa ata ata aca aga gca gac gga acc aga     432
Lys Gly Glu Val Ser Glu Lys Ile Ile Thr Arg Ala Asp Gly Thr Arg
    130                 135                 140 ctt gaa tac aca gga att aaa agc gat gga tct gga aaa gct aaa gag     480
Leu Glu Tyr Thr Gly Ile Lys Ser Asp Gly Ser Gly Lys Ala Lys Glu
145                 150                 155                 160 gtt tta aaa ggc tat gtt ctt gaa gga act cta act gct gaa aaa aca     528
Val Leu Lys Gly Tyr Val Leu Glu Gly Thr Leu Thr Ala Glu Lys Thr
                165                 170                 175 aca ttg gtg gtt aaa gaa gga act gtt act tta agc aaa aat att tca     576
Thr Leu Val Val Lys Glu Gly Thr Val Thr Leu Ser Lys Asn Ile Ser
            180                 185                 190 aaa tct ggg gaa gtt tca gtt gaa ctt aat gac act gac agt agt gct     624
Lys Ser Gly Glu Val Ser Val Glu Leu Asn Asp Thr Asp Ser Ser Ala
        195                 200                 205 gct act aaa aaa act gca gct tgg aat tca ggc act tca act tta aca     672
Ala Thr Lys Lys Thr Ala Ala Trp Asn Ser Gly Thr Ser Thr Leu Thr
    210                 215                 220 att act gta aac agt aaa aaa act aaa gac ctt gtg ttt aca aaa gaa     720
Ile Thr Val Asn Ser Lys Lys Thr Lys Asp Leu Val Phe Thr Lys Glu
```

```
Ile Thr Val Asn Ser Lys Lys Thr Lys Asp Leu Val Phe Thr Lys Glu
225                 230                 235                 240 aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255 ggg tca gca gtt gaa att aca aaa ctt gat gaa att aaa aac gct tta      816
Gly Ser Ala Val Glu Ile Thr Lys Leu Asp Glu Ile Lys Asn Ala Leu
                260                 265                 270 aaa taa                                                              822
Lys *

<210> SEQ ID NO 7
<211> LENGTH: 273
<212> TYPE: PRT
<213> ORGANISM: Borrelia burgdorferi

<400> SEQUENCE: 7

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
        50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys

<210> SEQ ID NO 8
<211> LENGTH: 825
<212> TYPE: DNA
<213> ORGANISM: Borrelia burgdorferi
```

```
<220> FEATURE:
<221> NAME/KEY: CDS
<222> LOCATION: (1)...(825)

<400> SEQUENCE: 8 atg aaa aaa tat tta ttg gga ata ggt cta ata tta gcc tta ata gca      48
Met Lys Lys Tyr Leu Leu Gly Ile Gly Leu Ile Leu Ala Leu Ile Ala
1               5                   10                  15 tgt aag caa aat gtt agc agc ctt gat gaa aaa aat agc gtt tca gta      96
Cys Lys Gln Asn Val Ser Ser Leu Asp Glu Lys Asn Ser Val Ser Val
            20                  25                  30 gat tta cct ggt gga atg aca gtt ctt gta agt aaa gaa aaa gac aaa     144
Asp Leu Pro Gly Gly Met Thr Val Leu Val Ser Lys Glu Lys Asp Lys
        35                  40                  45 gac ggt aaa tac agt cta gag gca aca gta gac aag ctt gag ctt aaa     192
Asp Gly Lys Tyr Ser Leu Glu Ala Thr Val Asp Lys Leu Glu Leu Lys
    50                  55                  60 gga act tct gat aaa aac aac ggt tct gga aca ctt gaa ggt gaa aaa     240
Gly Thr Ser Asp Lys Asn Asn Gly Ser Gly Thr Leu Glu Gly Glu Lys
65                  70                  75                  80 act gac aaa agt aaa gta aaa tta aca att gct gat gac cta agt caa     288
Thr Asp Lys Ser Lys Val Lys Leu Thr Ile Ala Asp Asp Leu Ser Gln
                85                  90                  95 act aaa ttt gaa att ttc aaa gaa gat gcc aaa aca tta gta tca aaa     336
Thr Lys Phe Glu Ile Phe Lys Glu Asp Ala Lys Thr Leu Val Ser Lys
            100                 105                 110 aaa gta acc ctt aaa gac aag tca tca aca gaa gaa aaa ttc aac gaa     384
Lys Val Thr Leu Lys Asp Lys Ser Ser Thr Glu Glu Lys Phe Asn Glu
        115                 120                 125 aag ggt gaa aca tct gaa aaa aca ata gta aga gca aat gga acc aga     432
Lys Gly Glu Thr Ser Glu Lys Thr Ile Val Arg Ala Asn Gly Thr Arg
    130                 135                 140 ctt gaa tac aca gac ata aaa agc gat gga tcc gga aaa gct aaa gaa     480
Leu Glu Tyr Thr Asp Ile Lys Ser Asp Gly Ser Gly Lys Ala Lys Glu
145                 150                 155                 160 gtt tta aaa gac ttt act ctt gaa gga act cta gct gct gac ggc aaa     528
Val Leu Lys Asp Phe Thr Leu Glu Gly Thr Leu Ala Ala Asp Gly Lys
                165                 170                 175 aca aca ttg aaa gtt aca gaa ggc act gtt gtt tta agc aag aac att     576
Thr Thr Leu Lys Val Thr Glu Gly Thr Val Val Leu Ser Lys Asn Ile
            180                 185                 190 tta aaa tcc gga gaa ata aca gtt gca ctt gat gac tct gac act act     624
Leu Lys Ser Gly Glu Ile Thr Val Ala Leu Asp Asp Ser Asp Thr Thr
        195                 200                 205 cag gct act aaa aaa act gga aaa tgg gat tca aaa act tcc act tta     672
Gln Ala Thr Lys Lys Thr Gly Lys Trp Asp Ser Lys Thr Ser Thr Leu
    210                 215                 220 aca att agt gtg aat agc caa aaa acc aaa aac ctt gta ttc aca aaa     720
Thr Ile Ser Val Asn Ser Gln Lys Thr Lys Asn Leu Val Phe Thr Lys
225                 230                 235                 240 gaa gac aca ata aca gta caa aaa tac gac tca gca ggc acc aat cta     768
Glu Asp Thr Ile Thr Val Gln Lys Tyr Asp Ser Ala Gly Thr Asn Leu
                245                 250                 255 gaa ggc aaa gca gtc gaa att aca aca ctt aaa gaa ctt aaa aac gct     816
Glu Gly Lys Ala Val Glu Ile Thr Thr Leu Lys Glu Leu Lys Asn Ala
            260                 265                 270 tta aaa taa                                                          825
Leu Lys *

<210> SEQ ID NO 9
<211> LENGTH: 274
```

```
<212> TYPE: PRT
<213> ORGANISM: Borrelia burgdorferi

<400> SEQUENCE: 9

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Gly Met Thr Val Leu Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Asp Asp Leu Ser Gln
                85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190

Leu Lys Ser Gly Glu Ile Thr Val Ala Leu Asp Asp Ser Asp Thr Thr
        195                 200                 205

Gln Ala Thr Lys Lys Thr Gly Lys Trp Asp Ser Lys Thr Ser Thr Leu
    210                 215                 220

Thr Ile Ser Val Asn Ser Gln Lys Thr Lys Asn Leu Val Phe Thr Lys
225                 230                 235                 240

Glu Asp Thr Ile Thr Val Gln Lys Tyr Asp Ser Ala Gly Thr Asn Leu
                245                 250                 255

Glu Gly Lys Ala Val Glu Ile Thr Thr Leu Lys Glu Leu Lys Asn Ala
            260                 265                 270

Leu Lys

<210> SEQ ID NO 10
<211> LENGTH: 822
<212> TYPE: DNA
<213> ORGANISM: Borrelia burgdorferi
<220> FEATURE:
<221> NAME/KEY: CDS
<222> LOCATION: (1)...(822)

<400> SEQUENCE: 10 atg aaa aaa tat tta ttg gga ata ggt cta ata tta gcc tta ata gca      48
Met Lys Lys Tyr Leu Leu Gly Ile Gly Leu Ile Leu Ala Leu Ile Ala
 1               5                  10                  15 tgc aag caa aat gtt agc agc ctt gat gaa aaa aac agc gct tca gta      96
Cys Lys Gln Asn Val Ser Ser Leu Asp Glu Lys Asn Ser Ala Ser Val
            20                  25                  30 gat ttg cct ggt gag atg aaa gtt ctt gta agt aaa gaa aaa gac aaa     144
Asp Leu Pro Gly Glu Met Lys Val Leu Val Ser Lys Glu Lys Asp Lys
        35                  40                  45
```

```
gac ggt aag tac agt cta aag gca aca gta gac aag att gag cta aaa      192
Asp Gly Lys Tyr Ser Leu Lys Ala Thr Val Asp Lys Ile Glu Leu Lys
        50                  55                  60 gga act tct gat aaa gac aat ggt tct gga gtg ctt gaa ggt aca aaa      240
Gly Thr Ser Asp Lys Asp Asn Gly Ser Gly Val Leu Glu Gly Thr Lys
 65                  70                  75                  80 gat gac aaa agt aaa gca aaa tta aca att gct gac gat cta agt aaa      288
Asp Asp Lys Ser Lys Ala Lys Leu Thr Ile Ala Asp Asp Leu Ser Lys
                 85                  90                  95 acc aca ttc gaa ctt tta aaa gaa gat ggc aaa aca tta gtg tca aga      336
Thr Thr Phe Glu Leu Leu Lys Glu Asp Gly Lys Thr Leu Val Ser Arg
            100                 105                 110 aaa gta agt tct aga gac aaa aca tca aca gat gaa atg ttc aat gaa      384
Lys Val Ser Ser Arg Asp Lys Thr Ser Thr Asp Glu Met Phe Asn Glu
        115                 120                 125 aaa ggt gaa ttg tct gca aaa acc atg aca aga gaa aat gga acc aaa      432
Lys Gly Glu Leu Ser Ala Lys Thr Met Thr Arg Glu Asn Gly Thr Lys
130                 135                 140 ctt gaa tat aca gaa atg aaa agc gat gga acc gga aaa gct aaa gaa      480
Leu Glu Tyr Thr Glu Met Lys Ser Asp Gly Thr Gly Lys Ala Lys Glu
145                 150                 155                 160 gtt tta aaa aag ttt act ctt gaa gga aaa gta gct aat gat aaa gta      528
Val Leu Lys Lys Phe Thr Leu Glu Gly Lys Val Ala Asn Asp Lys Val
                165                 170                 175 aca ttg gaa gta aaa gaa gga acc gtt act tta agt aag gaa att gca      576
Thr Leu Glu Val Lys Glu Gly Thr Val Thr Leu Ser Lys Glu Ile Ala
            180                 185                 190 aaa tct gga gaa gta aca gtt gct ctt aat gac act aac act act cag      624
Lys Ser Gly Glu Val Thr Val Ala Leu Asn Asp Thr Asn Thr Thr Gln
        195                 200                 205 gct act aaa aaa act ggc gca tgg gat tca aaa act tct act tta aca      672
Ala Thr Lys Lys Thr Gly Ala Trp Asp Ser Lys Thr Ser Thr Leu Thr
    210                 215                 220 att agt gtt aac agc aaa aaa act aca caa ctt gtg ttt act aaa caa      720
Ile Ser Val Asn Ser Lys Lys Thr Thr Gln Leu Val Phe Thr Lys Gln
225                 230                 235                 240 tac aca ata act gta aaa caa tac gac tcc gca ggt acc aat tta gaa      768
Tyr Thr Ile Thr Val Lys Gln Tyr Asp Ser Ala Gly Thr Asn Leu Glu
                245                 250                 255 ggc aca gca gtc gaa att aaa aca ctt gat gaa ctt aaa aac gct tta      816
Gly Thr Ala Val Glu Ile Lys Thr Leu Asp Glu Leu Lys Asn Ala Leu
            260                 265                 270 aaa taa                                                              822
Lys *

<210> SEQ ID NO 11
<211> LENGTH: 273
<212> TYPE: PRT
<213> ORGANISM: Borrelia burgdorferi

<400> SEQUENCE: 11

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Ala Ser Val
                 20                  25                  30

Asp Leu Pro Gly Glu Met Lys Val Leu Val Ser Lys Glu Lys Asp Lys
            35                  40                  45

Asp Gly Lys Tyr Ser Leu Lys Ala Thr Val Asp Lys Ile Glu Leu Lys
        50                  55                  60
```

```
Gly Thr Ser Asp Lys Asp Asn Gly Ser Gly Val Leu Glu Gly Thr Lys
 65                  70                  75                  80

Asp Asp Lys Ser Lys Ala Lys Leu Thr Ile Ala Asp Asp Leu Ser Lys
                 85                  90                  95

Thr Thr Phe Glu Leu Leu Lys Glu Asp Gly Lys Thr Leu Val Ser Arg
            100                 105                 110

Lys Val Ser Ser Arg Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Tyr Thr Ile Thr Val Lys Gln Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys

<210> SEQ ID NO 12
<211> LENGTH: 819
<212> TYPE: DNA
<213> ORGANISM: Borrelia burgdorferi
<220> FEATURE:
<221> NAME/KEY: CDS
<222> LOCATION: (1)...(819)

<400> SEQUENCE: 12 atg aaa aaa tat tta ttg gga ata ggt cta ata tta gct tta ata gca      48
Met Lys Lys Tyr Leu Leu Gly Ile Gly Leu Ile Leu Ala Leu Ile Ala
1               5                   10                  15 tgt aag caa aat gtt agc agc ctt gac gag aaa aac agc gtt tca gta      96
Cys Lys Gln Asn Val Ser Ser Leu Asp Glu Lys Asn Ser Val Ser Val
                20                  25                  30 gat ttg cct ggt gaa atg aaa gtt ctt gta agc aaa gaa aaa gac aaa     144
Asp Leu Pro Gly Glu Met Lys Val Leu Val Ser Lys Glu Lys Asp Lys
            35                  40                  45 gac ggc aag tac agt cta atg gca aca gta gac aag ctt gag ctt aaa     192
Asp Gly Lys Tyr Ser Leu Met Ala Thr Val Asp Lys Leu Glu Leu Lys
        50                  55                  60 gga aca tct gat aaa aac aat gga tct ggg gtg ctt gaa ggc gta aaa     240
Gly Thr Ser Asp Lys Asn Asn Gly Ser Gly Val Leu Glu Gly Val Lys
65                  70                  75                  80 gct gac aaa agc aaa gta aaa tta aca gtt tct gac gat cta agc aca     288
Ala Asp Lys Ser Lys Val Lys Leu Thr Val Ser Asp Asp Leu Ser Thr
                85                  90                  95 acc aca ctt gaa gtt tta aaa gaa gat ggc aaa aca tta gtg tca aaa     336
Thr Thr Leu Glu Val Leu Lys Glu Asp Gly Lys Thr Leu Val Ser Lys
            100                 105                 110
```

| | | | | | | | | | | | | | | | | |
|---|---|---|---|---|---|---|---|---|---|---|---|---|---|---|---|---|
| aaa | aga | act | tct | aaa | gat | aag | tca | tca | aca | gaa | gaa | aag | ttc | aat | gaa | 384 |
| Lys | Arg | Thr | Ser | Lys | Asp | Lys | Ser | Ser | Thr | Glu | Glu | Lys | Phe | Asn | Glu | |
| | 115 | | | | 120 | | | | | 125 | | | | | | |
| aaa | ggc | gaa | tta | gtt | gaa | aaa | ata | atg | gca | aga | gca | aac | gga | acc | ata | 432 |
| Lys | Gly | Glu | Leu | Val | Glu | Lys | Ile | Met | Ala | Arg | Ala | Asn | Gly | Thr | Ile | |
| 130 | | | | | 135 | | | | | 140 | | | | | | |
| ctt | gaa | tac | aca | gga | att | aaa | agc | gat | gga | tcc | gga | aaa | gct | aaa | gaa | 480 |
| Leu | Glu | Tyr | Thr | Gly | Ile | Lys | Ser | Asp | Gly | Ser | Gly | Lys | Ala | Lys | Glu | |
| 145 | | | | | 150 | | | | | 155 | | | | | 160 | |
| act | tta | aaa | gaa | tat | gtt | ctt | gaa | gga | act | cta | act | gct | gaa | aaa | gca | 528 |
| Thr | Leu | Lys | Glu | Tyr | Val | Leu | Glu | Gly | Thr | Leu | Thr | Ala | Glu | Lys | Ala | |
| | | | | 165 | | | | | 170 | | | | | 175 | | |
| aca | ttg | gtg | gtt | aaa | gaa | gga | act | gtt | act | tta | agt | aag | cac | att | tca | 576 |
| Thr | Leu | Val | Val | Lys | Glu | Gly | Thr | Val | Thr | Leu | Ser | Lys | His | Ile | Ser | |
| | | | 180 | | | | | 185 | | | | | 190 | | | |
| aaa | tct | gga | gaa | gta | aca | gct | gaa | ctt | aat | gac | act | gac | agt | act | caa | 624 |
| Lys | Ser | Gly | Glu | Val | Thr | Ala | Glu | Leu | Asn | Asp | Thr | Asp | Ser | Thr | Gln | |
| | | 195 | | | | | 200 | | | | | 205 | | | | |
| gct | act | aaa | aaa | act | ggg | aaa | tgg | gat | gca | ggc | act | tca | act | tta | aca | 672 |
| Ala | Thr | Lys | Lys | Thr | Gly | Lys | Trp | Asp | Ala | Gly | Thr | Ser | Thr | Leu | Thr | |
| 210 | | | | | 215 | | | | | 220 | | | | | | |
| att | act | gta | aac | aac | aaa | aaa | act | aaa | gcc | ctt | gta | ttt | aca | aaa | caa | 720 |
| Ile | Thr | Val | Asn | Asn | Lys | Lys | Thr | Lys | Ala | Leu | Val | Phe | Thr | Lys | Gln | |
| 225 | | | | | 230 | | | | | 235 | | | | | 240 | |
| gac | aca | att | aca | tca | caa | aaa | tac | gac | tca | gca | gga | acc | aac | ttg | gaa | 768 |
| Asp | Thr | Ile | Thr | Ser | Gln | Lys | Tyr | Asp | Ser | Ala | Gly | Thr | Asn | Leu | Glu | |
| | | | | 245 | | | | | 250 | | | | | 255 | | |
| ggc | aca | gca | gtc | gaa | att | aaa | aca | ctt | gat | gaa | ctt | aaa | aac | gct | tta | 816 |
| Gly | Thr | Ala | Val | Glu | Ile | Lys | Thr | Leu | Asp | Glu | Leu | Lys | Asn | Ala | Leu | |
| | | | 260 | | | | | 265 | | | | | 270 | | | |
| aga | | | | | | | | | | | | | | | | 819 |
| Arg | | | | | | | | | | | | | | | | |

<210> SEQ ID NO 13
<211> LENGTH: 273
<212> TYPE: PRT
<213> ORGANISM: Borrelia burgdorferi

<400> SEQUENCE: 13

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Lys Asp Lys
        35                  40                  45

Asp Gly Lys Tyr Ser Leu Met Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Val Ser Asp Asp Leu Ser Thr
                85                  90                  95

Thr Thr Leu Glu Val Leu Lys Glu Asp Gly Lys Thr Leu Val Ser Lys
            100                 105                 110

Lys Arg Thr Ser Lys Asp Lys Ser Ser Thr Glu Glu Lys Phe Asn Glu
        115                 120                 125

Lys Gly Glu Leu Val Glu Lys Ile Met Ala Arg Ala Asn Gly Thr Ile
    130                 135                 140

Leu Glu Tyr Thr Gly Ile Lys Ser Asp Gly Ser Gly Lys Ala Lys Glu
145                 150                 155                 160

```
Thr Leu Lys Glu Tyr Val Leu Glu Gly Thr Leu Thr Ala Glu Lys Ala
            165                 170                 175

Thr Leu Val Val Lys Glu Gly Thr Val Thr Leu Ser Lys His Ile Ser
        180                 185                 190

Lys Ser Gly Glu Val Thr Ala Glu Leu Asn Asp Thr Asp Ser Thr Gln
    195                 200                 205

Ala Thr Lys Lys Thr Gly Lys Trp Asp Ala Gly Thr Ser Thr Leu Thr
210                 215                 220

Ile Thr Val Asn Asn Lys Lys Thr Lys Ala Leu Val Phe Thr Lys Gln
225                 230                 235                 240

Asp Thr Ile Thr Ser Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Arg

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 14
gtctgcaaaa accatgacaa g                                              21

<210> SEQ ID NO 15
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 15
gtcatcaaca gaagaaaaat tc                                             22

<210> SEQ ID NO 16
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 16
ccggatccat atgaaaaaat atttattggg                                     30

<210> SEQ ID NO 17
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 17
ccgggatcca tatggctaag caaaatgtta gc                                  32

<210> SEQ ID NO 18
<211> LENGTH: 18
<212> TYPE: DNA
<213> ORGANISM: Artificial Sequence
<220> FEATURE:
<223> OTHER INFORMATION: Oligonucleotide Primer
```

```
<400> SEQUENCE: 18
gcgttcaagt actccaga                                                   18

<210> SEQ ID NO 19
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 19
gatatctaga tcttatttta aagcgtt                                         27

<210> SEQ ID NO 20
<211> LENGTH: 31
<212> TYPE: DNA
<213> ORGANISM: Artificial Sequence
<220> FEATURE:
<223> OTHER INFORMATION: Oligonucleotide Primer

<400> SEQUENCE: 20
ggatccggtg accttttaaa gcgttttaa t                                     31

<210> SEQ ID NO 21
<211> LENGTH: 825
<212> TYPE: DNA
<213> ORGANISM: Borrelia burgdorferi

<400> SEQUENCE: 21
atgaaaaaat atttattggg aataggtcta atattagcct aatagcatg taagcaaaat      60 gttagcagcc ttgatgaaaa aaatagcgtt tcagtagatt tacctggtgg aatgacagtt   120
cttgtaagta aagaaaaaga caaagacggt aaatacagtc tagaggcaac agtagacaag   180
cttgagctta aggaacttc tgataaaaac aacggttctg aacacttga aggtgaaaaa    240 actgacaaaa gtaaagtaaa atcaacaatt gctgatgacc taagtcaaac taaatttgaa   300
attttcaaag aagatggcaa aacattagta tcaaaaaag taacccttaa agacaagtca    360
tcaacagaag aaaaattcaa cggaaagggt gaaacatctg aaaaaacaat agtaagagca   420
aatggaacca gacttgaata cacagacata aaaagcgatg gatccggaaa agctaaagaa   480
gttttaaaag actttactct tgaaggaact ctagctgctg acggcaaaac aacattgaaa   540
gttacagaag gcactgttgt tttaagcaag aacatttaa atccggaga ataacagct      600 gcacttgatg actctgacac tactcgggct actaaaaaaa ctggaaaatg ggattccaaag  660 acttccactt taacaattag tgtgaatagc caaaaaacca aaaaccttgt attcacaaaa   720
gaagacacaa taacagtaca agatacgac tcagcaggca ccaatctaga aggcaaagca    780
gtcgaaatta caacacttaa agaacttaaa aacgctttaa aataa                    825

<210> SEQ ID NO 22
<211> LENGTH: 824
<212> TYPE: DNA
<213> ORGANISM: Borrelia burgdorferi

<400> SEQUENCE: 22
atgaaaaaat atttattggg aataggtcta atattagcat aatagcatg taagcaaaat      60 gttagcagcc ttgatgaaaa aaatagcgtt tcagtagatt tacctggtgg aatgcaagtt   120
cttgtaagta aagaaaaaga caaagatggt aaatacagtc taatggcaac agtagacaag   180
cttgagctta aggaacttc tgataaaaac aacggttctg aacacttga aggtgaaaaa    240
```

| | |
|---|---|
| actgacaaaa gtaaagcaaa attaacaatt gctgaggatc taagtaaaac cacatttgaa | 300 |
| atcttcaaag aagatggcaa acattagta tcaaaaaaag taacccttaa agacaagtca | 360 |
| tcaacagaag aaaaattcaa cgcaaagggt gaagcatctg aaaaaacaat agtaagagca | 420 |
| aatggaacca gacttgaata cacagacata aaaagcgata aaaccggaaa agctaaagaa | 480 |
| gttttaaaag actttgctct tgaaggaact ctagctgctg acggcaaaac aacattaaaa | 540 |
| gttacagaag gcactgttgt tttaagcaaa cacatttcaa actctggaga ataacagtt | 600 |
| gagcttaatg actctgacac tactcaggct actaaaaaaa ctggaacatg ggattcaaag | 660 |
| acttccactt taacaattag tgtgaatagc cgaaaaacca aaaaccttgt attcacaaaa | 720 |
| gaagacacaa taacagtaca aaaatacgac tcagcaggca ccaatctaga aggcaaagca | 780 |
| gtcgaaatta caacgcttaa agaacttaaa gatgctttaa aata | 824 |

<210> SEQ ID NO 23
<211> LENGTH: 821
<212> TYPE: DNA
<213> ORGANISM: Borrelia burgdorferi

<400> SEQUENCE: 23

| | |
|---|---|
| atgaaaaaat atttattggg aataggtcta atattagcct aatagcatg caagcaaaat | 60 |
| gttagcagcc ttgatgaaaa aaacagcgct tcagtagatt tgcctggtga gatgaaagtt | 120 |
| cttgtaagta aagaaaaaga caaagacggt aagtacagtc taaaggcaac agtagacaag | 180 |
| attgagctaa aaggaacttc tgataaagac aatggttctg ggtgcttga aggtacaaaa | 240 |
| gatgacaaaa gtaaagcaaa attaacaatt gctgacgatc taggtaaaac cacattcgaa | 300 |
| cttttcaaag aagatggcaa acattagtg tcaagaaaag taagttctaa agacaaaaca | 360 |
| tcaacagatg aaatgttcaa tgaaaaaggt gaattgtctg caaaaaccat gacaagagaa | 420 |
| aatggaacca aacttgaata tacagaaatg aaaagcgatg gaaccggaaa agctaaagaa | 480 |
| gttttaaaaa actttactct tgaaggaaaa gtagctaatg ataaagtaac attggaagta | 540 |
| aaagaaggaa ccgttacttt aagtaaggaa attgcaaat ctggagaagt aacagttgct | 600 |
| cttaatgaca ctaacactac tcaggctact aaaaaaactg gcgcatggga ttcaaaaact | 660 |
| tctactttaa caattagtgt taacagcaaa aaaactacac aacttgtgtt tactaaacaa | 720 |
| gacacaataa ctgtacaaaa atacgactcc gcaggtacca atttagaagg cacagcagtc | 780 |
| gaaattaaaa cacttgatga acttaaaaac gctttaaaat a | 821 |

<210> SEQ ID NO 24
<211> LENGTH: 821
<212> TYPE: DNA
<213> ORGANISM: Borrelia burgdorferi

<400> SEQUENCE: 24

| | |
|---|---|
| atgaaaaaat atttattggg aataggtcta atattagcct aatagcatg caagcaaaat | 60 |
| gttagcagcc ttgatgaaaa aaacagcgct tcagtagatt tgcctggtga gattaaagtt | 120 |
| cttgtaagta aagaaaaaga caaagacggt aagtacagtc taaaggcaac agtagacaag | 180 |
| attgagctaa aaggaacttc tgataaagac aatggttctg gagtgcttga aggtacaaaa | 240 |
| gatgacaaaa gtaaagcaaa attaacaatt gctgacgatc taagtaaaac cacattcgaa | 300 |
| cttttcaaag aagatggcaa acattagtg tcaagaaaag taagttctaa agacaaaaca | 360 |
| tcaacagatg aaatgttcaa tgaaaaaggt gaattgtctg caaaaaccat gacaagagaa | 420 |
| aatggaacca aacttgaata tacagaaatg aaaagcgatg gaaccggaaa agctaaagaa | 480 |

```
gttttaaaaa actttactct tgaaggaaaa gtagctaatg ataaagtaac attggaagta        540
aaagaaggaa ccgttacttt aagtaaggaa attgcaaaat ctggagaagt aacagttgct        600
cttaatgaca ctaacactac tcaggctact aaaaaaactg gcgcatggga ttcaaaaact        660
tctactttaa caattagtgt taacagtaaa aaaactacac aacttgtgtt tactaaacaa        720
gacacaataa ctgtacaaaa atacgactcc gcaggtacca atttagaagg cacagcagtc        780
gaaattaaaa cacttgatga acttaaaaac gctttaaaat a                            821
```

```
<210> SEQ ID NO 25
<211> LENGTH: 821
<212> TYPE: DNA
<213> ORGANISM: Borrelia burgdorferi

<400> SEQUENCE: 25
atgaaaaaat atttattggg aataggtcta atattagcct aatagcatg caagcaaaat          60 gttagcagcc ttgatgaaaa aaacagcgct tcagtagatt tgcctggtga gatgaaagtt        120
cttgtaagta aagaaaaaga caaagacggt aagtacagtc taaaggcaac agtagacaag        180
attgagctaa aaggaacttc tgataaagac aatggttctg gggtgcttga aggtacaaaa        240
gatgacaaaa gtaaagcaaa attaacaatt gctgacgatc taggtaaaac cacattcgaa        300
cttttcaaag aagatggcaa acattagtg tcaagaaaag taagttctaa agacaaaaca        360
tcaacagatg aaatgttcaa tgaaaaaggt gaattgtctg caaaaccat gacaagagaa        420 aatggaacca aacttgaata tacagaaatg aaagcgatg gaaccggaaa agctaaagaa        480
gttttaaaaa actttactct tgaaggaaaa gtagctaatg ataaagtaac attggaagta        540
aaagaaggaa ccgttacttt aagtaaggaa attgcaaaat ctggagaagt aacagttgct        600
cttaatgaca ctaacactac tcaggctact aaaaaaactg gcgcatggga ttcaaaaact        660
tctactttaa caattagtgt taacagcaaa aaaactacac aacttgtgtt tactaaacaa        720
gacacaataa ctgtacaaaa atacgactcc gcaggtacca atttagaagg cacagcagtc        780
gaaattaaaa cacttgatga acttaaaaac gctttaaaat a                            821
```

```
<210> SEQ ID NO 26
<211> LENGTH: 822
<212> TYPE: DNA
<213> ORGANISM: Borrelia burgdorferi

<400> SEQUENCE: 26
atgaaaaaat atttattggg aataggtcta atattagcct aatagcatg caagcaaaat          60 gttagcagcc ttgatgaaaa aaacagcgct tcagtagatt tgcctggtga gatgaaagtt        120
cttgtaagta aagaaaaaga caaagacggt aagtacagtc taaaggcaac agtagacaag        180
attgagctaa aaggaacttc tgataaagac aatggttctg gagtgcttga aggtacaaaa        240
gatgacaaaa gtaaagcaaa attaacaatt gctgacgatc taagtaaaac cacattcgaa        300
cttttcaaag aagatggcaa acattagtg tcaagaaaag taagttctaa agacaaaaca        360
tcaacagatg aaatgttcaa tgaaaaaggt gaattgtctg caaaaccat gacaagagaa        420 aatggaacca aacttgaata tacagaaatg aaagcgatg gaaccggaaa agctaaagaa        480
gttttaaaaa actttactct tgaaggaaaa gtagctaatg ataaagtaac attggaagta        540
aaagaaggaa ccgttacttt aagtaaggaa attgcaaaat ctggagaagt aacagttgct        600
cttaatgaca ctaacactac tcaggctact aaaaaaactg gcgcatggga ttcaaaaact        660
tctactttaa caattagtgt taacagcaaa aaaactacac aacttgtgtt tactaaacaa        720
```

```
gacacaataa ctgtacaaaa atacgactcc gcaggtacca atttagaagg cacagcagtc    780
gaaattaaaa cacttgatga acttaaaaac gctttgaaat aa                       822

<210> SEQ ID NO 27
<211> LENGTH: 38
<212> TYPE: DNA
<213> ORGANISM: Artificial Sequence
<220> FEATURE:
<223> OTHER INFORMATION: Oligonucleotide Primer

<400> SEQUENCE: 27
aaagtagaag tttttgaatc ccatttccca gttttttt                             38

<210> SEQ ID NO 28
<211> LENGTH: 825
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(825)

<400> SEQUENCE: 28 atg aaa aaa tat tta ttg gga ata ggt cta ata tta gcc tta ata gca      48
Met Lys Lys Tyr Leu Leu Gly Ile Gly Leu Ile Leu Ala Leu Ile Ala
1               5                   10                  15 tgt aag caa aat gtt agc agc ctt gat gaa aaa aat agc gtt tca gta      96
Cys Lys Gln Asn Val Ser Ser Leu Asp Glu Lys Asn Ser Val Ser Val
            20                  25                  30 gat tta cct ggt gga atg aca gtt ctt gta agt aaa gaa aaa gac aaa     144
Asp Leu Pro Gly Gly Met Thr Val Leu Val Ser Lys Glu Lys Asp Lys
        35                  40                  45 gac ggt aaa tac agt cta gag gca aca gta gac aag ctt gag ctt aaa     192
Asp Gly Lys Tyr Ser Leu Glu Ala Thr Val Asp Lys Leu Glu Leu Lys
    50                  55                  60 gga act tct gat aaa aac aac ggt tct gga aca ctt gaa ggt gaa aaa     240
Gly Thr Ser Asp Lys Asn Asn Gly Ser Gly Thr Leu Glu Gly Glu Lys
65                  70                  75                  80 act gac aaa agt aaa gta aaa tta aca att gct gat gac cta agt caa     288
Thr Asp Lys Ser Lys Val Lys Leu Thr Ile Ala Asp Asp Leu Ser Gln
                85                  90                  95 act aaa ttt gaa att ttc aaa gaa gat gcc aaa aca tta gta tca aaa     336
Thr Lys Phe Glu Ile Phe Lys Glu Asp Ala Lys Thr Leu Val Ser Lys
            100                 105                 110 aaa gta acc ctt aaa gac aag tca tca aca gaa gaa aaa ttc aac gaa     384
Lys Val Thr Leu Lys Asp Lys Ser Ser Thr Glu Glu Lys Phe Asn Glu
        115                 120                 125 aag ggt gaa aca tct gaa aaa aca ata gta aga gca aat gga acc aga     432
Lys Gly Glu Thr Ser Glu Lys Thr Ile Val Arg Ala Asn Gly Thr Arg
    130                 135                 140 ctt gaa tac aca gac ata aaa agc gat gga tcc gga aaa gct aaa gaa     480
Leu Glu Tyr Thr Asp Ile Lys Ser Asp Gly Ser Gly Lys Ala Lys Glu
145                 150                 155                 160 gtt tta aaa gac ttt act ctt gaa gga act cta gct gct gac ggc aaa     528
Val Leu Lys Asp Phe Thr Leu Glu Gly Thr Leu Ala Ala Asp Gly Lys
                165                 170                 175 aca aca ttg aaa gtt aca gaa ggc act gtt gtt tta agc aag aac att     576
Thr Thr Leu Lys Val Thr Glu Gly Thr Val Val Leu Ser Lys Asn Ile
            180                 185                 190 tta aaa tcc gga gaa ata aca gtt gca ctt gat gac tct gac act act     624
Leu Lys Ser Gly Glu Ile Thr Val Ala Leu Asp Asp Ser Asp Thr Thr
        195                 200                 205
```

```
cag gct act aaa aaa act gga aaa tgg gat tca aaa act tct act tta    672
Gln Ala Thr Lys Lys Thr Gly Lys Trp Asp Ser Lys Thr Ser Thr Leu
    210             215                 220 aca att agt gtt aac agc aaa aaa act aca caa ctt gtg ttt act aaa    720
Thr Ile Ser Val Asn Ser Lys Lys Thr Thr Gln Leu Val Phe Thr Lys
225             230                 235                 240 caa tac aca ata act gta aaa caa tac gac tcc gca ggt acc aat tta    768
Gln Tyr Thr Ile Thr Val Lys Gln Tyr Asp Ser Ala Gly Thr Asn Leu
            245                 250                 255 gaa ggc aca gca gtc gaa att aaa aca ctt gat gaa ctt aaa aac gct    816
Glu Gly Thr Ala Val Glu Ile Lys Thr Leu Asp Glu Leu Lys Asn Ala
        260                 265                 270 tta aaa taa                                                        825
Leu Lys  *

<210> SEQ ID NO 29
<211> LENGTH: 274
<212> TYPE: PRT
<213> ORGANISM: Artificial Sequence
<220> FEATURE:
<223> OTHER INFORMATION: Chimeric protein

<400> SEQUENCE: 29

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Thr Val Leu Val Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Thr Leu Glu Gly Glu Lys
65              70                  75                  80

Thr Asp Lys Ser Lys Val Lys Leu Thr Ile Ala Asp Asp Leu Ser Gln
            85                  90                  95

Thr Lys Phe Glu Ile Phe Lys Glu Asp Ala Lys Thr Leu Val Ser Lys
        100                 105                 110

Lys Val Thr Leu Lys Asp Lys Ser Ser Thr Glu Glu Lys Phe Asn Glu
    115                 120                 125

Lys Gly Glu Thr Ser Glu Lys Thr Ile Val Arg Ala Asn Gly Thr Arg
130                 135                 140

Leu Glu Tyr Thr Asp Ile Lys Ser Asp Gly Ser Gly Lys Ala Lys Glu
145             150                 155                 160

Val Leu Lys Asp Phe Thr Leu Glu Gly Thr Leu Ala Ala Asp Gly Lys
            165                 170                 175

Thr Thr Leu Lys Val Thr Glu Gly Thr Val Val Leu Ser Lys Asn Ile
        180                 185                 190

Leu Lys Ser Gly Glu Ile Thr Val Ala Leu Asp Asp Ser Asp Thr Thr
    195                 200                 205

Gln Ala Thr Lys Lys Thr Gly Lys Trp Asp Ser Lys Thr Ser Thr Leu
210                 215                 220

Thr Ile Ser Val Asn Ser Lys Lys Thr Thr Gln Leu Val Phe Thr Lys
225             230                 235                 240

Gln Tyr Thr Ile Thr Val Lys Gln Tyr Asp Ser Ala Gly Thr Asn Leu
            245                 250                 255

Glu Gly Thr Ala Val Glu Ile Lys Thr Leu Asp Glu Leu Lys Asn Ala
        260                 265                 270
```

Leu Lys

```
<210> SEQ ID NO 30
<211> LENGTH: 822
<212> TYPE: DNA
<213> ORGANISM: Artificial Sequence
<220> FEATURE:
<221> NAME/KEY: CDS
<222> LOCATION: (1)...(822)
<223> OTHER INFORMATION: Chimeric nucleic acid

<400> SEQUENCE: 30
```

| | | | | | | | | | | | | | | | | |
|---|---|---|---|---|---|---|---|---|---|---|---|---|---|---|---|---|
| atg | aaa | aaa | tat | tta | ttg | gga | ata | ggt | cta | ata | tta | gcc | tta | ata | gca | 48 |
| Met | Lys | Lys | Tyr | Leu | Leu | Gly | Ile | Gly | Leu | Ile | Leu | Ala | Leu | Ile | Ala | |
| 1 | | | | 5 | | | | | 10 | | | | | 15 | | |
| tgc | aag | caa | aat | gtt | agc | agc | ctt | gat | gaa | aaa | aac | agc | gct | tca | gta | 96 |
| Cys | Lys | Gln | Asn | Val | Ser | Ser | Leu | Asp | Glu | Lys | Asn | Ser | Ala | Ser | Val | |
| | | | 20 | | | | | 25 | | | | | 30 | | | |
| gat | ttg | cct | ggt | gag | atg | aaa | gtt | ctt | gta | agt | aaa | gaa | aaa | gac | aaa | 144 |
| Asp | Leu | Pro | Gly | Glu | Met | Lys | Val | Leu | Val | Ser | Lys | Glu | Lys | Asp | Lys | |
| | | 35 | | | | | 40 | | | | | 45 | | | | |
| gac | ggt | aag | tac | agt | cta | aag | gca | aca | gta | gac | aag | att | gag | cta | aaa | 192 |
| Asp | Gly | Lys | Tyr | Ser | Leu | Lys | Ala | Thr | Val | Asp | Lys | Ile | Glu | Leu | Lys | |
| 50 | | | | | 55 | | | | | 60 | | | | | | |
| gga | act | tct | gat | aaa | gac | aat | ggt | tct | gga | gtg | ctt | gaa | ggt | aca | aaa | 240 |
| Gly | Thr | Ser | Asp | Lys | Asp | Asn | Gly | Ser | Gly | Val | Leu | Glu | Gly | Thr | Lys | |
| 65 | | | | | 70 | | | | | 75 | | | | | 80 | |
| gat | gac | aaa | agt | aaa | gca | aaa | tta | aca | att | gct | gac | gat | cta | agt | aaa | 288 |
| Asp | Asp | Lys | Ser | Lys | Ala | Lys | Leu | Thr | Ile | Ala | Asp | Asp | Leu | Ser | Lys | |
| | | | | 85 | | | | | 90 | | | | | 95 | | |
| acc | aca | ttc | gaa | ctt | tta | aaa | gaa | gat | ggc | aaa | aca | tta | gtg | tca | aga | 336 |
| Thr | Thr | Phe | Glu | Leu | Leu | Lys | Glu | Asp | Gly | Lys | Thr | Leu | Val | Ser | Arg | |
| | | | 100 | | | | | 105 | | | | | 110 | | | |
| aaa | gta | agt | tct | aga | gac | aaa | aca | tca | aca | gat | gaa | atg | ttc | aat | gaa | 384 |
| Lys | Val | Ser | Ser | Arg | Asp | Lys | Thr | Ser | Thr | Asp | Glu | Met | Phe | Asn | Glu | |
| | | | 115 | | | | | 120 | | | | | 125 | | | |
| aaa | ggt | gaa | ttg | tct | gca | aaa | acc | atg | aca | aga | gaa | aat | gga | acc | aaa | 432 |
| Lys | Gly | Glu | Leu | Ser | Ala | Lys | Thr | Met | Thr | Arg | Glu | Asn | Gly | Thr | Lys | |
| | 130 | | | | | 135 | | | | | 140 | | | | | |
| ctt | gaa | tat | aca | gaa | atg | aaa | agc | gat | gga | acc | gga | aaa | gct | aaa | gaa | 480 |
| Leu | Glu | Tyr | Thr | Glu | Met | Lys | Ser | Asp | Gly | Thr | Gly | Lys | Ala | Lys | Glu | |
| 145 | | | | | 150 | | | | | 155 | | | | | 160 | |
| gtt | tta | aaa | aag | ttt | act | ctt | gaa | gga | aaa | gta | gct | aat | gat | aaa | gta | 528 |
| Val | Leu | Lys | Lys | Phe | Thr | Leu | Glu | Gly | Lys | Val | Ala | Asn | Asp | Lys | Val | |
| | | | | 165 | | | | | 170 | | | | | 175 | | |
| aca | ttg | gaa | gta | aaa | gaa | gga | acc | gtt | act | tta | agt | aag | gaa | att | gca | 576 |
| Thr | Leu | Glu | Val | Lys | Glu | Gly | Thr | Val | Thr | Leu | Ser | Lys | Glu | Ile | Ala | |
| | | | | 180 | | | | | 185 | | | | | 190 | | |
| aaa | tct | gga | gaa | gta | aca | gtt | gct | ctt | aat | gac | act | aac | act | act | cag | 624 |
| Lys | Ser | Gly | Glu | Val | Thr | Val | Ala | Leu | Asn | Asp | Thr | Asn | Thr | Thr | Gln | |
| | | 195 | | | | | 200 | | | | | 205 | | | | |
| gct | act | aaa | aaa | act | ggc | gca | tgg | gat | tca | aaa | act | tct | act | tta | aca | 672 |
| Ala | Thr | Lys | Lys | Thr | Gly | Ala | Trp | Asp | Ser | Lys | Thr | Ser | Thr | Leu | Thr | |
| | 210 | | | | | 215 | | | | | 220 | | | | | |
| att | agt | gtt | aac | agc | aaa | aaa | act | aca | caa | ctt | gtg | ttt | act | aaa | caa | 720 |
| Ile | Ser | Val | Asn | Ser | Lys | Lys | Thr | Thr | Gln | Leu | Val | Phe | Thr | Lys | Gln | |
| 225 | | | | | 230 | | | | | 235 | | | | | 240 | |
| tac | aca | ata | act | gta | aaa | caa | tac | gac | tcc | gca | ggt | acc | aat | tta | gaa | 768 |
| Tyr | Thr | Ile | Thr | Val | Lys | Gln | Tyr | Asp | Ser | Ala | Gly | Thr | Asn | Leu | Glu | |
| | | | | 245 | | | | | 250 | | | | | 255 | | |
| ggc | aca | gca | gtc | gaa | att | aaa | aca | ctt | gat | gaa | ctt | aaa | aac | gct | tta | 816 |
| Gly | Thr | Ala | Val | Glu | Ile | Lys | Thr | Leu | Asp | Glu | Leu | Lys | Asn | Ala | Leu | |

```
                    260                 265                 270
aaa taa                                                                      822
Lys  *

<210> SEQ ID NO 31
<211> LENGTH: 273
<212> TYPE: PRT
<213> ORGANISM: Artificial Sequence
<220> FEATURE:
<223> OTHER INFORMATION: Chimeric protein

<400> SEQUENCE: 31

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Ala Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Lys Ala Thr Val Asp Lys Ile Glu Leu Lys
    50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Leu Lys Glu Asp Gly Lys Thr Leu Val Ser Arg
            100                 105                 110

Lys Val Ser Ser Arg Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Tyr Thr Ile Thr Val Lys Gln Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys

<210> SEQ ID NO 32
<211> LENGTH: 822
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(822)

<400> SEQUENCE: 32
```

| | | | | | | | | | | | | | | | | |
|---|---|---|---|---|---|---|---|---|---|---|---|---|---|---|---|---|
| atg | aaa | aaa | tat | tta | ttg | gga | ata | ggt | cta | ata | tta | gcc | tta | ata | gca | 48 |
| Met | Lys | Lys | Tyr | Leu | Leu | Gly | Ile | Gly | Leu | Ile | Leu | Ala | Leu | Ile | Ala | |
| 1 | | | | 5 | | | | | 10 | | | | | 15 | | |
| tgt | aag | caa | aat | gtt | agc | agc | ctt | gac | gag | aaa | aac | agc | gtt | tca | gta | 96 |
| Cys | Lys | Gln | Asn | Val | Ser | Ser | Leu | Asp | Glu | Lys | Asn | Ser | Val | Ser | Val | |
| | | | 20 | | | | | 25 | | | | | 30 | | | |
| gat | ttg | cct | ggt | gaa | atg | aaa | gtt | ctt | gta | agc | aaa | gaa | aaa | aac | aaa | 144 |
| Asp | Leu | Pro | Gly | Glu | Met | Lys | Val | Leu | Val | Ser | Lys | Glu | Lys | Asn | Lys | |
| | | 35 | | | | | 40 | | | | | 45 | | | | |
| gac | ggc | aag | tac | gat | cta | att | gca | aca | gta | gac | aag | ctt | gag | ctt | aaa | 192 |
| Asp | Gly | Lys | Tyr | Asp | Leu | Ile | Ala | Thr | Val | Asp | Lys | Leu | Glu | Leu | Lys | |
| 50 | | | | | 55 | | | | | 60 | | | | | | |
| gga | act | tct | gat | aaa | aac | aat | gga | tct | gga | gta | ctt | gaa | ggc | gta | aaa | 240 |
| Gly | Thr | Ser | Asp | Lys | Asn | Asn | Gly | Ser | Gly | Val | Leu | Glu | Gly | Val | Lys | |
| 65 | | | | 70 | | | | | 75 | | | | | 80 | | |
| gct | gac | aaa | agt | aaa | gta | aaa | tta | aca | att | tct | gac | gat | cta | ggt | caa | 288 |
| Ala | Asp | Lys | Ser | Lys | Val | Lys | Leu | Thr | Ile | Ser | Asp | Asp | Leu | Gly | Gln | |
| | | | 85 | | | | | 90 | | | | | 95 | | | |
| acc | aca | ctt | gaa | gtt | ttc | aaa | gaa | gat | ggc | aaa | aca | cta | gta | tca | aaa | 336 |
| Thr | Thr | Leu | Glu | Val | Phe | Lys | Glu | Asp | Gly | Lys | Thr | Leu | Val | Ser | Lys | |
| | | | 100 | | | | | 105 | | | | | 110 | | | |
| aaa | gta | act | tcc | aaa | gac | aag | tca | tca | aca | gaa | gaa | aaa | ttc | aat | gaa | 384 |
| Lys | Val | Thr | Ser | Lys | Asp | Lys | Ser | Ser | Thr | Glu | Glu | Lys | Phe | Asn | Glu | |
| | | 115 | | | | | 120 | | | | | 125 | | | | |
| aaa | ggt | gaa | gta | tct | gaa | aaa | ata | ata | aca | aga | gca | gac | gga | acc | aga | 432 |
| Lys | Gly | Glu | Val | Ser | Glu | Lys | Ile | Ile | Thr | Arg | Ala | Asp | Gly | Thr | Arg | |
| 130 | | | | | 135 | | | | | 140 | | | | | | |
| ctt | gaa | tac | aca | gga | att | aaa | agc | gat | gga | tct | gga | aaa | gct | aaa | gag | 480 |
| Leu | Glu | Tyr | Thr | Gly | Ile | Lys | Ser | Asp | Gly | Ser | Gly | Lys | Ala | Lys | Glu | |
| 145 | | | | 150 | | | | | 155 | | | | | 160 | | |
| gtt | tta | aaa | ggc | tat | gtt | ctt | gaa | gga | act | cta | act | gct | gaa | aaa | aca | 528 |
| Val | Leu | Lys | Gly | Tyr | Val | Leu | Glu | Gly | Thr | Leu | Thr | Ala | Glu | Lys | Thr | |
| | | | 165 | | | | | 170 | | | | | 175 | | | |
| aca | ttg | gtg | gtt | aaa | gaa | gga | act | gtt | act | tta | agc | aaa | aat | att | tca | 576 |
| Thr | Leu | Val | Val | Lys | Glu | Gly | Thr | Val | Thr | Leu | Ser | Lys | Asn | Ile | Ser | |
| | | 180 | | | | | 185 | | | | | 190 | | | | |
| aaa | tct | ggg | gaa | gtt | tca | gtt | gaa | ctt | aat | gac | act | gac | agt | agt | gct | 624 |
| Lys | Ser | Gly | Glu | Val | Ser | Val | Glu | Leu | Asn | Asp | Thr | Asp | Ser | Ser | Ala | |
| | | 195 | | | | | 200 | | | | | 205 | | | | |
| gct | act | aaa | aaa | act | gca | gct | tgg | aat | tca | aaa | act | tcc | act | tta | aca | 672 |
| Ala | Thr | Lys | Lys | Thr | Ala | Ala | Trp | Asn | Ser | Lys | Thr | Ser | Thr | Leu | Thr | |
| 210 | | | | | 215 | | | | | 220 | | | | | | |
| att | agt | gtg | aat | agc | caa | aaa | acc | aaa | aac | ctt | gta | ttc | aca | aaa | gaa | 720 |
| Ile | Ser | Val | Asn | Ser | Gln | Lys | Thr | Lys | Asn | Leu | Val | Phe | Thr | Lys | Glu | |
| 225 | | | | | 230 | | | | | 235 | | | | | 240 | |
| gac | aca | ata | aca | gta | caa | aaa | tac | gac | tca | gca | ggc | acc | aat | cta | gaa | 768 |
| Asp | Thr | Ile | Thr | Val | Gln | Lys | Tyr | Asp | Ser | Ala | Gly | Thr | Asn | Leu | Glu | |
| | | | 245 | | | | | 250 | | | | | 255 | | | |
| ggc | aaa | gca | gtc | gaa | att | aca | aca | ctt | aaa | gaa | ctt | aaa | aac | gct | tta | 816 |
| Gly | Lys | Ala | Val | Glu | Ile | Thr | Thr | Leu | Lys | Glu | Leu | Lys | Asn | Ala | Leu | |
| | | 260 | | | | | 265 | | | | | 270 | | | | |
| aaa | taa | | | | | | | | | | | | | | | 822 |
| Lys | * | | | | | | | | | | | | | | | |

<210> SEQ ID NO 33
<211> LENGTH: 273
<212> TYPE: PRT
<213> ORGANISM: Artificial Sequence
<220> FEATURE:
<223> OTHER INFORMATION: Chimeric protein

<400> SEQUENCE: 33

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
50                  55                  60

Gly Thr Ser Asp Lys Asn Asn Gly Ser Val Leu Glu Gly Val Lys
65                  70                  75                  80

Ala Asp Lys Ser Lys Val Lys Leu Thr Ile Ser Asp Asp Leu Gly Gln
            85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
            115                 120                 125

Lys Gly Glu Val Ser Glu Lys Ile Ile Thr Arg Ala Asp Gly Thr Arg
130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
            195                 200                 205

Ala Thr Lys Lys Thr Ala Ala Trp Asn Ser Lys Thr Ser Thr Leu Thr
            210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys
```

<210> SEQ ID NO 34
<211> LENGTH: 819
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(819)

<400> SEQUENCE: 34

```
atg aaa aaa tat tta ttg gga ata ggt cta ata tta gcc tta ata gca      48
Met Lys Lys Tyr Leu Leu Gly Ile Gly Leu Ile Leu Ala Leu Ile Ala
1               5                   10                  15 tgt aag caa aat gtt agc agc ctt gac gag aaa aac agc gtt tca gta      96
Cys Lys Gln Asn Val Ser Ser Leu Asp Glu Lys Asn Ser Val Ser Val
            20                  25                  30 gat ttg cct ggt gaa atg aaa gtt ctt gta agc aaa gaa aaa aac aaa     144
Asp Leu Pro Gly Glu Met Lys Val Leu Val Ser Lys Glu Lys Asn Lys
            35                  40                  45 gac ggc aag tac gat cta att gca aca gta gac aag ctt gag ctt aaa     192
Asp Gly Lys Tyr Asp Leu Ile Ala Thr Val Asp Lys Leu Glu Leu Lys
```

| | | |
|---|---|---|
| gga act tct gat aaa aac aat gga tct gga gta ctt gaa ggc gta aaa<br>Gly Thr Ser Asp Lys Asn Asn Gly Ser Gly Val Leu Glu Gly Val Lys<br>65                              70                            75                            80 | 240 |
| gct gac aaa agt aaa gta aaa tta aca att tct gac gat cta ggt caa<br>Ala Asp Lys Ser Lys Val Lys Leu Thr Ile Ser Asp Asp Leu Gly Gln<br>85                                90                            95 | 288 |
| acc aca ctt gaa gtt ttc aaa gaa gat ggc aaa aca cta gta tca aaa<br>Thr Thr Leu Glu Val Phe Lys Glu Asp Gly Lys Thr Leu Val Ser Lys<br>100                              105                          110 | 336 |
| aaa gta act tcc aaa gac aag tca tca aca gaa gaa aaa ttc aat gaa<br>Lys Val Thr Ser Lys Asp Lys Ser Ser Thr Glu Glu Lys Phe Asn Glu<br>              115                          120                          125 | 384 |
| aaa ggt gaa gta tct gaa aaa ata ata aca aga gca gac gga acc aga<br>Lys Gly Glu Val Ser Glu Lys Ile Ile Thr Arg Ala Asp Gly Thr Arg<br>130                              135                          140 | 432 |
| ctt gaa tac aca gga att aaa agc gat gga tct gga aaa gct aaa gag<br>Leu Glu Tyr Thr Gly Ile Lys Ser Asp Gly Ser Gly Lys Ala Lys Glu<br>145                            150                          155                          160 | 480 |
| gtt tta aaa ggc tat gtt ctt gaa gga act cta act gct gaa aaa aca<br>Val Leu Lys Gly Tyr Val Leu Glu Gly Thr Leu Thr Ala Glu Lys Thr<br>              165                          170                          175 | 528 |
| aca ttg gtg gtt aaa gaa gga act gtt act tta agc aaa aat att tca<br>Thr Leu Val Val Lys Glu Gly Thr Val Thr Leu Ser Lys Asn Ile Ser<br>180                              185                          190 | 576 |
| aaa tct ggg gaa gtt tca gtt gaa ctt aat gac act gac agt agt gct<br>Lys Ser Gly Glu Val Ser Val Glu Leu Asn Asp Thr Asp Ser Ser Ala<br>              195                          200                          205 | 624 |
| gct act aaa aaa act gca gct tgg aat gca ggc act tca act tta aca<br>Ala Thr Lys Lys Thr Ala Ala Trp Asn Ala Gly Thr Ser Thr Leu Thr<br>210                              215                          220 | 672 |
| att act gta aac aac aaa aaa act aaa gcc ctt gta ttt aca aaa caa<br>Ile Thr Val Asn Asn Lys Lys Thr Lys Ala Leu Val Phe Thr Lys Gln<br>225                              230                          235                          240 | 720 |
| gac aca att aca tca caa aaa tac gac tca gca gga acc aac ttg gaa<br>Asp Thr Ile Thr Ser Gln Lys Tyr Asp Ser Ala Gly Thr Asn Leu Glu<br>              245                          250                          255 | 768 |
| ggc aca gca gtc gaa att aaa aca ctt gat gaa ctt aaa aac gct tta<br>Gly Thr Ala Val Glu Ile Lys Thr Leu Asp Glu Leu Lys Asn Ala Leu<br>260                              265                          270 | 816 |
| aga<br>Arg | 819 |

<210> SEQ ID NO 35
<211> LENGTH: 273
<212> TYPE: PRT
<213> ORGANISM: Artificial Sequence
<220> FEATURE:
<223> OTHER INFORMATION: Chimeric protein

<400> SEQUENCE: 35

Met Lys Lys Tyr Leu Leu Gly Ile Gly Leu Ile Leu Ala Leu Ile Ala
1                 5                   10                 15

Cys Lys Gln Asn Val Ser Ser Leu Asp Glu Lys Asn Ser Val Ser Val
             20                   25                   30

Asp Leu Pro Gly Glu Met Lys Val Leu Val Ser Lys Glu Lys Asn Lys
        35                   40                   45

Asp Gly Lys Tyr Asp Leu Ile Ala Thr Val Asp Lys Leu Glu Leu Lys
        50                   55                   60

Gly Thr Ser Asp Lys Asn Asn Gly Ser Gly Val Leu Glu Gly Val Lys

```
                65                  70                  75                  80
Ala Asp Lys Ser Lys Val Lys Leu Thr Ile Ser Asp Asp Leu Gly Gln
                    85                  90                  95

Thr Thr Leu Glu Val Phe Lys Glu Asp Gly Lys Thr Leu Val Ser Lys
                100                 105                 110

Lys Val Thr Ser Lys Asp Lys Ser Thr Glu Glu Lys Phe Asn Glu
            115                 120                 125

Lys Gly Glu Val Ser Glu Lys Ile Ile Thr Arg Ala Asp Gly Thr Arg
            130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
                180                 185                 190

Lys Ser Gly Glu Val Ser Val Glu Leu Asn Asp Thr Asp Ser Ser Ala
            195                 200                 205

Ala Thr Lys Lys Thr Ala Ala Trp Asn Ala Gly Thr Ser Thr Leu Thr
            210                 215                 220

Ile Thr Val Asn Asn Lys Lys Thr Lys Ala Leu Val Phe Thr Lys Gln
225                 230                 235                 240

Asp Thr Ile Thr Ser Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
                260                 265                 270

Arg

<210> SEQ ID NO 36
<211> LENGTH: 822
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(822)

<400> SEQUENCE: 36 atg aaa aaa tat tta ttg gga ata ggt cta ata tta gcc tta ata gca       48
Met Lys Lys Tyr Leu Leu Gly Ile Gly Leu Ile Leu Ala Leu Ile Ala
1               5                   10                  15 tgt aag caa aat gtt agc agc ctt gat gaa aaa aat agc gtt tca gta       96
Cys Lys Gln Asn Val Ser Ser Leu Asp Glu Lys Asn Ser Val Ser Val
            20                  25                  30 gat tta cct ggt gga atg aca gtt ctt gta agt aaa gaa aaa gac aaa      144
Asp Leu Pro Gly Gly Met Thr Val Leu Val Ser Lys Glu Lys Asp Lys
        35                  40                  45 gac ggt aaa tac agt cta gag gca aca gta gac aag ctt gag ctt aaa      192
Asp Gly Lys Tyr Ser Leu Glu Ala Thr Val Asp Lys Leu Glu Leu Lys
    50                  55                  60 gga act tct gat aaa aac aac ggt tct gga aca ctt gaa ggt gaa aaa      240
Gly Thr Ser Asp Lys Asn Asn Gly Ser Gly Thr Leu Glu Gly Glu Lys
65                  70                  75                  80 act gac aaa agt aaa gta aaa tta aca att gct gat gac cta agt caa      288
Thr Asp Lys Ser Lys Val Lys Leu Thr Ile Ala Asp Asp Leu Ser Gln
                85                  90                  95 act aaa ttt gaa att ttc aaa gaa gat gcc aaa aca tta gta tca aaa      336
Thr Lys Phe Glu Ile Phe Lys Glu Asp Ala Lys Thr Leu Val Ser Lys
                100                 105                 110
```

| | | | | |
|---|---|---|---|---|
| aaa gta acc ctt aaa gac aag tca tca aca gaa gaa aaa ttc aac gaa | | | | 384 |
| Lys Val Thr Leu Lys Asp Lys Ser Ser Thr Glu Glu Lys Phe Asn Glu | | | | |
| 115 120 125 | | | | |
| aag ggt gaa aca tct gaa aaa aca ata gta aga gca aat gga acc aga | | | | 432 |
| Lys Gly Glu Thr Ser Glu Lys Thr Ile Val Arg Ala Asn Gly Thr Arg | | | | |
| 130 135 140 | | | | |
| ctt gaa tac aca gac ata aaa agc gat gga tcc gga aaa gct aaa gaa | | | | 480 |
| Leu Glu Tyr Thr Asp Ile Lys Ser Asp Gly Ser Gly Lys Ala Lys Glu | | | | |
| 145 150 155 160 | | | | |
| gtt tta aaa gac ttt act ctt gaa gga act cta gct gct gac ggc aaa | | | | 528 |
| Val Leu Lys Asp Phe Thr Leu Glu Gly Thr Leu Ala Ala Asp Gly Lys | | | | |
| 165 170 175 | | | | |
| aca aca ttg aaa gtt aca gaa ggc act gtt gtt tta agc aag att tca | | | | 576 |
| Thr Thr Leu Lys Val Thr Glu Gly Thr Val Val Leu Ser Lys Ile Ser | | | | |
| 180 185 190 | | | | |
| aaa tct ggg gaa gtt tca gtt gaa ctt aat gac act gac agt agt gct | | | | 624 |
| Lys Ser Gly Glu Val Ser Val Glu Leu Asn Asp Thr Asp Ser Ser Ala | | | | |
| 195 200 205 | | | | |
| gct act aaa aaa act gca gct tgg aat tca aaa act tcc act tta aca | | | | 672 |
| Ala Thr Lys Lys Thr Ala Ala Trp Asn Ser Lys Thr Ser Thr Leu Thr | | | | |
| 210 215 220 | | | | |
| att agt gtg aat agc caa aaa acc aaa aac ctt gta ttc aca aaa gaa | | | | 720 |
| Ile Ser Val Asn Ser Gln Lys Thr Lys Asn Leu Val Phe Thr Lys Glu | | | | |
| 225 230 235 240 | | | | |
| gac aca ata aca gta caa aaa tac gac tca gca ggc acc aat cta gaa | | | | 768 |
| Asp Thr Ile Thr Val Gln Lys Tyr Asp Ser Ala Gly Thr Asn Leu Glu | | | | |
| 245 250 255 | | | | |
| ggc aaa gca gtc gaa att aca aca ctt aaa gaa ctt aaa aac gct tta | | | | 816 |
| Gly Lys Ala Val Glu Ile Thr Thr Leu Lys Glu Leu Lys Asn Ala Leu | | | | |
| 260 265 270 | | | | |
| aaa taa | | | | 822 |
| Lys * | | | | |

<210> SEQ ID NO 37
<211> LENGTH: 273
<212> TYPE: PRT
<213> ORGANISM: Artificial Sequence
<220> FEATURE:
<223> OTHER INFORMATION: Chimeric protein

<400> SEQUENCE: 37

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
                20                  25                  30

Asp Leu Pro Gly Gly Met Thr Val Leu Val Ser Lys Glu Lys Asp Lys
            35                  40                  45

Asp Gly Lys Tyr Ser Leu Glu Ala Thr Val Asp Lys Leu Glu Leu Lys
        50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Asp Asp Leu Ser Gln
                85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

```
Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys
```

```
<210> SEQ ID NO 38
<211> LENGTH: 822
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(822)

<400> SEQUENCE: 38
```

```
atg aaa aaa tat tta ttg gga ata ggt cta ata tta gcc tta ata gca      48
Met Lys Lys Tyr Leu Leu Gly Ile Gly Leu Ile Leu Ala Leu Ile Ala
1               5                   10                  15 tgt aag caa aat gtt agc agc ctt gat gaa aaa aat agc gtt tca gta      96
Cys Lys Gln Asn Val Ser Ser Leu Asp Glu Lys Asn Ser Val Ser Val
            20                  25                  30 gat tta cct ggt gga atg aca gtt ctt gta agt aaa gaa aaa gac aaa     144
Asp Leu Pro Gly Gly Met Thr Val Leu Val Ser Lys Glu Lys Asp Lys
        35                  40                  45 gac ggt aaa tac agt cta gag gca aca gta gac aag ctt gag ctt aaa     192
Asp Gly Lys Tyr Ser Leu Glu Ala Thr Val Asp Lys Leu Glu Leu Lys
    50                  55                  60 gga act tct gat aaa aac aac ggt tct gga aca ctt gaa ggt gaa aaa     240
Gly Thr Ser Asp Lys Asn Asn Gly Ser Gly Thr Leu Glu Gly Glu Lys
65                  70                  75                  80 act gac aaa agt aaa gta aaa tta aca att gct gat gac cta agt caa     288
Thr Asp Lys Ser Lys Val Lys Leu Thr Ile Ala Asp Asp Leu Ser Gln
                85                  90                  95 act aaa ttt gaa att ttc aaa gaa gat gcc aaa aca tta gta tca aaa     336
Thr Lys Phe Glu Ile Phe Lys Glu Asp Ala Lys Thr Leu Val Ser Lys
            100                 105                 110 aaa gta acc ctt aaa gac aag tca tca aca gaa gaa aaa ttc aac gaa     384
Lys Val Thr Leu Lys Asp Lys Ser Ser Thr Glu Glu Lys Phe Asn Glu
        115                 120                 125 aag ggt gaa aca tct gaa aaa aca ata gta aga gca aat gga acc aga     432
Lys Gly Glu Thr Ser Glu Lys Thr Ile Val Arg Ala Asn Gly Thr Arg
    130                 135                 140 ctt gaa tac aca gac ata aaa agc gat gga tcc gga aaa gct aaa gaa     480
Leu Glu Tyr Thr Asp Ile Lys Ser Asp Gly Ser Gly Lys Ala Lys Glu
145                 150                 155                 160 gtt tta aaa gac ttt act ctt gaa gga act cta gct gct gac ggc aaa     528
Val Leu Lys Asp Phe Thr Leu Glu Gly Thr Leu Ala Ala Asp Gly Lys
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     | 165 |     |     |     | 170 |     |     |     | 175 |     |     |     |     |     |
| aca | aca | ttg | aaa | gtt | aca | gaa | ggc | act | gtt | gtt | tta | agc | aag | att | tca | 576 |
| Thr | Thr | Leu | Lys | Val | Thr | Glu | Gly | Thr | Val | Val | Leu | Ser | Lys | Ile | Ser |     |
|     |     | 180 |     |     |     | 185 |     |     |     | 190 |     |     |     |     |     |     |
| aaa | tct | ggg | gaa | gtt | tca | gtt | gaa | ctt | aat | gac | act | gac | agt | agt | gct | 624 |
| Lys | Ser | Gly | Glu | Val | Ser | Val | Glu | Leu | Asn | Asp | Thr | Asp | Ser | Ser | Ala |     |
|     | 195 |     |     |     | 200 |     |     |     | 205 |     |     |     |     |     |     |     |
| gct | act | aaa | aaa | act | gca | gct | tgg | aat | tca | aaa | act | tcc | act | tta | aca | 672 |
| Ala | Thr | Lys | Lys | Thr | Ala | Ala | Trp | Asn | Ser | Lys | Thr | Ser | Thr | Leu | Thr |     |
| 210 |     |     |     |     | 215 |     |     |     |     | 220 |     |     |     |     |     |     |
| att | agt | gtg | aat | agc | caa | aaa | acc | aaa | aac | ctt | gta | ttc | aca | aaa | gaa | 720 |
| Ile | Ser | Val | Asn | Ser | Gln | Lys | Thr | Lys | Asn | Leu | Val | Phe | Thr | Lys | Glu |     |
| 225 |     |     |     | 230 |     |     |     | 235 |     |     |     | 240 |     |     |     |     |
| gac | aca | ata | aca | gta | caa | aaa | tac | gac | tca | gca | ggc | acc | aat | cta | gaa | 768 |
| Asp | Thr | Ile | Thr | Val | Gln | Lys | Tyr | Asp | Ser | Ala | Gly | Thr | Asn | Leu | Glu |     |
|     |     |     | 245 |     |     |     | 250 |     |     |     | 255 |     |     |     |     |     |
| ggc | aaa | gca | gtc | gaa | att | aca | aca | ctt | aaa | gaa | ctt | aaa | aac | gct | tta | 816 |
| Gly | Lys | Ala | Val | Glu | Ile | Thr | Thr | Leu | Lys | Glu | Leu | Lys | Asn | Ala | Leu |     |
|     | 260 |     |     |     | 265 |     |     |     | 270 |     |     |     |     |     |     |     |
| aaa | taa |     |     |     |     |     |     |     |     |     |     |     |     |     |     | 822 |
| Lys | *   |     |     |     |     |     |     |     |     |     |     |     |     |     |     |     |

<210> SEQ ID NO 39
<211> LENGTH: 273
<212> TYPE: PRT
<213> ORGANISM: Artificial Sequence
<220> FEATURE:
<223> OTHER INFORMATION: Chimeric protein

<400> SEQUENCE: 39

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
                20                  25                  30

Asp Leu Pro Gly Gly Met Thr Val Leu Val Ser Lys Glu Lys Asp Lys
            35                  40                  45

Asp Gly Lys Tyr Ser Leu Glu Ala Thr Val Asp Lys Leu Glu Leu Lys
        50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Asp Asp Leu Ser Gln
                85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

```
Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
            245                 250                 255

Gly Lys Ala Val Glu Ile Thr Thr Leu Lys Glu Leu Lys Asn Ala Leu
            260                 265                 270

Lys

<210> SEQ ID NO 40
<211> LENGTH: 822
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(822)

<400> SEQUENCE: 40 atg aaa aaa tat tta ttg gga ata ggt cta ata tta gcc tta ata gca      48
Met Lys Lys Tyr Leu Leu Gly Ile Gly Leu Ile Leu Ala Leu Ile Ala
1               5                   10                  15 tgt aag caa aat gtt agc agc ctt gac gag aaa aac agc gtt tca gta      96
Cys Lys Gln Asn Val Ser Ser Leu Asp Glu Lys Asn Ser Val Ser Val
                20                  25                  30 gat ttg cct ggt gaa atg aaa gtt ctt gta agc aaa gaa aaa aac aaa     144
Asp Leu Pro Gly Glu Met Lys Val Leu Val Ser Lys Glu Lys Asn Lys
            35                  40                  45 gac ggc aag tac gat cta att gca aca gta gac aag ctt gag ctt aaa     192
Asp Gly Lys Tyr Asp Leu Ile Ala Thr Val Asp Lys Leu Glu Leu Lys
        50                  55                  60 gga act tct gat aaa aac aat gga tct gga gta ctt gaa ggc gta aaa     240
Gly Thr Ser Asp Lys Asn Asn Gly Ser Gly Val Leu Glu Gly Val Lys
65                  70                  75                  80 gct gac aaa agt aaa gta aaa tta aca att tct gac gat cta ggt caa     288
Ala Asp Lys Ser Lys Val Lys Leu Thr Ile Ser Asp Asp Leu Gly Gln
                85                  90                  95 acc aca ctt gaa gtt ttc aaa gaa gat ggc aaa aca cta gta tca aaa     336
Thr Thr Leu Glu Val Phe Lys Glu Asp Gly Lys Thr Leu Val Ser Lys
            100                 105                 110 aaa gta act tcc aaa gac aag tca tca aca gaa gaa aaa ttc aat gaa     384
Lys Val Thr Ser Lys Asp Lys Ser Ser Thr Glu Glu Lys Phe Asn Glu
        115                 120                 125 aaa ggt gaa gta tct gaa aaa ata ata aca aga gca gac gga acc aga     432
Lys Gly Glu Val Ser Glu Lys Ile Ile Thr Arg Ala Asp Gly Thr Arg
    130                 135                 140 ctt gaa tac aca gga att aaa agc gat gga tct gga aaa gct aaa gag     480
Leu Glu Tyr Thr Gly Ile Lys Ser Asp Gly Ser Gly Lys Ala Lys Glu
145                 150                 155                 160 gtt tta aaa ggc tat gtt ctt gaa gga act cta act gct gaa aaa aca     528
Val Leu Lys Gly Tyr Val Leu Glu Gly Thr Leu Thr Ala Glu Lys Thr
                165                 170                 175 aca ttg gtg gtt aaa gaa gga act gtt act tta agc aaa aat att tca     576
Thr Leu Val Val Lys Glu Gly Thr Val Thr Leu Ser Lys Asn Ile Ser
            180                 185                 190 aaa tct ggg gaa gtt tca gtt gaa ctt aat gac act gac agt agt gct     624
Lys Ser Gly Glu Val Ser Val Glu Leu Asn Asp Thr Asp Ser Ser Ala
        195                 200                 205 gct act aaa aaa act gca gct tgg aat gac agt act agc act tta aca     672
Ala Thr Lys Lys Thr Ala Ala Trp Asn Asp Ser Thr Ser Thr Leu Thr
    210                 215                 220
```

```
att agt gct gac agc aaa aaa act aaa gat ttg gtg ttc tta aca gat    720
Ile Ser Ala Asp Ser Lys Lys Thr Lys Asp Leu Val Phe Leu Thr Asp
225             230                 235                 240 ggt aca att aca gta caa caa tac aac aca gct gga acc agc cta gaa    768
Gly Thr Ile Thr Val Gln Gln Tyr Asn Thr Ala Gly Thr Ser Leu Glu
            245                 250                 255 gga tca gca agt gaa att aaa aat ctt tca gag ctt aaa aac gct tta    816
Gly Ser Ala Ser Glu Ile Lys Asn Leu Ser Glu Leu Lys Asn Ala Leu
        260                 265                 270 aaa taa                                                            822
Lys *
```

<210> SEQ ID NO 41
<211> LENGTH: 273
<212> TYPE: PRT
<213> ORGANISM: Artificial Sequence
<220> FEATURE:
<223> OTHER INFORMATION: Chimeric protein

<400> SEQUENCE: 41

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Asp Ser Thr Ser Thr Leu Thr
    210                 215                 220

Ile Ser Ala Asp Ser Lys Lys Thr Lys Asp Leu Val Phe Leu Thr Asp
225                 230                 235                 240

Gly Thr Ile Thr Val Gln Gln Tyr Asn Thr Ala Gly Thr Ser Leu Glu
                245                 250                 255

Gly Ser Ala Ser Glu Ile Lys Asn Leu Ser Glu Leu Lys Asn Ala Leu
            260                 265                 270

Lys
```

<210> SEQ ID NO 42

```
<211> LENGTH: 822
<212> TYPE: DNA
<213> ORGANISM: Borrelia burgdorferi

<400> SEQUENCE: 42
atgaaaaaat atttattggg aataggtcta atattagcct taatagcatg taagcaaaat    60
gttagcagcc ttgacgagaa aaacagcgtt tcagtagatt tgcctggtga aatgaaagtt   120
cttgtaagca agaaaaaaaa caaagacggc aagtacgatc taattgcaac agtagacaag   180
cttgagctta aggaacttc  tgataaaaac aatggatctg gagtacttga aggcgtaaaa   240
gctgacaaaa gtaaagtaaa attaacaatt tctgacgatc taggtcaaac cacacttgaa   300
gttttcaaag aagatggcaa acactagta  tcaaaaaaag taacttccaa agacaagtca   360
tcaacagaag aaaaattcaa tgaaaaaggt gaagtatctg aaaaaataat aacaagagca   420
gacggaacca gacttgaata cacaggaatt aaaagcgatg gatctggaaa agctaaagag   480
gttttaaaag gctatgttct tgaaggaact ctaactgctg aaaaaacaac attggtggtt   540
aaagaaggaa ctgttacttt aagcaaaaat atttcaaaat ctggggaagt ttcagttgaa   600
cttaatgaca ctgacagtag tgctgctact aaaaaaactg cagcttggaa ttcaggcact   660
tcaactttaa caattactgt aaacagtaaa aaaactaaag accttgtgtt tacaaaagaa   720
aacacaatta cagtacaaca atacgactca aatggcacca aattagaggg gtcagcagtt   780
gaaattacaa aacttgatga aattaaaaac gctttaaaat aa                      822

<210> SEQ ID NO 43
<211> LENGTH: 822
<212> TYPE: DNA
<213> ORGANISM: Borrelia burgdorferi

<400> SEQUENCE: 43
atgaaaaaat atttattggg aataggtcta atattagcct taatagcatg taagcaaaat    60
gttagcagcc ttgacgagaa aaacagcgtt tcagtagatt tgcctggtga aatgaacgtt   120
cttgtaagca agaaaaaaaa caaagacggc aagtacgatc taattgcaac agtagacaag   180
cttgagctta aggaacttc  tgataaaaac aatggatctg gagtacttga aggcgtaaaa   240
gctgacaaaa gtaaagtaaa attaacaatt tctgacgatc taggtcaaac cacacttgaa   300
gttttcaaag aagatggcaa acactagta  tcaaaaaaag taacttccaa agacaagtca   360
tcaacagaag aaaaattcaa tgaaaaaggt gaagtatctg aaaaaataat aacaagagca   420
gacggaacca gacttgaata cacagaaatt aaaagcgatg gatctggaaa agctaaagag   480
gttttaaaag gctatgttct tgaaggaact ctaactgctg aaaaaacaac attggtggtt   540
aaagaaggaa ctgttacttt aagcaaaaat atttcaaaat ctggggaagt ttcagttgaa   600
cttaatgaca ctgacagtag tgctgctact aaaaaaactg cagcttggaa ttcaggcact   660
tcaactttaa caattactgt aaacagtaaa aaaactaaag accttgtgtt tacaaaagaa   720
aacacaatta cagtacaaca atacgactca aatggcacca aattagaggg gtcagcagtt   780
gaaattacaa aacttgatga aattaaaaac gctttaaaat aa                      822

<210> SEQ ID NO 44
<211> LENGTH: 822
<212> TYPE: DNA
<213> ORGANISM: Borrelia burgdorferi

<400> SEQUENCE: 44
atgaaaaaat atttattggg aataggtcta atattagcct taatagcatg taagcaaaat    60
```

```
gttagcagcc ttgacgagaa aaacagcgtt tcagtagatt tgcctggtga aatgaacgtt      120
cttgtaagca aagaaaaaaa caaagacggc aagtacgatc taattgcaac agtagacaag      180
cttgagctta aaggaacttc tgataaaaac aatggatctg gagtacttga aggcgtaaaa      240
gctgacaaaa gtaaagtaaa attaacaatt tctgacgatc taggtcaaac cacacttgaa      300
gttttcaaag aagatggcaa aacactagta tcaaaaaaag taacttccaa agacaagtca      360
tcaacagaag aaaaattcaa tgaaaaaggt gaagtatctg aaaaaataat aacaagagca      420
gacggaacca gacttgaata cacagaaatt aaaagcgatg gatctggaaa agctaaagag      480
gttttaaaaa gctatgttct tgaaggaact ttaactgctg aaaaaacaac attggtggtt      540
aaagaaggaa ctgttacttt aagcaaaaat atttcaaaat ctggggaagt tcagttgaa       600 cttaatgaca ctgacagtag tgctgctact aaaaaaactg cagcttggaa ttcaggcact      660
tcaactttaa caattactgt aaacagtaaa aaaactaaag accttgtgtt tacaaaagaa      720
aacacaatta cagtacaaca atacgactca aatggcacca aattagaggg gtcagcagtt      780
gaaattacaa aacttgatga aattaaaaac gctttaaaat aa                         822

<210> SEQ ID NO 45
<211> LENGTH: 821
<212> TYPE: DNA
<213> ORGANISM: Borrelia burgdorferi

<400> SEQUENCE: 45
atgaaaaaat atttattggg aataggtcta atattagcct taatagcatg taagcaaaat       60
gttagcagcc ttgatgagaa aaacagcgtt tcagtagatt tacctggtga aatgaaagtt      120
cttgtaagca aagaaaaaga caaagatggt aaatacagtc taatggcaac agtagacaag      180
ctagagctta aaggaacttc tgataaaagc aacggttctg aacacttga aggtgaaaaa       240 tctgacaaaa gtaaagcaaa attaacaatt tctgagatc taagtaaaac cacatttgaa       300
attttcaaag aagatggcaa aacattagta tcaaaaaaag taaattctaa agataagtca      360
tcaatagaag aaaaattcaa cgcaaaaggt gaattatctg aaaaaacaat actaagagca      420
aacggaacca ggcttgaata cacagaaata aaaagcgatg gaaccggaaa agctaaagaa      480
gctttaaaag actttgctct tgaaggaact ctagctgccg acaaaacaac attgaaagtt      540
acagaaggca ctgttgtttt aagcaaacac attccaaact ctggagaaat aacagttgag      600
cttaatgact ctaactctac tcaggctact aaaaaaactg gaaatgggga ttcaaatact       660
tccactttaa caattagtgt gaatagcaaa aaaactaaaa acattgtatt tacaaaagaa      720
gacacaataa cagtacaaaa atacgactca gcaggcacca atctagaagg caacgcagtc      780
gaaattaaaa cacttgatga acttaaaaac gctttaaaat a                          821

<210> SEQ ID NO 46
<211> LENGTH: 821
<212> TYPE: DNA
<213> ORGANISM: Borrelia burgdorferi

<400> SEQUENCE: 46
atgaaaaaat atttattggg aataggtcta atattagcct taatagcatg taagcaaaat       60
gttagcagcc ttgatgaaaa aaatagcgtt tcagtagatt tacctggtgg aatgaaagtt      120
cttgtaagta aagaaaaaga caaagatggt aaatacagtc taatggcaac agtagaaaag      180
cttgagctta aaggaacttc tgataaaaac aacggttctg aacacttga aggtgaaaaa       240 actgacaaaa gtaaagtaaa attaacaatt gctgaggatc taagtaaaac cacatttgaa      300
```

-continued

```
atcttcaaag aagatggcaa aacattagta tcgaaaaaag taacccttaa agacaagtca    360
tcaacagaag aaaaattcaa cgaaaagggt gaaatatctg aaaaaacaat agtaagagca    420
aatggaacca gacttgaata cacagacata aaaagcgata aaaccggaaa agctaaagaa    480
gttttaaaag actttactct tgaaggaact ctagctgctg acggcaaaac aacattgaaa    540
gttacagagg gcactgttac tttaagcaag aacatttcaa atccggaga ataacagtt    600 gcacttgatg acactgactc tagcggcaat aaaaaatccg gaacatggga ttcaggtact    660
tctactttaa caattagtaa aaacagacaa aaaactaaac aacttgtatt cacaaaagaa    720
gacacaataa cagtacaaaa ctacgactca gcaggcacca atctagaagg caaagcagtc    780
gaaattacaa cacttaaaga acttaaaaac gctttaaaat a    821
```

<210> SEQ ID NO 47
<211> LENGTH: 825
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(825)

<400> SEQUENCE: 47

```
atg aaa aaa tat tta ttg gga ata ggt cta ata tta gcc tta ata gca        48
Met Lys Lys Tyr Leu Leu Gly Ile Gly Leu Ile Leu Ala Leu Ile Ala
1               5                   10                  15 tgt aag caa aat gtt agc agc ctt gat gaa aaa aat agc gtt tca gta        96
Cys Lys Gln Asn Val Ser Ser Leu Asp Glu Lys Asn Ser Val Ser Val
                20                  25                  30 gat tta cct ggt gga atg aca gtt ctt gta agt aaa gaa aaa gac aaa       144
Asp Leu Pro Gly Gly Met Thr Val Leu Val Ser Lys Glu Lys Asp Lys
            35                  40                  45 gac ggt aaa tac agt cta gag gca aca gta gac aag ctt gag ctt aaa       192
Asp Gly Lys Tyr Ser Leu Glu Ala Thr Val Asp Lys Leu Glu Leu Lys
        50                  55                  60 gga act tct gat aaa aac aac ggt tct gga aca ctt gaa ggt gaa aaa       240
Gly Thr Ser Asp Lys Asn Asn Gly Ser Gly Thr Leu Glu Gly Glu Lys
65                  70                  75                  80 act gac aaa agt aaa gta aaa tta aca att gct gat gac cta agt caa       288
Thr Asp Lys Ser Lys Val Lys Leu Thr Ile Ala Asp Asp Leu Ser Gln
                85                  90                  95 act aaa ttt gaa att ttc aaa gaa gat gcc aaa aca tta gta tca aaa       336
Thr Lys Phe Glu Ile Phe Lys Glu Asp Ala Lys Thr Leu Val Ser Lys
                100                 105                 110 aaa gta acc ctt aaa gac aag tca tca aca gaa gaa aaa ttc aac gaa       384
Lys Val Thr Leu Lys Asp Lys Ser Ser Thr Glu Glu Lys Phe Asn Glu
            115                 120                 125 aag ggt gaa aca tct gaa aaa aca ata gta aga gca aat gga acc aga       432
Lys Gly Glu Thr Ser Glu Lys Thr Ile Val Arg Ala Asn Gly Thr Arg
        130                 135                 140 ctt gaa tac aca gac ata aaa agc gat gga tcc gga aaa gct aaa gaa       480
Leu Glu Tyr Thr Asp Ile Lys Ser Asp Gly Ser Gly Lys Ala Lys Glu
145                 150                 155                 160 gtt tta aaa gac ttt act ctt gaa gga act cta gct gct gac ggc aaa       528
Val Leu Lys Asp Phe Thr Leu Glu Gly Thr Leu Ala Ala Asp Gly Lys
                165                 170                 175 aca aca ttg aaa gtt aca gag ggc act gtt gtt tta agc aag aac att       576
Thr Thr Leu Lys Val Thr Glu Gly Thr Val Val Leu Ser Lys Asn Ile
            180                 185                 190 tta aaa tcc gga gaa ata aca gtt gca ctt gat gac tct gac act act       624
Leu Lys Ser Gly Glu Ile Thr Val Ala Leu Asp Asp Ser Asp Thr Thr
```

```
                       195                 200                 205
cag gct act aaa aaa act gga aaa tgg gat tca aat act tcc act tta      672
Gln Ala Thr Lys Lys Thr Gly Lys Trp Asp Ser Asn Thr Ser Thr Leu
    210                 215                 220 aca att agt gtg aat agc aaa aaa act aaa aac att gta ttt aca aaa      720
Thr Ile Ser Val Asn Ser Lys Lys Thr Lys Asn Ile Val Phe Thr Lys
225                 230                 235                 240 gaa gac aca ata aca gta caa aaa tac gac tca gca ggc acc aat cta      768
Glu Asp Thr Ile Thr Val Gln Lys Tyr Asp Ser Ala Gly Thr Asn Leu
                245                 250                 255 gaa ggc aac gca gtc gaa att aaa aca ctt gat gaa ctt aaa aac gct      816
Glu Gly Asn Ala Val Glu Ile Lys Thr Leu Asp Glu Leu Lys Asn Ala
            260                 265                 270 tta aaa tag                                                           825
Leu Lys  *

<210> SEQ ID NO 48
<211> LENGTH: 274
<212> TYPE: PRT
<213> ORGANISM: Artificial Sequence
<220> FEATURE:
<223> OTHER INFORMATION: Chimeric protein

<400> SEQUENCE: 48

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                20                  25                  30

Asp Leu Pro Gly Gly Met Thr Val Leu Val Ser Lys Glu Lys Asp Lys
            35                  40                  45

Asp Gly Lys Tyr Ser Leu Glu Ala Thr Val Asp Lys Leu Glu Leu Lys
        50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Asp Asp Leu Ser Gln
                85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190

Leu Lys Ser Gly Glu Ile Thr Val Ala Leu Asp Asp Ser Asp Thr Thr
        195                 200                 205

Gln Ala Thr Lys Lys Thr Gly Lys Trp Asp Ser Asn Thr Ser Thr Leu
    210                 215                 220

Thr Ile Ser Val Asn Ser Lys Lys Thr Lys Asn Ile Val Phe Thr Lys
225                 230                 235                 240

Glu Asp Thr Ile Thr Val Gln Lys Tyr Asp Ser Ala Gly Thr Asn Leu
                245                 250                 255

Glu Gly Asn Ala Val Glu Ile Lys Thr Leu Asp Glu Leu Lys Asn Ala
```

<210> SEQ ID NO 49
<211> LENGTH: 822
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(822)

<400> SEQUENCE: 49

| | | | | | | | | | | | | | | | | |
|---|---|---|---|---|---|---|---|---|---|---|---|---|---|---|---|---|
| atg | aaa | aaa | tat | tta | ttg | gga | ata | ggt | cta | ata | tta | gcc | tta | ata | gca | 48 |
| Met | Lys | Lys | Tyr | Leu | Leu | Gly | Ile | Gly | Leu | Ile | Leu | Ala | Leu | Ile | Ala | |
| 1 | | | | 5 | | | | | 10 | | | | | 15 | | |
| tgc | aag | caa | aat | gtt | agc | agc | ctt | gat | gaa | aaa | aac | agc | gct | tca | gta | 96 |
| Cys | Lys | Gln | Asn | Val | Ser | Ser | Leu | Asp | Glu | Lys | Asn | Ser | Ala | Ser | Val | |
| | | | 20 | | | | | 25 | | | | | 30 | | | |
| gat | ttg | cct | ggt | gag | atg | aaa | gtt | ctt | gta | agt | aaa | gaa | aaa | gac | aaa | 144 |
| Asp | Leu | Pro | Gly | Glu | Met | Lys | Val | Leu | Val | Ser | Lys | Glu | Lys | Asp | Lys | |
| | | 35 | | | | | 40 | | | | | 45 | | | | |
| gac | ggt | aag | tac | agt | cta | aag | gca | aca | gta | gac | aag | att | gag | cta | aaa | 192 |
| Asp | Gly | Lys | Tyr | Ser | Leu | Lys | Ala | Thr | Val | Asp | Lys | Ile | Glu | Leu | Lys | |
| | 50 | | | | | 55 | | | | | 60 | | | | | |
| gga | act | tct | gat | aaa | gac | aat | ggt | tct | gga | gtg | ctt | gaa | ggt | aca | aaa | 240 |
| Gly | Thr | Ser | Asp | Lys | Asp | Asn | Gly | Ser | Gly | Val | Leu | Glu | Gly | Thr | Lys | |
| 65 | | | | | 70 | | | | | 75 | | | | | 80 | |
| gat | gac | aaa | agt | aaa | gca | aaa | tta | aca | att | gct | gac | gat | cta | agt | aaa | 288 |
| Asp | Asp | Lys | Ser | Lys | Ala | Lys | Leu | Thr | Ile | Ala | Asp | Asp | Leu | Ser | Lys | |
| | | | 85 | | | | | 90 | | | | | 95 | | | |
| acc | aca | ttc | gaa | ctt | tta | aaa | gaa | gat | ggc | aaa | aca | tta | gtg | tca | aga | 336 |
| Thr | Thr | Phe | Glu | Leu | Leu | Lys | Glu | Asp | Gly | Lys | Thr | Leu | Val | Ser | Arg | |
| | | 100 | | | | | 105 | | | | | 110 | | | | |
| aaa | gta | agt | tct | aga | gac | aaa | aca | tca | aca | gat | gaa | atg | ttc | aat | gaa | 384 |
| Lys | Val | Ser | Ser | Arg | Asp | Lys | Thr | Ser | Thr | Asp | Glu | Met | Phe | Asn | Glu | |
| | 115 | | | | | 120 | | | | | 125 | | | | | |
| aaa | ggt | gaa | ttg | tct | gca | aaa | acc | atg | aca | aga | gaa | aat | gga | acc | aaa | 432 |
| Lys | Gly | Glu | Leu | Ser | Ala | Lys | Thr | Met | Thr | Arg | Glu | Asn | Gly | Thr | Lys | |
| 130 | | | | | 135 | | | | | 140 | | | | | | |
| ctt | gaa | tat | aca | gaa | atg | aaa | agc | gat | gga | acc | gga | aaa | gct | aaa | gaa | 480 |
| Leu | Glu | Tyr | Thr | Glu | Met | Lys | Ser | Asp | Gly | Thr | Gly | Lys | Ala | Lys | Glu | |
| 145 | | | | | 150 | | | | | 155 | | | | | 160 | |
| gtt | tta | aaa | aag | ttt | act | ctt | gaa | gga | aaa | gta | gct | aat | gat | aaa | gta | 528 |
| Val | Leu | Lys | Lys | Phe | Thr | Leu | Glu | Gly | Lys | Val | Ala | Asn | Asp | Lys | Val | |
| | | | | 165 | | | | | 170 | | | | | 175 | | |
| aca | ttg | gaa | gta | aaa | gaa | gga | acc | gtt | act | tta | agt | aag | gaa | att | gca | 576 |
| Thr | Leu | Glu | Val | Lys | Glu | Gly | Thr | Val | Thr | Leu | Ser | Lys | Glu | Ile | Ala | |
| | | | 180 | | | | | 185 | | | | | 190 | | | |
| aaa | tct | gga | gaa | gta | aca | gtt | gct | ctt | aat | gac | act | aac | act | act | cag | 624 |
| Lys | Ser | Gly | Glu | Val | Thr | Val | Ala | Leu | Asn | Asp | Thr | Asn | Thr | Thr | Gln | |
| | | 195 | | | | | 200 | | | | | 205 | | | | |
| gct | act | aaa | aaa | act | ggc | gca | tgg | gat | tca | aaa | act | tct | act | tta | aca | 672 |
| Ala | Thr | Lys | Lys | Thr | Gly | Ala | Trp | Asp | Ser | Lys | Thr | Ser | Thr | Leu | Thr | |
| | 210 | | | | | 215 | | | | | 220 | | | | | |
| att | agt | gtt | aac | agc | aaa | aaa | act | aca | caa | ctt | gtg | ttt | act | aaa | caa | 720 |
| Ile | Ser | Val | Asn | Ser | Lys | Lys | Thr | Thr | Gln | Leu | Val | Phe | Thr | Lys | Gln | |
| 225 | | | | | 230 | | | | | 235 | | | | | 240 | |
| gac | aca | ata | act | gta | caa | aaa | tac | gac | tcc | gca | ggt | acc | aat | tta | gaa | 768 |
| Asp | Thr | Ile | Thr | Val | Gln | Lys | Tyr | Asp | Ser | Ala | Gly | Thr | Asn | Leu | Glu | |
| | | | | 245 | | | | | 250 | | | | | 255 | | |

```
ggt aca gca gtc gaa att aaa aca ctt gat gaa ctt aaa aac gct tta      816
Gly Thr Ala Val Glu Ile Lys Thr Leu Asp Glu Leu Lys Asn Ala Leu
        260                 265                 270 aaa tag                                                              822
Lys *

<210> SEQ ID NO 50
<211> LENGTH: 273
<212> TYPE: PRT
<213> ORGANISM: Artificial Sequence
<220> FEATURE:
<223> OTHER INFORMATION: Chimeric protein

<400> SEQUENCE: 50

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Ala Ser Val
                20                  25                  30

Asp Leu Pro Gly Glu Met Lys Val Leu Ser Lys Glu Lys Asp Lys
            35                  40                  45

Asp Gly Lys Tyr Ser Leu Lys Ala Thr Val Asp Lys Ile Glu Leu Lys
    50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Leu Lys Gly Asp Gly Lys Thr Leu Val Ser Arg
            100                 105                 110

Lys Val Ser Ser Arg Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys

<210> SEQ ID NO 51
<211> LENGTH: 822
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(822)
```

<400> SEQUENCE: 51

```
atg aaa aaa tat tta ttg gga ata ggt cta ata tta gcc tta ata gca      48
Met Lys Lys Tyr Leu Leu Gly Ile Gly Leu Ile Leu Ala Leu Ile Ala
1               5                   10                  15 tgc aag caa aat gtt agc agc ctt gat gaa aaa aac agc gct tca gta      96
Cys Lys Gln Asn Val Ser Ser Leu Asp Glu Lys Asn Ser Ala Ser Val
            20                  25                  30 gat ttg cct ggt gag atg aaa gtt ctt gta agt aaa gaa aaa gac aaa     144
Asp Leu Pro Gly Glu Met Lys Val Leu Val Ser Lys Glu Lys Asp Lys
        35                  40                  45 gac ggt aag tac agt cta aag gca aca gta gac aag att gag cta aaa     192
Asp Gly Lys Tyr Ser Leu Lys Ala Thr Val Asp Lys Ile Glu Leu Lys
    50                  55                  60 gga act tct gat aaa gac aat ggt tct gga gtg ctt gaa ggt aca aaa     240
Gly Thr Ser Asp Lys Asp Asn Gly Ser Gly Val Leu Glu Gly Thr Lys
65                  70                  75                  80 gat gac aaa agt aaa gca aaa tta aca att gct gac gat cta agt aaa     288
Asp Asp Lys Ser Lys Ala Lys Leu Thr Ile Ala Asp Asp Leu Ser Lys
                85                  90                  95 acc aca ttc gaa ctt tta aaa gaa gat ggc aaa aca tta gtg tca aga     336
Thr Thr Phe Glu Leu Leu Lys Glu Asp Gly Lys Thr Leu Val Ser Arg
            100                 105                 110 aaa gta agt tct aga gac aaa aca tca aca gat gaa atg ttc aat gaa     384
Lys Val Ser Ser Arg Asp Lys Thr Ser Thr Asp Glu Met Phe Asn Glu
        115                 120                 125 aaa ggt gaa ttg tct gca aaa acc atg aca aga gaa aat gga acc aaa     432
Lys Gly Glu Leu Ser Ala Lys Thr Met Thr Arg Glu Asn Gly Thr Lys
    130                 135                 140 ctt gaa tat aca gaa atg aaa agc gat gga acc gga aaa gct aaa gaa     480
Leu Glu Tyr Thr Glu Met Lys Ser Asp Gly Thr Gly Lys Ala Lys Glu
145                 150                 155                 160 gtt tta aaa aag ttt act ctt gaa gga aaa gta gct aat gat aaa gta     528
Val Leu Lys Lys Phe Thr Leu Glu Gly Lys Val Ala Asn Asp Lys Val
                165                 170                 175 aca ttg gaa gta aaa gaa gga acc gtt act tta agt aag gaa att tca     576
Thr Leu Glu Val Lys Glu Gly Thr Val Thr Leu Ser Lys Glu Ile Ser
            180                 185                 190 aaa tct ggg gaa gtt tca gtt gaa ctt aat gac act gac agt agt gct     624
Lys Ser Gly Glu Val Ser Val Glu Leu Asn Asp Thr Asp Ser Ser Ala
        195                 200                 205 gct act aaa aaa act gca gct tgg aat tca aaa act tcc act tta aca     672
Ala Thr Lys Lys Thr Ala Ala Trp Asn Ser Lys Thr Ser Thr Leu Thr
    210                 215                 220 att agt gtg aat agc caa aaa acc aaa aac ctt gta ttc aca aaa gaa     720
Ile Ser Val Asn Ser Gln Lys Thr Lys Asn Leu Val Phe Thr Lys Glu
225                 230                 235                 240 gac aca ata aca gta caa aaa tac gac tca gca ggc acc aat cta gaa     768
Asp Thr Ile Thr Val Gln Lys Tyr Asp Ser Ala Gly Thr Asn Leu Glu
                245                 250                 255 ggc aaa gca gtc gaa att aca aca ctt aaa gaa ctt aaa aac gct tta     816
Gly Lys Ala Val Glu Ile Thr Thr Leu Lys Glu Leu Lys Asn Ala Leu
            260                 265                 270 aaa taa                                                              822
Lys *
```

<210> SEQ ID NO 52
<211> LENGTH: 273
<212> TYPE: PRT
<213> ORGANISM: Artificial Sequence
<220> FEATURE:
<223> OTHER INFORMATION: Chimeric protein

```
<400> SEQUENCE: 52

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Ala Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Lys Ala Thr Val Asp Lys Ile Glu Leu Lys
    50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Leu Lys Glu Asp Gly Lys Thr Leu Val Ser Arg
            100                 105                 110

Lys Val Ser Ser Arg Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys

<210> SEQ ID NO 53
<211> LENGTH: 822
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(822)

<400> SEQUENCE: 53 atg aaa aaa tat tta ttg gga ata ggt cta ata tta gcc tta ata gca      48
Met Lys Lys Tyr Leu Leu Gly Ile Gly Leu Ile Leu Ala Leu Ile Ala
 1               5                  10                  15 tgt aag caa aat gtt agc agc ctt gac gag aaa aac agc gtt tca gta      96
Cys Lys Gln Asn Val Ser Ser Leu Asp Glu Lys Asn Ser Val Ser Val
            20                  25                  30 gat ttg cct ggt gaa atg aaa gtt ctt gta agc aaa gaa aaa aac aaa     144
Asp Leu Pro Gly Glu Met Lys Val Leu Val Ser Lys Glu Lys Asn Lys
        35                  40                  45
```

```
gac ggc aag tac gat cta att gca aca gta gac aag ctt gag ctt aaa      192
Asp Gly Lys Tyr Asp Leu Ile Ala Thr Val Asp Lys Leu Glu Leu Lys
         50                  55                  60 gga act tct gat aaa aac aat gga tct gga gta ctt gaa ggc gta aaa      240
Gly Thr Ser Asp Lys Asn Asn Gly Ser Gly Val Leu Glu Gly Val Lys
 65                  70                  75                  80 gct gac aaa agt aaa gta aaa tta aca att tct gac gat cta ggt caa      288
Ala Asp Lys Ser Lys Val Lys Leu Thr Ile Ser Asp Asp Leu Gly Gln
                 85                  90                  95 acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110 aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125 aaa ggt gaa gta tct gaa aaa ata ata aca aga gca aat gga acc aaa      432
Lys Gly Glu Val Ser Glu Lys Ile Ile Thr Arg Ala Asn Gly Thr Lys
    130                 135                 140 ctt gaa tat aca gaa atg aaa agc gat gga acc gga aaa gct aaa gaa      480
Leu Glu Tyr Thr Glu Met Lys Ser Asp Gly Thr Gly Lys Ala Lys Glu
145                 150                 155                 160 gtt tta aaa aag ttt act ctt gaa gga aaa gta gct aat gat aaa gta      528
Val Leu Lys Lys Phe Thr Leu Glu Gly Lys Val Ala Asn Asp Lys Val
                165                 170                 175 aca ttg gaa gta aaa gaa gga acc gtt act tta agt aag gaa att tca      576
Thr Leu Glu Val Lys Glu Gly Thr Val Thr Leu Ser Lys Glu Ile Ser
            180                 185                 190 aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205 gct act aaa aaa act gca gct tgg aat tca aaa act tcc act tta aca      672
Ala Thr Lys Lys Thr Ala Ala Trp Asn Ser Lys Thr Ser Thr Leu Thr
    210                 215                 220 att agt gtg aat agc caa aaa acc aaa aac ctt gta ttc aca aaa gaa      720
Ile Ser Val Asn Ser Gln Lys Thr Lys Asn Leu Val Phe Thr Lys Glu
225                 230                 235                 240 gac aca ata aca gta caa aaa tac gac tca gca ggc acc aat cta gaa      768
Asp Thr Ile Thr Val Gln Lys Tyr Asp Ser Ala Gly Thr Asn Leu Glu
                245                 250                 255 ggc aaa gca gtc gaa att aca aca ctt aaa gaa ctt aaa aac gct tta      816
Gly Lys Ala Val Glu Ile Thr Thr Leu Lys Glu Leu Lys Asn Ala Leu
            260                 265                 270 aaa taa                                                              822
Lys *
```

<210> SEQ ID NO 54
<211> LENGTH: 273
<212> TYPE: PRT
<213> ORGANISM: Artificial Sequence
<220> FEATURE:
<223> OTHER INFORMATION: Chimeric protein

<400> SEQUENCE: 54

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
        50                  55                  60
```

```
Gly Thr Ser Asp Lys Asn Asn Gly Ser Gly Val Leu Glu Gly Val Lys
 65                  70                  75                  80

Ala Asp Lys Ser Lys Val Lys Leu Thr Ile Ser Asp Leu Gly Gln
             85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys

<210> SEQ ID NO 55
<211> LENGTH: 1362
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1362)

<400> SEQUENCE: 55 atg gct tgt aat aat tca ggg aaa gat ggg aat aca tct gca aat tct    48
Met Ala Cys Asn Asn Ser Gly Lys Asp Gly Asn Thr Ser Ala Asn Ser
1               5                  10                  15 gct gat gag tct gtt aaa ggg cct aat ctt aca gaa ata aat aaa aaa    96
Ala Asp Glu Ser Val Lys Gly Pro Asn Leu Thr Glu Ile Asn Lys Lys
            20                  25                  30 att acg gat tct aat gcg gtt tta ctt gct gtg aaa gag gtt gaa gcg   144
Ile Thr Asp Ser Asn Ala Val Leu Leu Ala Val Lys Glu Val Glu Ala
        35                  40                  45 ttg ctg tca tct ata gat gaa att gct gct aaa gct att ggt aaa aaa   192
Leu Leu Ser Ser Ile Asp Glu Ile Ala Ala Lys Ala Ile Gly Lys Lys
    50                  55                  60 ata cac caa aat aat ggt ttg gat acc gaa aat aat cac aat gga tca   240
Ile His Gln Asn Asn Gly Leu Asp Thr Glu Asn Asn His Asn Gly Ser
65                  70                  75                  80 ttg tta gcg gga gct tat gca ata tca acc cta ata aaa caa aaa tta   288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag   336
Asp Gly Leu Lys Asn Glu Gly Leu Lys Glu Lys Ile Asp Ala Ala Lys
```

-continued

```
                100                 105                 110
aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
130                 135                 140 aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa      576
Asn Ser Val Lys Glu Leu Thr Ser Pro Val Val Ala Glu Ser Pro Lys
        180                 185                 190 aaa cct tcc atg gcc aag caa aat gtt agc agc ctt gac gag aaa aac      624
Lys Pro Ser Met Ala Lys Gln Asn Val Ser Ser Leu Asp Glu Lys Asn
        195                 200                 205 agc gtt tca gta gat ttg cct ggt gaa atg aaa gtt ctt gta agc aaa      672
Ser Val Ser Val Asp Leu Pro Gly Glu Met Lys Val Leu Val Ser Lys
210                 215                 220 gaa aaa aac aaa gac ggc aag tac gat cta att gca aca gta gac aag      720
Glu Lys Asn Lys Asp Gly Lys Tyr Asp Leu Ile Ala Thr Val Asp Lys
225                 230                 235                 240 ctt gag ctt aaa gga act tct gat aaa aac aat gga tct gga gta ctt      768
Leu Glu Leu Lys Gly Thr Ser Asp Lys Asn Asn Gly Ser Gly Val Leu
                245                 250                 255 gaa ggc gta aaa gct gac aaa agt aaa gta aaa tta aca att tct gac      816
Glu Gly Val Lys Ala Asp Lys Ser Lys Val Lys Leu Thr Ile Ser Asp
        260                 265                 270 gat cta ggt caa acc aca ctt gaa gtt ttc aaa gaa gat ggc aaa aca      864
Asp Leu Gly Gln Thr Thr Leu Glu Val Phe Lys Glu Asp Gly Lys Thr
        275                 280                 285 cta gta tca aaa aaa gta act tcc aaa gac aag tca tca aca gaa gaa      912
Leu Val Ser Lys Lys Val Thr Ser Lys Asp Lys Ser Ser Thr Glu Glu
290                 295                 300 aaa ttc aat gaa aaa ggt gaa gta tct gaa aaa ata ata aca aga gca      960
Lys Phe Asn Glu Lys Gly Glu Val Ser Glu Lys Ile Ile Thr Arg Ala
305                 310                 315                 320 gac gga acc aga ctt gaa tac aca gga att aaa agc gat gga tct gga     1008
Asp Gly Thr Arg Leu Glu Tyr Thr Gly Ile Lys Ser Asp Gly Ser Gly
                325                 330                 335 aaa gct aaa gag gtt tta aaa ggc tat gtt ctt gaa gga act cta act     1056
Lys Ala Lys Glu Val Leu Lys Gly Tyr Val Leu Glu Gly Thr Leu Thr
        340                 345                 350 gct gaa aaa aca aca ttg gtg gtt aaa gaa gga act gtt act tta agc     1104
Ala Glu Lys Thr Thr Leu Val Val Lys Glu Gly Thr Val Thr Leu Ser
        355                 360                 365 aaa aat att tca aaa tct ggg gaa gtt tca gtt gaa ctt aat gac act     1152
Lys Asn Ile Ser Lys Ser Gly Glu Val Ser Val Glu Leu Asn Asp Thr
370                 375                 380 gac agt agt gct gct act aaa aaa act gca gct tgg aat tca ggc act     1200
Asp Ser Ser Ala Ala Thr Lys Lys Thr Ala Ala Trp Asn Ser Gly Thr
385                 390                 395                 400 tca act tta aca att act gta aac agt aaa aaa act aaa gac ctt gtg     1248
Ser Thr Leu Thr Ile Thr Val Asn Ser Lys Lys Thr Lys Asp Leu Val
                405                 410                 415 ttt aca aaa gaa aac aca att aca gta caa caa tac gac tca aat ggc     1296
Phe Thr Lys Glu Asn Thr Ile Thr Val Gln Gln Tyr Asp Ser Asn Gly
```

|  |  |  |  |  |  | 420 |  |  |  |  | 425 |  |  |  |  | 430 |  |  |  |
|---|---|---|---|---|---|---|---|---|---|---|---|---|---|---|---|---|---|---|---|
| acc | aaa | tta | gag | ggg | tca | gca | gtt | gaa | att | aca | aaa | ctt | gat | gaa | att |  |  |  | 1344 |
| Thr | Lys | Leu | Glu | Gly | Ser | Ala | Val | Glu | Ile | Thr | Lys | Leu | Asp | Glu | Ile |  |  |  |  |
|  |  | 435 |  |  |  |  | 440 |  |  |  |  | 445 |  |  |  |  |  |  |  |
| aaa | aac | gct | tta | aaa | taa |  |  |  |  |  |  |  |  |  |  |  |  |  | 1362 |
| Lys | Asn | Ala | Leu | Lys | * |  |  |  |  |  |  |  |  |  |  |  |  |  |  |
|  |  | 450 |  |  |  |  |  |  |  |  |  |  |  |  |  |  |  |  |  |

<210> SEQ ID NO 56
<211> LENGTH: 453
<212> TYPE: PRT
<213> ORGANISM: Artificial Sequence
<220> FEATURE:
<223> OTHER INFORMATION: Chimeric protein

<400> SEQUENCE: 56

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Ser Leu Asp Glu Lys Asn
        195                 200                 205

Ser Val Ser Val Asp Leu Pro Gly Glu Met Lys Val Leu Val Ser Lys
    210                 215                 220

Glu Lys Asn Lys Asp Gly Lys Tyr Asp Leu Ile Ala Thr Val Asp Lys
225                 230                 235                 240

Leu Glu Leu Lys Gly Thr Ser Asp Lys Asn Asn Gly Ser Gly Val Leu
                245                 250                 255

Glu Gly Val Lys Ala Asp Lys Ser Lys Val Lys Leu Thr Ile Ser Asp
            260                 265                 270

Asp Leu Gly Gln Thr Thr Leu Glu Val Phe Lys Glu Asp Gly Lys Thr
        275                 280                 285

Leu Val Ser Lys Lys Val Thr Ser Lys Asp Lys Ser Ser Thr Glu Glu
    290                 295                 300

Lys Phe Asn Glu Lys Gly Glu Val Ser Glu Lys Ile Ile Thr Arg Ala
305                 310                 315                 320

```
Asp Gly Thr Arg Leu Glu Tyr Thr Gly Ile Lys Ser Asp Gly Ser Gly
            325                 330                 335

Lys Ala Lys Glu Val Leu Lys Gly Tyr Val Leu Glu Gly Thr Leu Thr
        340                 345                 350

Ala Glu Lys Thr Thr Leu Val Val Lys Glu Gly Thr Val Thr Leu Ser
    355                 360                 365

Lys Asn Ile Ser Lys Ser Gly Glu Val Ser Val Glu Leu Asn Asp Thr
370                 375                 380

Asp Ser Ser Ala Ala Thr Lys Lys Thr Ala Ala Trp Asn Ser Gly Thr
385                 390                 395                 400

Ser Thr Leu Thr Ile Thr Val Asn Ser Lys Thr Lys Asp Leu Val
            405                 410                 415

Phe Thr Lys Glu Asn Thr Ile Thr Val Gln Gln Tyr Asp Ser Asn Gly
        420                 425                 430

Thr Lys Leu Glu Gly Ser Ala Val Glu Ile Thr Lys Leu Asp Glu Ile
    435                 440                 445

Lys Asn Ala Leu Lys
    450

<210> SEQ ID NO 57
<211> LENGTH: 1353
<212> TYPE: DNA
<213> ORGANISM: Artificial Sequence
<220> FEATURE:
<223> OTHER INFORMATION: Chimeric  nucleic acid
<221> NAME/KEY: CDS
<222> LOCATION: (1)...(1353)

<400> SEQUENCE: 57 atg gct tgt aat aat tca ggg aaa gat ggg aat aca tct gca aat tct      48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata aat aaa aaa      96
Ala Asp Glu Ser Val Lys Gly Pro Asn Leu Thr Glu Ile Asn Lys Lys
            20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
        35                  40                  45 ttg ctg tca tct ata gat gaa att gct gct aaa gct att ggt aaa aaa     192
Leu Leu Ser Ser Ile Asp Glu Ile Ala Ala Lys Ala Ile Gly Lys Lys
    50                  55                  60 ata cac caa aat aat ggt ttg gat acc gaa aat aat cac aat gga tca     240
Ile His Gln Asn Asn Gly Leu Asp Thr Glu Asn Asn His Asn Gly Ser
65                  70                  75                  80 ttg tta gcg gga gct tat gca ata tca acc cta ata aaa caa aaa tta     288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag     336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat     384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta     432
Leu Gly Lys Glu Gly Val Thr Asp Ala Asp Ala Lys Glu Ala Ile Leu
    130                 135                 140 aaa gca aat ggt act aaa act aaa ggt gct gaa gaa ctt gga aaa tta     480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct     528
Phe Glu Ser Val Glu Val Leu Ser Lys Ala Ala Lys Glu Met Leu Ala
```

```
                Phe Glu Ser Val Glu Val Leu Ser Lys Ala Ala Lys Glu Met Leu Ala
                                165                 170                 175 aat tca gtt aaa gag ctt aca agc cct gtt gtg gca gaa agt cca gcc         576
Asn Ser Val Lys Glu Leu Thr Ser Pro Val Val Ala Glu Ser Pro Ala
                180                 185                 190 atg gcc aag caa aat gtt agc agc ctt gac gag aaa aac agc gtt tca         624
Met Ala Lys Gln Asn Val Ser Ser Leu Asp Glu Lys Asn Ser Val Ser
                195                 200                 205 gta gat ttg cct ggt gaa atg aaa gtt ctt gta agc aaa gaa aaa aac         672
Val Asp Leu Pro Gly Glu Met Lys Val Leu Val Ser Lys Glu Lys Asn
                210                 215                 220 aaa gac ggc aag tac gat cta att gca aca gta gac aag ctt gag ctt         720
Lys Asp Gly Lys Tyr Asp Leu Ile Ala Thr Val Asp Lys Leu Glu Leu
225                 230                 235                 240 aaa gga act tct gat aaa aac aat gga tct gga gta ctt gaa ggc gta         768
Lys Gly Thr Ser Asp Lys Asn Asn Gly Ser Gly Val Leu Glu Gly Val
                245                 250                 255 aaa gct gac aaa agt aaa gta aaa tta aca att tct gac gat cta ggt         816
Lys Ala Asp Lys Ser Lys Val Lys Leu Thr Ile Ser Asp Asp Leu Gly
                260                 265                 270 caa acc aca ctt gaa gtt ttc aaa gaa gat ggc aaa aca cta gta tca         864
Gln Thr Thr Leu Glu Val Phe Lys Glu Asp Gly Lys Thr Leu Val Ser
                275                 280                 285 aaa aaa gta act tcc aaa gac aag tca tca aca gaa gaa aaa ttc aat         912
Lys Lys Val Thr Ser Lys Asp Lys Ser Ser Thr Glu Glu Lys Phe Asn
                290                 295                 300 gaa aaa ggt gaa gta tct gaa aaa ata ata aca aga gca gac gga acc         960
Glu Lys Gly Glu Val Ser Glu Lys Ile Ile Thr Arg Ala Asp Gly Thr
305                 310                 315                 320 aga ctt gaa tac aca gga att aaa agc gat gga tct gga aaa gct aaa        1008
Arg Leu Glu Tyr Thr Gly Ile Lys Ser Asp Gly Ser Gly Lys Ala Lys
                325                 330                 335 gag gtt tta aaa ggc tat gtt ctt gaa gga act cta act gct gaa aaa        1056
Glu Val Leu Lys Gly Tyr Val Leu Glu Gly Thr Leu Thr Ala Glu Lys
                340                 345                 350 aca aca ttg gtg gtt aaa gaa gga act gtt act tta agc aaa aat att        1104
Thr Thr Leu Val Val Lys Glu Gly Thr Val Thr Leu Ser Lys Asn Ile
                355                 360                 365 tca aaa tct ggg gaa gtt tca gtt gaa ctt aat gac act gac agt agt        1152
Ser Lys Ser Gly Glu Val Ser Val Glu Leu Asn Asp Thr Asp Ser Ser
                370                 375                 380 gct gct act aaa aaa act gca gct tgg aat tca ggc act tca act tta        1200
Ala Ala Thr Lys Lys Thr Ala Ala Trp Asn Ser Gly Thr Ser Thr Leu
385                 390                 395                 400 aca att act gta aac agt aaa aaa act aaa gac ctt gtg ttt aca aaa        1248
Thr Ile Thr Val Asn Ser Lys Lys Thr Lys Asp Leu Val Phe Thr Lys
                405                 410                 415 gaa aac aca att aca gta caa caa tac gac tca aat ggc acc aaa tta        1296
Glu Asn Thr Ile Thr Val Gln Gln Tyr Asp Ser Asn Gly Thr Lys Leu
                420                 425                 430 gag ggg tca gca gtt gaa att aca aaa ctt gat gaa att aaa aac gct        1344
Glu Gly Ser Ala Val Glu Ile Thr Lys Leu Asp Glu Ile Lys Asn Ala
                435                 440                 445 tta aaa taa                                                            1353
Leu Lys  *
    450

<210> SEQ ID NO 58
<211> LENGTH: 450
<212> TYPE: PRT
<213> ORGANISM: Artificial Sequence
```

<220> FEATURE:
<223> OTHER INFORMATION: Chimeric protein

<400> SEQUENCE: 58

```
Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Ala
            180                 185                 190

Met Ala Lys Gln Asn Val Ser Ser Leu Asp Glu Lys Asn Ser Val Ser
        195                 200                 205

Val Asp Leu Pro Gly Glu Met Lys Val Leu Val Ser Lys Glu Lys Asn
    210                 215                 220

Lys Asp Gly Lys Tyr Asp Leu Ile Ala Thr Val Asp Lys Leu Glu Leu
225                 230                 235                 240

Lys Gly Thr Ser Asp Lys Asn Asn Gly Ser Gly Val Leu Glu Gly Val
                245                 250                 255

Lys Ala Asp Lys Ser Lys Val Lys Leu Thr Ile Ser Asp Asp Leu Gly
            260                 265                 270

Gln Thr Thr Leu Glu Val Phe Lys Glu Asp Gly Lys Thr Leu Val Ser
        275                 280                 285

Lys Lys Val Thr Ser Lys Asp Lys Ser Ser Thr Glu Glu Lys Phe Asn
    290                 295                 300

Glu Lys Gly Glu Val Ser Glu Lys Ile Ile Thr Arg Ala Asp Gly Thr
305                 310                 315                 320

Arg Leu Glu Tyr Thr Gly Ile Lys Ser Asp Gly Ser Gly Lys Ala Lys
                325                 330                 335

Glu Val Leu Lys Gly Tyr Val Leu Glu Gly Thr Leu Thr Ala Glu Lys
            340                 345                 350

Thr Thr Leu Val Val Lys Glu Gly Thr Val Thr Leu Ser Lys Asn Ile
        355                 360                 365

Ser Lys Ser Gly Glu Val Ser Val Glu Leu Asn Asp Thr Asp Ser Ser
    370                 375                 380

Ala Ala Thr Lys Lys Thr Ala Ala Trp Asn Ser Gly Thr Ser Thr Leu
385                 390                 395                 400
```

```
Thr Ile Thr Val Asn Ser Lys Lys Thr Lys Asp Leu Val Phe Thr Lys
            405                 410                 415

Glu Asn Thr Ile Thr Val Gln Gln Tyr Asp Ser Asn Gly Thr Lys Leu
        420                 425                 430

Glu Gly Ser Ala Val Glu Ile Thr Lys Leu Asp Glu Ile Lys Asn Ala
    435                 440                 445

Leu Lys
    450

<210> SEQ ID NO 59
<211> LENGTH: 1341
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1341)

<400> SEQUENCE: 59 atg gct tgt aat aat tca ggg aaa gat ggg aat aca tct gca aat tct      48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
            20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
        35                  40                  45 ttg ctg tca tct ata gat gag ctt gct aaa gct att ggt aaa aaa ata     192
Leu Leu Ser Ser Ile Asp Glu Leu Ala Lys Ala Ile Gly Lys Lys Ile
    50                  55                  60 aaa aac gat ggt agt tta gat aat gaa gca aat cgc aac gag tca ttg     240
Lys Asn Asp Gly Ser Leu Asp Asn Glu Ala Asn Arg Asn Glu Ser Leu
65                  70                  75                  80 tta gca gga gct tat aca ata tca acc tta ata aca caa aaa tta agt     288
Leu Ala Gly Ala Tyr Thr Ile Ser Thr Leu Ile Thr Gln Lys Leu Ser
                85                  90                  95 aaa tta aac gga tca gaa ggt tta aag gaa aag att gcc gca gct aag     336
Lys Leu Asn Gly Ser Glu Gly Leu Lys Glu Lys Ile Ala Ala Ala Lys
            100                 105                 110 aaa tgc tct gaa gag ttt agt act aaa cta aaa gat aat cat gca cag     384
Lys Cys Ser Glu Glu Phe Ser Thr Lys Leu Lys Asp Asn His Ala Gln
        115                 120                 125 ctt ggt ata cag ggc gtt act gat gaa aat gca aaa aaa gct att tta     432
Leu Gly Ile Gln Gly Val Thr Asp Glu Asn Ala Lys Lys Ala Ile Leu
    130                 135                 140 aaa gca aat gca gcg ggt aaa gat aag ggc gtt gaa gaa ctt gaa aag     480
Lys Ala Asn Ala Ala Gly Lys Asp Lys Gly Val Glu Glu Leu Glu Lys
145                 150                 155                 160 ttg tcc gga tca tta gaa agc tta tca aaa gca gct aaa gag atg ctt     528
Leu Ser Gly Ser Leu Glu Ser Leu Ser Lys Ala Ala Lys Glu Met Leu
                165                 170                 175 gct aat tca gtt aaa gag ctt aca agc cct gtt gtc cat ggc aag caa     576
Ala Asn Ser Val Lys Glu Leu Thr Ser Pro Val Val His Gly Lys Gln
            180                 185                 190 aat gtt agc agc ctt gac gag aaa aac agc gtt tca gta gat ttg cct     624
Asn Val Ser Ser Leu Asp Glu Lys Asn Ser Val Ser Val Asp Leu Pro
        195                 200                 205 ggt gaa atg aaa gtt ctt gta agc aaa gaa aaa aac aaa gac ggc aag     672
Gly Glu Met Lys Val Leu Val Ser Lys Glu Lys Asn Lys Asp Gly Lys
    210                 215                 220
```

```
tac gat cta att gca aca gta gac aag ctt gag ctt aaa gga act tct    720
Tyr Asp Leu Ile Ala Thr Val Asp Lys Leu Glu Leu Lys Gly Thr Ser
225                 230                 235                 240 gat aaa aac aat gga tct gga gta ctt gaa ggc gta aaa gct gac aaa    768
Asp Lys Asn Asn Gly Ser Gly Val Leu Glu Gly Val Lys Ala Asp Lys
            245                 250                 255 agt aaa gta aaa tta aca att tct gac gat cta ggt caa acc aca ctt    816
Ser Lys Val Lys Leu Thr Ile Ser Asp Asp Leu Gly Gln Thr Thr Leu
        260                 265                 270 gaa gtt ttc aaa gaa gat ggc aaa aca cta gta tca aaa aaa gta act    864
Glu Val Phe Lys Glu Asp Gly Lys Thr Leu Val Ser Lys Lys Val Thr
    275                 280                 285 tcc aaa gac aag tca tca aca gaa gaa aaa ttc aat gaa aaa ggt gaa    912
Ser Lys Asp Lys Ser Ser Thr Glu Glu Lys Phe Asn Glu Lys Gly Glu
290                 295                 300 gta tct gaa aaa ata ata aca aga gca gac gga acc aga ctt gaa tac    960
Val Ser Glu Lys Ile Ile Thr Arg Ala Asp Gly Thr Arg Leu Glu Tyr
305                 310                 315                 320 aca gga att aaa agc gat gga tct gga aaa gct aaa gag gtt tta aaa   1008
Thr Gly Ile Lys Ser Asp Gly Ser Gly Lys Ala Lys Glu Val Leu Lys
            325                 330                 335 ggc tat gtt ctt gaa gga act cta act gct gaa aaa aca aca ttg gtg   1056
Gly Tyr Val Leu Glu Gly Thr Leu Thr Ala Glu Lys Thr Thr Leu Val
        340                 345                 350 gtt aaa gaa gga act gtt act tta agc aaa aat att tca aaa tct ggg   1104
Val Lys Glu Gly Thr Val Thr Leu Ser Lys Asn Ile Ser Lys Ser Gly
    355                 360                 365 gaa gtt tca gtt gaa ctt aat gac act gac agt agt gct gct act aaa   1152
Glu Val Ser Val Glu Leu Asn Asp Thr Asp Ser Ser Ala Ala Thr Lys
370                 375                 380 aaa act gca gct tgg aat tca ggc act tca act tta aca att act gta   1200
Lys Thr Ala Ala Trp Asn Ser Gly Thr Ser Thr Leu Thr Ile Thr Val
385                 390                 395                 400 aac agt aaa aaa act aaa gac ctt gtg ttt aca aaa gaa aac aca att   1248
Asn Ser Lys Lys Thr Lys Asp Leu Val Phe Thr Lys Glu Asn Thr Ile
            405                 410                 415 aca gta caa caa tac gac tca aat ggc acc aaa tta gag ggg tca gca   1296
Thr Val Gln Gln Tyr Asp Ser Asn Gly Thr Lys Leu Glu Gly Ser Ala
        420                 425                 430 gtt gaa att aca aaa ctt gat gaa att aaa aac gct tta aaa taa       1341
Val Glu Ile Thr Lys Leu Asp Glu Ile Lys Asn Ala Leu Lys *
    435                 440                 445
```

<210> SEQ ID NO 60
<211> LENGTH: 446
<212> TYPE: PRT
<213> ORGANISM: Artificial Sequence
<220> FEATURE:
<223> OTHER INFORMATION: Chimeric protein

<400> SEQUENCE: 60

```
Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80
```

Leu Ala Gly Ala Tyr Thr Ile Ser Thr Leu Ile Thr Gln Lys Leu Ser
            85                  90                  95

Lys Leu Asn Gly Ser Glu Gly Leu Lys Glu Lys Ile Ala Ala Ala Lys
            100                 105                 110

Lys Cys Ser Glu Glu Phe Ser Thr Lys Leu Lys Asp Asn His Ala Gln
            115                 120                 125

Leu Gly Ile Gln Gly Val Thr Asp Glu Asn Ala Lys Lys Ala Ile Leu
            130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Lys Gln
            180                 185                 190

Asn Val Ser Ser Leu Asp Glu Lys Asn Ser Val Ser Val Asp Leu Pro
            195                 200                 205

Gly Glu Met Lys Val Leu Val Ser Lys Glu Lys Asn Lys Asp Gly Lys
            210                 215                 220

Tyr Asp Leu Ile Ala Thr Val Asp Lys Leu Glu Leu Lys Gly Thr Ser
225                 230                 235                 240

Asp Lys Asn Asn Gly Ser Gly Val Leu Glu Gly Val Lys Ala Asp Lys
                245                 250                 255

Ser Lys Val Lys Leu Thr Ile Ser Asp Asp Leu Gly Gln Thr Thr Leu
            260                 265                 270

Glu Val Phe Lys Glu Asp Gly Lys Thr Leu Val Ser Lys Lys Val Thr
            275                 280                 285

Ser Lys Asp Lys Ser Ser Thr Glu Glu Lys Phe Asn Glu Lys Gly Glu
            290                 295                 300

Val Ser Glu Lys Ile Ile Thr Arg Ala Asp Gly Thr Arg Leu Glu Tyr
305                 310                 315                 320

Thr Gly Ile Lys Ser Asp Gly Ser Gly Lys Ala Lys Glu Val Leu Lys
                325                 330                 335

Gly Tyr Val Leu Glu Gly Thr Leu Thr Ala Glu Lys Thr Thr Leu Val
            340                 345                 350

Val Lys Glu Gly Thr Val Thr Leu Ser Lys Asn Ile Ser Lys Ser Gly
            355                 360                 365

Glu Val Ser Val Glu Leu Asn Asp Thr Asp Ser Ser Ala Ala Thr Lys
            370                 375                 380

Lys Thr Ala Ala Trp Asn Ser Gly Thr Ser Thr Leu Thr Ile Thr Val
385                 390                 395                 400

Asn Ser Lys Lys Thr Lys Asp Leu Val Phe Thr Lys Glu Asn Thr Ile
                405                 410                 415

Thr Val Gln Gln Tyr Asp Ser Asn Gly Thr Lys Leu Glu Gly Ser Ala
            420                 425                 430

Val Glu Ile Thr Lys Leu Asp Glu Ile Lys Asn Ala Leu Lys
            435                 440                 445

<210> SEQ ID NO 61
<211> LENGTH: 1362
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1362)

<400> SEQUENCE: 61

```
atg gct tgt aat aat tca ggg aaa gat ggg aat aca tct gca aat tct      48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata aat aaa aaa      96
Ala Asp Glu Ser Val Lys Gly Pro Asn Leu Thr Glu Ile Asn Lys Lys
            20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
        35                  40                  45 ttg ctg tca tct ata gat gaa att gct gct aaa gct att ggt aaa aaa     192
Leu Leu Ser Ser Ile Asp Glu Ile Ala Ala Lys Ala Ile Gly Lys Lys
    50                  55                  60 ata cac caa aat aat ggt ttg gat acc gaa aat aat cac aat gga tca     240
Ile His Gln Asn Asn Gly Leu Asp Thr Glu Asn Asn His Asn Gly Ser
65                  70                  75                  80 ttg tta gcg gga gct tat gca ata tca acc cta ata aaa caa aaa tta     288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag     336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat     384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta     432
Leu Gly Lys Glu Gly Val Thr Asp Ala Asp Ala Lys Glu Ala Ile Leu
    130                 135                 140 aaa gca aat ggt act aaa act aaa ggt gct gaa gaa ctt gga aaa tta     480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct     528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa     576
Asn Ser Val Lys Glu Leu Thr Ser Pro Val Val Ala Glu Ser Pro Lys
            180                 185                 190 aaa cct tcc atg gcc aag caa aat gtt agc agc ctt gac gag aaa aac     624
Lys Pro Ser Met Ala Lys Gln Asn Val Ser Ser Leu Asp Glu Lys Asn
        195                 200                 205 agc gtt tca gta gat ttg cct ggt gaa atg aaa gtt ctt gta agc aaa     672
Ser Val Ser Val Asp Leu Pro Gly Glu Met Lys Val Leu Val Ser Lys
    210                 215                 220 gaa aaa aac aaa gac ggc aag tac gat cta att gca aca gta gac aag     720
Glu Lys Asn Lys Asp Gly Lys Tyr Asp Leu Ile Ala Thr Val Asp Lys
225                 230                 235                 240 ctt gag ctt aaa gga act tct gat aaa aac aat gga tct gga gta ctt     768
Leu Glu Leu Lys Gly Thr Ser Asp Lys Asn Asn Gly Ser Gly Val Leu
                245                 250                 255 gaa ggc gta aaa gct gac aaa agt aaa gta aaa tta aca att tct gac     816
Glu Gly Val Lys Ala Asp Lys Ser Lys Val Lys Leu Thr Ile Ser Asp
            260                 265                 270 gat cta ggt caa acc aca ctt gaa gtt ttc aaa gaa gat ggc aaa aca     864
Asp Leu Gly Gln Thr Thr Leu Glu Val Phe Lys Glu Asp Gly Lys Thr
        275                 280                 285 cta gta tca aaa aaa gta act tcc aaa gac aag tca tca aca gaa gaa     912
Leu Val Ser Lys Lys Val Thr Ser Lys Asp Lys Ser Ser Thr Glu Glu
    290                 295                 300 aaa ttc aat gaa aaa ggt gaa gta tct gaa aaa ata ata aca aga gca     960
Lys Phe Asn Glu Lys Gly Glu Val Ser Glu Lys Ile Ile Thr Arg Ala
```

```
                305                 310                 315                 320
gac gga acc aga ctt gaa tac aca gga att aaa agc gat gga tct gga      1008
Asp Gly Thr Arg Leu Glu Tyr Thr Gly Ile Lys Ser Asp Gly Ser Gly
                325                 330                 335 aaa gct aaa gag gtt tta aaa ggc tat gtt ctt gaa gga act cta act      1056
Lys Ala Lys Glu Val Leu Lys Gly Tyr Val Leu Glu Gly Thr Leu Thr
            340                 345                 350 gct gaa aaa aca aca ttg gtg gtt aaa gaa gga act gtt act tta agc      1104
Ala Glu Lys Thr Thr Leu Val Val Lys Glu Gly Thr Val Thr Leu Ser
        355                 360                 365 aaa aat att tca aaa tct ggg gaa gtt tca gtt gaa ctt aat gac act      1152
Lys Asn Ile Ser Lys Ser Gly Glu Val Ser Val Glu Leu Asn Asp Thr
    370                 375                 380 gac agt agt gct gct act aaa aaa act gca gct tgg aat tca aaa act      1200
Asp Ser Ser Ala Ala Thr Lys Lys Thr Ala Ala Trp Asn Ser Lys Thr
385                 390                 395                 400 tcc act tta aca att agt gtg aat agc caa aaa acc aaa aac ctt gta      1248
Ser Thr Leu Thr Ile Ser Val Asn Ser Gln Lys Thr Lys Asn Leu Val
                405                 410                 415 ttc aca aaa gaa gac aca ata aca gta caa aaa tac gac tca gca ggc      1296
Phe Thr Lys Glu Asp Thr Ile Thr Val Gln Lys Tyr Asp Ser Ala Gly
            420                 425                 430 acc aat cta gaa ggc aaa gca gtc gaa att aca aca ctt aaa gaa ctt      1344
Thr Asn Leu Glu Gly Lys Ala Val Glu Ile Thr Thr Leu Lys Glu Leu
        435                 440                 445 aaa aac gct tta aaa taa                                              1362
Lys Asn Ala Leu Lys *
    450

<210> SEQ ID NO 62
<211> LENGTH: 453
<212> TYPE: PRT
<213> ORGANISM: Artificial Sequence
<220> FEATURE:
<223> OTHER INFORMATION: Chimeric protein

<400> SEQUENCE: 62

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175
```

```
Asn Ser Val Lys Glu Leu Thr Ser Pro Val Ala Glu Ser Pro Lys
            180                 185                 190

Lys Pro Ser Met Ala Lys Gln Asn Val Ser Ser Leu Asp Glu Lys Asn
        195                 200                 205

Ser Val Ser Val Asp Leu Pro Gly Glu Met Lys Val Leu Val Ser Lys
    210                 215                 220

Glu Lys Asn Lys Asp Gly Lys Tyr Asp Leu Ile Ala Thr Val Asp Lys
225                 230                 235                 240

Leu Glu Leu Lys Gly Thr Ser Asp Lys Asn Asn Gly Ser Gly Val Leu
                245                 250                 255

Glu Gly Val Lys Ala Asp Lys Ser Lys Val Lys Leu Thr Ile Ser Asp
            260                 265                 270

Asp Leu Gly Gln Thr Thr Leu Glu Val Phe Lys Glu Asp Gly Lys Thr
        275                 280                 285

Leu Val Ser Lys Lys Val Thr Ser Lys Asp Lys Ser Ser Thr Glu Glu
    290                 295                 300

Lys Phe Asn Glu Lys Gly Glu Val Ser Glu Lys Ile Ile Thr Arg Ala
305                 310                 315                 320

Asp Gly Thr Arg Leu Glu Tyr Thr Gly Ile Lys Ser Asp Gly Ser Gly
                325                 330                 335

Lys Ala Lys Glu Val Leu Lys Gly Tyr Val Leu Glu Gly Thr Leu Thr
            340                 345                 350

Ala Glu Lys Thr Thr Leu Val Val Lys Glu Gly Thr Val Thr Leu Ser
        355                 360                 365

Lys Asn Ile Ser Lys Ser Gly Glu Val Ser Val Glu Leu Asn Asp Thr
    370                 375                 380

Asp Ser Ser Ala Ala Thr Lys Lys Thr Ala Ala Trp Asn Ser Lys Thr
385                 390                 395                 400

Ser Thr Leu Thr Ile Ser Val Asn Ser Gln Lys Thr Lys Asn Leu Val
                405                 410                 415

Phe Thr Lys Glu Asp Thr Ile Thr Val Gln Lys Tyr Asp Ser Ala Gly
            420                 425                 430

Thr Asn Leu Glu Gly Lys Ala Val Glu Ile Thr Thr Leu Lys Glu Leu
        435                 440                 445

Lys Asn Ala Leu Lys
    450

<210> SEQ ID NO 63
<211> LENGTH: 1341
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1341)

<400> SEQUENCE: 63 atg gct tgt aat aat tca ggg aaa gat ggg aat aca tct gca aat tct      48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
                20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
            35                  40                  45 ttg ctg tca tct ata gat gag ctt gct aaa gct att ggt aaa aaa ata     192
```

-continued

| | | | | | | | | | | | | | | | | |
|---|---|---|---|---|---|---|---|---|---|---|---|---|---|---|---|---|
| Leu | Leu | Ser | Ser | Ile | Asp | Glu | Leu | Ala | Lys | Ala | Ile | Gly | Lys | Lys | Ile | |
| | 50 | | | | 55 | | | | 60 | | | | | | | |

| aaa | aac | gat | ggt | agt | tta | gat | aat | gaa | gca | aat | cgc | aac | gag | tca | ttg | 240 |
|---|---|---|---|---|---|---|---|---|---|---|---|---|---|---|---|---|
| Lys | Asn | Asp | Gly | Ser | Leu | Asp | Asn | Glu | Ala | Asn | Arg | Asn | Glu | Ser | Leu | |
| 65 | | | | | 70 | | | | | 75 | | | | | 80 | |

| tta | gca | gga | gct | tat | aca | ata | tca | acc | tta | ata | aca | caa | aaa | tta | agt | 288 |
|---|---|---|---|---|---|---|---|---|---|---|---|---|---|---|---|---|
| Leu | Ala | Gly | Ala | Tyr | Thr | Ile | Ser | Thr | Leu | Ile | Thr | Gln | Lys | Leu | Ser | |
| | | | | 85 | | | | | 90 | | | | | 95 | | |

| aaa | tta | aac | gga | tca | gaa | ggt | tta | aag | gaa | aag | att | gcc | gca | gct | aag | 336 |
|---|---|---|---|---|---|---|---|---|---|---|---|---|---|---|---|---|
| Lys | Leu | Asn | Gly | Ser | Glu | Gly | Leu | Lys | Glu | Lys | Ile | Ala | Ala | Ala | Lys | |
| | | | 100 | | | | | 105 | | | | | 110 | | | |

| aaa | tgc | tct | gaa | gag | ttt | agt | act | aaa | cta | aaa | gat | aat | cat | gca | cag | 384 |
|---|---|---|---|---|---|---|---|---|---|---|---|---|---|---|---|---|
| Lys | Cys | Ser | Glu | Glu | Phe | Ser | Thr | Lys | Leu | Lys | Asp | Asn | His | Ala | Gln | |
| | | 115 | | | | | 120 | | | | | 125 | | | | |

| ctt | ggt | ata | cag | ggc | gtt | act | gat | gaa | aat | gca | aaa | aaa | gct | att | tta | 432 |
|---|---|---|---|---|---|---|---|---|---|---|---|---|---|---|---|---|
| Leu | Gly | Ile | Gln | Gly | Val | Thr | Asp | Glu | Asn | Ala | Lys | Lys | Ala | Ile | Leu | |
| | 130 | | | | | 135 | | | | | 140 | | | | | |

| aaa | gca | aat | gca | gcg | ggt | aaa | gat | aag | ggc | gtt | gaa | gaa | ctt | gaa | aag | 480 |
|---|---|---|---|---|---|---|---|---|---|---|---|---|---|---|---|---|
| Lys | Ala | Asn | Ala | Ala | Gly | Lys | Asp | Lys | Gly | Val | Glu | Glu | Leu | Glu | Lys | |
| 145 | | | | | 150 | | | | | 155 | | | | | 160 | |

| ttg | tcc | gga | tca | tta | gaa | agc | tta | tca | aaa | gca | gct | aaa | gag | atg | ctt | 528 |
|---|---|---|---|---|---|---|---|---|---|---|---|---|---|---|---|---|
| Leu | Ser | Gly | Ser | Leu | Glu | Ser | Leu | Ser | Lys | Ala | Ala | Lys | Glu | Met | Leu | |
| | | | | 165 | | | | | 170 | | | | | 175 | | |

| gct | aat | tca | gtt | aaa | gag | ctt | aca | agc | cct | gtt | gtc | cat | ggc | aag | caa | 576 |
|---|---|---|---|---|---|---|---|---|---|---|---|---|---|---|---|---|
| Ala | Asn | Ser | Val | Lys | Glu | Leu | Thr | Ser | Pro | Val | Val | His | Gly | Lys | Gln | |
| | | 180 | | | | | 185 | | | | | 190 | | | | |

| aat | gtt | agc | agc | ctt | gac | gag | aaa | aac | agc | gtt | tca | gta | gat | ttg | cct | 624 |
|---|---|---|---|---|---|---|---|---|---|---|---|---|---|---|---|---|
| Asn | Val | Ser | Ser | Leu | Asp | Glu | Lys | Asn | Ser | Val | Ser | Val | Asp | Leu | Pro | |
| | | 195 | | | | | 200 | | | | | 205 | | | | |

| ggt | gaa | atg | aaa | gtt | ctt | gta | agc | aaa | gaa | aaa | aac | aaa | gac | ggc | aag | 672 |
|---|---|---|---|---|---|---|---|---|---|---|---|---|---|---|---|---|
| Gly | Glu | Met | Lys | Val | Leu | Val | Ser | Lys | Glu | Lys | Asn | Lys | Asp | Gly | Lys | |
| | 210 | | | | | 215 | | | | | 220 | | | | | |

| tac | gat | cta | att | gca | aca | gta | gac | aag | ctt | gag | ctt | aaa | gga | act | tct | 720 |
|---|---|---|---|---|---|---|---|---|---|---|---|---|---|---|---|---|
| Tyr | Asp | Leu | Ile | Ala | Thr | Val | Asp | Lys | Leu | Glu | Leu | Lys | Gly | Thr | Ser | |
| 225 | | | | | 230 | | | | | 235 | | | | | 240 | |

| gat | aaa | aac | aat | gga | tct | gga | gta | ctt | gaa | ggc | gta | aaa | gct | gac | aaa | 768 |
|---|---|---|---|---|---|---|---|---|---|---|---|---|---|---|---|---|
| Asp | Lys | Asn | Asn | Gly | Ser | Gly | Val | Leu | Glu | Gly | Val | Lys | Ala | Asp | Lys | |
| | | | | 245 | | | | | 250 | | | | | 255 | | |

| agt | aaa | gta | aaa | tta | aca | att | tct | gac | gat | cta | ggt | caa | acc | aca | ctt | 816 |
|---|---|---|---|---|---|---|---|---|---|---|---|---|---|---|---|---|
| Ser | Lys | Val | Lys | Leu | Thr | Ile | Ser | Asp | Asp | Leu | Gly | Gln | Thr | Thr | Leu | |
| | | | 260 | | | | | 265 | | | | | 270 | | | |

| gaa | gtt | ttc | aaa | gaa | gat | ggc | aaa | aca | cta | gta | tca | aaa | aaa | gta | act | 864 |
|---|---|---|---|---|---|---|---|---|---|---|---|---|---|---|---|---|
| Glu | Val | Phe | Lys | Glu | Asp | Gly | Lys | Thr | Leu | Val | Ser | Lys | Lys | Val | Thr | |
| | | 275 | | | | | 280 | | | | | 285 | | | | |

| tcc | aaa | gac | aag | tca | tca | aca | gaa | gaa | aaa | ttc | aat | gaa | aaa | ggt | gaa | 912 |
|---|---|---|---|---|---|---|---|---|---|---|---|---|---|---|---|---|
| Ser | Lys | Asp | Lys | Ser | Ser | Thr | Glu | Glu | Lys | Phe | Asn | Glu | Lys | Gly | Glu | |
| | 290 | | | | | 295 | | | | | 300 | | | | | |

| gta | tct | gaa | aaa | ata | ata | aca | aga | gca | gac | gga | acc | aga | ctt | gaa | tac | 960 |
|---|---|---|---|---|---|---|---|---|---|---|---|---|---|---|---|---|
| Val | Ser | Glu | Lys | Ile | Ile | Thr | Arg | Ala | Asp | Gly | Thr | Arg | Leu | Glu | Tyr | |
| 305 | | | | | 310 | | | | | 315 | | | | | 320 | |

| aca | gga | att | aaa | agc | gat | gga | tct | gga | aaa | gct | aaa | gag | gtt | tta | aaa | 1008 |
|---|---|---|---|---|---|---|---|---|---|---|---|---|---|---|---|---|
| Thr | Gly | Ile | Lys | Ser | Asp | Gly | Ser | Gly | Lys | Ala | Lys | Glu | Val | Leu | Lys | |
| | | | | 325 | | | | | 330 | | | | | 335 | | |

| ggc | tat | gtt | ctt | gaa | gga | act | cta | act | gct | gaa | aaa | aca | aca | ttg | gtg | 1056 |
|---|---|---|---|---|---|---|---|---|---|---|---|---|---|---|---|---|
| Gly | Tyr | Val | Leu | Glu | Gly | Thr | Leu | Thr | Ala | Glu | Lys | Thr | Thr | Leu | Val | |
| | | | 340 | | | | | 345 | | | | | 350 | | | |

| gtt | aaa | gaa | gga | act | gtt | act | tta | agc | aaa | aat | att | tca | aaa | tct | ggg | 1104 |
|---|---|---|---|---|---|---|---|---|---|---|---|---|---|---|---|---|
| Val | Lys | Glu | Gly | Thr | Val | Thr | Leu | Ser | Lys | Asn | Ile | Ser | Lys | Ser | Gly | |
| | | 355 | | | | | 360 | | | | | 365 | | | | |

| gaa | gtt | tca | gtt | gaa | ctt | aat | gac | act | gac | agt | agt | gct | gct | act | aaa | 1152 |
|---|---|---|---|---|---|---|---|---|---|---|---|---|---|---|---|---|

-continued

```
            Glu Val Ser Val Glu Leu Asn Asp Thr Asp Ser Ser Ala Ala Thr Lys
                370                 375                 380 aaa act gca gct tgg aat tca aaa act tcc act tta aca att agt gtg       1200
Lys Thr Ala Ala Trp Asn Ser Lys Thr Ser Thr Leu Thr Ile Ser Val
385                 390                 395                 400 aat agc caa aaa acc aaa aac ctt gta ttc aca aaa gaa gac aca ata       1248
Asn Ser Gln Lys Thr Lys Asn Leu Val Phe Thr Lys Glu Asp Thr Ile
                405                 410                 415 aca gta caa aaa tac gac tca gca ggc acc aat cta gaa ggc aaa gca       1296
Thr Val Gln Lys Tyr Asp Ser Ala Gly Thr Asn Leu Glu Gly Lys Ala
                420                 425                 430 gtc gaa att aca aca ctt aaa gaa ctt aaa aac gct tta aaa taa           1341
Val Glu Ile Thr Thr Leu Lys Glu Leu Lys Asn Ala Leu Lys *
                435                 440                 445
```

<210> SEQ ID NO 64
<211> LENGTH: 446
<212> TYPE: PRT
<213> ORGANISM: Artificial Sequence
<220> FEATURE:
<223> OTHER INFORMATION: Chimeric protein

<400> SEQUENCE: 64

```
Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
                20                  25                  30

Ile Thr Asp Ser Asn Ala Val Leu Leu Ala Val Lys Glu Val Glu Ala
                35                  40                  45

Leu Leu Ser Ser Ile Asp Glu Leu Ala Lys Ala Ile Gly Lys Lys Ile
        50                  55                  60

Lys Asn Asp Gly Ser Leu Asp Asn Glu Ala Asn Arg Asn Glu Ser Leu
65              70                  75                  80

Leu Ala Gly Ala Tyr Thr Ile Ser Thr Leu Ile Thr Gln Lys Leu Ser
                85                  90                  95

Lys Leu Asn Gly Ser Glu Gly Leu Lys Glu Lys Ile Ala Ala Ala Lys
                100                 105                 110

Lys Cys Ser Glu Glu Phe Ser Thr Lys Leu Lys Asp Asn His Ala Gln
                115                 120                 125

Leu Gly Ile Gln Gly Val Thr Asp Glu Asn Ala Lys Lys Ala Ile Leu
        130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Lys Gln
                180                 185                 190

Asn Val Ser Ser Leu Asp Glu Lys Asn Ser Val Ser Val Asp Leu Pro
                195                 200                 205

Gly Glu Met Lys Val Leu Val Ser Lys Glu Lys Asn Lys Asp Gly Lys
        210                 215                 220

Tyr Asp Leu Ile Ala Thr Val Asp Lys Leu Glu Leu Lys Gly Thr Ser
225                 230                 235                 240

Asp Lys Asn Asn Gly Ser Gly Val Leu Glu Gly Val Lys Ala Asp Lys
                245                 250                 255

Ser Lys Val Lys Leu Thr Ile Ser Asp Asp Leu Gly Gln Thr Thr Leu
                260                 265                 270
```

```
Glu Val Phe Lys Glu Asp Gly Lys Thr Leu Val Ser Lys Val Thr
        275                 280                 285

Ser Lys Asp Lys Ser Ser Thr Glu Glu Lys Phe Asn Glu Lys Gly Glu
290                 295                 300

Val Ser Glu Lys Ile Ile Thr Arg Ala Asp Gly Thr Arg Leu Glu Tyr
305                 310                 315                 320

Thr Gly Ile Lys Ser Asp Gly Ser Gly Lys Ala Lys Glu Val Leu Lys
                325                 330                 335

Gly Tyr Val Leu Glu Gly Thr Leu Thr Ala Glu Lys Thr Thr Leu Val
        340                 345                 350

Val Lys Glu Gly Thr Val Thr Leu Ser Lys Asn Ile Ser Lys Ser Gly
            355                 360                 365

Glu Val Ser Val Glu Leu Asn Asp Thr Asp Ser Ser Ala Ala Thr Lys
        370                 375                 380

Lys Thr Ala Ala Trp Asn Ser Lys Thr Ser Thr Leu Thr Ile Ser Val
385                 390                 395                 400

Asn Ser Gln Lys Thr Lys Asn Leu Val Phe Thr Lys Glu Asp Thr Ile
                405                 410                 415

Thr Val Gln Lys Tyr Asp Ser Ala Gly Thr Asn Leu Glu Gly Lys Ala
            420                 425                 430

Val Glu Ile Thr Thr Leu Lys Glu Leu Lys Asn Ala Leu Lys
        435                 440                 445

<210> SEQ ID NO 65
<211> LENGTH: 1362
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1362)

<400> SEQUENCE: 65 atg gct tgt aat aat tca ggg aaa gat ggg aat aca tct gca aat tct    48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata aat aaa aaa    96
Ala Asp Glu Ser Val Lys Gly Pro Asn Leu Thr Glu Ile Asn Lys Lys
            20                  25                  30 att acg tca tct aat gcg gtt tta ctt gct gtg aaa gag gtt gaa gcg   144
Ile Thr Ser Ser Asn Ala Val Leu Leu Ala Val Lys Glu Val Glu Ala
        35                  40                  45 ttg ctg gat tct ata gat gaa att gct gct aaa gct att ggt aaa aaa   192
Leu Leu Asp Ser Ile Asp Glu Ile Ala Ala Lys Ala Ile Gly Lys Lys
    50                  55                  60 ata cac caa aat aat ggt ttg gat acc gaa aat aat cac aat gga tca   240
Ile His Gln Asn Asn Gly Leu Asp Thr Glu Asn Asn His Asn Gly Ser
65                  70                  75                  80 ttg tta gcg gga gct tat gca ata tca acc cta ata aaa caa aaa tta   288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag   336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat   384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta   432
Leu Gly Lys Glu Gly Val Thr Asp Ala Asp Ala Lys Glu Ala Ile Leu
    130                 135                 140
```

-continued

| | |
|---|---|
| aaa gca aat ggt act aaa act aaa ggt gct gaa gaa ctt gga aaa tta<br>Lys Ala Asn Gly Thr Lys Thr Lys Gly Ala Glu Glu Leu Gly Lys Leu<br>145     150     155     160 | 480 |
| ttt gaa tca gta gag gtc ttg tca aaa gca gct aaa gag atg ctt gct<br>Phe Glu Ser Val Glu Val Leu Ser Lys Ala Ala Lys Glu Met Leu Ala<br>     165     170     175 | 528 |
| aat tca gtt aaa gag ctt aca agc cct gtt gtg gca gaa agt cca aaa<br>Asn Ser Val Lys Glu Leu Thr Ser Pro Val Val Ala Glu Ser Pro Lys<br>  180     185     190 | 576 |
| aaa cct tcc atg gcc aag caa aat gtt agc agc ctt gac gag aaa aac<br>Lys Pro Ser Met Ala Lys Gln Asn Val Ser Ser Leu Asp Glu Lys Asn<br>195     200     205 | 624 |
| agc gtt tca gta gat ttg cct ggt gaa atg aaa gtt ctt gta agc aaa<br>Ser Val Ser Val Asp Leu Pro Gly Glu Met Lys Val Leu Val Ser Lys<br>210     215     220 | 672 |
| gaa aaa aac aaa gac ggc aag tac gat cta att gca aca gta gac aag<br>Glu Lys Asn Lys Asp Gly Lys Tyr Asp Leu Ile Ala Thr Val Asp Lys<br>225     230     235     240 | 720 |
| ctt gag ctt aaa gga act tct gat aaa aac aat gga tct gga gta ctt<br>Leu Glu Leu Lys Gly Thr Ser Asp Lys Asn Asn Gly Ser Gly Val Leu<br>     245     250     255 | 768 |
| gaa ggc gta aaa gct gac aaa agt aaa gta aaa tta aca att tct gac<br>Glu Gly Val Lys Ala Asp Lys Ser Lys Val Lys Leu Thr Ile Ser Asp<br>  260     265     270 | 816 |
| gat cta ggt caa acc aca ctt gaa gtt ttc aaa gaa gat ggc aaa aca<br>Asp Leu Gly Gln Thr Thr Leu Glu Val Phe Lys Glu Asp Gly Lys Thr<br>275     280     285 | 864 |
| cta gta tca aaa aaa gta act tcc aaa gac aag tca tca aca gaa gaa<br>Leu Val Ser Lys Lys Val Thr Ser Lys Asp Lys Ser Ser Thr Glu Glu<br>290     295     300 | 912 |
| aaa ttc aat gaa aaa ggt gaa gta tct gaa aaa ata ata aca aga gca<br>Lys Phe Asn Glu Lys Gly Glu Val Ser Glu Lys Ile Ile Thr Arg Ala<br>305     310     315     320 | 960 |
| gac gga acc aga ctt gaa tac aca gga att aaa agc gat gga tct gga<br>Asp Gly Thr Arg Leu Glu Tyr Thr Gly Ile Lys Ser Asp Gly Ser Gly<br>     325     330     335 | 1008 |
| aaa gct aaa gag gtt tta aaa ggc tat gtt ctt gaa gga act cta act<br>Lys Ala Lys Glu Val Leu Lys Gly Tyr Val Leu Glu Gly Thr Leu Thr<br>  340     345     350 | 1056 |
| gct gaa aaa aca aca ttg gtg gtt aaa gaa gga act gtt act tta agc<br>Ala Glu Lys Thr Thr Leu Val Val Lys Glu Gly Thr Val Thr Leu Ser<br>355     360     365 | 1104 |
| aaa aat att tca aaa tct ggg gaa gtt tca gtt gaa ctt aat gac act<br>Lys Asn Ile Ser Lys Ser Gly Glu Val Ser Val Glu Leu Asn Asp Thr<br>370     375     380 | 1152 |
| gac agt agt gct gct act aaa aaa act gca gct tgg aat tca aaa act<br>Asp Ser Ser Ala Ala Thr Lys Lys Thr Ala Ala Trp Asn Ser Lys Thr<br>385     390     395     400 | 1200 |
| tct act tta aca att agt gtt aac agc aaa aaa act aca caa ctt gtg<br>Ser Thr Leu Thr Ile Ser Val Asn Ser Lys Lys Thr Thr Gln Leu Val<br>     405     410     415 | 1248 |
| ttt act aaa caa gac aca ata act gta caa aaa tac gac tcc gca ggt<br>Phe Thr Lys Gln Asp Thr Ile Thr Val Gln Lys Tyr Asp Ser Ala Gly<br>  420     425     430 | 1296 |
| acc aat tta gaa ggc aca gca gtc gaa att aaa aca ctt gat gaa ctt<br>Thr Asn Leu Glu Gly Thr Ala Val Glu Ile Lys Thr Leu Asp Glu Leu<br>435     440     445 | 1344 |
| aaa aac gct tta aaa taa<br>Lys Asn Ala Leu Lys *<br>     450 | 1362 |

<210> SEQ ID NO 66
<211> LENGTH: 453
<212> TYPE: PRT
<213> ORGANISM: Artificial Sequence
<220> FEATURE:
<223> OTHER INFORMATION: Chimeric protein

<400> SEQUENCE: 66

```
Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
             20                  25                  30

Ile Thr Ser Ser Asn Ala Val Leu Leu Ala Val Lys Glu Val Glu Ala
         35                  40                  45

Leu Leu Asp Ser Ile Asp Glu Ile Ala Ala Lys Ala Ile Gly Lys Lys
 50                  55                  60

Ile His Gln Asn Asn Gly Leu Asp Thr Glu Asn Asn His Asn Gly Ser
 65                  70                  75                  80

Leu Leu Ala Gly Ala Tyr Ala Ile Ser Thr Leu Ile Lys Gln Lys Leu
                 85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Ser Leu Asp Glu Lys Asn
        195                 200                 205

Ser Val Ser Val Asp Leu Pro Gly Glu Met Lys Val Leu Val Ser Lys
    210                 215                 220

Glu Lys Asn Lys Asp Gly Lys Tyr Asp Leu Ile Ala Thr Val Asp Lys
225                 230                 235                 240

Leu Glu Leu Lys Gly Thr Ser Asp Lys Asn Asn Gly Ser Gly Val Leu
                245                 250                 255

Glu Gly Val Lys Ala Asp Lys Ser Lys Val Lys Leu Thr Ile Ser Asp
            260                 265                 270

Asp Leu Gly Gln Thr Thr Leu Glu Val Phe Lys Glu Asp Gly Lys Thr
        275                 280                 285

Leu Val Ser Lys Lys Val Thr Ser Lys Asp Lys Ser Ser Thr Glu Glu
    290                 295                 300

Lys Phe Asn Glu Lys Gly Glu Val Ser Glu Lys Ile Ile Thr Arg Ala
305                 310                 315                 320

Asp Gly Thr Arg Leu Glu Tyr Thr Gly Ile Lys Ser Asp Gly Ser Gly
                325                 330                 335

Lys Ala Lys Glu Val Leu Lys Gly Tyr Val Leu Glu Gly Thr Leu Thr
            340                 345                 350

Ala Glu Lys Thr Thr Leu Val Val Lys Glu Gly Thr Val Thr Leu Ser
        355                 360                 365
```

```
Lys Asn Ile Ser Lys Ser Gly Glu Val Ser Val Glu Leu Asn Asp Thr
        370                 375                 380

Asp Ser Ser Ala Ala Thr Lys Lys Thr Ala Ala Trp Asn Ser Lys Thr
385                 390                 395                 400

Ser Thr Leu Thr Ile Ser Val Asn Ser Lys Lys Thr Thr Gln Leu Val
                405                 410                 415

Phe Thr Lys Gln Asp Thr Ile Thr Val Gln Lys Tyr Asp Ser Ala Gly
            420                 425                 430

Thr Asn Leu Glu Gly Thr Ala Val Glu Ile Lys Thr Leu Asp Glu Leu
        435                 440                 445

Lys Asn Ala Leu Lys
        450

<210> SEQ ID NO 67
<211> LENGTH: 1341
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1341)

<400> SEQUENCE: 67 atg gct tgt aat aat tca ggg aaa gat ggg aat aca tct gca aat tct      48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
            20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
        35                  40                  45 ttg ctg tca tct ata gat gag ctt gct aaa gct att ggt aaa aaa ata     192
Leu Leu Ser Ser Ile Asp Glu Leu Ala Lys Ala Ile Gly Lys Lys Ile
    50                  55                  60 aaa aac gat ggt agt tta gat aat gaa gca aat cgc aac gag tca ttg     240
Lys Asn Asp Gly Ser Leu Asp Asn Glu Ala Asn Arg Asn Glu Ser Leu
65                  70                  75                  80 tta gca gga gct tat aca ata tca acc tta ata aca caa aaa tta agt     288
Leu Ala Gly Ala Tyr Thr Ile Ser Thr Leu Ile Thr Gln Lys Leu Ser
                85                  90                  95 aaa tta aac gga tca gaa ggt tta aag gaa aag att gcc gca gct aag     336
Lys Leu Asn Gly Ser Glu Gly Leu Lys Glu Lys Ile Ala Ala Ala Lys
            100                 105                 110 aaa tgc tct gaa gag ttt agt act aaa cta aaa gat aat cat gca cag     384
Lys Cys Ser Glu Glu Phe Ser Thr Lys Leu Lys Asp Asn His Ala Gln
        115                 120                 125 ctt ggt ata cag ggc gtt act gat gaa aat gca aaa aaa gct att tta     432
Leu Gly Ile Gln Gly Val Thr Asp Glu Asn Ala Lys Lys Ala Ile Leu
    130                 135                 140 aaa gca aat gca gcg ggt aaa gat aag ggc gtt gaa gaa ctt gaa aag     480
Lys Ala Asn Ala Ala Gly Lys Asp Lys Gly Val Glu Glu Leu Glu Lys
145                 150                 155                 160 ttg tcc gga tca tta gaa agc tta tca aaa gca gct aaa gag atg ctt     528
Leu Ser Gly Ser Leu Glu Ser Leu Ser Lys Ala Ala Lys Glu Met Leu
                165                 170                 175 gct aat tca gtt aaa gag ctt aca agc cct gtt gtc cat ggc aag caa     576
Ala Asn Ser Val Lys Glu Leu Thr Ser Pro Val Val His Gly Lys Gln
            180                 185                 190 aat gtt agc agc ctt gac gag aaa aac agc gtt tca gta gat ttg cct     624
Asn Val Ser Ser Leu Asp Glu Lys Asn Ser Val Ser Val Asp Leu Pro
```

```
                    195                 200                 205
ggt gaa atg aaa gtt ctt gta agc aaa gaa aaa aac aaa gac ggc aag       672
Gly Glu Met Lys Val Leu Val Ser Lys Glu Lys Asn Lys Asp Gly Lys
        210                 215                 220 tac gat cta att gca aca gta gac aag ctt gag ctt aaa gga act tct       720
Tyr Asp Leu Ile Ala Thr Val Asp Lys Leu Glu Leu Lys Gly Thr Ser
225                 230                 235                 240 gat aaa aac aat gga tct gga gta ctt gaa ggc gta aaa gct gac aaa       768
Asp Lys Asn Asn Gly Ser Gly Val Leu Glu Gly Val Lys Ala Asp Lys
                245                 250                 255 agt aaa gta aaa tta aca att tct gac gat cta ggt caa acc aca ctt       816
Ser Lys Val Lys Leu Thr Ile Ser Asp Asp Leu Gly Gln Thr Thr Leu
            260                 265                 270 gaa gtt ttc aaa gaa gat ggc aaa aca cta gta tca aaa aaa gta act       864
Glu Val Phe Lys Glu Asp Gly Lys Thr Leu Val Ser Lys Lys Val Thr
        275                 280                 285 tcc aaa gac aag tca tca aca gaa gaa aaa ttc aat gaa aaa ggt gaa       912
Ser Lys Asp Lys Ser Ser Thr Glu Glu Lys Phe Asn Glu Lys Gly Glu
    290                 295                 300 gta tct gaa aaa ata ata aca aga gca gac gga acc aga ctt gaa tac       960
Val Ser Glu Lys Ile Ile Thr Arg Ala Asp Gly Thr Arg Leu Glu Tyr
305                 310                 315                 320 aca gga att aaa agc gat gga tct gga aaa gct aaa gag gtt tta aaa      1008
Thr Gly Ile Lys Ser Asp Gly Ser Gly Lys Ala Lys Glu Val Leu Lys
                325                 330                 335 ggc tat gtt ctt gaa gga act cta act gct gaa aaa aca aca ttg gtg      1056
Gly Tyr Val Leu Glu Gly Thr Leu Thr Ala Glu Lys Thr Thr Leu Val
            340                 345                 350 gtt aaa gaa gga act gtt act tta agc aaa aat att tca aaa tct ggg      1104
Val Lys Glu Gly Thr Val Thr Leu Ser Lys Asn Ile Ser Lys Ser Gly
        355                 360                 365 gaa gtt tca gtt gaa ctt aat gac act gac agt agt gct gct act aaa      1152
Glu Val Ser Val Glu Leu Asn Asp Thr Asp Ser Ser Ala Ala Thr Lys
    370                 375                 380 aaa act gca gct tgg aat tca aaa act tct act tta aca att agt gtt      1200
Lys Thr Ala Ala Trp Asn Ser Lys Thr Ser Thr Leu Thr Ile Ser Val
385                 390                 395                 400 aac agc aaa aaa act aca caa ctt gtg ttt act aaa caa tac aca ata      1248
Asn Ser Lys Lys Thr Thr Gln Leu Val Phe Thr Lys Gln Tyr Thr Ile
                405                 410                 415 act gta aaa caa tac gac tcc gca ggt acc aat tta gaa ggc aca gca      1296
Thr Val Lys Gln Tyr Asp Ser Ala Gly Thr Asn Leu Glu Gly Thr Ala
            420                 425                 430 gtc gaa att aaa aca ctt gat gaa ctt aaa aac gct tta aaa taa          1341
Val Glu Ile Lys Thr Leu Asp Glu Leu Lys Asn Ala Leu Lys *
        435                 440                 445

<210> SEQ ID NO 68
<211> LENGTH: 446
<212> TYPE: PRT
<213> ORGANISM: Artificial Sequence
<220> FEATURE:
<223> OTHER INFORMATION: Chimeric protein

<400> SEQUENCE: 68

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45
```

Leu Leu Ser Ser Ile Asp Glu Leu Ala Lys Ala Ile Gly Lys Lys Ile
 50                  55                  60

Lys Asn Asp Gly Ser Leu Asp Asn Glu Ala Asn Arg Asn Glu Ser Leu
 65                  70                  75                  80

Leu Ala Gly Ala Tyr Thr Ile Ser Thr Leu Ile Thr Gln Lys Leu Ser
                 85                  90                  95

Lys Leu Asn Gly Ser Glu Gly Leu Lys Glu Lys Ile Ala Ala Ala Lys
             100                 105                 110

Lys Cys Ser Glu Glu Phe Ser Thr Lys Leu Lys Asp Asn His Ala Gln
         115                 120                 125

Leu Gly Ile Gln Gly Val Thr Asp Glu Asn Ala Lys Lys Ala Ile Leu
 130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Lys Gln
            180                 185                 190

Asn Val Ser Ser Leu Asp Glu Lys Asn Ser Val Ser Val Asp Leu Pro
        195                 200                 205

Gly Glu Met Lys Val Leu Val Ser Lys Glu Lys Asn Lys Asp Gly Lys
210                 215                 220

Tyr Asp Leu Ile Ala Thr Val Asp Lys Leu Glu Leu Lys Gly Thr Ser
225                 230                 235                 240

Asp Lys Asn Asn Gly Ser Gly Val Leu Glu Gly Val Lys Ala Asp Lys
                245                 250                 255

Ser Lys Val Lys Leu Thr Ile Ser Asp Asp Leu Gly Gln Thr Thr Leu
            260                 265                 270

Glu Val Phe Lys Glu Asp Gly Lys Thr Leu Val Ser Lys Lys Val Thr
        275                 280                 285

Ser Lys Asp Lys Ser Ser Thr Glu Glu Lys Phe Asn Glu Lys Gly Glu
290                 295                 300

Val Ser Glu Lys Ile Ile Thr Arg Ala Asp Gly Thr Arg Leu Glu Tyr
305                 310                 315                 320

Thr Gly Ile Lys Ser Asp Gly Ser Gly Lys Ala Lys Glu Val Leu Lys
                325                 330                 335

Gly Tyr Val Leu Glu Gly Thr Leu Thr Ala Glu Lys Thr Thr Leu Val
            340                 345                 350

Val Lys Glu Gly Thr Val Thr Leu Ser Lys Asn Ile Ser Lys Ser Gly
        355                 360                 365

Glu Val Ser Val Glu Leu Asn Asp Thr Asp Ser Ser Ala Ala Thr Lys
370                 375                 380

Lys Thr Ala Ala Trp Asn Ser Lys Thr Ser Thr Leu Thr Ile Ser Val
385                 390                 395                 400

Asn Ser Lys Lys Thr Thr Gln Leu Val Phe Thr Lys Gln Tyr Thr Ile
                405                 410                 415

Thr Val Lys Gln Tyr Asp Ser Ala Gly Thr Asn Leu Glu Gly Thr Ala
            420                 425                 430

Val Glu Ile Lys Thr Leu Asp Glu Leu Lys Asn Ala Leu Lys
        435                 440                 445

<210> SEQ ID NO 69
<211> LENGTH: 1365
<212> TYPE: DNA

<213> ORGANISM: Artificial Sequence
<220> FEATURE:
<223> OTHER INFORMATION: Chimeric nucleic acid
<221> NAME/KEY: CDS
<222> LOCATION: (1)...(1365)

<400> SEQUENCE: 69

```
atg gct tgt aat aat tca ggg aaa gat ggg aat aca tct gca aat tct      48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
            20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
        35                  40                  45 ttg ctg tca tct ata gat gaa att gct gct aaa gct att ggt aaa aaa     192
Leu Leu Ser Ser Ile Asp Glu Ile Ala Ala Lys Ala Ile Gly Lys Lys
    50                  55                  60 ata cac caa aat aat ggt ttg gat acc gaa tat aat cac aat gga tca     240
Ile His Gln Asn Asn Gly Leu Asp Thr Glu Tyr Asn His Asn Gly Ser
65                  70                  75                  80 ttg tta gcg gga gct tat gca ata tca acc cta ata aaa caa aaa tta     288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag     336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat     384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta     432
Leu Gly Lys Glu Gly Val Thr Asp Ala Asp Ala Lys Glu Ala Ile Leu
    130                 135                 140 aaa aca aat ggt act aaa act aaa ggt gct gaa gaa ctt gga aaa tta     480
Lys Thr Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct     528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa     576
Asn Ser Val Lys Glu Leu Thr Ser Pro Val Val Ala Glu Ser Pro Lys
            180                 185                 190 aaa cct tcc atg gcc aag caa aat gtt agc agc ctt gat gaa aaa aat     624
Lys Pro Ser Met Ala Lys Gln Asn Val Ser Ser Leu Asp Glu Lys Asn
        195                 200                 205 agc gtt tca gta gat tta cct ggt gga atg aca gtt ctt gta agt aaa     672
Ser Val Ser Val Asp Leu Pro Gly Gly Met Thr Val Leu Val Ser Lys
    210                 215                 220 gaa aaa gac aaa gac ggt aaa tac agt cta gag gca aca gta gac aag     720
Glu Lys Asp Lys Asp Gly Lys Tyr Ser Leu Glu Ala Thr Val Asp Lys
225                 230                 235                 240 ctt gag ctt aaa gga act tct gat aaa aac aac ggt tct gga aca ctt     768
Leu Glu Leu Lys Gly Thr Ser Asp Lys Asn Asn Gly Ser Gly Thr Leu
                245                 250                 255 gaa ggt gaa aaa act gac aaa agt aaa gta aaa tta aca att gct gat     816
Glu Gly Glu Lys Thr Asp Lys Ser Lys Val Lys Leu Thr Ile Ala Asp
            260                 265                 270 gac cta agt caa act aaa ttt gaa att ttc aaa gaa gat gcc aaa aca     864
Asp Leu Ser Gln Thr Lys Phe Glu Ile Phe Lys Glu Asp Ala Lys Thr
        275                 280                 285
```

```
tta gta tca aaa aaa gta acc ctt aaa gac aag tca tca aca gaa gaa      912
Leu Val Ser Lys Lys Val Thr Leu Lys Asp Lys Ser Ser Thr Glu Glu
    290                 295                 300 aaa ttc aac gaa aag ggt gaa aca tct gaa aaa aca ata gta aga gca      960
Lys Phe Asn Glu Lys Gly Glu Thr Ser Glu Lys Thr Ile Val Arg Ala
305                 310                 315                 320 aat gga acc aga ctt gaa tac aca gac ata aaa agc gat gga tcc gga     1008
Asn Gly Thr Arg Leu Glu Tyr Thr Asp Ile Lys Ser Asp Gly Ser Gly
                325                 330                 335 aaa gct aaa gaa gtt tta aaa gac ttt act ctt gaa gga act cta gct     1056
Lys Ala Lys Glu Val Leu Lys Asp Phe Thr Leu Glu Gly Thr Leu Ala
            340                 345                 350 gct gac ggc aaa aca aca ttg aaa gtt aca gaa gga act gtt gtt tta     1104
Ala Asp Gly Lys Thr Thr Leu Lys Val Thr Glu Gly Thr Val Val Leu
        355                 360                 365 agc aag aac att tta aaa tcc gga gaa ata aca gtt gca ctt gat gac     1152
Ser Lys Asn Ile Leu Lys Ser Gly Glu Ile Thr Val Ala Leu Asp Asp
    370                 375                 380 tct gac act act cag gct act aaa aaa act gga aaa tgg gat tca aat     1200
Ser Asp Thr Thr Gln Ala Thr Lys Lys Thr Gly Lys Trp Asp Ser Asn
385                 390                 395                 400 act tcc act tta aca att agt gtg aat agc aaa aaa act aaa aac att     1248
Thr Ser Thr Leu Thr Ile Ser Val Asn Ser Lys Lys Thr Lys Asn Ile
                405                 410                 415 gta ttt aca aaa gaa gac aca ata aca gta caa aaa tac gac tca gca     1296
Val Phe Thr Lys Glu Asp Thr Ile Thr Val Gln Lys Tyr Asp Ser Ala
            420                 425                 430 ggc acc aat cta gaa ggc aac gca gtc gaa att aaa aca ctt gat gaa     1344
Gly Thr Asn Leu Glu Gly Asn Ala Val Glu Ile Lys Thr Leu Asp Glu
        435                 440                 445 ctt aaa aac gct tta aaa tag                                          1365
Leu Lys Asn Ala Leu Lys  *
    450

<210> SEQ ID NO 70
<211> LENGTH: 454
<212> TYPE: PRT
<213> ORGANISM: Artificial Sequence
<220> FEATURE:
<223> OTHER INFORMATION: Chimeric protein

<400> SEQUENCE: 70

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Tyr Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Leu Glu Lys His Thr Asp
        115                 120                 125

Leu Gly Lys Glu Gly Val Thr Asp Ala Asp Ala Lys Glu Ala Ile Leu
    130                 135                 140
```

```
Lys Thr Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Ser Leu Asp Glu Lys Asn
        195                 200                 205

Ser Val Ser Val Asp Leu Pro Gly Gly Met Thr Val Leu Val Ser Lys
    210                 215                 220

Glu Lys Asp Lys Asp Gly Lys Tyr Ser Leu Glu Ala Thr Val Asp Lys
225                 230                 235                 240

Leu Glu Leu Lys Gly Thr Ser Asp Lys Asn Asn Gly Ser Gly Thr Leu
                245                 250                 255

Glu Gly Glu Lys Thr Asp Lys Ser Lys Val Lys Leu Thr Ile Ala Asp
            260                 265                 270

Asp Leu Ser Gln Thr Lys Phe Glu Ile Phe Lys Glu Asp Ala Lys Thr
        275                 280                 285

Leu Val Ser Lys Lys Val Thr Leu Lys Asp Lys Ser Ser Thr Glu Glu
    290                 295                 300

Lys Phe Asn Glu Lys Gly Glu Thr Ser Glu Lys Thr Ile Val Arg Ala
305                 310                 315                 320

Asn Gly Thr Arg Leu Glu Tyr Thr Asp Ile Lys Ser Asp Gly Ser Gly
                325                 330                 335

Lys Ala Lys Glu Val Leu Lys Asp Phe Thr Leu Glu Gly Thr Leu Ala
            340                 345                 350

Ala Asp Gly Lys Thr Thr Leu Lys Val Thr Glu Gly Thr Val Val Leu
        355                 360                 365

Ser Lys Asn Ile Leu Lys Ser Gly Glu Ile Thr Val Ala Leu Asp Asp
    370                 375                 380

Ser Asp Thr Thr Gln Ala Thr Lys Lys Thr Gly Lys Trp Asp Ser Asn
385                 390                 395                 400

Thr Ser Thr Leu Thr Ile Ser Val Asn Ser Lys Lys Thr Lys Asn Ile
                405                 410                 415

Val Phe Thr Lys Glu Asp Thr Ile Thr Val Gln Lys Tyr Asp Ser Ala
            420                 425                 430

Gly Thr Asn Leu Glu Gly Asn Ala Val Glu Ile Lys Thr Leu Asp Glu
        435                 440                 445

Leu Lys Asn Ala Leu Lys
    450

<210> SEQ ID NO 71
<211> LENGTH: 1344
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1344)

<400> SEQUENCE: 71 atg gct tgt aat aat tca ggg aaa gat ggg aat aca tct gca aat tct      48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
            20                  25                  30
```

| | | | | | | | | | | | | | | | | |
|---|---|---|---|---|---|---|---|---|---|---|---|---|---|---|---|---|
| att | acg | gat | tct | aat | gcg | gtt | tta | ctt | gct | gtg | aaa | gag | gtt | gaa | gcg | 144 |
| Ile | Thr | Asp | Ser | Asn | Ala | Val | Leu | Leu | Ala | Val | Lys | Glu | Val | Glu | Ala | |
| | | 35 | | | | 40 | | | | 45 | | | | | | |
| ttg | ctg | tca | tct | ata | gat | gag | ctt | gct | aaa | gct | att | ggt | aaa | aaa | ata | 192 |
| Leu | Leu | Ser | Ser | Ile | Asp | Glu | Leu | Ala | Lys | Ala | Ile | Gly | Lys | Lys | Ile | |
| 50 | | | | | 55 | | | | | 60 | | | | | | |
| aaa | aac | gat | ggt | agt | tta | gat | aat | gaa | gca | aat | cgc | aac | gag | tca | ttg | 240 |
| Lys | Asn | Asp | Gly | Ser | Leu | Asp | Asn | Glu | Ala | Asn | Arg | Asn | Glu | Ser | Leu | |
| 65 | | | | 70 | | | | | 75 | | | | | 80 | | |
| tta | gca | gga | gct | tat | aca | ata | tca | acc | tta | ata | aca | caa | aaa | tta | agt | 288 |
| Leu | Ala | Gly | Ala | Tyr | Thr | Ile | Ser | Thr | Leu | Ile | Thr | Gln | Lys | Leu | Ser | |
| | | | | 85 | | | | 90 | | | | | 95 | | | |
| aaa | tta | aac | gga | tca | gaa | ggt | tta | aag | gaa | aag | att | gcc | gca | gct | aag | 336 |
| Lys | Leu | Asn | Gly | Ser | Glu | Gly | Leu | Lys | Glu | Lys | Ile | Ala | Ala | Ala | Lys | |
| | | | 100 | | | | | 105 | | | | | 110 | | | |
| aaa | tgc | tct | gaa | gag | ttt | agt | act | aaa | cta | aaa | gat | aat | cat | gca | cag | 384 |
| Lys | Cys | Ser | Glu | Glu | Phe | Ser | Thr | Lys | Leu | Lys | Asp | Asn | His | Ala | Gln | |
| | | 115 | | | | | 120 | | | | | 125 | | | | |
| ctt | ggt | ata | cag | ggc | gtt | act | gat | gaa | aat | gca | aaa | aaa | gct | att | tta | 432 |
| Leu | Gly | Ile | Gln | Gly | Val | Thr | Asp | Glu | Asn | Ala | Lys | Lys | Ala | Ile | Leu | |
| 130 | | | | | 135 | | | | | 140 | | | | | | |
| aaa | gca | aat | gca | gcg | ggt | aaa | gat | aag | ggc | gtt | gaa | gaa | ctt | gaa | aag | 480 |
| Lys | Ala | Asn | Ala | Ala | Gly | Lys | Asp | Lys | Gly | Val | Glu | Glu | Leu | Glu | Lys | |
| 145 | | | | | 150 | | | | | 155 | | | | | 160 | |
| ttg | tcc | gga | tca | tta | gaa | agc | tta | tca | aaa | gca | gct | aaa | gag | atg | ctt | 528 |
| Leu | Ser | Gly | Ser | Leu | Glu | Ser | Leu | Ser | Lys | Ala | Ala | Lys | Glu | Met | Leu | |
| | | | | 165 | | | | | 170 | | | | | 175 | | |
| gct | aat | tca | gtt | aaa | gag | ctt | aca | agc | cct | gtt | gtc | cat | ggc | aag | caa | 576 |
| Ala | Asn | Ser | Val | Lys | Glu | Leu | Thr | Ser | Pro | Val | Val | His | Gly | Lys | Gln | |
| | | | 180 | | | | | 185 | | | | | 190 | | | |
| aat | gtt | agc | agc | ctt | gat | gaa | aaa | aat | agc | gtt | tca | gta | gat | tta | cct | 624 |
| Asn | Val | Ser | Ser | Leu | Asp | Glu | Lys | Asn | Ser | Val | Ser | Val | Asp | Leu | Pro | |
| | | 195 | | | | | 200 | | | | | 205 | | | | |
| ggt | gga | atg | aca | gtt | ctt | gta | agt | aaa | gaa | aaa | gac | aaa | gac | ggt | aaa | 672 |
| Gly | Gly | Met | Thr | Val | Leu | Val | Ser | Lys | Glu | Lys | Asp | Lys | Asp | Gly | Lys | |
| 210 | | | | | 215 | | | | | 220 | | | | | | |
| tac | agt | cta | gag | gca | aca | gta | gac | aag | ctt | gag | ctt | aaa | gga | act | tct | 720 |
| Tyr | Ser | Leu | Glu | Ala | Thr | Val | Asp | Lys | Leu | Glu | Leu | Lys | Gly | Thr | Ser | |
| 225 | | | | 230 | | | | | 235 | | | | | 240 | | |
| gat | aaa | aac | aac | ggt | tct | gga | aca | ctt | gaa | ggt | gaa | aaa | act | gac | aaa | 768 |
| Asp | Lys | Asn | Asn | Gly | Ser | Gly | Thr | Leu | Glu | Gly | Glu | Lys | Thr | Asp | Lys | |
| | | | | 245 | | | | | 250 | | | | | 255 | | |
| agt | aaa | gta | aaa | tta | aca | att | gct | gat | gac | cta | agt | caa | act | aaa | ttt | 816 |
| Ser | Lys | Val | Lys | Leu | Thr | Ile | Ala | Asp | Asp | Leu | Ser | Gln | Thr | Lys | Phe | |
| | | | 260 | | | | | 265 | | | | | 270 | | | |
| gaa | att | ttc | aaa | gaa | gat | gcc | aaa | aca | tta | gta | tca | aaa | aaa | gta | acc | 864 |
| Glu | Ile | Phe | Lys | Glu | Asp | Ala | Lys | Thr | Leu | Val | Ser | Lys | Lys | Val | Thr | |
| | | 275 | | | | | 280 | | | | | 285 | | | | |
| ctt | aaa | gac | aag | tca | tca | aca | gaa | gaa | aaa | ttc | aac | gaa | aag | ggt | gaa | 912 |
| Leu | Lys | Asp | Lys | Ser | Ser | Thr | Glu | Glu | Lys | Phe | Asn | Glu | Lys | Gly | Glu | |
| | | 290 | | | | | 295 | | | | | 300 | | | | |
| aca | tct | gaa | aaa | aca | ata | gta | aga | gca | aat | gga | acc | aga | ctt | gaa | tac | 960 |
| Thr | Ser | Glu | Lys | Thr | Ile | Val | Arg | Ala | Asn | Gly | Thr | Arg | Leu | Glu | Tyr | |
| 305 | | | | | 310 | | | | | 315 | | | | | 320 | |
| aca | gac | ata | aaa | agc | gat | gga | tcc | gga | aaa | gct | aaa | gaa | gtt | tta | aaa | 1008 |
| Thr | Asp | Ile | Lys | Ser | Asp | Gly | Ser | Gly | Lys | Ala | Lys | Glu | Val | Leu | Lys | |
| | | | | 325 | | | | | 330 | | | | | 335 | | |
| gac | ttt | act | ctt | gaa | gga | act | cta | gct | gct | gac | ggc | aaa | aca | aca | ttg | 1056 |
| Asp | Phe | Thr | Leu | Glu | Gly | Thr | Leu | Ala | Ala | Asp | Gly | Lys | Thr | Thr | Leu | |
| | | | 340 | | | | | 345 | | | | | 350 | | | |

```
aaa gtt aca gaa ggc act gtt gtt tta agc aag aac att tta aaa tcc       1104
Lys Val Thr Glu Gly Thr Val Val Leu Ser Lys Asn Ile Leu Lys Ser
        355                 360                 365 gga gaa ata aca gtt gca ctt gat gac tct gac act act cag gct act       1152
Gly Glu Ile Thr Val Ala Leu Asp Asp Ser Asp Thr Thr Gln Ala Thr
370                 375                 380 aaa aaa act gga aaa tgg gat tca aat act tcc act tta aca att agt       1200
Lys Lys Thr Gly Lys Trp Asp Ser Asn Thr Ser Thr Leu Thr Ile Ser
385                 390                 395                 400 gtg aat agc aaa aaa act aaa aac att gta ttt aca aaa gaa gac aca       1248
Val Asn Ser Lys Lys Thr Lys Asn Ile Val Phe Thr Lys Glu Asp Thr
            405                 410                 415 ata aca gta caa aaa tac gac tca gca ggc acc aat cta gaa ggc aac       1296
Ile Thr Val Gln Lys Tyr Asp Ser Ala Gly Thr Asn Leu Glu Gly Asn
        420                 425                 430 gca gtc gaa att aaa aca ctt gat gaa ctt aaa aac gct tta aaa tag       1344
Ala Val Glu Ile Lys Thr Leu Asp Glu Leu Lys Asn Ala Leu Lys  *
    435                 440                 445
```

<210> SEQ ID NO 72
<211> LENGTH: 447
<212> TYPE: PRT
<213> ORGANISM: Artificial Sequence
<220> FEATURE:
<223> OTHER INFORMATION: Chimeric protein

<400> SEQUENCE: 72

```
Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80

Leu Ala Gly Ala Tyr Thr Ile Ser Thr Leu Ile Thr Gln Lys Leu Ser
                85                  90                  95

Lys Leu Asn Gly Ser Glu Gly Leu Lys Glu Ile Ala Ala Ala Lys
            100                 105                 110

Lys Cys Ser Glu Glu Phe Ser Thr Lys Leu Lys Asp Asn His Ala Gln
        115                 120                 125

Leu Gly Ile Gln Gly Val Thr Asp Glu Asn Ala Lys Lys Ala Ile Leu
    130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Lys Gln
            180                 185                 190

Asn Val Ser Ser Leu Asp Glu Lys Asn Ser Val Ser Val Asp Leu Pro
        195                 200                 205

Gly Gly Met Thr Val Leu Val Ser Lys Glu Lys Asp Lys Asp Gly Lys
    210                 215                 220

Tyr Ser Leu Glu Ala Thr Val Asp Lys Leu Glu Leu Lys Gly Thr Ser
225                 230                 235                 240
```

```
Asp Lys Asn Asn Gly Ser Gly Thr Leu Glu Gly Glu Lys Thr Asp Lys
                245                 250                 255

Ser Lys Val Lys Leu Thr Ile Ala Asp Leu Ser Gln Thr Lys Phe
        260                 265                 270

Glu Ile Phe Lys Glu Asp Ala Lys Thr Leu Val Ser Lys Lys Val Thr
            275                 280                 285

Leu Lys Asp Lys Ser Ser Thr Glu Glu Lys Phe Asn Glu Lys Gly Glu
    290                 295                 300

Thr Ser Glu Lys Thr Ile Val Arg Ala Asn Gly Thr Arg Leu Glu Tyr
305                 310                 315                 320

Thr Asp Ile Lys Ser Asp Gly Ser Gly Lys Ala Lys Glu Val Leu Lys
                325                 330                 335

Asp Phe Thr Leu Glu Gly Thr Leu Ala Ala Asp Gly Lys Thr Thr Leu
            340                 345                 350

Lys Val Thr Glu Gly Thr Val Val Leu Ser Lys Asn Ile Leu Lys Ser
    355                 360                 365

Gly Glu Ile Thr Val Ala Leu Asp Asp Ser Asp Thr Thr Gln Ala Thr
370                 375                 380

Lys Lys Thr Gly Lys Trp Asp Ser Asn Thr Ser Thr Leu Thr Ile Ser
385                 390                 395                 400

Val Asn Ser Lys Lys Thr Lys Asn Ile Val Phe Thr Lys Glu Asp Thr
                405                 410                 415

Ile Thr Val Gln Lys Tyr Asp Ser Ala Gly Thr Asn Leu Glu Gly Asn
            420                 425                 430

Ala Val Glu Ile Lys Thr Leu Asp Glu Leu Lys Asn Ala Leu Lys
    435                 440                 445

<210> SEQ ID NO 73
<211> LENGTH: 1305
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1305)

<400> SEQUENCE: 73 atg gct tgt aat aat tca gga aaa gat ggg aat aca tct gca aat tct        48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata agt aaa aaa        96
Ala Asp Glu Ser Val Lys Gly Pro Asn Leu Thr Glu Ile Ser Lys Lys
                20                  25                  30 att aca gaa tct aac gca gtt gtt ctg gct gtg aaa gaa att gaa act       144
Ile Thr Glu Ser Asn Ala Val Val Leu Ala Val Lys Glu Ile Glu Thr
            35                  40                  45 ttg ctt gca tct ata gat gaa ctt gct act aaa gct att ggt aaa aaa       192
Leu Leu Ala Ser Ile Asp Glu Leu Ala Thr Lys Ala Ile Gly Lys Lys
        50                  55                  60 ata caa caa aat ggt ggt tta gct gtc gaa gcg ggg cat aat gga aca       240
Ile Gln Gln Asn Gly Gly Leu Ala Val Glu Ala Gly His Asn Gly Thr
65                  70                  75                  80 ttg tta gca ggt gct tat aca ata tca aaa cta ata aca caa aaa tta       288
Leu Leu Ala Gly Ala Tyr Thr Ile Ser Lys Leu Ile Thr Gln Lys Leu
                85                  90                  95 gat gga ttg aaa aat tca gaa aaa tta aag gaa aaa att gaa aat gct       336
Asp Gly Leu Lys Asn Ser Glu Lys Leu Lys Glu Lys Ile Glu Asn Ala
            100                 105                 110 aag aaa tgt tct gaa gat ttt act aaa aaa cta gaa gga gaa cat gcg       384
Lys Lys Cys Ser Glu Asp Phe Thr Lys Lys Leu Glu Gly Glu His Ala
```

-continued

```
Lys Lys Cys Ser Glu Asp Phe Thr Lys Lys Leu Glu Gly Glu His Ala
        115                 120                 125 caa ctt gga att gaa aat gtt act gat gag aat gca aaa aaa gct att    432
Gln Leu Gly Ile Glu Asn Val Thr Asp Glu Asn Ala Lys Lys Ala Ile
130                 135                 140 tta ata aca gat gca gct aaa gat aag ggc gct gca gag ctt gaa aag    480
Leu Ile Thr Asp Ala Ala Lys Asp Lys Gly Ala Ala Glu Leu Glu Lys
145                 150                 155                 160 cta ttt aaa gca gta gaa aac ttg gca aaa gca gct aaa gag atg ctt    528
Leu Phe Lys Ala Val Glu Asn Leu Ala Lys Ala Ala Lys Glu Met Leu
        165                 170                 175 gct aat tca gtt aaa gag ctt aca agt cct att gtg cat ggc gtt tca    576
Ala Asn Ser Val Lys Glu Leu Thr Ser Pro Ile Val His Gly Val Ser
        180                 185                 190 gta gat ttg cct ggt gaa atg aaa gtt ctt gta agc aaa gaa aaa aac    624
Val Asp Leu Pro Gly Glu Met Lys Val Leu Val Ser Lys Glu Lys Asn
        195                 200                 205 aaa gac ggc aag tac gat cta att gca aca gta gac aag ctt gag ctt    672
Lys Asp Gly Lys Tyr Asp Leu Ile Ala Thr Val Asp Lys Leu Glu Leu
210                 215                 220 aaa gga act tct gat aaa aac aat gga tct gga gta ctt gaa ggc gta    720
Lys Gly Thr Ser Asp Lys Asn Asn Gly Ser Gly Val Leu Glu Gly Val
225                 230                 235                 240 aaa gct gac aaa agt aaa gta aaa tta aca att tct gac gat cta ggt    768
Lys Ala Asp Lys Ser Lys Val Lys Leu Thr Ile Ser Asp Asp Leu Gly
        245                 250                 255 caa acc aca ctt gaa gtt ttc aaa gaa gat ggc aaa aca cta gta tca    816
Gln Thr Thr Leu Glu Val Phe Lys Glu Asp Gly Lys Thr Leu Val Ser
        260                 265                 270 aaa aaa gta act tcc aaa gac aag tca tca aca gaa gaa aaa ttc aat    864
Lys Lys Val Thr Ser Lys Asp Lys Ser Ser Thr Glu Glu Lys Phe Asn
        275                 280                 285 gaa aaa ggt gaa gta tct gaa aaa ata ata aca aga gca gac gga acc    912
Glu Lys Gly Glu Val Ser Glu Lys Ile Ile Thr Arg Ala Asp Gly Thr
290                 295                 300 aga ctt gaa tac aca gga att aaa agc gat gga tct gga aaa gct aaa    960
Arg Leu Glu Tyr Thr Gly Ile Lys Ser Asp Gly Ser Gly Lys Ala Lys
305                 310                 315                 320 gag gtt tta aaa aaa ttt act ctt gaa gga aaa gta gct aat gat aaa   1008
Glu Val Leu Lys Lys Phe Thr Leu Glu Gly Lys Val Ala Asn Asp Lys
        325                 330                 335 gta aca ttg gaa gta aaa gaa gga acc gtt act tta agt aag aac att   1056
Val Thr Leu Glu Val Lys Glu Gly Thr Val Thr Leu Ser Lys Asn Ile
        340                 345                 350 tca aaa tct ggg gaa gtt tca gtt gaa ctt aat gac act gac agt agt   1104
Ser Lys Ser Gly Glu Val Ser Val Glu Leu Asn Asp Thr Asp Ser Ser
        355                 360                 365 gct gct act aaa aaa act gca gct tgg aat tca ggc act tca act tta   1152
Ala Ala Thr Lys Lys Thr Ala Ala Trp Asn Ser Gly Thr Ser Thr Leu
370                 375                 380 aca att act gta aac agt aaa aaa act aaa gac ctt gtg ttt aca aaa   1200
Thr Ile Thr Val Asn Ser Lys Lys Thr Lys Asp Leu Val Phe Thr Lys
385                 390                 395                 400 gaa aac aca att aca gta caa caa tac gac tca aat ggc acc aaa tta   1248
Glu Asn Thr Ile Thr Val Gln Gln Tyr Asp Ser Asn Gly Thr Lys Leu
        405                 410                 415 gag ggg tca gca gtt gaa att aca aaa ctt gat gaa att aaa aac gct   1296
Glu Gly Ser Ala Val Glu Ile Thr Lys Leu Asp Glu Ile Lys Asn Ala
        420                 425                 430 tta aaa taa                                                       1305
```

Leu Lys *

<210> SEQ ID NO 74
<211> LENGTH: 434
<212> TYPE: PRT
<213> ORGANISM: Artificial Sequence
<220> FEATURE:
<223> OTHER INFORMATION: Chimeric protein

<400> SEQUENCE: 74

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile Thr Glu Ser Asn Ala Val Val Leu Ala Val Lys Glu Ile Glu Thr
        35                  40                  45

Leu Leu Ala Ser Ile Asp Glu Leu Ala Thr Lys Ala Ile Gly Lys Lys
    50                  55                  60

Ile Gln Gln Asn Gly Gly Leu Ala Val Glu Ala Gly His Asn Gly Thr
65                  70                  75                  80

Leu Leu Ala Gly Ala Tyr Thr Ile Ser Lys Leu Ile Thr Gln Lys Leu
                85                  90                  95

Asp Gly Leu Lys Asn Ser Glu Lys Leu Lys Glu Lys Ile Glu Asn Ala
            100                 105                 110

Lys Lys Cys Ser Glu Asp Phe Thr Lys Lys Leu Glu Gly Glu His Ala
        115                 120                 125

Gln Leu Gly Ile Glu Asn Val Thr Asp Glu Asn Ala Lys Lys Ala Ile
    130                 135                 140

Leu Ile Thr Asp Ala Ala Lys Asp Lys Gly Ala Ala Glu Leu Glu Lys
145                 150                 155                 160

Leu Phe Lys Ala Val Glu Asn Leu Ala Lys Ala Ala Lys Glu Met Leu
                165                 170                 175

Ala Asn Ser Val Lys Glu Leu Thr Ser Pro Ile Val His Gly Val Ser
            180                 185                 190

Val Asp Leu Pro Gly Glu Met Lys Val Leu Val Ser Lys Glu Lys Asn
        195                 200                 205

Lys Asp Gly Lys Tyr Asp Leu Ile Ala Thr Val Asp Lys Leu Glu Leu
    210                 215                 220

Lys Gly Thr Ser Asp Lys Asn Asn Gly Ser Gly Val Leu Glu Gly Val
225                 230                 235                 240

Lys Ala Asp Lys Ser Lys Val Lys Leu Thr Ile Ser Asp Asp Leu Gly
                245                 250                 255

Gln Thr Thr Leu Glu Val Phe Lys Glu Asp Gly Lys Thr Leu Val Ser
            260                 265                 270

Lys Lys Val Thr Ser Lys Asp Lys Ser Ser Thr Glu Glu Lys Phe Asn
        275                 280                 285

Glu Lys Gly Glu Val Ser Glu Lys Ile Ile Thr Arg Ala Asp Gly Thr
    290                 295                 300

Arg Leu Glu Tyr Thr Gly Ile Lys Ser Asp Gly Ser Gly Lys Ala Lys
305                 310                 315                 320

Glu Val Leu Lys Lys Phe Thr Leu Glu Gly Lys Val Ala Asn Asp Lys
                325                 330                 335

Val Thr Leu Glu Val Lys Glu Gly Thr Val Thr Leu Ser Lys Asn Ile
            340                 345                 350

Ser Lys Ser Gly Glu Val Ser Val Glu Leu Asn Asp Thr Asp Ser Ser
        355                 360                 365

```
Ala Ala Thr Lys Lys Thr Ala Ala Trp Asn Ser Gly Thr Ser Thr Leu
    370             375                 380

Thr Ile Thr Val Asn Ser Lys Lys Thr Lys Asp Leu Val Phe Thr Lys
385                 390                 395                 400

Glu Asn Thr Ile Thr Val Gln Gln Tyr Asp Ser Asn Gly Thr Lys Leu
                405                 410                 415

Glu Gly Ser Ala Val Glu Ile Thr Lys Leu Asp Glu Ile Lys Asn Ala
            420                 425                 430

Leu Lys

<210> SEQ ID NO 75
<211> LENGTH: 1332
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1332)

<400> SEQUENCE: 75 atg gct tgt agt aat tca ggg aaa ggt ggg gat tct gca tct act aat     48
Met Ala Cys Ser Asn Ser Gly Lys Gly Gly Asp Ser Ala Ser Thr Asn
1               5                   10                  15 cct gct gac gag tct gcg aaa ggg cct aat ctt aca gaa ata agc aaa     96
Pro Ala Asp Glu Ser Ala Lys Gly Pro Asn Leu Thr Glu Ile Ser Lys
            20                  25                  30 aaa att aca gat tct aat gca ttt gta ctt gct gtt aaa gaa gtt gag    144
Lys Ile Thr Asp Ser Asn Ala Phe Val Leu Ala Val Lys Glu Val Glu
        35                  40                  45 act ttg gtt tta tct ata gat gaa ctt gct aag aaa gct att ggt caa    192
Thr Leu Val Leu Ser Ile Asp Glu Leu Ala Lys Lys Ala Ile Gly Gln
    50                  55                  60 aaa ata gac aat aat aat ggt tta gct gct tta aat aat cag aat gga    240
Lys Ile Asp Asn Asn Asn Gly Leu Ala Ala Leu Asn Asn Gln Asn Gly
65                  70                  75                  80 tcg ttg tta gca gga gcc tat gca ata tca acc cta ata aca gaa aaa    288
Ser Leu Leu Ala Gly Ala Tyr Ala Ile Ser Thr Leu Ile Thr Glu Lys
                85                  90                  95 ttg agt aaa ttg aaa aat tta gaa gaa tta aag aca gaa att gca aag    336
Leu Ser Lys Leu Lys Asn Leu Glu Glu Leu Lys Thr Glu Ile Ala Lys
            100                 105                 110 gct aag aaa tgt tcc gaa gaa ttt act aat aaa cta aaa agt ggt cat    384
Ala Lys Lys Cys Ser Glu Glu Phe Thr Asn Lys Leu Lys Ser Gly His
        115                 120                 125 gca gat ctt ggc aaa cag gat gct acc gat gat cat gca aaa gca gct    432
Ala Asp Leu Gly Lys Gln Asp Ala Thr Asp Asp His Ala Lys Ala Ala
    130                 135                 140 att tta aaa aca cat gca act acc gat aaa ggt gct aaa gaa ttt aaa    480
Ile Leu Lys Thr His Ala Thr Thr Asp Lys Gly Ala Lys Glu Phe Lys
145                 150                 155                 160 gat tta ttt gaa tca gta gaa ggt ttg tta aaa gca gct caa gta gca    528
Asp Leu Phe Glu Ser Val Glu Gly Leu Leu Lys Ala Ala Gln Val Ala
                165                 170                 175 cta act aat tca gtt aaa gaa ctt aca agt cct gtt gta gca gaa agt    576
Leu Thr Asn Ser Val Lys Glu Leu Thr Ser Pro Val Val Ala Glu Ser
            180                 185                 190 cca aaa aaa cct tcc atg gcc gtt tca gta gat ttg cct ggt gaa atg    624
Pro Lys Lys Pro Ser Met Ala Val Ser Val Asp Leu Pro Gly Glu Met
        195                 200                 205 aaa gtt ctt gta agc aaa gaa aaa aac aaa gac ggc aag tac gat cta    672
```

```
                                                                                             -continued
Lys Val Leu Val Ser Lys Glu Lys Asn Lys Asp Gly Lys Tyr Asp Leu
            210                 215                 220 att gca aca gta gac aag ctt gag ctt aaa gga act tct gat aaa aac      720
Ile Ala Thr Val Asp Lys Leu Glu Leu Lys Gly Thr Ser Asp Lys Asn
225                 230                 235                 240 aat gga tct gga gta ctt gaa ggc gta aaa gct gac aaa agt aaa gta      768
Asn Gly Ser Gly Val Leu Glu Gly Val Lys Ala Asp Lys Ser Lys Val
                245                 250                 255 aaa tta aca att tct gac gat cta ggt caa acc aca ctt gaa gtt ttc      816
Lys Leu Thr Ile Ser Asp Asp Leu Gly Gln Thr Thr Leu Glu Val Phe
            260                 265                 270 aaa gaa gat ggc aaa aca cta gta tca aaa aaa gta act tcc aaa gac      864
Lys Glu Asp Gly Lys Thr Leu Val Ser Lys Lys Val Thr Ser Lys Asp
        275                 280                 285 aag tca tca aca gaa gaa aaa ttc aat gaa aaa ggt gaa gta tct gaa      912
Lys Ser Ser Thr Glu Glu Lys Phe Asn Glu Lys Gly Glu Val Ser Glu
    290                 295                 300 aaa ata ata aca aga gca gac gga acc aga ctt gaa tac aca gga att      960
Lys Ile Ile Thr Arg Ala Asp Gly Thr Arg Leu Glu Tyr Thr Gly Ile
305                 310                 315                 320 aaa agc gat gga tct gga aaa gct aaa gag gtt tta aaa aaa ttt act     1008
Lys Ser Asp Gly Ser Gly Lys Ala Lys Glu Val Leu Lys Lys Phe Thr
                325                 330                 335 ctt gaa gga aaa gta gct aat gat aaa gta aca ttg gaa gta aaa gaa     1056
Leu Glu Gly Lys Val Ala Asn Asp Lys Val Thr Leu Glu Val Lys Glu
            340                 345                 350 gga acc gtt act tta agt aag aat att tca aaa tct ggg gaa gtt tca     1104
Gly Thr Val Thr Leu Ser Lys Asn Ile Ser Lys Ser Gly Glu Val Ser
        355                 360                 365 gtt gaa ctt aat gac act gac agt agt gct gct act aaa aaa act gca     1152
Val Glu Leu Asn Asp Thr Asp Ser Ser Ala Ala Thr Lys Lys Thr Ala
    370                 375                 380 gct tgg aat tca aaa act tcc act tta aca att agt gtg aat agc caa     1200
Ala Trp Asn Ser Lys Thr Ser Thr Leu Thr Ile Ser Val Asn Ser Gln
385                 390                 395                 400 aaa acc aaa aac ctt gta ttc aca aaa gaa gac aca ata aca gta caa     1248
Lys Thr Lys Asn Leu Val Phe Thr Lys Glu Asp Thr Ile Thr Val Gln
                405                 410                 415 aaa tac gac tca gca ggc acc aat cta gaa ggc aaa gca gtc gaa att     1296
Lys Tyr Asp Ser Ala Gly Thr Asn Leu Glu Gly Lys Ala Val Glu Ile
            420                 425                 430 aca aca ctt aaa gaa ctt aaa aac gct tta aaa taa                     1332
Thr Thr Leu Lys Glu Leu Lys Asn Ala Leu Lys *
        435                 440

<210> SEQ ID NO 76
<211> LENGTH: 443
<212> TYPE: PRT
<213> ORGANISM: Artificial Sequence
<220> FEATURE:
<223> OTHER INFORMATION: Chimeric protein

<400> SEQUENCE: 76

Met Ala Cys Ser Asn Ser Gly Lys Gly Gly Asp Ser Ala Ser Thr Asn
1               5                   10                  15

Pro Ala Asp Glu Ser Ala Lys Gly Pro Asn Leu Thr Glu Ile Ser Lys
            20                  25                  30

Lys Ile Thr Asp Ser Asn Ala Phe Val Leu Ala Val Lys Glu Val Glu
        35                  40                  45

Thr Leu Val Leu Ser Ile Asp Glu Leu Ala Lys Lys Ala Ile Gly Gln
    50                  55                  60
```

```
Lys Ile Asp Asn Asn Gly Leu Ala Ala Leu Asn Asn Gln Asn Gly
 65                  70                  75                  80

Ser Leu Leu Ala Gly Ala Tyr Ala Ile Ser Thr Leu Ile Thr Glu Lys
                 85                  90                  95

Leu Ser Lys Leu Lys Asn Leu Glu Glu Leu Lys Thr Glu Ile Ala Lys
            100                 105                 110

Ala Lys Lys Cys Ser Glu Glu Phe Thr Asn Lys Leu Lys Ser Gly His
        115                 120                 125

Ala Asp Leu Gly Lys Gln Asp Ala Thr Asp His Ala Lys Ala Ala
    130                 135                 140

Ile Leu Lys Thr His Ala Thr Thr Asp Lys Gly Ala Lys Glu Phe Lys
145                 150                 155                 160

Asp Leu Phe Glu Ser Val Glu Gly Leu Leu Lys Ala Ala Gln Val Ala
                165                 170                 175

Leu Thr Asn Ser Val Lys Glu Leu Thr Ser Pro Val Val Ala Glu Ser
            180                 185                 190

Pro Lys Lys Pro Ser Met Ala Val Ser Val Asp Leu Pro Gly Glu Met
        195                 200                 205

Lys Val Leu Val Ser Lys Glu Lys Asn Lys Asp Gly Lys Tyr Asp Leu
    210                 215                 220

Ile Ala Thr Val Asp Lys Leu Glu Leu Lys Gly Thr Ser Asp Lys Asn
225                 230                 235                 240

Asn Gly Ser Gly Val Leu Glu Gly Val Lys Ala Asp Lys Ser Lys Val
                245                 250                 255

Lys Leu Thr Ile Ser Asp Asp Leu Gly Gln Thr Thr Leu Glu Val Phe
            260                 265                 270

Lys Glu Asp Gly Lys Thr Leu Val Ser Lys Lys Val Thr Ser Lys Asp
        275                 280                 285

Lys Ser Ser Thr Glu Glu Lys Phe Asn Glu Lys Gly Glu Val Ser Glu
    290                 295                 300

Lys Ile Ile Thr Arg Ala Asp Gly Thr Arg Leu Glu Tyr Thr Gly Ile
305                 310                 315                 320

Lys Ser Asp Gly Ser Gly Lys Ala Lys Glu Val Leu Lys Lys Phe Thr
                325                 330                 335

Leu Glu Gly Lys Val Ala Asn Asp Lys Val Thr Leu Glu Val Lys Glu
            340                 345                 350

Gly Thr Val Thr Leu Ser Lys Asn Ile Ser Lys Ser Gly Glu Val Ser
        355                 360                 365

Val Glu Leu Asn Asp Thr Asp Ser Ser Ala Ala Thr Lys Lys Thr Ala
    370                 375                 380

Ala Trp Asn Ser Lys Thr Ser Thr Leu Thr Ile Ser Val Asn Ser Gln
385                 390                 395                 400

Lys Thr Lys Asn Leu Val Phe Thr Lys Glu Asp Thr Ile Thr Val Gln
                405                 410                 415

Lys Tyr Asp Ser Ala Gly Thr Asn Leu Glu Gly Lys Ala Val Glu Ile
            420                 425                 430

Thr Thr Leu Lys Glu Leu Lys Asn Ala Leu Lys
        435                 440

<210> SEQ ID NO 77
<211> LENGTH: 1317
<212> TYPE: DNA
<213> ORGANISM: Artificial Sequence
<220> FEATURE:
<223> OTHER INFORMATION: Chimeric nucleic acid
```

<221> NAME/KEY: CDS
<222> LOCATION: (1)...(1317)

<400> SEQUENCE: 77

```
atg gct tgt aat aat tca ggt ggg gat tct gca tct act aat cct gat      48
Met Ala Cys Asn Asn Ser Gly Gly Asp Ser Ala Ser Thr Asn Pro Asp
1               5                  10                  15 gag tct gca aaa gga cct aat ctt acc gta ata agc aaa aaa att aca      96
Glu Ser Ala Lys Gly Pro Asn Leu Thr Val Ile Ser Lys Lys Ile Thr
            20                  25                  30 gat tct aat gca ttt tta ctg gct gtg aaa gaa gtt gag gct ttg ctt     144
Asp Ser Asn Ala Phe Leu Leu Ala Val Lys Glu Val Glu Ala Leu Leu
        35                  40                  45 tca tct ata gat gaa ctt tct aaa gct att ggt aaa aaa ata aaa aat     192
Ser Ser Ile Asp Glu Leu Ser Lys Ala Ile Gly Lys Lys Ile Lys Asn
    50                  55                  60 gat ggt act tta gat aac gaa gca aat cga aac gaa tca ttg ata gca     240
Asp Gly Thr Leu Asp Asn Glu Ala Asn Arg Asn Glu Ser Leu Ile Ala
65                  70                  75                  80 gga gct tat gaa ata tca aaa cta ata aca caa aaa tta agt gta ttg     288
Gly Ala Tyr Glu Ile Ser Lys Leu Ile Thr Gln Lys Leu Ser Val Leu
                85                  90                  95 aat tca gaa gaa tta aag gaa aaa att aaa gag gct aag gat tgt tcc     336
Asn Ser Glu Glu Leu Lys Glu Lys Ile Lys Glu Ala Lys Asp Cys Ser
            100                 105                 110 gaa aaa ttt act act aag cta aaa gat agt cat gca gag ctt ggt ata     384
Glu Lys Phe Thr Thr Lys Leu Lys Asp Ser His Ala Glu Leu Gly Ile
        115                 120                 125 caa agc gtt cag gat gat aat gca aaa aaa gct att tta aaa aca cat     432
Gln Ser Val Gln Asp Asp Asn Ala Lys Lys Ala Ile Leu Lys Thr His
    130                 135                 140 gga act aaa gac aag ggt gct aaa gaa ctt gaa gag tta ttt aaa tca     480
Gly Thr Lys Asp Lys Gly Ala Lys Glu Leu Glu Glu Leu Phe Lys Ser
145                 150                 155                 160 cta gaa agc ttg tca aaa gca gcg caa gca gca tta act aat tca gtt     528
Leu Glu Ser Leu Ser Lys Ala Ala Gln Ala Ala Leu Thr Asn Ser Val
                165                 170                 175 aaa gag ctt aca aat cct gtt gtg gca gaa agt cca aaa aaa cct tcc     576
Lys Glu Leu Thr Asn Pro Val Val Ala Glu Ser Pro Lys Lys Pro Ser
            180                 185                 190 atg gcc gtt tca gta gat ttg cct ggt gaa atg aaa gtt ctt gta agc     624
Met Ala Val Ser Val Asp Leu Pro Gly Glu Met Lys Val Leu Val Ser
        195                 200                 205 aaa gaa aaa aac aaa gac ggc aag tac gat cta att gca aca gta gac     672
Lys Glu Lys Asn Lys Asp Gly Lys Tyr Asp Leu Ile Ala Thr Val Asp
    210                 215                 220 aag ctt gag ctt aaa gga act tct gat aaa aac aat gga tct gga gta     720
Lys Leu Glu Leu Lys Gly Thr Ser Asp Lys Asn Asn Gly Ser Gly Val
225                 230                 235                 240 ctt gaa ggc gta aaa gct gac aaa agt aaa gta aaa tta aca att tct     768
Leu Glu Gly Val Lys Ala Asp Lys Ser Lys Val Lys Leu Thr Ile Ser
                245                 250                 255 gac gat cta ggt caa acc aca ctt gaa gtt ttc aaa gaa gat ggc aaa     816
Asp Asp Leu Gly Gln Thr Thr Leu Glu Val Phe Lys Glu Asp Gly Lys
            260                 265                 270 aca cta gta tca aaa aaa gta act tcc aaa gac aag tca tca aca gaa     864
Thr Leu Val Ser Lys Lys Val Thr Ser Lys Asp Lys Ser Ser Thr Glu
        275                 280                 285 gaa aaa ttc aat gaa aaa ggt gaa gta tct gaa aaa ata ata aca aga     912
Glu Lys Phe Asn Glu Lys Gly Glu Val Ser Glu Lys Ile Ile Thr Arg
    290                 295                 300
```

```
gca gac gga acc aga ctt gaa tac aca gga att aaa agc gat gga tct      960
Ala Asp Gly Thr Arg Leu Glu Tyr Thr Gly Ile Lys Ser Asp Gly Ser
305                 310                 315                 320 gga aaa gct aaa gag gtt tta aaa aaa ttt act ctt gaa gga aaa gta     1008
Gly Lys Ala Lys Glu Val Leu Lys Lys Phe Thr Leu Glu Gly Lys Val
            325                 330                 335 gct aat gat aaa gta aca ttg gaa gta aaa gaa gga acc gtt act tta     1056
Ala Asn Asp Lys Val Thr Leu Glu Val Lys Glu Gly Thr Val Thr Leu
        340                 345                 350 agt aag aac att tca aaa tct ggg gaa gtt tca gtt gaa ctt aat gac     1104
Ser Lys Asn Ile Ser Lys Ser Gly Glu Val Ser Val Glu Leu Asn Asp
    355                 360                 365 act gac agt agt gct gct act aaa aaa act gca gct tgg aat tca aaa     1152
Thr Asp Ser Ser Ala Ala Thr Lys Lys Thr Ala Ala Trp Asn Ser Lys
370                 375                 380 act tct act tta aca att agt gtt aac agc aaa aaa act aca caa ctt     1200
Thr Ser Thr Leu Thr Ile Ser Val Asn Ser Lys Lys Thr Thr Gln Leu
385                 390                 395                 400 gtg ttt act aaa caa gac aca ata act gta caa aaa tac gac tcc gca     1248
Val Phe Thr Lys Gln Asp Thr Ile Thr Val Gln Lys Tyr Asp Ser Ala
            405                 410                 415 ggt acc aat tta gaa ggc aca gca gtc gaa att aaa aca ctt gat gaa     1296
Gly Thr Asn Leu Glu Gly Thr Ala Val Glu Ile Lys Thr Leu Asp Glu
        420                 425                 430 ctt aaa aac gct tta aaa taa                                         1317
Leu Lys Asn Ala Leu Lys  *
    435
```

<210> SEQ ID NO 78
<211> LENGTH: 438
<212> TYPE: PRT
<213> ORGANISM: Artificial Sequence
<220> FEATURE:
<223> OTHER INFORMATION: Chimeric protein

<400> SEQUENCE: 78

```
Met Ala Cys Asn Asn Ser Gly Gly Asp Ser Ala Ser Thr Asn Pro Asp
1               5                   10                  15

Glu Ser Ala Lys Gly Pro Asn Leu Thr Val Ile Ser Lys Lys Ile Thr
            20                  25                  30

Asp Ser Asn Ala Phe Leu Leu Ala Val Lys Glu Val Glu Ala Leu Leu
        35                  40                  45

Ser Ser Ile Asp Glu Leu Ser Lys Ala Ile Gly Lys Lys Ile Lys Asn
    50                  55                  60

Asp Gly Thr Leu Asp Asn Glu Ala Asn Arg Asn Glu Ser Leu Ile Ala
65                  70                  75                  80

Gly Ala Tyr Glu Ile Ser Lys Leu Ile Thr Gln Lys Leu Ser Val Leu
                85                  90                  95

Asn Ser Glu Glu Leu Lys Glu Lys Ile Lys Glu Ala Lys Asp Cys Ser
            100                 105                 110

Glu Lys Phe Thr Thr Lys Leu Lys Asp Ser His Ala Glu Leu Gly Ile
        115                 120                 125

Gln Ser Val Gln Asp Asp Asn Ala Lys Lys Ala Ile Leu Lys Thr His
    130                 135                 140

Gly Thr Lys Asp Lys Gly Ala Lys Glu Leu Glu Leu Phe Lys Ser
145                 150                 155                 160

Leu Glu Ser Leu Ser Lys Ala Ala Gln Ala Ala Leu Thr Asn Ser Val
                165                 170                 175
```

```
Lys Glu Leu Thr Asn Pro Val Ala Glu Ser Pro Lys Lys Pro Ser
            180                 185                 190

Met Ala Val Ser Val Asp Leu Pro Gly Glu Met Lys Val Leu Val Ser
        195                 200                 205

Lys Glu Lys Asn Lys Asp Gly Lys Tyr Asp Leu Ile Ala Thr Val Asp
    210                 215                 220

Lys Leu Glu Leu Lys Gly Thr Ser Asp Lys Asn Asn Gly Ser Gly Val
225                 230                 235                 240

Leu Glu Gly Val Lys Ala Asp Lys Ser Lys Val Lys Leu Thr Ile Ser
                245                 250                 255

Asp Asp Leu Gly Gln Thr Thr Leu Glu Val Phe Lys Glu Asp Gly Lys
            260                 265                 270

Thr Leu Val Ser Lys Lys Val Thr Ser Lys Asp Lys Ser Ser Thr Glu
        275                 280                 285

Glu Lys Phe Asn Glu Lys Gly Glu Val Ser Glu Lys Ile Ile Thr Arg
    290                 295                 300

Ala Asp Gly Thr Arg Leu Glu Tyr Thr Gly Ile Lys Ser Asp Gly Ser
305                 310                 315                 320

Gly Lys Ala Lys Glu Val Leu Lys Lys Phe Thr Leu Glu Gly Lys Val
                325                 330                 335

Ala Asn Asp Lys Val Thr Leu Glu Val Lys Glu Gly Thr Val Thr Leu
            340                 345                 350

Ser Lys Asn Ile Ser Lys Ser Gly Glu Val Ser Val Glu Leu Asn Asp
        355                 360                 365

Thr Asp Ser Ser Ala Ala Thr Lys Lys Thr Ala Ala Trp Asn Ser Lys
    370                 375                 380

Thr Ser Thr Leu Thr Ile Ser Val Asn Ser Lys Lys Thr Thr Gln Leu
385                 390                 395                 400

Val Phe Thr Lys Gln Asp Thr Ile Thr Val Gln Lys Tyr Asp Ser Ala
                405                 410                 415

Gly Thr Asn Leu Glu Gly Thr Ala Val Glu Ile Lys Thr Leu Asp Glu
            420                 425                 430

Leu Lys Asn Ala Leu Lys
        435

<210> SEQ ID NO 79
<211> LENGTH: 1029
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1029)

<400> SEQUENCE: 79 atg gct tgt aat aat tca ggg aaa gat ggg aat aca tct gca aat tct    48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata aat aaa aaa    96
Ala Asp Glu Ser Val Lys Gly Pro Asn Leu Thr Glu Ile Asn Lys Lys
            20                  25                  30 att acg gat tct aat gcg gtt tta ctt gct gtg aaa gag gtt gaa gcg   144
Ile Thr Asp Ser Asn Ala Val Leu Leu Ala Val Lys Glu Val Glu Ala
        35                  40                  45 ttg ctg tca tct ata gat gaa att gct gct aaa gct att ggt aaa aaa   192
Leu Leu Ser Ser Ile Asp Glu Ile Ala Ala Lys Ala Ile Gly Lys Lys
    50                  55                  60 ata cac caa aat aat ggt ttg gat acc gaa aat aat cac aat gga tca   240
```

```
                Ile His Gln Asn Asn Gly Leu Asp Thr Glu Asn Asn His Asn Gly Ser
                 65                  70                  75                  80 ttg tta gcg gga gct tat gca ata tca acc cta ata aaa caa aaa tta          288
Leu Leu Ala Gly Ala Tyr Ala Ile Ser Thr Leu Ile Lys Gln Lys Leu
                     85                  90                  95 gat gga ttg aaa aat gaa gga tta aag gaa aaa att gat gcg gct aag          336
Asp Gly Leu Lys Asn Glu Gly Leu Lys Glu Lys Ile Asp Ala Ala Lys
                100                 105                 110 aaa tgt tct gaa aca ttt act aat aaa tta aaa gaa aaa cac aca gat          384
Lys Cys Ser Glu Thr Phe Thr Asn Lys Leu Lys Glu Lys His Thr Asp
            115                 120                 125 ctt ggt aaa gaa ggt gtt act gat gct gat gca aaa gaa gcc att tta          432
Leu Gly Lys Glu Gly Val Thr Asp Ala Asp Ala Lys Glu Ala Ile Leu
        130                 135                 140 aaa gca aat ggt act aaa act aaa ggt gct gaa gaa ctt gga aaa tta          480
Lys Ala Asn Gly Thr Lys Thr Lys Gly Ala Glu Glu Leu Gly Lys Leu
    145                 150                 155                 160 ttt gaa tca gta gag gtc ttg tca aaa gca gct aaa gag atg ctt gct          528
Phe Glu Ser Val Glu Val Leu Ser Lys Ala Ala Lys Glu Met Leu Ala
                    165                 170                 175 aat tca gtt aaa gag ctt aca agc cct gtt gtg gca gaa agt cca aaa          576
Asn Ser Val Lys Glu Leu Thr Ser Pro Val Val Ala Glu Ser Pro Lys
                180                 185                 190 aaa cct tcc atg gcc aag caa aat gtt tct gaa aaa ata ata aca aga          624
Lys Pro Ser Met Ala Lys Gln Asn Val Ser Glu Lys Ile Ile Thr Arg
            195                 200                 205 gca gac gga acc aga ctt gaa tac aca gga att aaa agc gat gga tct          672
Ala Asp Gly Thr Arg Leu Glu Tyr Thr Gly Ile Lys Ser Asp Gly Ser
        210                 215                 220 gga aaa gct aaa gag gtt tta aaa ggc tat gtt ctt gaa gga act cta          720
Gly Lys Ala Lys Glu Val Leu Lys Gly Tyr Val Leu Glu Gly Thr Leu
225                 230                 235                 240 act gct gaa aaa aca aca ttg gtg gtt aaa gaa gga act gtt act tta          768
Thr Ala Glu Lys Thr Thr Leu Val Val Lys Glu Gly Thr Val Thr Leu
                    245                 250                 255 agc aaa aat att tca aaa tct ggg gaa gtt tca gtt gaa ctt aat gac          816
Ser Lys Asn Ile Ser Lys Ser Gly Glu Val Ser Val Glu Leu Asn Asp
                260                 265                 270 act gac agt agt gct gct act aaa aaa act gca gct tgg aat tca ggc          864
Thr Asp Ser Ser Ala Ala Thr Lys Lys Thr Ala Ala Trp Asn Ser Gly
            275                 280                 285 act tca act tta aca att act gta aac agt aaa aaa act aaa gac ctt          912
Thr Ser Thr Leu Thr Ile Thr Val Asn Ser Lys Lys Thr Lys Asp Leu
        290                 295                 300 gtg ttt aca aaa gaa aac aca att aca gta caa caa tac gac tca aat          960
Val Phe Thr Lys Glu Asn Thr Ile Thr Val Gln Gln Tyr Asp Ser Asn
305                 310                 315                 320 ggc acc aaa tta gag ggg tca gca gtt gaa att aca aaa ctt gat gaa         1008
Gly Thr Lys Leu Glu Gly Ser Ala Val Glu Ile Thr Lys Leu Asp Glu
                    325                 330                 335 att aaa aac gct tta aaa taa                                             1029
Ile Lys Asn Ala Leu Lys  *
                340

<210> SEQ ID NO 80
<211> LENGTH: 342
<212> TYPE: PRT
<213> ORGANISM: Artificial Sequence
<220> FEATURE:
<223> OTHER INFORMATION: Chimeric protein

<400> SEQUENCE: 80
```

| | | | | | | | | | | | | | | |
|---|---|---|---|---|---|---|---|---|---|---|---|---|---|---|
| Met | Ala | Cys | Asn | Asn | Ser | Gly | Lys | Asp | Gly | Asn | Thr | Ser | Ala | Asn | Ser |
| 1 | | | | 5 | | | | | 10 | | | | | 15 | |
| Ala | Asp | Glu | Ser | Val | Lys | Gly | Pro | Asn | Leu | Thr | Glu | Ile | Asn | Lys | Lys |
| | | | 20 | | | | | 25 | | | | | 30 | | |
| Ile | Thr | Asp | Ser | Asn | Ala | Val | Leu | Leu | Ala | Val | Lys | Val | Glu | Ala | |
| | | 35 | | | | | 40 | | | | | 45 | | | |
| Leu | Leu | Ser | Ser | Ile | Asp | Glu | Ile | Ala | Ala | Lys | Ala | Ile | Gly | Lys | Lys |
| | 50 | | | | | 55 | | | | | 60 | | | | |
| Ile | His | Gln | Asn | Asn | Gly | Leu | Asp | Thr | Glu | Asn | Asn | His | Asn | Gly | Ser |
| 65 | | | | | 70 | | | | | 75 | | | | | 80 |
| Leu | Leu | Ala | Gly | Ala | Tyr | Ala | Ile | Ser | Thr | Leu | Ile | Lys | Gln | Lys | Leu |
| | | | | 85 | | | | | 90 | | | | | 95 | |
| Asp | Gly | Leu | Lys | Asn | Glu | Gly | Leu | Lys | Glu | Lys | Ile | Asp | Ala | Ala | Lys |
| | | | 100 | | | | | 105 | | | | | 110 | | |
| Lys | Cys | Ser | Glu | Thr | Phe | Thr | Asn | Lys | Leu | Lys | Glu | Lys | His | Thr | Asp |
| | | 115 | | | | | 120 | | | | | 125 | | | |
| Leu | Gly | Lys | Glu | Gly | Val | Thr | Asp | Ala | Asp | Ala | Lys | Glu | Ala | Ile | Leu |
| | 130 | | | | | 135 | | | | | 140 | | | | |
| Lys | Ala | Asn | Gly | Thr | Lys | Thr | Lys | Gly | Ala | Glu | Glu | Leu | Gly | Lys | Leu |
| 145 | | | | | 150 | | | | | 155 | | | | | 160 |
| Phe | Glu | Ser | Val | Glu | Val | Leu | Ser | Lys | Ala | Ala | Lys | Glu | Met | Leu | Ala |
| | | | | 165 | | | | | 170 | | | | | 175 | |
| Asn | Ser | Val | Lys | Glu | Leu | Thr | Ser | Pro | Val | Val | Ala | Glu | Ser | Pro | Lys |
| | | | 180 | | | | | 185 | | | | | 190 | | |
| Lys | Pro | Ser | Met | Ala | Lys | Gln | Asn | Val | Ser | Glu | Lys | Ile | Ile | Thr | Arg |
| | | 195 | | | | | 200 | | | | | 205 | | | |
| Ala | Asp | Gly | Thr | Arg | Leu | Glu | Tyr | Thr | Gly | Ile | Lys | Ser | Asp | Gly | Ser |
| | 210 | | | | | 215 | | | | | 220 | | | | |
| Gly | Lys | Ala | Lys | Glu | Val | Leu | Lys | Gly | Tyr | Val | Leu | Glu | Gly | Thr | Leu |
| 225 | | | | | 230 | | | | | 235 | | | | | 240 |
| Thr | Ala | Glu | Lys | Thr | Thr | Leu | Val | Val | Lys | Glu | Gly | Thr | Val | Thr | Leu |
| | | | | 245 | | | | | 250 | | | | | 255 | |
| Ser | Lys | Asn | Ile | Ser | Lys | Ser | Gly | Glu | Val | Ser | Val | Glu | Leu | Asn | Asp |
| | | | 260 | | | | | 265 | | | | | 270 | | |
| Thr | Asp | Ser | Ser | Ala | Ala | Thr | Lys | Lys | Thr | Ala | Ala | Trp | Asn | Ser | Gly |
| | | 275 | | | | | 280 | | | | | 285 | | | |
| Thr | Ser | Thr | Leu | Thr | Ile | Thr | Val | Asn | Ser | Lys | Lys | Thr | Lys | Asp | Leu |
| | 290 | | | | | 295 | | | | | 300 | | | | |
| Val | Phe | Thr | Lys | Glu | Asn | Thr | Ile | Thr | Val | Gln | Gln | Tyr | Asp | Ser | Asn |
| 305 | | | | | 310 | | | | | 315 | | | | | 320 |
| Gly | Thr | Lys | Leu | Glu | Gly | Ser | Ala | Val | Glu | Ile | Thr | Lys | Leu | Asp | Glu |
| | | | | 325 | | | | | 330 | | | | | 335 | |
| Ile | Lys | Asn | Ala | Leu | Lys | | | | | | | | | | |
| | | | 340 | | | | | | | | | | | | |

<210> SEQ ID NO 81
<211> LENGTH: 1029
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1029)

<400> SEQUENCE: 81 atg gct tgt aat aat tca ggg aaa gat ggg aat aca tct gca aat tct     48

-continued

| | | | |
|---|---|---|---|
| Met Ala Cys Asn Asn Ser Gly Lys Asp Gly Asn Thr Ser Ala Asn Ser<br>1               5                   10                  15 | | | |
| gct gat gag tct gtt aaa ggg cct aat ctt aca gaa ata aat aaa aaa<br>Ala Asp Glu Ser Val Lys Gly Pro Asn Leu Thr Glu Ile Asn Lys Lys<br>            20                  25                  30 | | | 96 |
| att acg gat tct aat gcg gtt tta ctt gct gtg aaa gag gtt gaa gcg<br>Ile Thr Asp Ser Asn Ala Val Leu Leu Ala Val Lys Glu Val Glu Ala<br>        35                  40                  45 | | | 144 |
| ttg ctg tca tct ata gat gaa att gct gct aaa gct att ggt aaa aaa<br>Leu Leu Ser Ser Ile Asp Glu Ile Ala Ala Lys Ala Ile Gly Lys Lys<br>    50                  55                  60 | | | 192 |
| ata cac caa aat aat ggt ttg gat acc gaa aat aat cac aat gga tca<br>Ile His Gln Asn Asn Gly Leu Asp Thr Glu Asn Asn His Asn Gly Ser<br>65                  70                  75                  80 | | | 240 |
| ttg tta gcg gga gct tat gca ata tca acc cta ata aaa caa aaa tta<br>Leu Leu Ala Gly Ala Tyr Ala Ile Ser Thr Leu Ile Lys Gln Lys Leu<br>                85                  90                  95 | | | 288 |
| gat gga ttg aaa aat gaa gga tta aag gaa aaa att gat gcg gct aag<br>Asp Gly Leu Lys Asn Glu Gly Leu Lys Glu Lys Ile Asp Ala Ala Lys<br>            100                 105                 110 | | | 336 |
| aaa tgt tct gaa aca ttt act aat aaa tta aaa gaa aaa cac aca gat<br>Lys Cys Ser Glu Thr Phe Thr Asn Lys Leu Lys Glu Lys His Thr Asp<br>        115                 120                 125 | | | 384 |
| ctt ggt aaa gaa ggt gtt act gat gct gat gca aaa gaa gcc att tta<br>Leu Gly Lys Glu Gly Val Thr Asp Ala Asp Ala Lys Glu Ala Ile Leu<br>    130                 135                 140 | | | 432 |
| aaa gca aat ggt act aaa act aaa ggt gct gaa gaa ctt gga aaa tta<br>Lys Ala Asn Gly Thr Lys Thr Lys Gly Ala Glu Glu Leu Gly Lys Leu<br>145                 150                 155                 160 | | | 480 |
| ttt gaa tca gta gag gtc ttg tca aaa gca gct aaa gag atg ctt gct<br>Phe Glu Ser Val Glu Val Leu Ser Lys Ala Ala Lys Glu Met Leu Ala<br>                165                 170                 175 | | | 528 |
| aat tca gtt aaa gag ctt aca agc cct gtt gtg gca gaa agt cca aaa<br>Asn Ser Val Lys Glu Leu Thr Ser Pro Val Val Ala Glu Ser Pro Lys<br>            180                 185                 190 | | | 576 |
| aaa cct tcc atg gcc aag caa aat gtt tct gaa aaa ata ata aca aga<br>Lys Pro Ser Met Ala Lys Gln Asn Val Ser Glu Lys Ile Ile Thr Arg<br>        195                 200                 205 | | | 624 |
| gca gac gga acc aga ctt gaa tac aca gga att aaa agc gat gga tct<br>Ala Asp Gly Thr Arg Leu Glu Tyr Thr Gly Ile Lys Ser Asp Gly Ser<br>    210                 215                 220 | | | 672 |
| gga aaa gct aaa gag gtt tta aaa ggc tat gtt ctt gaa gga act cta<br>Gly Lys Ala Lys Glu Val Leu Lys Gly Tyr Val Leu Glu Gly Thr Leu<br>225                 230                 235                 240 | | | 720 |
| act gct gaa aaa aca aca ttg gtg gtt aaa gaa gga act gtt act tta<br>Thr Ala Glu Lys Thr Thr Leu Val Val Lys Glu Gly Thr Val Thr Leu<br>                245                 250                 255 | | | 768 |
| agc aaa aat att tca aaa tct ggg gaa gtt tca gtt gaa ctt aat gac<br>Ser Lys Asn Ile Ser Lys Ser Gly Glu Val Ser Val Glu Leu Asn Asp<br>            260                 265                 270 | | | 816 |
| act gac agt agt gct gct act aaa aaa act gca gct tgg aat tca aaa<br>Thr Asp Ser Ser Ala Ala Thr Lys Lys Thr Ala Ala Trp Asn Ser Lys<br>        275                 280                 285 | | | 864 |
| act tcc act tta aca att agt gtg aat agc caa aaa acc aaa aac ctt<br>Thr Ser Thr Leu Thr Ile Ser Val Asn Ser Gln Lys Thr Lys Asn Leu<br>    290                 295                 300 | | | 912 |
| gta ttc aca aaa gaa gac aca ata aca gta caa aaa tac gac tca gca<br>Val Phe Thr Lys Glu Asp Thr Ile Thr Val Gln Lys Tyr Asp Ser Ala<br>305                 310                 315                 320 | | | 960 |
| ggc acc aat cta gaa ggc aaa gca gtc gaa att aca aca ctt aaa gaa | | | 1008 |

```
Gly Thr Asn Leu Glu Gly Lys Ala Val Glu Ile Thr Thr Leu Lys Glu
                325                 330                 335 ctt aaa aac gct tta aaa taa                                              1029
Leu Lys Asn Ala Leu Lys *
            340

<210> SEQ ID NO 82
<211> LENGTH: 342
<212> TYPE: PRT
<213> ORGANISM: Artificial Sequence
<220> FEATURE:
<223> OTHER INFORMATION: Chimeric protein

<400> SEQUENCE: 82

Met Ala Cys Asn Asn Ser Gly Lys Asp Gly Asn Thr Ser Ala Asn Ser
  1               5                  10                  15

Ala Asp Glu Ser Val Lys Gly Pro Asn Leu Thr Glu Ile Asn Lys Lys
                 20                  25                  30

Ile Thr Asp Ser Asn Ala Val Leu Leu Ala Val Lys Glu Val Glu Ala
             35                  40                  45

Leu Leu Ser Ser Ile Asp Glu Ile Ala Ala Lys Ala Ile Gly Lys Lys
 50                  55                  60

Ile His Gln Asn Asn Gly Leu Asp Thr Glu Asn Asn His Asn Gly Ser
 65                  70                  75                  80

Leu Leu Ala Gly Ala Tyr Ala Ile Ser Thr Leu Ile Lys Gln Lys Leu
                 85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Glu Lys Ile Ile Thr Arg
        195                 200                 205

Ala Asp Gly Thr Arg Leu Glu Tyr Thr Gly Ile Lys Ser Asp Gly Ser
210                 215                 220

Gly Lys Ala Lys Glu Val Leu Lys Gly Tyr Val Leu Glu Gly Thr Leu
225                 230                 235                 240

Thr Ala Glu Lys Thr Thr Leu Val Val Lys Glu Gly Thr Val Thr Leu
                245                 250                 255

Ser Lys Asn Ile Ser Lys Ser Gly Glu Val Ser Val Glu Leu Asn Asp
            260                 265                 270

Thr Asp Ser Ser Ala Ala Thr Lys Lys Thr Ala Ala Trp Asn Ser Lys
        275                 280                 285

Thr Ser Thr Leu Thr Ile Ser Val Asn Ser Gln Lys Thr Lys Asn Leu
290                 295                 300

Val Phe Thr Lys Glu Asp Thr Ile Thr Val Gln Lys Tyr Asp Ser Ala
305                 310                 315                 320

Gly Thr Asn Leu Glu Gly Lys Ala Val Glu Ile Thr Thr Leu Lys Glu
                325                 330                 335
```

<210> SEQ ID NO 83
<211> LENGTH: 1029
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1029)

<400> SEQUENCE: 83

```
atg gct tgt aat aat tca ggg aaa gat ggg aat aca tct gca aat tct      48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata aat aaa aaa      96
Ala Asp Glu Ser Val Lys Gly Pro Asn Leu Thr Glu Ile Asn Lys Lys
                20                  25                  30 att acg gat tct aat gcg gtt tta ctt gct gtg aaa gag gtt gaa gcg      144
Ile Thr Asp Ser Asn Ala Val Leu Leu Ala Val Lys Glu Val Glu Ala
            35                  40                  45 ttg ctg tca tct ata gat gaa att gct gct aaa gct att ggt aaa aaa      192
Leu Leu Ser Ser Ile Asp Glu Ile Ala Ala Lys Ala Ile Gly Lys Lys
        50                  55                  60 ata cac caa aat aat ggt ttg gat acc gaa aat aat cac aat gga tca      240
Ile His Gln Asn Asn Gly Leu Asp Thr Glu Asn Asn His Asn Gly Ser
65                  70                  75                  80 ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag      336
Asp Gly Leu Lys Asn Glu Gly Leu Lys Glu Lys Ile Asp Ala Ala Lys
                100                 105                 110 aaa tgt tct gaa aca ttt act aat aaa tta aaa gaa aaa cac aca gat      384
Lys Cys Ser Glu Thr Phe Thr Asn Lys Leu Lys Glu Lys His Thr Asp
            115                 120                 125 ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
        130                 135                 140 aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa      576
Asn Ser Val Lys Glu Leu Thr Ser Pro Val Val Ala Glu Ser Pro Lys
                180                 185                 190 aaa cct tcc atg gcc aag caa aat gtt tct gaa aaa ata ata aca aga      624
Lys Pro Ser Met Ala Lys Gln Asn Val Ser Glu Lys Ile Ile Thr Arg
            195                 200                 205 gca gac gga acc aga ctt gaa tac aca gga att aaa agc gat gga tct      672
Ala Asp Gly Thr Arg Leu Glu Tyr Thr Gly Ile Lys Ser Asp Gly Ser
        210                 215                 220 gga aaa gct aaa gag gtt tta aaa ggc tat gtt ctt gaa gga act cta      720
Gly Lys Ala Lys Glu Val Leu Lys Gly Tyr Val Leu Glu Gly Thr Leu
225                 230                 235                 240 act gct gaa aaa aca aca ttg gtg gtt aaa gaa gga act gtt act tta      768
Thr Ala Glu Lys Thr Thr Leu Val Val Lys Glu Gly Thr Val Thr Leu
                245                 250                 255 agc aaa aat att tca aaa tct ggg gaa gtt tca gtt gaa ctt aat gac      816
Ser Lys Asn Ile Ser Lys Ser Gly Glu Val Ser Val Glu Leu Asn Asp
```

```
Ser Lys Asn Ile Ser Lys Ser Gly Glu Val Ser Val Glu Leu Asn Asp
            260                 265                 270 act gac agt agt gct gct act aaa aaa act gca gct tgg aat tca aaa      864
Thr Asp Ser Ser Ala Ala Thr Lys Lys Thr Ala Ala Trp Asn Ser Lys
            275                 280                 285 act tct act tta aca att agt gtt aac agc aaa aaa act aca caa ctt      912
Thr Ser Thr Leu Thr Ile Ser Val Asn Ser Lys Lys Thr Thr Gln Leu
            290                 295                 300 gtg ttt act aaa caa gac aca ata act gta caa aaa tac gac tcc gca      960
Val Phe Thr Lys Gln Asp Thr Ile Thr Val Gln Lys Tyr Asp Ser Ala
305                 310                 315                 320 ggt acc aat tta gaa ggc aca gca gtc gaa att aaa aca ctt gat gaa     1008
Gly Thr Asn Leu Glu Gly Thr Ala Val Glu Ile Lys Thr Leu Asp Glu
            325                 330                 335 ctt aaa aac gct tta aaa taa                                          1029
Leu Lys Asn Ala Leu Lys  *
            340

<210> SEQ ID NO 84
<211> LENGTH: 342
<212> TYPE: PRT
<213> ORGANISM: Artificial Sequence
<220> FEATURE:
<223> OTHER INFORMATION: Chimeric protein

<400> SEQUENCE: 84

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Glu Lys Ile Ile Thr Arg
        195                 200                 205

Ala Asp Gly Thr Arg Leu Glu Tyr Thr Gly Ile Lys Ser Asp Gly Ser
    210                 215                 220

Gly Lys Ala Lys Glu Val Leu Lys Gly Tyr Val Leu Glu Gly Thr Leu
225                 230                 235                 240

Thr Ala Glu Lys Thr Thr Leu Val Val Lys Glu Gly Thr Val Thr Leu
                245                 250                 255
```

```
Ser Lys Asn Ile Ser Lys Ser Gly Glu Val Ser Val Glu Leu Asn Asp
            260                 265                 270

Thr Asp Ser Ser Ala Ala Thr Lys Lys Thr Ala Ala Trp Asn Ser Lys
        275                 280                 285

Thr Ser Thr Leu Thr Ile Ser Val Asn Ser Lys Lys Thr Thr Gln Leu
    290                 295                 300

Val Phe Thr Lys Gln Asp Thr Ile Thr Val Gln Lys Tyr Asp Ser Ala
305                 310                 315                 320

Gly Thr Asn Leu Glu Gly Thr Ala Val Glu Ile Lys Thr Leu Asp Glu
                325                 330                 335

Leu Lys Asn Ala Leu Lys
            340

<210> SEQ ID NO 85
<211> LENGTH: 1035
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1035)

<400> SEQUENCE: 85 atg gct tgt aat aat tca ggg aaa gat ggg aat aca tct gca aat tct      48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
            20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
        35                  40                  45 ttg ctg tca tct ata gat gaa att gct gct aaa gct att ggt aaa aaa     192
Leu Leu Ser Ser Ile Asp Glu Ile Ala Ala Lys Ala Ile Gly Lys Lys
    50                  55                  60 ata cac caa aat aat ggt ttg gat acc gaa tat aat cac aat gga tca     240
Ile His Gln Asn Asn Gly Leu Asp Thr Glu Tyr Asn His Asn Gly Ser
65                  70                  75                  80 ttg tta gcg gga gct tat gca ata tca acc cta ata aaa caa aaa tta     288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag     336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat     384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta     432
Leu Gly Lys Glu Gly Val Thr Asp Ala Asp Ala Lys Glu Ala Ile Leu
    130                 135                 140 aaa aca aat ggt act aaa act aaa ggt gct gaa gaa ctt gga aaa tta     480
Lys Thr Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct     528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa     576
Asn Ser Val Lys Glu Leu Thr Ser Pro Val Val Ala Glu Ser Pro Lys
            180                 185                 190 aaa cct tcc atg gcc aag caa aat gtt aca tct gaa aaa aca ata gta     624
```

```
                                           -continued
Lys Pro Ser Met Ala Lys Gln Asn Val Thr Ser Glu Lys Thr Ile Val
        195                 200                 205 aga gca aat gga acc aga ctt gaa tac aca gac ata aaa agc gat gga     672
Arg Ala Asn Gly Thr Arg Leu Glu Tyr Thr Asp Ile Lys Ser Asp Gly
210                 215                 220 tcc gga aaa gct aaa gaa gtt tta aaa gac ttt act ctt gaa gga act     720
Ser Gly Lys Ala Lys Glu Val Leu Lys Asp Phe Thr Leu Glu Gly Thr
225                 230                 235                 240 cta gct gct gac ggc aaa aca aca ttg aaa gtt aca gaa ggc act gtt     768
Leu Ala Ala Asp Gly Lys Thr Thr Leu Lys Val Thr Glu Gly Thr Val
            245                 250                 255 gtt tta agc aag aac att tta aaa tcc gga gaa ata aca gtt gca ctt     816
Val Leu Ser Lys Asn Ile Leu Lys Ser Gly Glu Ile Thr Val Ala Leu
        260                 265                 270 gat gac tct gac act act cag gct act aaa aaa act gga aaa tgg gat     864
Asp Asp Ser Asp Thr Thr Gln Ala Thr Lys Lys Thr Gly Lys Trp Asp
    275                 280                 285 tca aat act tcc act tta aca att agt gtg aat agc aaa aaa act aaa     912
Ser Asn Thr Ser Thr Leu Thr Ile Ser Val Asn Ser Lys Lys Thr Lys
290                 295                 300 aac att gta ttt aca aaa gaa gac aca ata aca gta caa aaa tac gac     960
Asn Ile Val Phe Thr Lys Glu Asp Thr Ile Thr Val Gln Lys Tyr Asp
305                 310                 315                 320 tca gca ggc acc aat cta gaa ggc aac gca gtc gaa att aaa aca ctt    1008
Ser Ala Gly Thr Asn Leu Glu Gly Asn Ala Val Glu Ile Lys Thr Leu
            325                 330                 335 gat gaa ctt aaa aac gct tta aaa tag                                 1035
Asp Glu Leu Lys Asn Ala Leu Lys *
        340

<210> SEQ ID NO 86
<211> LENGTH: 344
<212> TYPE: PRT
<213> ORGANISM: Artificial Sequence
<220> FEATURE:
<223> OTHER INFORMATION: Chimeric protein

<400> SEQUENCE: 86

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Tyr Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Thr Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
```

```
                            165                 170                 175
Asn Ser Val Lys Glu Leu Thr Ser Pro Val Ala Glu Ser Pro Lys
            180                 185                 190

Lys Pro Ser Met Ala Lys Gln Asn Val Thr Ser Glu Lys Thr Ile Val
            195                 200                 205

Arg Ala Asn Gly Thr Arg Leu Glu Tyr Thr Asp Ile Lys Ser Asp Gly
            210                 215                 220

Ser Gly Lys Ala Lys Glu Val Leu Lys Asp Phe Thr Leu Glu Gly Thr
225                 230                 235                 240

Leu Ala Ala Asp Gly Lys Thr Thr Leu Lys Val Thr Glu Gly Thr Val
                245                 250                 255

Val Leu Ser Lys Asn Ile Leu Lys Ser Gly Glu Ile Thr Val Ala Leu
            260                 265                 270

Asp Asp Ser Asp Thr Thr Gln Ala Thr Lys Lys Thr Gly Lys Trp Asp
            275                 280                 285

Ser Asn Thr Ser Thr Leu Thr Ile Ser Val Asn Ser Lys Lys Thr Lys
            290                 295                 300

Asn Ile Val Phe Thr Lys Glu Asp Thr Ile Thr Val Gln Lys Tyr Asp
305                 310                 315                 320

Ser Ala Gly Thr Asn Leu Glu Gly Asn Ala Val Glu Ile Lys Thr Leu
                325                 330                 335

Asp Glu Leu Lys Asn Ala Leu Lys
            340

<210> SEQ ID NO 87
<211> LENGTH: 1323
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1323)

<400> SEQUENCE: 87 atg gct tgt aat aat tca ggg aaa gat ggg aat aca tct gca aat tct      48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata aat aaa aaa      96
Ala Asp Glu Ser Val Lys Gly Pro Asn Leu Thr Glu Ile Asn Lys Lys
            20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
        35                  40                  45 ttg ctg tca tct ata gat gaa att gct gct aaa gct att ggt aaa aaa     192
Leu Leu Ser Ser Ile Asp Glu Ile Ala Ala Lys Ala Ile Gly Lys Lys
    50                  55                  60 ata cac caa aat aat ggt ttg gat acc gaa aat aat cac aat gga tca     240
Ile His Gln Asn Asn Gly Leu Asp Thr Glu Asn Asn His Asn Gly Ser
65                  70                  75                  80 ttg tta gcg gga gct tat gca ata tca acc cta ata aaa caa aaa tta     288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag     336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat     384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta     432
```

```
Leu Gly Lys Glu Gly Val Thr Asp Ala Asp Ala Lys Glu Ala Ile Leu
    130                 135                 140 aaa gca aat ggt act aaa act aaa ggt gct gaa gaa ctt gga aaa tta    480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct    528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa    576
Asn Ser Val Lys Glu Leu Thr Ser Pro Val Val Ala Glu Ser Pro Lys
            180                 185                 190 aaa cct tcc atg gcc gtt tca gta gat ttg cct ggt gaa atg aaa gtt    624
Lys Pro Ser Met Ala Val Ser Val Asp Leu Pro Gly Glu Met Lys Val
        195                 200                 205 ctt gta agc aaa gaa aaa aac aaa gac ggc aag tac gat cta att gca    672
Leu Val Ser Lys Glu Lys Asn Lys Asp Gly Lys Tyr Asp Leu Ile Ala
    210                 215                 220 aca gta gac aag ctt gag ctt aaa gga act tct gat aaa aac aat gga    720
Thr Val Asp Lys Leu Glu Leu Lys Gly Thr Ser Asp Lys Asn Asn Gly
225                 230                 235                 240 tct gga gta ctt gaa ggc gta aaa gct gac aaa agt aaa gta aaa tta    768
Ser Gly Val Leu Glu Gly Val Lys Ala Asp Lys Ser Lys Val Lys Leu
                245                 250                 255 aca att tct gac gat cta ggt caa acc aca ctt gaa gtt ttc aaa gaa    816
Thr Ile Ser Asp Asp Leu Gly Gln Thr Thr Leu Glu Val Phe Lys Glu
            260                 265                 270 gat ggc aaa aca cta gta tca aaa aaa gta act tcc aaa gac aag tca    864
Asp Gly Lys Thr Leu Val Ser Lys Lys Val Thr Ser Lys Asp Lys Ser
        275                 280                 285 tca aca gaa gaa aaa ttc aat gaa aaa ggt gaa gta tct gaa aaa ata    912
Ser Thr Glu Glu Lys Phe Asn Glu Lys Gly Glu Val Ser Glu Lys Ile
    290                 295                 300 ata aca aga gca gac gga acc aga ctt gaa tac aca gga att aaa agc    960
Ile Thr Arg Ala Asp Gly Thr Arg Leu Glu Tyr Thr Gly Ile Lys Ser
305                 310                 315                 320 gat gga tct gga aaa gct aaa gag gtt tta aaa ggc ttt act ctt gaa   1008
Asp Gly Ser Gly Lys Ala Lys Glu Val Leu Lys Gly Phe Thr Leu Glu
                325                 330                 335 gga aaa gta gct aat gat aaa gta aca ttg gaa gta aaa gaa gga acc   1056
Gly Lys Val Ala Asn Asp Lys Val Thr Leu Glu Val Lys Glu Gly Thr
            340                 345                 350 gtt act tta agt aag att tca aaa tct ggg gaa gtt tca gtt gaa ctt   1104
Val Thr Leu Ser Lys Ile Ser Lys Ser Gly Glu Val Ser Val Glu Leu
        355                 360                 365 aat gac act gac agt agt gct gct act aaa aaa act gca gct tgg aat   1152
Asn Asp Thr Asp Ser Ser Ala Ala Thr Lys Lys Thr Ala Ala Trp Asn
    370                 375                 380 tca aaa act tct act tta aca att agt gtt aac agc aaa aaa act aca   1200
Ser Lys Thr Ser Thr Leu Thr Ile Ser Val Asn Ser Lys Lys Thr Thr
385                 390                 395                 400 caa ctt gtg ttt act aaa caa gac aca ata act gta caa aaa tac gac   1248
Gln Leu Val Phe Thr Lys Gln Asp Thr Ile Thr Val Gln Lys Tyr Asp
                405                 410                 415 tcc gca ggt acc aat tta gaa ggc aca gca gtc gaa att aaa aca ctt   1296
Ser Ala Gly Thr Asn Leu Glu Gly Thr Ala Val Glu Ile Lys Thr Leu
            420                 425                 430 gat gaa ctt aaa aac gct tta aaa taa                                1323
Asp Glu Leu Lys Asn Ala Leu Lys *
        435                 440
```

```
<210> SEQ ID NO 88
<211> LENGTH: 440
<212> TYPE: PRT
<213> ORGANISM: Artificial Sequence
<220> FEATURE:
<223> OTHER INFORMATION: Chimeric protein

<400> SEQUENCE: 88

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Ala Glu Ser Pro Lys
            180                 185                 190

Lys Pro Ser Met Ala Val Ser Val Asp Leu Pro Gly Glu Met Lys Val
        195                 200                 205

Leu Val Ser Lys Glu Lys Asn Lys Asp Gly Lys Tyr Asp Leu Ile Ala
    210                 215                 220

Thr Val Asp Lys Leu Glu Leu Lys Gly Thr Ser Asp Lys Asn Asn Gly
225                 230                 235                 240

Ser Gly Val Leu Glu Gly Val Lys Ala Asp Lys Ser Lys Val Lys Leu
                245                 250                 255

Thr Ile Ser Asp Asp Leu Gly Gln Thr Thr Leu Glu Val Phe Lys Glu
            260                 265                 270

Asp Gly Lys Thr Leu Val Ser Lys Lys Val Thr Ser Lys Asp Lys Ser
        275                 280                 285

Ser Thr Glu Glu Lys Phe Asn Glu Lys Gly Glu Val Ser Glu Lys Ile
    290                 295                 300

Ile Thr Arg Ala Asp Gly Thr Arg Leu Glu Tyr Thr Gly Ile Lys Ser
305                 310                 315                 320

Asp Gly Ser Gly Lys Ala Lys Glu Val Leu Lys Gly Phe Thr Leu Glu
                325                 330                 335

Gly Lys Val Ala Asn Asp Lys Val Thr Leu Glu Val Lys Glu Gly Thr
            340                 345                 350

Val Thr Leu Ser Lys Ile Ser Lys Ser Gly Glu Val Ser Val Glu Leu
        355                 360                 365

Asn Asp Thr Asp Ser Ser Ala Ala Thr Lys Lys Thr Ala Ala Trp Asn
    370                 375                 380
```

```
Ser Lys Thr Ser Thr Leu Thr Ile Ser Val Asn Ser Lys Lys Thr Thr
385                 390                 395                 400

Gln Leu Val Phe Thr Lys Gln Asp Thr Ile Thr Val Gln Lys Tyr Asp
            405                 410                 415

Ser Ala Gly Thr Asn Leu Glu Gly Thr Ala Val Glu Ile Lys Thr Leu
            420                 425                 430

Asp Glu Leu Lys Asn Ala Leu Lys
            435                 440

<210> SEQ ID NO 89
<211> LENGTH: 1302
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1302)

<400> SEQUENCE: 89 atg gct tgt aat aat tca ggg aaa gat ggg aat aca tct gca aat tct      48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
            20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
        35                  40                  45 ttg ctg tca tct ata gat gag ctt gct aaa gct att ggt aaa aaa ata     192
Leu Leu Ser Ser Ile Asp Glu Leu Ala Lys Ala Ile Gly Lys Lys Ile
    50                  55                  60 aaa aac gat ggt agt tta gat aat gaa gca aat cgc aac gag tca ttg     240
Lys Asn Asp Gly Ser Leu Asp Asn Glu Ala Asn Arg Asn Glu Ser Leu
65                  70                  75                  80 tta gca gga gct tat aca ata tca acc tta ata aca caa aaa tta agt     288
Leu Ala Gly Ala Tyr Thr Ile Ser Thr Leu Ile Thr Gln Lys Leu Ser
                85                  90                  95 aaa tta aac gga tca gaa ggt tta aag gaa aag att gcc gca gct aag     336
Lys Leu Asn Gly Ser Glu Gly Leu Lys Glu Lys Ile Ala Ala Ala Lys
            100                 105                 110 aaa tgc tct gaa gag ttt agt act aaa cta aaa gat aat cat gca cag     384
Lys Cys Ser Glu Glu Phe Ser Thr Lys Leu Lys Asp Asn His Ala Gln
        115                 120                 125 ctt ggt ata cag ggc gtt act gat gaa aat gca aaa aaa gct att tta     432
Leu Gly Ile Gln Gly Val Thr Asp Glu Asn Ala Lys Lys Ala Ile Leu
    130                 135                 140 aaa gca aat gca gcg ggt aaa gat aag ggc gtt gaa gaa ctt gaa aag     480
Lys Ala Asn Ala Ala Gly Lys Asp Lys Gly Val Glu Glu Leu Glu Lys
145                 150                 155                 160 ttg tcc gga tca tta gaa agc tta tca aaa gca gct aaa gag atg ctt     528
Leu Ser Gly Ser Leu Glu Ser Leu Ser Lys Ala Ala Lys Glu Met Leu
                165                 170                 175 gct aat tca gtt aaa gag ctt aca agc cct gtt gtc cat ggc gtt tca     576
Ala Asn Ser Val Lys Glu Leu Thr Ser Pro Val Val His Gly Val Ser
            180                 185                 190 gta gat ttg cct ggt gaa atg aaa gtt ctt gta agc aaa gaa aaa aac     624
Val Asp Leu Pro Gly Glu Met Lys Val Leu Val Ser Lys Glu Lys Asn
        195                 200                 205 aaa gac ggc aag tac gat cta att gca aca gta gac aag ctt gag ctt     672
Lys Asp Gly Lys Tyr Asp Leu Ile Ala Thr Val Asp Lys Leu Glu Leu
    210                 215                 220
```

```
aaa gga act tct gat aaa aac aat gga tct gga gta ctt gaa ggc gta      720
Lys Gly Thr Ser Asp Lys Asn Asn Gly Ser Gly Val Leu Glu Gly Val
225                 230                 235                 240 aaa gct gac aaa agt aaa gta aaa tta aca att tct gac gat cta ggt      768
Lys Ala Asp Lys Ser Lys Val Lys Leu Thr Ile Ser Asp Asp Leu Gly
            245                 250                 255 caa acc aca ctt gaa gtt ttc aaa gaa gat ggc aaa aca cta gta tca      816
Gln Thr Thr Leu Glu Val Phe Lys Glu Asp Gly Lys Thr Leu Val Ser
        260                 265                 270 aaa aaa gta act tcc aaa gac aag tca tca aca gaa gaa aaa ttc aat      864
Lys Lys Val Thr Ser Lys Asp Lys Ser Ser Thr Glu Glu Lys Phe Asn
    275                 280                 285 gaa aaa ggt gaa gta tct gaa aaa ata ata aca aga gca gac gga acc      912
Glu Lys Gly Glu Val Ser Glu Lys Ile Ile Thr Arg Ala Asp Gly Thr
290                 295                 300 aga ctt gaa tac aca gga att aaa agc gat gga tct gga aaa gct aaa      960
Arg Leu Glu Tyr Thr Gly Ile Lys Ser Asp Gly Ser Gly Lys Ala Lys
305                 310                 315                 320 gag gtt tta aaa ggc ttt act ctt gaa gga aaa gta gct aat gat aaa     1008
Glu Val Leu Lys Gly Phe Thr Leu Glu Gly Lys Val Ala Asn Asp Lys
            325                 330                 335 gta aca ttg gaa gta aaa gaa gga acc gtt act tta agt aag att tca     1056
Val Thr Leu Glu Val Lys Glu Gly Thr Val Thr Leu Ser Lys Ile Ser
        340                 345                 350 aaa tct ggg gaa gtt tca gtt gaa ctt aat gac act gac agt agt gct     1104
Lys Ser Gly Glu Val Ser Val Glu Leu Asn Asp Thr Asp Ser Ser Ala
    355                 360                 365 gct act aaa aaa act gca gct tgg aat tca aaa act tct act tta aca     1152
Ala Thr Lys Lys Thr Ala Ala Trp Asn Ser Lys Thr Ser Thr Leu Thr
370                 375                 380 att agt gtt aac agc aaa aaa act aca caa ctt gtg ttt act aaa caa     1200
Ile Ser Val Asn Ser Lys Lys Thr Thr Gln Leu Val Phe Thr Lys Gln
385                 390                 395                 400 gac aca ata act gta caa aaa tac gac tcc gca ggt acc aat tta gaa     1248
Asp Thr Ile Thr Val Gln Lys Tyr Asp Ser Ala Gly Thr Asn Leu Glu
            405                 410                 415 ggc aca gca gtc gaa att aaa aca ctt gat gaa ctt aaa aac gct tta     1296
Gly Thr Ala Val Glu Ile Lys Thr Leu Asp Glu Leu Lys Asn Ala Leu
        420                 425                 430 aaa taa                                                              1302
Lys *

<210> SEQ ID NO 90
<211> LENGTH: 433
<212> TYPE: PRT
<213> ORGANISM: Artificial Sequence
<220> FEATURE:
<223> OTHER INFORMATION: Chimeric protein

<400> SEQUENCE: 90

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80
```

```
Leu Ala Gly Ala Tyr Thr Ile Ser Thr Leu Ile Thr Gln Lys Leu Ser
            85                  90                  95
Lys Leu Asn Gly Ser Glu Gly Leu Lys Glu Lys Ile Ala Ala Ala Lys
            100                 105                 110
Lys Cys Ser Glu Glu Phe Ser Thr Lys Leu Lys Asp Asn His Ala Gln
            115                 120                 125
Leu Gly Ile Gln Gly Val Thr Asp Glu Asn Ala Lys Lys Ala Ile Leu
            130                 135                 140
Lys Ala Asn Ala Ala Gly Lys Asp Lys Gly Val Glu Glu Leu Glu Lys
145                 150                 155                 160
Leu Ser Gly Ser Leu Glu Ser Leu Ser Lys Ala Ala Lys Glu Met Leu
                165                 170                 175
Ala Asn Ser Val Lys Glu Leu Thr Ser Pro Val Val His Gly Val Ser
            180                 185                 190
Val Asp Leu Pro Gly Glu Met Lys Val Leu Val Ser Lys Glu Lys Asn
            195                 200                 205
Lys Asp Gly Lys Tyr Asp Leu Ile Ala Thr Val Asp Lys Leu Glu Leu
            210                 215                 220
Lys Gly Thr Ser Asp Lys Asn Asn Gly Ser Gly Val Leu Glu Gly Val
225                 230                 235                 240
Lys Ala Asp Lys Ser Lys Val Lys Leu Thr Ile Ser Asp Asp Leu Gly
            245                 250                 255
Gln Thr Thr Leu Glu Val Phe Lys Glu Asp Gly Lys Thr Leu Val Ser
            260                 265                 270
Lys Lys Val Thr Ser Lys Asp Lys Ser Ser Thr Glu Glu Lys Phe Asn
            275                 280                 285
Glu Lys Gly Glu Val Ser Glu Lys Ile Ile Thr Arg Ala Asp Gly Thr
            290                 295                 300
Arg Leu Glu Tyr Thr Gly Ile Lys Ser Asp Gly Ser Gly Lys Ala Lys
305                 310                 315                 320
Glu Val Leu Lys Gly Phe Thr Leu Glu Gly Lys Val Ala Asn Asp Lys
            325                 330                 335
Val Thr Leu Glu Val Lys Glu Gly Thr Val Thr Leu Ser Lys Ile Ser
            340                 345                 350
Lys Ser Gly Glu Val Ser Val Glu Leu Asn Asp Thr Asp Ser Ser Ala
            355                 360                 365
Ala Thr Lys Lys Thr Ala Ala Trp Asn Ser Lys Thr Ser Thr Leu Thr
            370                 375                 380
Ile Ser Val Asn Ser Lys Lys Thr Thr Gln Leu Val Phe Thr Lys Gln
385                 390                 395                 400
Asp Thr Ile Thr Val Gln Lys Tyr Asp Ser Ala Gly Thr Asn Leu Glu
            405                 410                 415
Gly Thr Ala Val Glu Ile Lys Thr Leu Asp Glu Leu Lys Asn Ala Leu
            420                 425                 430
Lys
```

<210> SEQ ID NO 91
<211> LENGTH: 31
<212> TYPE: DNA
<213> ORGANISM: Artificial Sequence
<220> FEATURE:
<223> OTHER INFORMATION: Oligonucleotide Primer

<400> SEQUENCE: 91
gtcatatggc ttgtaataat tcagggaaag a    31

```
<210> SEQ ID NO 92
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 92
tttccatgga aggttttttt ggactttctg                                      30

<210> SEQ ID NO 93
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 93
tttccatggc caagcaaaat gttagcagcc                                      30

<210> SEQ ID NO 94
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 94
taaggatcct tattttaaag cgttttt                                         27

<210> SEQ ID NO 95
<211> LENGTH: 822
<212> TYPE: DNA
<213> ORGANISM: Artificial Sequence
<220> FEATURE:
<223> OTHER INFORMATION: Altered OspA N

```
aaa ggt gaa gta tct gaa aaa ata ata aca atg gca gac gga acc aga       432
Lys Gly Glu Val Ser Glu Lys Ile Ile Thr Met Ala Asp Gly Thr Arg
        130                 135                 140 ctt gaa tac aca gga att aaa agc gat gga tct gga aaa gct aaa gag       480
Leu Glu Tyr Thr Gly Ile Lys Ser Asp Gly Ser Gly Lys Ala Lys Glu
145                 150                 155                 160 gtt tta aaa ggc tat gtt ctt gaa gga act cta act gct gaa aaa aca       528
Val Leu Lys Gly Tyr Val Leu Glu Gly Thr Leu Thr Ala Glu Lys Thr
                165                 170                 175 aca ttg gtg gtt aaa gaa gga act gtt act tta agc aaa aat att tca       576
Thr Leu Val Val Lys Glu Gly Thr Val Thr Leu Ser Lys Asn Ile Ser
        180                 185                 190 aaa tct ggg gaa gtt tca gtt gaa ctt aat gac act gac agt agt gct       624
Lys Ser Gly Glu Val Ser Val Glu Leu Asn Asp Thr Asp Ser Ser Ala
195                 200                 205 gct act aaa aaa act gca gct tgg aat tca ggc act tca act tta aca       672
Ala Thr Lys Lys Thr Ala Ala Trp Asn Ser Gly Thr Ser Thr Leu Thr
        210                 215                 220 att act gta aac agt aaa aaa act aaa gac ctt gtg ttt aca aaa gaa       720
Ile Thr Val Asn Ser Lys Lys Thr Lys Asp Leu Val Phe Thr Lys Glu
225                 230                 235                 240 aac aca att aca gta caa caa tac gac tca aat ggc acc aaa tta gag       768
Asn Thr Ile Thr Val Gln Gln Tyr Asp Ser Asn Gly Thr Lys Leu Glu
                245                 250                 255 ggg tca gca gtt gaa att aca aaa ctt gat gaa att aaa aac gct tta       816
Gly Ser Ala Val Glu Ile Thr Lys Leu Asp Glu Ile Lys Asn Ala Leu
        260                 265                 270 aaa taa                                                               822
Lys *

<210> SEQ ID NO 96
<211> LENGTH: 273
<212> TYPE: PRT
<213> ORGANISM: Artificial Sequence
<220> FEATURE:
<223> OTHER INFORMATION: Altered OspA protein

<400> SEQUENCE: 96

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
                20

```
Val Leu Lys Gly Tyr Val Leu Glu Gly Thr Leu Thr Ala Glu Lys Thr
            165                 170                 175

Thr Leu Val Val Lys Glu Gly Thr Val Thr Leu Ser Lys Asn Ile Ser
        180                 185                 190

Lys Ser Gly Glu Val Ser Val Glu Leu Asn Asp Thr Asp Ser Ser Ala
    195                 200                 205

Ala Thr Lys Lys Thr Ala Ala Trp Asn Ser Gly Thr Ser Thr Leu Thr
210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys

<210> SEQ ID NO 97
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 97 atg aaa aaa tat tta ttg gga ata ggt cta ata tta gcc tta ata gca      48
Met Lys Lys Tyr Leu Leu Gly Ile Gly Leu Ile Leu Ala Leu Ile Ala
1               5                   10                  15 tgt

```
Thr Leu Val Val Lys Glu Gly Thr Val Thr Leu Ser Lys Asn Ile Ser
            180                 185                 190 aaa tct ggg gaa gtt tca gtt gaa ctt aat gac act gac agt agt gct     624
Lys Ser Gly Glu Val Ser Val Glu Leu Asn Asp Thr Asp Ser Ser Ala
        195                 200                 205 gct act aaa aaa act gca gct tgg aat tca ggc act tca act tta aca     672
Ala Thr Lys Lys Thr Ala Ala Trp Asn Ser Gly Thr Ser Thr Leu Thr
    210                 215                 220 att act gta aac agt aaa aaa act aaa gac ctt gtg ttt aca aaa gaa     720
Ile Thr Val Asn Ser Lys Lys Thr Lys Asp Leu Val Phe Thr Lys Glu
225                 230                 235                 240 aac aca att aca gta caa caa tac gac tca aat ggc acc aaa tta gag     768
Asn Thr Ile Thr Val Gln Gln Tyr Asp Ser Asn Gly Thr Lys Leu Glu
                245                 250                 255 ggg tca gca gtt gaa att aca aaa ctt gat gaa att aaa aac gct tta     816
Gly Ser Ala Val Glu Ile Thr Lys Leu Asp Glu Ile Lys Asn Ala Leu
            260                 265                 270 aaa taa                                                             822
Lys *

<210> SEQ ID NO 98
<211> LENGTH: 273
<212> TYPE: PRT
<213> ORGANISM: Artificial Sequence
<220> FEATURE:
<223> OTHER INFORMATION: Altered OspA protein

<400> SEQUENCE: 98

Met Lys Lys Tyr Leu Leu Gly Ile Gly Leu Ile Leu Ala Leu Ile Ala
1

```
Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys

<210> SEQ ID NO 99
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 99 atg aaa aaa tat tta ttg gga ata ggt cta ata tta gcc tta ata gca     48
Met Lys Lys Tyr Leu Leu Gly Ile Gly Leu Ile Leu Ala Leu Ile Ala
1               5                   10                  15 tgt aag caa aat gtt ag

-continued

```
aac aca att aca gta caa caa tac gac tca aat ggc acc aaa tta gag    768
Asn Thr Ile Thr Val Gln Gln Tyr Asp Ser Asn Gly Thr Lys Leu Glu
            245                 250                 255 ggg tca gca gtt gaa att aca aaa ctt gat gaa att aaa aac gct tta    816
Gly Ser Ala Val Glu Ile Thr Lys Leu Asp Glu Ile Lys Asn Ala Leu
        260                 265                 270 aaa taa                                                             822
Lys  *
```

<210> SEQ ID NO 100
<211> LENGTH: 273
<212> TYPE: PRT
<213> ORGANISM: Artificial Sequence
<220> FEATURE:
<223> OTHER INFORMATION: Altered OspA Protein

<400> SEQUENCE: 100

```

<220> FEATURE:
<223> OTHER INFORMATION: Altered OspA Nucleic Acid
<221> NAME/KEY: CDS
<222> LOCATION: (1

<211> LENGTH: 273
<212> TYPE: PRT
<213> ORGANISM: Artificial Sequence
<220> FEATURE:
<223> OTHER INFORMATION: Altered OspA Protein

<400> SEQUENCE: 102

Met Lys Lys Tyr Leu Leu Gly Ile Gly Leu Ile Leu Ala Leu Ile Ala
1               5                   10                  15

```
gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45 gac ggc aag tac gat cta att gca aca gta gac aag ctt gag ctt aaa      192
Asp Gly Lys Tyr Asp Leu Ile Ala Thr Val Asp Lys Leu Glu Leu Lys
    50                  55                  60 gga act tct gat aaa aac aat gga tct gga gta ctt gaa ggc gta aaa      240
Gly Thr Ser Asp Lys Asn Asn Gly Ser Gly Val Leu Glu Gly Val Lys
65                  70                  75                  80 gct gac aaa agt aaa gta aaa tta aca att tct gac gat cta ggt caa      288
Ala Asp Lys Ser Lys Val Lys Leu Thr Ile Ser Asp Asp Leu Gly Gln
                85                  90                  95 acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110 aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125 aaa ggt gaa gta tct gaa aaa ata ata aca atg gca gac gga acc aga      432
Lys Gly Glu Val Ser Glu Lys Ile Ile Thr Met Ala Asp Gly Thr Arg
130                 135                 140 ctt gaa tac aca gga att aaa agc gat gga tct gga aaa gct aaa tat      480
Leu Glu Tyr Thr Gly Ile Lys Ser Asp Gly Ser Gly Lys Ala Lys Tyr
145                 150                 155                 160 gtt tta aaa ggc tat gtt ctt gaa gga act cta act gct gaa aaa aca      528
Val Leu Lys Gly Tyr Val Leu Glu Gly Thr Leu Thr Ala Glu Lys Thr
                165                 170                 175 aca ttg gtg gtt aaa gaa gga act gtt act tta agc aug aat att tca      576
Thr Leu Val Val Lys Glu Gly Thr Val Thr Leu Ser Met Asn Ile Ser
            180                 185                 190 aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205 gct act aaa aaa act gca gct tgg aat tca ggc act tca act tta aca      672
Ala Thr Lys Lys Thr Ala Ala Trp Asn Ser Gly Thr Ser Thr Leu Thr
210                 215                 220 att act gta aac agt aaa aaa act aaa gac ctt gtg ttt aca aaa gaa      720
Ile Thr Val Asn Ser Lys Lys Thr Lys Asp Leu Val Phe Thr Lys Glu
225                 230                 235                 240 aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255 ggg tca gca gtt gaa att aca aaa ctt gat gaa att aaa aac gct tta      816
Gly Ser Ala Val Glu Ile Thr Lys Leu Asp Glu Ile Lys Asn Ala Leu
            260                 265                 270 aaa taa                                                              822
Lys *
```

<210> SEQ ID NO 104
<211> LENGTH: 273
<212> TYPE: PRT
<213> ORGANISM: Artificial Sequence
<220> FEATURE:
<223> OTHER INFORMATION: Altered OspA Protein

<400> SEQUENCE: 104

```
Met Lys Lys Tyr Leu Leu Gly Ile Gly Leu Ile Leu

```
Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
 50                  55                  60

Gly Thr Ser Asp Lys Asn Asn Gly Ser Gly Val Leu Glu Gly Val Lys
 65                  70                  75                  80

Ala Asp Lys Ser Lys Val Lys Leu Thr Ile Ser Asp Asp Leu Gly Gln
                 85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Met Ala Asp Gly Thr Arg
130                 135                 140

Leu Glu Tyr Thr Gly Ile Lys Ser Asp Gly Ser Gly Lys Ala Lys Tyr
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Met Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys

<210> SEQ ID NO 105
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 105

```
Ala Asp Lys Ser Lys Val Lys Leu Thr Ile Ser Asp Leu Gly Gln
             85                  90                  95 acc aca ctt gaa gtt ttc aaa gaa gat ggc aaa aca cta gta tca aaa        336
Thr Thr Leu Glu Val Phe Lys Glu Asp Gly Lys Thr Leu Val Ser Lys
            100                 105                 110 aaa gta act tcc aaa gac aag tca tca aca gaa gaa aaa ttc aat gaa        384
Lys Val Thr Ser Lys Asp Lys Ser Ser Thr Glu Glu Lys Phe Asn Glu
            115                 120                 125 aaa ggt gaa gta tct gaa aaa ata ata aca aga gca gac gga acc aga        432
Lys Gly Glu Val Ser Glu Lys Ile Ile Thr Arg Ala Asp Gly Thr Arg
        130                 135                 140 ctt gaa tac aca gga att aaa agc gat gga tct gga aaa gct aaa gag        480
Leu Glu Tyr Thr Gly Ile Lys Ser Asp Gly Ser Gly Lys Ala Lys Glu
145                 150                 155                 160 gtt tta aaa ggc ttt gtt ctt gaa gga act cta act gct gaa aaa aca        528
Val Leu Lys Gly Phe Val Leu Glu Gly Thr Leu Thr Ala Glu Lys Thr
                165                 170                 175 aca ttg gtg gtt aaa gaa gga act gtt act tta agc aaa aat att tca        576
Thr Leu Val Val Lys Glu Gly Thr Val Thr Leu Ser Lys Asn Ile Ser
            180                 185                 190 aaa tct ggg gaa gtt tca gtt gaa ctt aat gac act gac agt agt gct        624
Lys Ser Gly Glu Val Ser Val Glu Leu Asn Asp Thr Asp Ser Ser Ala
            195                 200                 205 gct act aaa aaa act gca gct tgg aat tca ggc act tca act tta aca        672
Ala Thr Lys Lys Thr Ala Ala Trp Asn Ser Gly Thr Ser Thr Leu Thr
        210                 215                 220 att act gta aac agt aaa aaa act aaa gac ctt gtg ttt aca aaa gaa        720
Ile Thr Val Asn Ser Lys Lys Thr Lys Asp Leu Val Phe Thr Lys Glu
225                 230                 235                 240 aac aca att aca gta caa caa tac gac tca aat ggc acc aaa tta gag        768
Asn Thr Ile Thr Val Gln Gln Tyr Asp Ser Asn Gly Thr Lys Leu Glu
                245                 250                 255 ggg tca gca gtt gaa att aca aaa ctt gat gaa att aaa aac gct tta        816
Gly Ser Ala Val Glu Ile Thr Lys Leu Asp Glu Ile Lys Asn Ala Leu
            260                 265                 270 aaa taa                                                                822
Lys *

<210> SEQ ID NO 106
<211> LENGTH: 273
<212> TYPE: PRT
<213> ORGANISM: Artificial Sequence
<220> FEATURE:
<223> OTHER INFORMATION: Altered OspA protein

<400> SEQUENCE: 106

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25

```
Lys Val Thr Ser Lys Asp Lys Ser Ser Thr Glu Glu Lys Phe Asn Glu
            115                 120                 125

Lys Gly Glu Val Ser Glu Lys Ile Ile Thr Arg Ala Asp Gly Thr Arg
            130                 135                 140

Leu Glu Tyr Thr Gly Ile Lys Ser Asp Gly Ser Gly Lys Ala Lys Glu
145                 150                 155                 160

Val Leu Lys Gly Phe Val Leu Glu Gly Thr Leu Thr Ala Glu Lys Thr
                165                 170                 175

Thr Leu Val Val Lys Glu Gly Thr Val Thr Leu Ser Lys Asn Ile Ser
                180                 185                 190

Lys Ser Gly Glu Val Ser Val Glu Leu Asn Asp Thr Asp Ser Ser Ala
            195                 200                 205

Ala Thr Lys Lys Thr Ala Ala Trp Asn Ser Gly Thr Ser Thr Leu Thr
            210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
                260                 265                 270

Lys
```

```
<210> SEQ ID NO 107
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 107
```

```
atg aaa aaa tat tta ttg gga ata ggt cta ata tta gcc tta ata gca      48
Met Lys Lys Tyr Leu Leu Gly Ile Gly Leu Ile Leu Ala Leu Ile Ala
1               5                   10                  15 tgt aag caa aat gtt agc agc

| | | |
|---|---|---|
| ctt gaa tac aca gga att aaa agc gat gga tct gga aaa gct aaa gag<br>Leu Glu Tyr Thr Gly Ile Lys Ser Asp Gly Ser Gly Lys Ala Lys Glu<br>145                       150                   155                     160 | | 480 |
| gtt tta aaa ggc ttt act ctt gaa gga act cta act gct gaa aaa aca<br>Val Leu Lys Gly Phe Thr Leu Glu Gly Thr Leu Thr Ala Glu Lys Thr<br>                   165                      170                   175 | | 528 |
| aca ttg gtg gtt aaa gaa gga act gtt act tta agc aaa aat att tca<br>Thr Leu Val Val Lys Glu Gly Thr Val Thr Leu Ser Lys Asn Ile Ser<br>                180                     185                   190 | | 576 |
| aaa tct ggg gaa gtt tca gtt gaa ctt aat gac act gac agt agt gct<br>Lys Ser Gly Glu Val Ser Val Glu Leu Asn Asp Thr Asp Ser Ser Ala<br>         195                   200                   205 | | 624 |
| gct act aaa aaa act gca gct tgg aat tca ggc act tca act tta aca<br>Ala Thr Lys Lys Thr Ala Ala Trp Asn Ser Gly Thr Ser Thr Leu Thr<br>210                       215                   220 | | 672 |
| att act gta aac agt aaa aaa act aaa gac ctt gtg ttt aca aaa gaa<br>Ile Thr Val Asn Ser Lys Lys Thr Lys Asp Leu Val Phe Thr Lys Glu<br>225                       230                   235                   240 | | 720 |
| aac aca att aca gta caa caa tac gac tca aat ggc acc aaa tta gag<br>Asn Thr Ile Thr Val Gln Gln Tyr Asp Ser Asn Gly Thr Lys Leu Glu<br>                245                     250                   255 | | 768 |
| ggg tca gca gtt gaa att aca aaa ctt gat gaa att aaa aac gct tta<br>Gly Ser Ala Val Glu Ile Thr Lys Leu Asp Glu Ile Lys Asn Ala Leu<br>         260                   265                   270 | | 816 |
| aaa taa<br>Lys  * | | 822 |

<210> SEQ ID NO 108
<211> LENGTH: 273
<212> TYPE: PRT
<213> ORGANISM: Artificial Sequence
<220> FEATURE:
<223> OTHER INFORMATION: Altered OspA Protein

<400> SEQUENCE: 108

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met L

|  |  |  |  | 180 |  |  |  | 185 |  |  |  | 190 |  |  |  |  |
|---|---|---|---|---|---|---|---|---|---|---|---|---|---|---|---|---|
| Lys | Ser | Gly | Glu | Val | Ser | Val | Glu | Leu | Asn | Asp | Thr | Asp | Ser | Ser | Ala | |
|  |  |  | 195 |  |  |  | 200 |  |  |  | 205 |  |  |  |  |  |

Ala Thr Lys Lys Thr Ala Ala Trp Asn Ser Gly Thr Ser Thr Leu Thr
    210                215                220

Ile Thr Val Asn Ser Lys Lys Thr Lys Asp Leu Val Phe Thr Lys Glu
225                230                235                240

Asn Thr Ile Thr Val Gln Gln Tyr Asp Ser Asn Gly Thr Lys Leu Glu
                245                250                255

Gly Ser Ala Val Glu Ile Thr Lys Leu Asp Glu Ile Lys Asn Ala Leu
        260                265                270

Lys

```
<210> SEQ ID NO 109
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 109
```

| atg | aaa | aaa | tat | tta | ttg | gga | ata | ggt | cta | ata | tta | gcc | tta | ata | gca | 48 |
|---|---|---|---|---|---|---|---|---|---|---|---|---|---|---|---|---|
| Met | Lys | Lys | Tyr | Leu | Leu | Gly | Ile | Gly | Leu | Ile | Leu | Ala | Leu | Ile | Ala | |
| 1 |

```
Lys Ser Gly Glu Val Ser Val Glu Leu Asn Asp Thr Asp Ser Ser Ala
            195                 200                 205 gct act aaa aaa act gca gct tgg aat tca ggc act tca act tta aca    672
Ala Thr Lys Lys Thr Ala Ala Trp Asn Ser Gly Thr Ser Thr Leu Thr
        210                 215                 220 att act gta aac agt aaa aaa act aaa gac ctt gtg ttt aca aaa gaa    720
Ile Thr Val Asn Ser Lys Lys Thr Lys Asp Leu Val Phe Thr Lys Glu
225                 230                 235                 240 aac aca att aca gta caa caa tac gac tca aat ggc acc aaa tta gag    768
Asn Thr Ile Thr Val Gln Gln Tyr Asp Ser Asn Gly Thr Lys Leu Glu
                245                 250                 255 ggg tca gca gtt gaa att aca aaa ctt gat gaa att aaa aac gct tta    816
Gly Ser Ala Val Glu Ile Thr Lys Leu Asp Glu Ile Lys Asn Ala Leu
            260                 265                 270 aaa taa                                                             822
Lys *

<210> SEQ ID NO 110
<211> LENGTH: 273
<212> TYPE: PRT
<213> ORGANISM: Artificial Sequence
<220> FEATURE:
<223> OTHER INFORMATION: Altered OspA Protein

<400>

```
Gly Ser Ala Val Glu Ile Thr Lys Leu Asp Glu Ile Lys Asn Ala Leu
            260                 265                 270

Lys

<210> SEQ ID NO 111
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 111 atg aaa aaa tat tta ttg gga ata ggt cta ata tta gcc tta ata gca      48
Met Lys Lys Tyr Leu Leu Gly Ile Gly Leu Ile Leu Ala Leu Ile

| | | | | | | | | | | | | |
|---|---|---|---|---|---|---|---|---|---|---|---|---|
| ggg | tca | gca | gtt | gaa | att | aca | aaa | ctt | gat | gaa | att | |
| Gly | Ser | Ala | Val | Glu | Ile | Thr | Lys | Leu | Asp | Glu | Ile | |
| | | 260 | | | | | 265 | | | | | |
| | | | | | | | | | | | | |
| aaa | aac | gct | tta | | | | | | | | | 816 |
| Lys | Asn | Ala | Leu | | | | | | | | | |
| | | 270 | | | | | | | | | | | aaa taa                                                                    822
Lys *

```
<210> SEQ ID NO 112
<211> LENGTH: 273
<212> TYPE: PRT
<213> ORGANISM: Artificial Sequence
<220> FEATURE:
<223> OTHER INFORMATION: Altered OspA Protein

<400> SEQUENCE: 112
```

Met Lys Lys T

<400> SEQUENCE: 113

```
atg aaa aaa tat tta ttg gga ata ggt cta ata tta gcc tta ata gca    48
Met Lys Lys Tyr Leu Leu Gly Ile Gly Leu Ile Leu Ala Leu Ile Ala
1               5                   10                  15 tgt aag caa aat gtt agc agc ctt gac gag aaa aac agc gtt tca gta    96
Cys Lys Gln Asn Val Ser Ser Leu Asp Glu Lys Asn Ser Val Ser Val
            20                  25                  30 gat ttg cct ggt gaa atg aaa gtt ctt gta agc aaa gaa aaa aac aaa   144
Asp Leu Pro Gly Glu Met Lys Val Leu Val Ser Lys Glu Lys Asn Lys
        35                  40                  45 gac ggc aag tac gat cta att gca aca gta gac aag ctt gag ctt aaa   192
Asp Gly Lys Tyr Asp Leu Ile Ala Thr Val Asp Lys Leu Glu Leu Lys
    50                  55                  60 gga act tct gat aaa aac aat gga tct gga gta ctt gaa ggc gta aaa   240
Gly Thr Ser Asp Lys Asn Asn Gly Ser Gly Val Leu Glu Gly Val Lys
65                  70                  75                  80 gct gac aaa agt aaa gta aaa tta aca att tct gac gat cta ggt caa   288
Ala Asp Lys Ser Lys Val Lys Leu Thr Ile Ser Asp Asp Leu Gly Gln
                85                  90                  95 acc aca ctt gaa gtt ttc aaa gaa gat ggc aaa aca cta gta tca aaa   336
Thr Thr Leu Glu Val Phe Lys Glu Asp Gly Lys Thr Leu Val Ser Lys
            100                 105                 110 aaa gta act tcc aaa gac aag tca tca aca gaa gaa aaa ttc aat gaa   384
Lys Val Thr Ser Lys Asp Lys Ser Ser Thr Glu Glu Lys Phe Asn Glu
        115                 120                 125 aaa ggt gaa gta tct gaa aaa ata ata aca aga gca gac gga acc aga   432
Lys Gly Glu Val Ser Glu Lys Ile Ile Thr Arg Ala Asp Gly Thr Arg
    130                 135                 140 ctt gaa tac aca gga att aaa agc gat gga tct gga aaa gct aaa gag   480
Leu Glu Tyr Thr Gly Ile Lys Ser Asp Gly Ser Gly Lys Ala Lys Glu
145                 150                 155                 160 gtt tta aaa ggc ttt act ctt gaa gga aag cta act gct gaa aaa aca   528
Val Leu Lys Gly Phe Thr Leu Glu Gly Lys Leu Thr Ala Glu Lys Thr
                165                 170                 175 aca ttg gtg gtt aaa gaa gga act gtt act tta agc aaa aat att tca   576
Thr Leu Val Val Lys Glu Gly Thr Val Thr Leu Ser Lys Asn Ile Ser
            180                 185                 190 aaa tct ggg gaa gtt tca gtt gaa ctt aat gac act gac agt agt gct   624
Lys Ser Gly Glu Val Ser Val Glu Leu Asn Asp Thr Asp Ser Ser Ala
        195                 200                 205 gct act aaa aaa act gca gct tgg aat tca ggc act tca act tta aca   672
Ala Thr Lys Lys Thr Ala Ala Trp Asn Ser Gly Thr Ser Thr Leu Thr
    210                 215                 220 att act gta aac agt aaa aaa act aaa gac ctt gtg ttt aca aaa gaa   720
Ile Thr Val Asn Ser Lys Lys Thr Lys Asp Leu Val Phe Thr Lys Glu
225                 230                 235                 240 aac aca att aca gta caa caa tac gac tca aat ggc acc aaa tta gag   768
Asn Thr Ile Thr Val Gln Gln Tyr Asp Ser Asn Gly Thr Lys Leu Glu
                245                 250                 255 ggg tca gca gtt gaa att aca aaa ctt gat gaa att aaa aac gct tta   816
Gly Ser Ala Val Glu Ile Thr Lys Leu Asp Glu Ile Lys Asn Ala Leu
            260                 265                 270 aaa taa                                                           822
Lys *
```

<210> SEQ ID NO 114
<211> LENGTH: 273
<212> TYPE: PRT
<213> ORGANISM: Artificial Sequence
<220> FEATURE:

<223> OTHER INFORMATION: Altered OspA protein

<400> SEQUENCE: 114

```
Met Lys Lys Tyr Leu Leu Gly Ile Gly Leu Ile Leu Ala Leu Ile Ala
  1               5                  10                  15
Cys Lys Gln Asn Val Ser Ser Leu Asp Glu L

-continued

```
gac ggc aag tac gat cta att gca aca gta gac aag ctt gag ctt aaa      192
Asp Gly Lys Tyr Asp Leu Ile Ala Thr Val Asp Lys Leu Glu Leu Lys
        50                  55                  60 gga act tct gat aaa aac aat gga tct gga gta ctt gaa ggc gta aaa      240
Gly Thr Ser Asp Lys Asn Asn Gly Ser Gly Val Leu Glu Gly Val Lys
 65                  70                  75                  80 gct gac aaa agt aaa gta aaa tta aca att tct gac gat cta ggt caa      288
Ala Asp Lys Ser Lys Val Lys Leu Thr Ile Ser Asp Asp Leu Gly Gln
                 85                  90                  95 acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110 aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125 aaa ggt gaa gta tct gaa aaa ata ata aca atg gca gac gga acc aga      432
Lys Gly Glu Val Ser Glu Lys Ile Ile Thr Met Ala Asp Gly Thr Arg
130                 135                 140 ctt gaa tac aca gga att aaa agc gat gga tct gga aaa gct aaa tat      480
Leu Glu Tyr Thr Gly Ile Lys Ser Asp Gly Ser Gly Lys Ala Lys Tyr
145                 150                 155                 160 gtt tta aaa ggc ttt act ctt gaa gga aag cta act gct gaa aaa aca      528
Val Leu Lys Gly Phe Thr Leu Glu Gly Lys Leu Thr Ala Glu Lys Thr
                165                 170                 175 aca ttg gtg gtt aaa gaa gga act gtt act tta agc atg aat att tca      576
Thr Leu Val Val Lys Glu Gly Thr Val Thr Leu Ser Met Asn Ile Ser
            180                 185                 190 aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205 gct act aaa aaa act gca gct tgg aat tca ggc act tca act tta aca      672
Ala Thr Lys Lys Thr Ala Ala Trp Asn Ser Gly Thr Ser Thr Leu Thr
    210                 215                 220 att act gta aac agt aaa aaa act aaa gac ctt gtg ttt aca aaa gaa      720
Ile Thr Val Asn Ser Lys Lys Thr Lys Asp Leu Val Phe Thr Lys Glu
225                 230                 235                 240 aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255 ggg tca gca gtt gaa att aca aaa ctt gat gaa att aaa aac gct tta      816
Gly Ser Ala Val Glu Ile Thr Lys Leu Asp Glu Ile Lys Asn Ala Leu
            260                 265                 270 aaa taa                                                               822
Lys *
```

<210> SEQ ID NO 116
<211> LENGTH: 273
<212> TYPE: PRT
<213> ORGANISM: Artificial Sequence
<220> FEATURE:
<223> OTHER INFORMATION: Altered OspA protein

<400> SEQUENCE: 116

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
```

```
                    50                  55                  60
Gly Thr Ser Asp Lys Asn Asn Gly Ser Gly Val Leu Glu Gly Val Lys
 65                  70                  75                  80

Ala Asp Lys Ser Lys Val Lys Leu Thr Ile Ser Asp Asp Leu Gly Gln
                 85                  90                  95

Thr Thr Leu Glu Val Phe Lys Glu Asp Gly Lys Thr Leu Val Ser Lys
                100                 105                 110

Lys Val Thr Ser Lys Asp Lys Ser Ser Thr Glu Glu Lys Phe Asn Glu
            115                 120                 125

Lys Gly Glu Val Ser Glu Lys Ile Ile Thr Met Ala Asp Gly Thr Arg
130                 135                 140

Leu Glu Tyr Thr Gly Ile Lys Ser Asp Gly Ser Gly Lys Ala Lys Tyr
145                 150                 155                 160

Val Leu Lys Gly Phe Thr Leu Glu Gly Lys Leu Thr Ala Glu Lys Thr
                165                 170                 175

Thr Leu Val Val Lys Glu Gly Thr Val Thr Leu Ser Met Asn Ile Ser
                180                 185                 190

Lys Ser Gly Glu Val Ser Val Glu Leu Asn Asp Thr Asp Ser Ser Ala
            195                 200                 205

Ala Thr Lys Lys Thr Ala Ala Trp Asn Ser Gly Thr Ser Thr Leu Thr
        210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys

<210> SEQ ID NO 117
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 117
gaaaaaataa taacaatggc agacggaacc                                      30

<210> SEQ ID NO 118
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 118
ggttccgtct gccattgtta ttattttttc                                      30

<210> SEQ ID NO 119
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 119
ggaaaagcta atatgttttt aaaaggc                                         27
```

```
<210> SEQ ID NO 120
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 120 gcctttaaa acatatttag cttttcc                                        27

<210> SEQ ID NO 121
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 121
gttactttaa gcatgaatat ttcaaaatc                                     29

<210> SEQ ID NO 122
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 122
gattttgaaa tattcatgct taaagtaac                                     29

<210> SEQ ID NO 123
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 123
gaggttttaa aaggctttac tcttgaagga actc                               34

<210> SEQ ID NO 124
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 124
gagttccttc aagagtaaag ccttttaaaa cctg                               34

<210> SEQ ID NO 125
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 125
tcttgaagga aagctaactg ctg                                           23

<210> SEQ ID NO 126
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 126
```

```
cagcagttag ctttccttca aga                                                   23

<210> SEQ ID NO 127
<211> LENGTH: 819
<212> TYPE: DNA
<213> ORGANISM: Borrelia burgdorferi
<220> FEATURE:
<221> NAME/KEY: CDS
<222> LOCATION: (1)...(819)

<400> SEQUENCE: 127 atg aaa aaa tat tta ttg gga ata ggt cta ata tta gcc tta ata gca      48
Met Lys Lys Tyr Leu Leu Gly Ile Gly Leu Ile Leu Ala Leu Ile Ala
1               5                   10                  15 tgt aag caa aat gtt agc agc ctt gac gag aaa aac agc gtt tca gta      96
Cys Lys Gln Asn Val Ser Ser Leu Asp Glu Lys Asn Ser Val Ser Val
            20                  25                  30 gat ttg cct ggt gaa atg aaa gtt ctt gta agc aaa gaa aaa aac aaa     144
Asp Leu Pro Gly Glu Met Lys Val Leu Val Ser Lys Glu Lys Asn Lys
        35                  40                  45 gac ggc aag tac gat cta att gca aca gta gac aag ctt gag ctt aaa     192
Asp Gly Lys Tyr Asp Leu Ile Ala Thr Val Asp Lys Leu Glu Leu Lys
    50                  55                  60 gga act tct gat aaa aac aat gga tct gga gta ctt gaa ggc gta aaa     240
Gly Thr Ser Asp Lys Asn Asn Gly Ser Gly Val Leu Glu Gly Val Lys
65                  70                  75                  80 gct gac aaa agt aaa gta aaa tta aca att tct gac gat cta ggt caa     288
Ala Asp Lys Ser Lys Val Lys Leu Thr Ile Ser Asp Asp Leu Gly Gln
                85                  90                  95 acc aca ctt gaa gtt ttc aaa gaa gat ggc aaa aca cta gta tca aaa     336
Thr Thr Leu Glu Val Phe Lys Glu Asp Gly Lys Thr Leu Val Ser Lys
            100                 105                 110 aaa gta act tcc aaa gac aag tca tca aca gaa gaa aaa ttc aat gaa     384
Lys Val Thr Ser Lys Asp Lys Ser Ser Thr Glu Glu Lys Phe Asn Glu
        115                 120                 125 aaa ggt gaa gta tct gaa aaa ata ata aca aga gca gac gga acc aga     432
Lys Gly Glu Val Ser Glu Lys Ile Ile Thr Arg Ala Asp Gly Thr Arg
    130                 135                 140 ctt gaa tac aca gga att aaa agc gat gga tct gga aaa gct aaa gag     480
Leu Glu Tyr Thr Gly Ile Lys Ser Asp Gly Ser Gly Lys Ala Lys Glu
145                 150                 155                 160 gtt tta aaa ggc tat gtt ctt gaa gga act cta act gct gaa aaa aca     528
Val Leu Lys Gly Tyr Val Leu Glu Gly Thr Leu Thr Ala Glu Lys Thr
                165                 170                 175 aca ttg gtg gtt aaa gaa gga act gtt act tta agc aaa aat att tca     576
Thr Leu Val Val Lys Glu Gly Thr Val Thr Leu Ser Lys Asn Ile Ser
            180                 185                 190 aaa tct ggg gaa gtt tca gtt gaa ctt aat gac act gac agt agt gct     624
Lys Ser Gly Glu Val Ser Val Glu Leu Asn Asp Thr Asp Ser Ser Ala
        195                 200                 205 gct act aaa aaa act gca gct tgg aat gca ggc act tca act tta aca     672
Ala Thr Lys Lys Thr Ala Ala Trp Asn Ala Gly Thr Ser Thr Leu Thr
    210                 215                 220 att act gta aac aac aaa aaa act aaa gcc ctt gta ttt aca aaa caa     720
Ile Thr Val Asn Asn Lys Lys Thr Lys Ala Leu Val Phe Thr Lys Gln
225                 230                 235                 240 gac aca att aca tca caa aaa tac gac tca gca gga acc aac ttg gaa     768
Asp Thr Ile Thr Ser Gln Lys Tyr Asp Ser Ala Gly Thr Asn Leu Glu
                245                 250                 255 ggc aca gca gtc gaa att aaa aca ctt gat gaa ctt aaa aac gct tta     816
Gly Thr Ala Val Glu Ile Lys Thr Leu Asp Glu Leu Lys Asn Ala Leu
``` aga       819
Arg

<210> SEQ ID NO 128
<211> LENGTH: 273
<212> TYPE: PRT
<213> ORGANISM: Borrelia burgdorferi

<400> SEQUENCE: 128

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ala Gly Thr Ser Thr Leu Thr
    210                 215                 220

Ile Thr Val Asn Asn Lys Lys Thr Lys Ala Leu Val Phe Thr Lys Gln
225                 230                 235                 240

Asp Thr Ile Thr Ser Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Arg

<210> SEQ ID NO 129
<211> LENGTH: 9
<212> TYPE: PRT
<213> ORGANISM: Artificial Sequence
<220> FEATURE:
<223> OTHER INFORMATION: Residue 165-173 of B31 OspA

<400> SEQUENCE: 129

Tyr Val Leu Glu Gly Thr Leu Thr Ala
1               5

```
<210> SEQ ID NO 130
<211> LENGTH: 9
<212> TYPE: PRT
<213> ORGANISM: Artificial Sequence
<220> FEATURE:
<223> OTHER INFORMATION: Residue 332-340 of hLFA-1

<400> SEQUENCE: 130

Tyr Val Ile Glu Gly Thr Ser Lys Gln
 1               5

<210> SEQ ID NO 131
<211> LENGTH: 8
<212> TYPE: PRT
<213> ORGANISM: Borrelia burgdorferi

<400> SEQUENCE: 131

Leu Pro Gly Glu Met Lys Val Leu
 1               5

<210> SEQ ID NO 132
<211> LENGTH: 8
<212> TYPE: PRT
<213> ORGANISM: Borrelia burgdorferi

<400> SEQUENCE: 132

Leu Pro Gly Glu Met Lys Val Leu
 1               5

<210> SEQ ID NO 133
<211> LENGTH: 8
<212> TYPE: PRT
<213> ORGANISM: Borrelia burgdorferi

<400> SEQUENCE: 133

Leu Pro Gly Gly Met Thr Val Leu
 1               5

<210> SEQ ID NO 134
<211> LENGTH: 8
<212> TYPE: PRT
<213> ORGANISM: Borrelia burgdorferi

<400> SEQUENCE: 134

Leu Pro Gly Gly Met Thr Val Leu
 1               5

<210> SEQ ID NO 135
<211> LENGTH: 8
<212> TYPE: PRT
<213> ORGANISM: Borrelia burgdorferi

<400> SEQUENCE: 135

Leu Pro Gly Glu Met Lys Val Leu
 1               5

<210> SEQ ID NO 136
<211> LENGTH: 8
<212> TYPE: PRT
<213> ORGANISM: Borrelia burgdorferi

<400> SEQUENCE: 136

Leu Pro Gly Glu Met Lys Val Leu
 1               5

<210> SEQ ID NO 137
```

```
<211> LENGTH: 8
<212> TYPE: PRT
<213> ORGANISM: Borrelia burgdorferi

<400> SEQUENCE: 137

Leu Pro Gly Glu Ile Lys Val Leu
1               5

<210> SEQ ID NO 138
<211> LENGTH: 8
<212> TYPE: PRT
<213> ORGANISM: Borrelia burgdorferi

<400> SEQUENCE: 138

Leu Pro Gly Gly Met Gly Val Leu
1               5

<210> SEQ ID NO 139
<211> LENGTH: 8
<212> TYPE: PRT
<213> ORGANISM: Borrelia burgdorferi

<400> SEQUENCE: 139

Leu Pro Gly Glu Met Lys Val Leu
1               5

<210> SEQ ID NO 140
<211> LENGTH: 11
<212> TYPE: PRT
<213> ORGANISM: Borrelia burgdorferi

<400> SEQUENCE: 140

Gly Thr Ser Asp Lys Asn Asn Gly Ser Gly Val
1               5                   10

<210> SEQ ID NO 141
<211> LENGTH: 11
<212> TYPE: PRT
<213> ORGANISM: Borrelia burgdorferi

<400> SEQUENCE: 141

Gly Thr Ser Asp Lys Ser Asn Gly Ser Gly Thr
1               5                   10

<210> SEQ ID NO 142
<211> LENGTH: 11
<212> TYPE: PRT
<213> ORGANISM: Borrelia burgdorferi

<400> SEQUENCE: 142

Gly Thr Ser Asp Lys Asn Asn Gly Ser Gly Thr
1               5                   10

<210> SEQ ID NO 143
<211> LENGTH: 11
<212> TYPE: PRT
<213> ORGANISM: Borrelia burgdorferi

<400> SEQUENCE: 143

Gly Thr Ser Asp Lys Asn Asn Gly Ser Gly Thr
1               5                   10

<210> SEQ ID NO 144
<211> LENGTH: 11
<212> TYPE: PRT
<213> ORGANISM: Borrelia burgdorferi
```

```
<400> SEQUENCE: 14

Gly Thr Ser Asp Lys Asp Asn Gly Ser Gly Thr
1               5                   10

<210> SEQ ID NO 145
<211> LENGTH: 11
<212> TYPE: PRT
<213> ORGANISM: Borrelia burgdorferi

<400> SEQUENCE: 145

Gly Thr Ser Asp Lys Asp Asn Gly Ser Gly Thr
1               5                   10

<210> SEQ ID NO 146
<211> LENGTH: 11
<212> TYPE: PRT
<213> ORGANISM: Borrelia burgdorferi

<400> SEQUENCE: 146

Gly Thr Ser Asp Lys Asp Asn Gly Ser Gly Val
1               5                   10

<210> SEQ ID NO 147
<211> LENGTH: 11
<212> TYPE: PRT
<213> ORGANISM: Borrelia burgdorferi

<400> SEQUENCE: 147

Gly Thr Ser Asp Lys Asn Asn Gly Ser Gly Thr
1               5                   10

<210> SEQ ID NO 148
<211> LENGTH: 11
<212> TYPE: PRT
<213> ORGANISM: Borrelia burgdorferi

<400> SEQUENCE: 148

Gly Thr Ser Asp Lys Asn Asn Gly Ser Gly Val
1               5                   10

<210> SEQ ID NO 149
<211> LENGTH: 31
<212> TYPE: PRT
<213> ORGANISM: Borrelia burgdorferi

<400> SEQUENCE: 149

Asn Ile Ser Lys Ser Gly Glu Val Ser Val Glu Leu Asn Asp Thr Asp
1               5                   10                  15

Ser Ser Ala Ala Thr Lys Lys Thr Ala Ala Trp Asn Ser Gly Thr
            20                  25                  30

<210> SEQ ID NO 150
<211> LENGTH: 31
<212> TYPE: PRT
<213> ORGANISM: Borrelia burgdorferi

<400> SEQUENCE: 150

His Ile Pro Asn Ser Gly Glu Ile Thr Val Glu Leu Asn Asp Ser Asn
1               5                   10                  15

Ser Thr Gln Ala Thr Lys Lys Thr Gly Lys Trp Asp Ser Asn Thr
            20                  25                  30

<210> SEQ ID NO 151
```

```
<211> LENGTH: 29
<212> TYPE: PRT
<213> ORGANISM: Borrelia burgdorferi

<400> SEQUENCE: 151

Asn Ile Leu Lys Ser Gly Glu Ile Thr Val Asp Asp Ser Asp Thr
 1               5                  10                  15

Gln Ala Thr Lys Lys Thr Gly Lys Trp Asp Ser Lys Thr
            20                  25

<210> SEQ ID NO 152
<211> LENGTH: 31
<212> TYPE: PRT
<213> ORGANISM: Borrelia burgdorferi

<400> SEQUENCE: 152

Asn Ile Leu Lys Ser Gly Glu Ile Thr Ala Ala Leu Asp Asp Ser Asp
 1               5                  10                  15

Thr Thr Arg Ala Thr Lys Lys Thr Gly Lys Trp Asp Ser Lys Thr
                20                  25                  30

<210> SEQ ID NO 153
<211> LENGTH: 29
<212> TYPE: PRT
<213> ORGANISM: Borrelia burgdorferi

<400> SEQUENCE: 153

Glu Ile Ala Lys Ser Gly Glu Val Thr Val Asn Asp Thr Asn Thr Thr
 1               5                  10                  15

Gln Ala Thr Lys Lys Thr Gly Ala Trp Asp Ser Lys Thr
            20                  25

<210> SEQ ID NO 154
<211> LENGTH: 29
<212> TYPE: PRT
<213> ORGANISM: Borrelia burgdorferi

<400> SEQUENCE: 154

Glu Ile Ala Lys Ser Gly Glu Val Thr Val Asn Asp Thr Asn Thr Thr
 1               5                  10                  15

Gln Ala Thr Lys Lys Thr Gly Ala Trp Asp Ser Lys Thr
            20                  25

<210> SEQ ID NO 155
<211> LENGTH: 29
<212> TYPE: PRT
<213> ORGANISM: Borrelia burgdorferi

<400> SEQUENCE: 155

Glu Ile Ala Lys Ser Gly Glu Val Thr Val Asn Asp Thr Asn Thr Thr
 1               5                  10                  15

Gln Ala Thr Lys Lys Thr Gly Ala Trp Asp Ser Lys Thr
            20                  25

<210> SEQ ID NO 156
<211> LENGTH: 29
<212> TYPE: PRT
<213> ORGANISM: Borrelia burgdorferi

<400> SEQUENCE: 156

His Asn Ser Gly Glu Ile Thr Val Glu Leu Asn Asp Ser Asp Thr Thr
 1               5                  10                  15

Gln Ala Thr Lys Lys Thr Gly Thr Trp Asp Ser Lys Thr
```

```
                    20                  25

<210> SEQ ID NO 157
<211> LENGTH: 29
<212> TYPE: PRT
<213> ORGANISM: Borrelia burgdorferi

<400> SEQUENCE: 157

His Lys Ser Gly Glu Val Thr Ala Glu Leu Asn Asp Thr Asp Ser Thr
1               5                   10                  15

Gln Ala Thr Lys Lys Thr Gly Lys Trp Asp Ala Gly Thr
            20                  25

<210> SEQ ID NO 158
<211> LENGTH: 21
<212> TYPE: PRT
<213> ORGANISM: Borrelia burgdorferi

<400> SEQUENCE: 158

Ser Asn Gly Thr Lys Leu Glu Gly Ser Ala Val Glu Ile Thr Lys Leu
1               5                   10                  15

Asp Glu Ile Lys Asn
            20

<210> SEQ ID NO 159
<211> LENGTH: 21
<212> TYPE: PRT
<213> ORGANISM: Borrelia burgdorferi

<400> SEQUENCE: 159

Ser Ala Gly Thr Asn Leu Glu Gly Asn Ala Val Glu Ile Lys Thr Leu
1               5                   10                  15

Asp Glu Leu Lys Asn
            20

<210> SEQ ID NO 160
<211> LENGTH: 21
<212> TYPE: PRT
<213> ORGANISM: Borrelia burgdorferi

<400> SEQUENCE: 160

Ser Ala Gly Thr Asn Leu Glu Gly Lys Ala Val Glu Ile Thr Thr Leu
1               5                   10                  15

Lys Glu Leu Lys Asn
            20

<210> SEQ ID NO 161
<211> LENGTH: 21
<212> TYPE: PRT
<213> ORGANISM: Borrelia burgdorferi

<400> SEQUENCE: 161

Ser Ala Gly Thr Asn Leu Glu Gly Lys Ala Val Glu Ile Thr Thr Leu
1               5                   10                  15

Lys Glu Leu Lys Asn
            20

<210> SEQ ID NO 162
<211> LENGTH: 21
<212> TYPE: PRT
<213> ORGANISM: Borrelia burgdorferi

<400> SEQUENCE: 162
```

```
Ser Ala Gly Thr Asn Leu Glu Gly Thr Ala Val Glu Ile Lys Thr Leu
1               5                   10                  15

Asp Glu Leu Lys Asn
            20
```

<210> SEQ ID NO 163
<211> LENGTH: 21
<212> TYPE: PRT
<213> ORGANISM: Borrelia burgdorferi

<400> SEQUENCE: 163

```
Ser Ala Gly Thr Asn Leu Glu Gly Thr Ala Val Glu Ile Lys Thr Leu
1               5                   10                  15

Asp Glu Leu Lys Asn
            20
```

<210> SEQ ID NO 164
<211> LENGTH: 21
<212> TYPE: PRT
<213> ORGANISM: Borrelia burgdorferi

<400> SEQUENCE: 164

```
Ser Ala Gly Thr Asn Leu Glu Gly Thr Ala Val Glu Ile Lys Thr Leu
1               5                   10                  15

Asp Glu Leu Lys Asn
            20
```

<210> SEQ ID NO 165
<211> LENGTH: 21
<212> TYPE: PRT
<213> ORGANISM: Borrelia burgdorferi

<400> SEQUENCE: 165

```
Ser Ala Gly Thr Asn Leu Glu Gly Lys Ala Val Glu Ile Thr Thr Leu
1               5                   10                  15

Lys Glu Leu Lys Asn
            20
```

<210> SEQ ID NO 166
<211> LENGTH: 21
<212> TYPE: PRT
<213> ORGANISM: Borrelia burgdorferi

<400> SEQUENCE: 166

```
Ser Ala Gly Thr Asn Leu Glu Gly Thr Ala Val Glu Ile Lys Thr Leu
1               5                   10                  15

Asp Glu Ile Lys Asn
            20
```

<210> SEQ ID NO 167
<211> LENGTH: 21
<212> TYPE: PRT
<213> ORGANISM: Borrelia burgdorferi

<400> SEQUENCE: 167

```
Glu Leu Asn Asp Thr Asp Ser Ser Ala Ala Thr Lys Lys Thr Ala Ala
1               5                   10                  15

Trp Asn Ser Gly Thr
            20
```

<210> SEQ ID NO 168
<211> LENGTH: 21
<212> TYPE: PRT

<213> ORGANISM: Borrelia burgdorferi

<400> SEQUENCE: 168

Ala Leu Asp Asp Ser Asp Thr Thr Gln Ala Thr Lys Lys Thr Gly Lys
1               5                   10                  15

Trp Asp Ser Lys Thr
            20

<210> SEQ ID NO 169
<211> LENGTH: 21
<212> TYPE: PRT
<213> ORGANISM: Borrelia burgdorferi

<400> SEQUENCE: 169

Glu Leu Asn Asp Ser Asp Thr Ser Ala Ala Thr Lys Lys Thr Ala Ala
1               5                   10                  15

Trp Asn Ser Gly Thr
            20

<210> SEQ ID NO 170
<211> LENGTH: 21
<212> TYPE: PRT
<213> ORGANISM: Borrelia burgdorferi

<400> SEQUENCE: 170

Glu Leu Asn Asp Thr Asp Ser Ser Ala Ala Thr Lys Lys Thr Gly Lys
1               5                   10                  15

Trp Asn Ser Gly Thr
            20

<210> SEQ ID NO 171
<211> LENGTH: 21
<212> TYPE: PRT
<213> ORGANISM: Borrelia burgdorferi

<400> SEQUENCE: 171

Glu Leu Asn Asp Thr Asp Ser Ser Ala Ala Thr Lys Lys Thr Ala Ala
1               5                   10                  15

Trp Asp Ser Lys Thr
            20

<210> SEQ ID NO 172
<211> LENGTH: 21
<212> TYPE: PRT
<213> ORGANISM: Borrelia burgdorferi

<400> SEQUENCE: 172

Glu Leu Asn Asp Ser Asp Thr Ser Ala Ala Thr Lys Lys Thr Gly Lys
1               5                   10                  15

Trp Asn Ser Gly Thr
            20

<210> SEQ ID NO 173
<211> LENGTH: 21
<212> TYPE: PRT
<213> ORGANISM: Borrelia burgdorferi

<400> SEQUENCE: 173

Glu Leu Asn Asp Ser Asp Thr Ser Ala Ala Thr Lys Lys Thr Ala Ala
1               5                   10                  15

Trp Asp Ser Lys Thr
            20

What is claimed is:

1. A purified polypeptide comprising an OspA protein from a sensu stricto strain of *Borrelia burgdorferi*, wherein the OspA protein comprises SEQ ID NO:7 in which there are alterations consisting of: residue 165 of SEQ ID NO:7 being phenylalanine, residue 166 of SEQ ID NO:7 being threonine, and residue 170 of SEQ ID NO:7 being lysine.

2. A purified polypeptide selected from the group consisting of: SEQ ID NO:96, 98, 100, 102, 104, 106, 108, 110, 112, 114 and 116.

3. A method of generating an altered *Borrelia burgdorferi* OspA protein with reduced cross-reactivity with an hLFA-1 molecule, compared to the cross-reactivity with an hLFA-1 molecule of a corresponding unaltered *Borrelia burgdorferi* OspA protein (SEQ ID NO:7), comprising;

a) providing an expression vector comprising a regulatory sequence operably linked to a polynucleotide encoding a polypeptide comprising an OspA protein from *Borrelia burgdorferi* comprising SEQ ID NO:7;

b) altering the polynucleotide such that encoded residue 165 of SEQ ID NO:7 is phenylalanine, encoded residue 166 of SEQ ID NO:7 is threonine and encoded residue of SEQ ID NO:7 170 is lysine; and c) expressing the polynucleotide of step b);

thereby generating the altered *Borrelia burgdorferi* OspA protein.

4. A purified polypeptide comprising an OspA protein from a sensu stricto strain of *Borrelia burgdorferi*, wherein the OspA protein comprises SEQ ID NO:7 in which there are alterations consisting of: residue 165 of SEQ ID NO:7 being phenylalanine, residue 166 of SEQ ID NO:7 being threonine, residue 170 of SEQ ID NO:7 being lysine, residue 139 of SEQ ID NO:7 being methionine, residue 160 of SEQ ID NO:7 being tyrosine and residue 189 of SEQ ID NO:7 being methionine.

* * * * *

UNITED STATES PATENT AND TRADEMARK OFFICE
CERTIFICATE OF CORRECTION

| | | |
|---|---|---|
| PATENT NO. | : 8,680,236 B2 | Page 1 of 1 |
| APPLICATION NO. | : 12/313443 | |
| DATED | : March 25, 2014 | |
| INVENTOR(S) | : Luft et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 763 days.

Signed and Sealed this
Twenty-first Day of July, 2015

Michelle K. Lee
*Director of the United States Patent and Trademark Office*